US005310737A

United States Patent [19]
Fisher et al.

[11] Patent Number: 5,310,737
[45] Date of Patent: May 10, 1994

[54] BENZO-FUSED LACTAMS THAT PROMOTE THE RELEASE OF GROWTH HORMONE

[75] Inventors: Michael H. Fisher, Ringoes; William R. Schoen, Edison; Matthew J. Wyvratt, Mountainside; Robert J. DeVita, Westfield, all of N.J.

[73] Assignee: Merck & Co., Inc., Rahway, N.J.

[21] Appl. No.: 12,190

[22] Filed: Feb. 2, 1993

Related U.S. Application Data

[60] Division of Ser. No. 839,742, Feb. 28, 1992, Pat. No. 5,206,235, which is a continuation-in-part of Ser. No. 673,695, Mar. 20, 1991, abandoned.

[51] Int. Cl.$^5$ .................... A61K 31/55; C07D 281/02
[52] U.S. Cl. .................................... 514/215; 540/491
[58] Field of Search ................ 540/491; 514/213, 211, 514/215

[56] References Cited

U.S. PATENT DOCUMENTS

| | | | |
|---|---|---|---|
| 3,239,345 | 8/1966 | Hodge et al. | 514/450 |
| 4,036,979 | 7/1977 | Asato | 514/443 |
| 4,411,890 | 10/1983 | Momany | 514/17 |
| 4,539,150 | 9/1985 | Katakami et al. | 540/491 |
| 4,882,326 | 11/1989 | Murakami et al. | 540/491 |
| 5,206,234 | 4/1993 | Bock et al. | 514/213 |

FOREIGN PATENT DOCUMENTS 166357  6/1984  European Pat. Off. .
349949  7/1988  European Pat. Off. .

OTHER PUBLICATIONS

Parsons, W. H., *Med. Chem.* vol. 32 pp. 1681–1685, yr 1989/Sep.
Jones, et al, *J. Chem. Soc. C* pp. 2176–2181 (1969).
Davis, et al *Arch. Biochem. Biophys 102* pp. 48–51 (1963).
Wattley, et al *J. Med. Chem. 28* 1511–1516 (1985).
Slade, et al *J. Med. Chem 28* pp. 1517–1521 (1985).
Ott, *Arch. Pharm* (Weinheim, Gen) 325 (9) pp. 601–603 (1990).
Huang, et al *Synthesis 10* p. 851 (1984).
Australia J. Chem. 33 pp. 633–640 (1980).
Still, et al *J. Org. Chem. 43* p. 2923 (1978).

*Primary Examiner*—Mukund J. Shah
*Assistant Examiner*—Pavanaram R. Sripada
*Attorney, Agent, or Firm*—David L. Rose; Joseph F. DiPrima

[57] ABSTRACT

There are disclosed certain novel compounds identified as benzo-fused lactams which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such benzo-fused lactams as the active ingredient thereof are also disclosed.

9 Claims, No Drawings

BENZO-FUSED LACTAMS THAT PROMOTE THE RELEASE OF GROWTH HORMONE

CROSS REFERENCE TO RELATED APPLICATIONS

This is a division of application Ser. No. 07/839,742, filed Feb. 28, 1992, now U.S. Pat. No. 5,206,235, which is a continuation-in-part of our copending application Ser. No. 673694, filed 20 Mar. 1991 now abandoned.

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,390. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures for the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

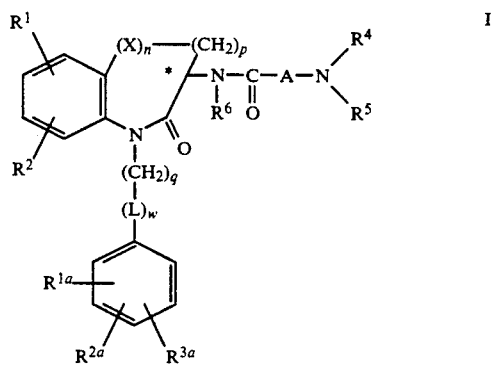

where L is

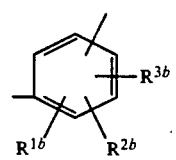

X is C=O, O, S(O)$_m$, $-\overset{OH}{\underset{|}{CH}}-$, $-\overset{R^{10}}{\underset{|}{N}}-$, $-CH=CH-$;

m is 0 to 2;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, $C_1$-$C_3$ perfluoroalkoxy. $-S(O)_mR^{7a}$, cyano, nitro, $R^{7b}O(CH_2)_r$-, $R^{7b}COO(CH_2)_r$-, $R^{7b}O$-$CO(CH_2)_v$, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen, $C_1$-$C_6$ alkyl, $C_1$-$C_6$ alkoxy, or hydroxy and v is 0 to 3;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$;

$R^9$ is 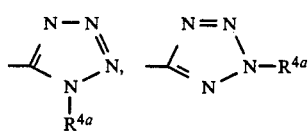

$R^{7b}O(CH_2)_r$-, $R^{7b}COO(CH_2)_r$-, $R^{7b}OCO(CH_2)_r$-, $R^{7b}CO(CH_2)_r$-, $R^{7b}O(CH_2)_vCO$-, $R^4R^5N(CH_2)_r$-, $R^{7b}CON(R^4)(CH_2)_r$-, $R^4R^5NCO(CH_2)_r$-, $R^4R^5NCS(CH_2)_r$-, $R^4R^5NN(R^5)CO(CH_2)_r$-, $R^4R^5NN(R^5)CS(CH_2)_r$-, $R^{7b}CON(R^4)N(R^5)CO(CH_2)_r$-, $R^{7b}CON(R^4)N(R^5)CS(CH_2)_r$-, $R^4N(OR^{7b})CO(CH_2)_r$- or $R^{7a}CON(OR^{7b})CO(CH_2)_r$-;

and v is as defined above;

$R^4$, $R^{4a}$, $R^5$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl, or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, phenyl $C_1$-$C_3$ alkoxy, fluoro, $R^1$ substituted or $R^1$, $R^2$ independently disubstituted phenyl $C_1$-$C_3$ alkoxy, phenyl, $R^1$ substituted or $R^1$, $R^2$ independently disubstituted phenyl, where the substituents on the phenyl are as defined above, $C_1$-$C_5$-alkanoyloxy, $C_1$-$C_5$ alkoxycarbonyl, carboxy, formyl, or —$NR^{10}R^{11}$ where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl, or $C_1$-$C_5$-alkanoyl-$C_1$-$C_6$ alkyl; or $R^4$ and $R^5$ can be taken together to form —$(CH_2)_rB(CH_2)_s$— where B is $CH_2$, O or $S(O)_m$ or N—$R^{10}$, r and s are independently 1 to 3 and $R^{10}$ is as defined above;

$R^6$ is hydrogen, $C_1$-$C_{10}$ alkyl, phenyl or phenyl $C_1$-$C_{10}$ alkyl;

A is

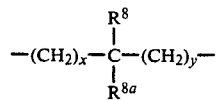

where x and y are independently 0-3;

$R^8$ and $R^{8a}$ are independently hydrogen, $C_1$-$C_{10}$ alkyl, trifluoromethyl, phenyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $C_3$-$C_7$ cycloalkyl, phenyl $C_1$-$C_3$ alkoxy, $R^1$ substituted or $R^1$, $R^2$ independently disubstituted phenyl $C_1$-$C_3$ alkoxy, phenyl, $R^1$ substituted or $R^1$, $R^2$ independently disubstituted phenyl, $C_1$-$C_5$-alkanoyloxy, $C_1$-$C_5$ alkoxycarbonyl, carboxy, formyl, or —$NR^{10}R^{11}$ where $R^{10}$ and $R^{11}$ are as defined above; or $R^8$ and $R^{8a}$ can be taken together to form —$(CH_2)_t$—where t is 2 to 6; and $R^8$ and $R^{8a}$ can independently be joined to one or both of $R^4$ and $R^5$ to form alkyl bridges between the terminal nitrogen and the alkyl portion of the A group wherein the bridge contains from 1 to 5 carbon atoms; and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atom fluorine, chlorine, bromine and iodine.

Certain of the above defined terms may occur more than once in the above formula and upon such occurrence each term shall be defined independently of the other.

Preferred compounds of the instant invention are realized when in the above structural formula:

n is 0 or 1;
p is 0 to 3;
q is 0 to 2;
w is 0 or 1;

X is O, $S(O)_m$, 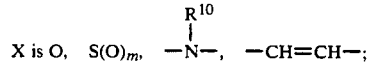

m is 0 to 2;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_r$-, $R^{7b}COO(CH_2)_r$-, $R^{7b}OCO(CH_2)_v$, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl; phenyl and v is 0 to 2;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$;

$R^9$ is 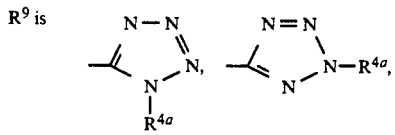

$R^{7b}O(CH_2)_r$-, $R^{7b}COO(CH_2)_r$-, $R^{7b}OCO(CH_2)_r$-, $R^{7b}CO(CH_2)_r$-, $R^4R^5N(CH_2)_r$-, $R^{7b}CON(R^4)(CH_2)_v$, $R^4R^5NCO(CH_2)_v$, $R^4R^5NCS(CH_2)_v$, $R^4R^5NN(R^5)CO(CH_2)_v$, $R^{7b}CON(R^4)N(R^5)CO(CH_2)_v$, $R^4N(OR^{7b})CO(CH_2)_v$ or $R^{7a}CON(OR^{7b})CO(CH_2)_v$; where v is as defined above; $R^4$, $R^{4a}$, $R^5$ are independently hydrogen, $C_1-C_{10}$ alkyl, substituted $C_1-C_{10}$ alkyl, where the substituents on the alkyl are from 1 to 5 of hydroxy, $C_1-C_6$ alkoxy, $C_3-C_7$ cycloalkyl, phenyl $C_1-C_3$ alkoxy, fluoro, $R^1$ substituted or $R^1$, $R^2$ independently disubstituted phenyl $C_1-C_3$ alkoxy, phenyl, $R^1$ substituted or $R^1$, $R^2$ independently disubstituted phenyl, where the substituents on the phenyl are as defined above, $C_1-C_5$-alkanoyloxy, $C_1-C_5$ alkoxycarbonyl, carboxy or formyl;

$R^4$ and $R^5$ can be taken together to form $-(CH_2)_rB(CH_2)_s-$ where B is $CH_2$, O or $S(O)_m$ or $N-R^{10}$ r and s are independently 1 to 3 and $R^{10}$ is as defined above;

$R^6$ is hydrogen, $C_1-C_{10}$ alkyl or phenyl $C_1-C_{10}$ alkyl; A is

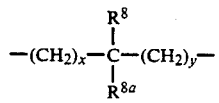

where x and y are independently 0-2;

$R^8$ and $R^{8a}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_mR^{7a}$, $C_1-C_6$ alkoxy, phenyl, $R^1$ substituted or $R^1$, $R^2$ independently disubstituted phenyl, $C_1-C_5$-alkanoyloxy, $C_1-C_5$ alkoxycarbonyl, carboxy, formyl, or $-NR^{10}R^{11}$ where $R^{10}$ and $R^{11}$ are independently hydrogen, $C_1-C_6$ alkyl, or $C_1-C_5$ alkanoyl-$C_1-C_6$ alkyl; or $R^8$ and $R^{8a}$ can be taken together to form $-(CH_2)_t-$ where t is 2 to 4; and $R^8$ and $R^{8a}$ can independently be joined to one or both of $R^4$ and $R^5$ to form alkyl bridges between the terminal nitrogen and the alkyl portion of the A group wherein the bridge contains from 1 to 5 carbon atoms; and pharmaceutically acceptable salts thereof.

Additional preferred compounds are realized in the above structural formula when:

n is 0 or 1;
p is 0 to 2;
q is 0 to 2;
w is 0 or 1;
X is $S(O)_m$, $-CH=CH-$;
m is 0 or 1;
$R^1$, $R^2$, $R^{1a}$, $R^{2a}$, $R^{1b}$, and $R^{2b}$ are independently hydrogen, halogen, $C_1-C_7$ alkyl, $C_1-C_3$ perfluoroalkyl, $-S(O)_mR^{7a}$, $R^{7b}O(CH_2)_v$, $R^{7b}COO(CH_2)_v$, $R^{7b}OCO(CH_2)_v$, phenyl or substituted phenyl where the substituents are from 1 to 3 of halogen, $C_1-C_6$ alkyl, $C_1-C_6$ alkoxy, or hydroxy;

$R^{7a}$ and $R^{7b}$ are independently hydrogen, $C_1-C_6$ alkyl, substituted $C_1-C_6$ alkyl, where the substituents are phenyl and v is 0 to 2;

$R^{3a}$ and $R^{3b}$ are independently hydrogen, $R^9$, $C_1-C_6$ alkyl substituted with $R^9$, phenyl substituted with $R^9$ or phenoxy substituted with $R^9$;

$R^9$ is

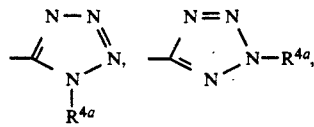

$R^{7b}O(CH_2)_v$, $R^{7b}COO(CH_2)_v$, $R^{7b}OCO(CH_2)_v$, $R^{7b}CO(CH_2)_v$, $R^4R^5N(CH_2)_v$, $R^{7b}CON(R^4)(CH_2)_v$, $R^4R^5NCO(CH_2)_v$, $R^4R^5NCS(CH_2)_v$, $R^4N(OR^{7b})CO(CH_2)_v$ or $R^{7a}CON(OR^{7b})CO(CH_2)_v$; where v is as defined above; $R^4$, $R^{4a}$, $R^5$ are independently hydrogen, $C_1-C_{10}$ alkyl, substituted $C_1-C_{10}$ alkyl, where the substituents on the alkyl are from 1 to 5 of hydroxy, $C_1-C_6$ alkoxy, fluoro, phenyl, $R^1$ substituted or $R^1$, $R^2$ independently disubstituted phenyl, where the substituents on the phenyl are as defined above, $C_1-C_5$-alkanoyloxy, $C_1-C_5$ alkoxycarbonyl, carboxy;

$R^6$ is hydrogen, $C_1-C_{10}$ alkyl;
A is

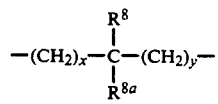

where x and y are independently 0-2;

$R^8$ and $R^{8a}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_mR^{7a}$, $C_1-C_6$ alkoxy, phenyl, $R^1$ substituted or $R^1$, $R^2$ independently disubstituted phenyl, $C_1-C_5$-alkanoyloxy, $C_1-C_5$ alkoxycarbonyl, carboxy; or $R^8$ and $R^{8a}$ can be taken together to form $-(CH_2)_t-$ where t is 2; and $R^8$ and $R^{8a}$ can independently be joined to one or both of $R^4$ and $R^5$ to form alkyl bridges between the terminal nitrogen and the alkyl portion of the A group wherein the bridge contains from 1 to 5 carbon atoms;

and pharmaceutically acceptable salts thereof.

Still further preferred compounds of the instant invention are realized in the above structural formula when;

n is 0 or 1;
p is 0 to 2;
q is 1;
w is 1;
X is $S(O)_m$, $-CH=CH-$;
m is 0 or 1;
$R^1$, $R^2$, $R^{1a}$, $R^{2a}$, $R^{1b}$, and $R^{2b}$ are independently hydrogen, halogen, $C_1-C_7$ alkyl, $C_1-C_3$ perfluoroalkyl, $-S(O)_mR^{7a}$, $R^{7b}O(CH_2)_v$, $R^{7b}COO(CH_2)_v$, phenyl or substituted phenyl where the substituents are from 1 to 3 of halogen, $C_1-C_6$ alkyl, $C_1-C_6$ alkoxy, or hydroxy;

$R^{7a}$ and $R^{7b}$ are independently hydrogen, $C_1-C_6$ alkyl, substituted $C_1-C_6$ alkyl, where the substituents are phenyl, phenyl and v is 0 or 1;

$R^{3a}$ and $R^{3b}$ are independently hydrogen or $R^9$;
$R^9$ is

R⁹ is

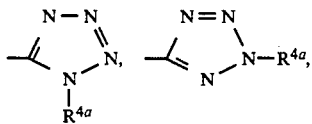

R⁷ᵇO(CH₂)ᵥ-, R⁷ᵇCOO(CH₂)ᵥ-, R⁷ᵇOCO(CH₂)ᵥ-, R⁷ᵇCO(CH₂)ᵥ-, R⁴R⁵N(CH₂)ᵥ-, R⁷ᵇCON(R⁴)(CH₂)ᵥ-, R⁴R⁵NCO(CH₂)ᵥ-, or R⁴N(OR⁷ᵇ)CO(CH₂)ᵥ-; where v is as defined above;

R⁴, R⁵ are independently hydrogen, $C_1$-$C_{10}$ alkyl, substituted $C_1$-$C_{10}$ alkyl, where the substituents on the alkyl are from 1 to 3 of hydroxy, $C_1$-$C_3$ alkoxy, fluoro, phenyl, R¹ substituted or R¹, R² independently disubstituted phenyl, where the substituents on the phenyl are as defined above; $C_1$-$C_5$-alkanoyloxy, $C_1$-$C_5$ alkoxycarbonyl, carboxy;

R⁴ᵃ is hydrogen, $C_1$-$C_{10}$ alkyl, substituted $C_1$-$C_{10}$ alkyl where the substituents on the alkyl are from 1 to 3 of hydroxy;

R⁶ is hydrogen;

A is

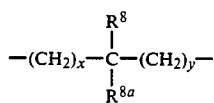

where x and y are independently 0-1;

R⁸ and R⁸ᵃ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, phenyl, R¹ substituted or R¹, R² independently disubstituted phenyl, $C_1$-$C_5$-alkanoyloxy, $C_1$-$C_5$ alkoxycarbonyl, carboxy; or R⁸ and R⁸ᵃ can be taken together to form —(CH₂)ₜ— where t is 2; and R⁸ and R⁸ᵃ can independently be joined to one or both of R⁴ and R⁵ to form alkyl bridges between the terminal nitrogen and the alkyl portion of the A group wherein the bridge contains from 1 to 5 carbon atoms;

and pharmaceutically acceptable salts thereof.

Representative preferred growth hormone releasing compounds of the present invention include the following:

1. 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
2. 2(R)-amino-3-hydroxy-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide
3. 2(R)-amino-3-phenyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide
4. 2(R)-amino-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide
5. 3-(2-hydroxyethyl)amino-3-methyl-N-[2,3,4,5-tetrahydro-2-oxo-1-[[2'-[1-(2-hydroxyethyl)-tetrazol-5-yl)[1,1'-biphenyl]-4-yl]methyl]-1H-1-benzazepin-3(R)-yl]-butanamide
6. 3-(2-hydroxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
7. 2-amino-2-methyl-N-[2,3,4,5-tetrahydro-2-oxo-1-[[2'-(1H-tetrazol-5-yl)[1,1'-biphenyl]-4-yl]-methyl]-1H-1-benzazepin-3(R)-yl]-propanamide
8. 3-amino-3-methyl-N-[7-fluoro-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
9. 3-amino-3-methyl-N-[7-trifluoromethyl-2,3,4,5-tetrahydro-2-oxo-1-[[2'-(1H-tetrazol-5-yl[1,1'-biphenyl]-4-yl]methyl]-1H-1-benzazepin-3(R)-yl]-butanamide
10. 3-amino-3-methyl-N-[6-fluoro-2,3,4,5-tetrahydro-2-oxo-1-[[2'-(1H-tetrazol-5-yl[1,1'-biphenyl]-4-yl]methyl]-1H-1-benzazepin-3(R)-yl]-butanamide
11. 3-benzylamino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
12. 3-amino-3-methyl-N-[3,4-dihydro-4-oxo-5-[[2'-(1H-tetrazol-5-yl)[1,1'-biphenyl]-4-yl]methyl]-1,4-benzopthiazepin-3(S)-yl]-butanamide
13. 3-(2(R)-hydroxypropyl)amino-3-methyl-N-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
14. 3-(2(S)-hydroxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
15. 3-(2(R),3-dihydroxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
16. 3-(2(S),3-dihydroxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
17. 3-(3(S)-hydroxybutyl)amino-3-methyl-N-[7-fluoro-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
18. 3-(3(S)-hydroxybutyl)amino-3-methyl-N-[2,3,4,5-tetrahydro-2-oxo-1-[[2'-(1H-tetrazol-5-yl[1,1'-biphenyl]-4-yl]methyl]-1H-1-benzazepin-3(R)-yl]-butanamide
19. 3-amino-3-methyl-N-[7-hydroxy-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
20. 3-(2(R)-hydroxypropyl)amino-3-methyl-N-[7-hydroxy-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
21. 3-(2(R)-hydroxypropyl)amino-3-methyl-N-[7-fluoro-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
22. 2-(3(R)-hydroxybutyl)amino-2-methyl-N-[2,3,4,5-tetrahydro-2-oxo-1-[[2'-(1H-tetrazol-5-yl)1,1'-biphenyl]-4-yl]methyl]-1H-1-benzazepin-3(R)-yl]-propanamide
23. 2-(3(S)-hydroxybutyl)amino-2-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide
24. 3-Amino-3-methyl-N-[7-methoxy-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
25. 3-(2(R)-hydroxypropyl)amino-3-methyl-N-[7-methoxy-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide 26. 3-(3(S)-hydroxybutyl)amino-3-methyl-N-[7-methoxy-2,3,4,5-tetrahydro-2-oxo-1-[[2'-(1H-tetrazol-5-yl) [1,1'-biphenyl]-4-yl]methyl]-1H-1-benzazepin-3(R)-yl]butanamide
27. Quinuclidine-N'-[2,3,4,5-tetrahydro-2-oxo-1-[[2'-(1H-tetrazol-5-yl)[1,1'-biphenyl]-4-yl]methyl]-1H-1-benzazepin-3(R)-yl]-3-carboxamide
28. 3-(2-fluoropropyl)amino-3-methyl-N-[2,3,4,5-tetrahydro-2-oxo-1-[[2'-(1H-tetrazol-5-yl)[1,1'-biphenyl]-4-yl]methyl-1H-1-benzazepin-3(R)-yl]-butanamide
29. 3-(2-methoxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
30. 3-(2-hydroxy-2-methylpropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide
31. 4'-[[3(R)-[(3-amino-3-methyl-1-oxobutyl)amino]-2,3,4,5-tetrahydro-2-oxo-1H-1-benzazepin-1-yl]methyl]-[1,1'-biphenyl]-2-carboxamide
32. 4'-[[3(R)-[[3-[(2(R)-hydroxypropyl)amino]-3-methyl-1-oxobutyl]amino]-2,3,4,5-tetrahydro-2-oxo-1H-1-benzazepin-1-yl]methyl]-[1,1'-biphenyl]-2-carboxamide
33. 4'-[[3(R)-[[3-[(2(S),3-dihydroxypropyl)amino]-3-methyl-1-oxobutyl]amino]-2,3,4,5-tetrahydro-2-oxo-1H-1-benzazepin-1-yl]methyl]-[1,1'-biphenyl]-2-carboxamide
34. N-ethyl-4'-[[3(R)-[(3-amino-3-methyl-1-oxobutyl)amino]-2,3,4,5-tetrahydro-2-oxo-1H-1-yl]methyl]-[1,1'-biphenyl]-2-carboxamide
35. N-ethyl-4'-[[3(R)-[[3[(2(S),3-dihydroxypropyl)amino]-3-methyl-1-oxobutyl]amino]-2,3,4,5-tetrahydro-2-oxo-1H-1-benzazepin-1-yl]methyl]-1,1'-biphenyl]-2-carboxamide
36. N-methyl-4'-[[3(R)-[[3-[(2(S),3-dihydroxypropyl)amino]-3-methyl-1-oxobutyl]amino]-2,3,4,5-tetrahydro-2-oxo-1H-1-benzazepin-1-yl]methyl]-1,1'-biphenyl]-2-carboxamide
37. 3-amino-3-methyl-N-[2,3,4,5-tetrahydro-2-oxo-1-[[2'-hydroxymethyl[1,1'-biphenyl]-4-yl]methyl]-1H-1-benzazepin-3(R)-yl]butanamide
38. 3-(2(R)-hydroxypropyl)amino-3-methyl-N-[2,3,4,5-tetrahydro-2-oxo-1-[[2'-hydroxymethyl[1,1'-biphenyl]-4-yl]methyl]-1H-1-benzazepin-3(R)-yl]butanamide
39. 3-Amino-3-methyl-N-[2,3,4,5-tetrahydro-2-oxo-1-[[2'-aminomethyl[1,1'-biphenyl]-4-yl]methyl]-1H-1-benzazepin-3(R)-yl]butanamide
40. 3-(2(R)-hydroxypropyl)amino-3-methyl-N-[2,3,4,5-tetrahydro-2-oxo-1-[[2'-aminomethyl[1,1'-biphenyl]-4-yl]methyl]-1H-1-benzazepin-3(R)-yl]butanamide
41. 4'-[[3(R)-[[3-[(2(S),3(S),4-trihydroxybutyl)amino]-3-methyl-1-oxobutyl]amino]-2,3,4,5-tetrahydro-2-oxo-1H-benzazepin-1-yl]methyl]-[1,1'-biphenyl]-2-carboxamide
42. 4'-[[3(R)-[[3[(3-hydroxybutyl)amino]-3-methyl-1-oxobutyl]amino]-2,3,4,5-tetrahydro-2-oxo-1H-1-benzazepin-1-yl]methyl]-[1,1'-biphenyl]-2-carboxamide
43. 3-Amino-3-methyl-N-[2,3-dihydro-2-oxo-1-[[2'-(1H-tetrazol-5-yl)[1,1'-biphenyl]-4-yl]methyl]-1H-1-benzazepin-3(R)-yl]butanamide
44. 3-(2(R)-hydroxypropyl)amino-3-methyl-N-[2,3-dihydro-2-oxo-1-[[2'-(1H-tetrazol-5-yl)[1,1'-biphenyl]-4-yl]methyl]-1H-1-benzazepin-3(R)-yl]butanamide
45. N-ethyl-4'-[[3(R)-[[3-[(2(S),3-dihydroxypropyl)amino]-3-methyl-1-oxobutyl]amino]-2,3-dihydro-2-oxo-1H-1-benzazepin-1-yl]methyl]-[1,1'-biphenyl]-2-carboxamide
46. 3-(2(R)-hydroxypropyl)amino-3-methyl-N-[3,4-dihydro-4-oxo-4-[[2'-(1H-tetrazol-5-yl)[1,1'-biphenyl]-4-yl]methyl]-1,5-benzothiazepin-3(S)-yl]-butanamide
47. 3-(2(S)-hydroxypropyl)amino-3-methyl-N-[3,4-dihydro-4-oxo-5-[[2'-(1H-tetrazol-5-yl)[1,1'-biphenyl]-4-yl]methyl]-1,5-benzothiazepin-3(S)-yl]-butanamide
48. N-ethyl-4'-[[3(S)-[[3[(2(S),3-dihydroxypropyl)amino]-3-methyl-1-oxobutyl]amino]-3,4-dihydro-4-oxo-1,5-benzothiazepin-5(2H)-yl]methyl]-[1,1'-biphenyl]-2-carboxamide
49. 4'-[[3(S)-[(3-amino-3-methyl-1-oxobutyl)amino]-3,4-dihydro-4-oxo-1,5-benzothiazepin-5(2H)-yl]methyl]-[1,1'-biphenyl]-2-carboxamide
50. 4'-[[3(R)-[(3-amino-3-methyl-1-oxobutyl)amino]-2,3,4,5-tetrahydro-2-oxo-1H-1-benzazepin-1-yl]methyl]-[1,1'-biphenyl]-2-thioamide
51. N-hydroxy-4'-[[3(R)-[(3-amino-3-methyl-1-oxobutyl)amino]-2,3,4,5-tetrahydro-2-oxo-1H-1-benzazepin-1-yl]methyl]-[1,1'-biphenyl]-2-carboxamide
52. N-hydroxy-4'-[[3(R)-[[3-[(2(S),3-dihydroxypropyl)amino]-3-methyl-1-oxobutyl]amino]-2,3,4,5-tetrahydro-2-oxo-1H-1-benzazepin-1-yl]methyl]-[1,1'-biphenyl]-2-carboxamide
53. N-hydroxy-4'-[[3(R)-[[3-[(2(R)-hydroxypropyl)amino]-3-methyl-1-oxobutyl]amino]-2,3,4,5-tetrahydro-2-oxo-1H-1-benzazepin-1-yl]methyl]-[1,1'-biphenyl]-2-carboxamide
54. 3-(2(R)-hydroxypropyl)amino-3-methyl-N-[3,4-dihydro-1,4-dioxo-5-[[2'-(1H-tetrazol-5-yl)[1,1'-biphenyl]-4-yl]methyl]-1,5-benzothiazepin-3(S)-yl]-butanamide
55. 3-amino-3-methyl-N-[3,4-dihydro-1,4-dioxo-5-[[2'-(1H-tetrazol-5-yl)[1,1'-biphenyl]-4-yl]methyl]-1,5-benzothiazepin-3(S)-yl]-butanamide
56. 3-amino-3-methyl-N-[7-methylthio-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
57. 3-(2(R)-hydroxypropyl)amino-3-methyl-N-[7-methylthio-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
58. 3-(2(R)-hydroxypropyl)amino-3-methyl-N-[7-methylsulfinyl-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
59. 3-amino-3-methyl-N-[7-methylsulfinyl-2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide
60. 3-amino-3-methyl-N-[2,3,4,5-tetrahydro-2-oxo-1-[[2'-(acetylaminomethyl)[1,1'-biphenyl]-4-yl] methyl]-1H-1-benzazepin-3(R)-yl]butanamide
61. 3-(2(R)-hydroxypropyl)amino-3-methyl-N-[2,3,4,5-tetrahydro-2-oxo-1-[[2'-(acetylaminomethyl)[1,1'-biphenyl]-4-yl]methyl]-1H-1-benzazepin-3(R)-yl] butanamide
62. 3-amino-3-methyl-N-[2,3,4,5-tetrahydro-2-oxo-1-[[2'-(benzoylaminomethyl)[1,1'-biphenyl]-4-yl] methyl]-1H-1-benzazepin-3(R)-yl]butanamide
63. 3-(2(R)-hydroxypropyl)amino-3-methyl-N-[2,3,4,5-tetrahydro-2-oxo-1-[[2'-(benzoylaminomethyl)[1,1'- biphenyl]-4-yl]methyl]-1H-1-benzazepin-3(R)-yl]
butanamide 64. 3-amino-3-methyl-4-hydroxy-N-[2,3,4,5-tetrahydro-
2-oxo-1-[[2'-(1H-tetrazol-5-yl)[1,1'-biphenyl]-4-
yl]methyl]-1H-1-benzazepin-3(R)-yl]butanamide 65. 2-amino-2-methyl-3-hydroxy-N-[2,3,4,5-tetrahydro-
2-oxo-1-[[2'-(1H-tetrazol-5-yl)[1,1'-biphenyl]-4-
yl]methyl]-1H-1-benzazepin-3(R)-yl]propanamide 66. 3-(2(R)-hydroxypropyl)amino-3-methyl-4-hydroxy-
N-2,3,4,5-tetrahydro-2-oxo-1-[[2'-(1H-tetrazol-5-
yl)[1,1'-biphenyl]-4-yl]methyl]-1H-1-benzazepin-
3(R)-yl]butanamide 67. 2-(3-hydroxybutyl)amino-2-methyl-3-hydroxy-N-
[2,3,4,5-tetrahydro-2-oxo-1-[[2'-(1H-tetrazol-5-
yl)[1,1'-biphenyl]-4-yl]methyl]-1H-1-benzazepin-
3(R)-yl]propanamide Representative examples of the nomenclature employed are given below:

3-amino-3-methyl-N-[2,3,4,5-tetrahydro-2-oxo-1-[[2'-
(1H-tetrazol-5-yl)[1,1'-biphenyl]-4-yl]methyl]-1H-1-
benzazepin-3(R)-yl]butanamide

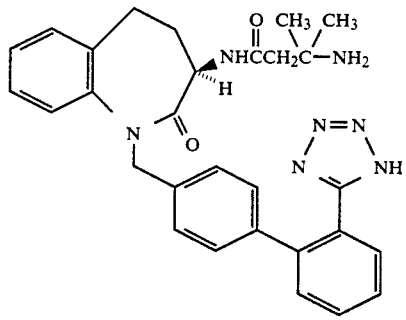

3-(2(R)-hydroxypropyl)amino-3-methyl-N-[2,3,4,5-tetra-
hydro-2-oxo-1-[[2'-(1H-tetrazol-5-yl)[1,1'-biphenyl]-
4-yl]methyl]-1H-1-benzazepin-3(R)-yl]butanamide

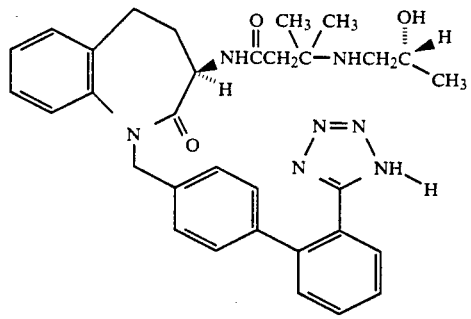

4'-[[3(R)[(3-amino-3-methyl-1-oxobutyl)amino]-
2,3,4,5-tetrahydro-2-oxo-1H-1-benzazepin-1-yl]methyl]-
[1,1'-biphenyl]-2-carboxamide

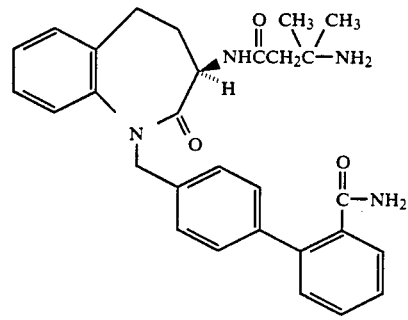

-continued 3-amino-3-methyl-N-[3,4-dihydro-4-oxo-5-[[2'-(1H-
tetrazol-5-yl)[1,1'-biphenyl]-4-yl]methyl]-1,5-
benzothiazepin-3(S)-yl]butanamide

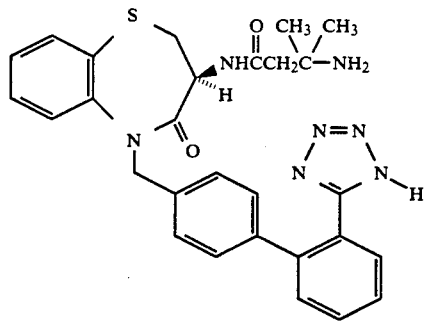

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. In the substituent $(X)_n$, when $n=0$, the asymmetric center is designated as the R-isomer. When $n=1$, this center will be designated according to the R/S rules as either R or S depending upon the value of X.

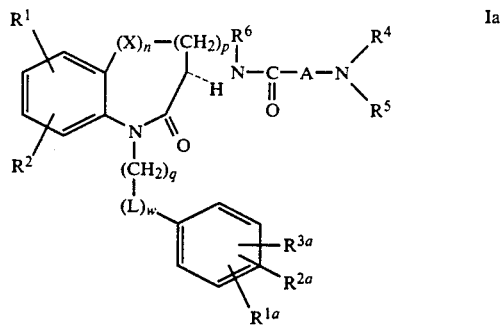

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

The compounds (I) of the present invention are prepared from aminolactam intermediates such as those of formula II. The preparation of these intermediates is described in the following reaction Schemes.

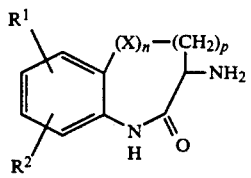

II

Benzo-fused lactams 3 wherein the lactam is a seven-membered ring are conveniently prepared from substituted tetralones 2 using known procedures. The substituted tetralones are, in some cases, commercially available or are prepared from a suitably substituted derivation of 4-phenylbutyric acid 1. Cyclization of 1 can be achieved by a number of methods well known in the literature including treatment with polyphosphoric acid at elevated temperatures as shown in Scheme 1.

Scheme 1

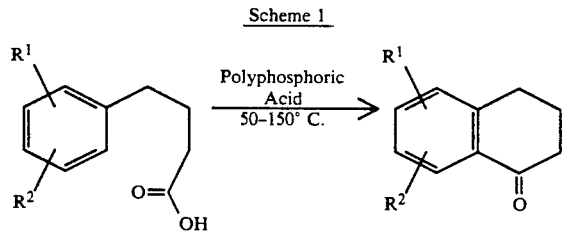

1    2

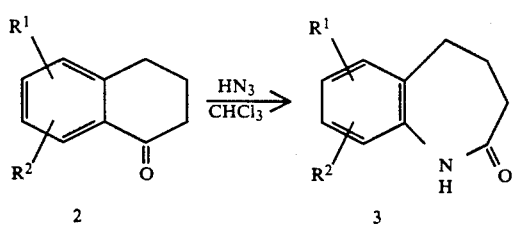

2    3

Conversion of substituted tetralones 2 to benzolactams 3 can be achieved by a number of methods familiar to those skilled in the art. A suitable method involves the use of hydrazoic acid (Schmidt reaction) to form the substituted benzolactam 3.

Benzo-fused lactams wherein the lactam is an eight-membered ring (6) are prepared as described by D. H. Jones, et al, J. Chem. Soc. C, 2176-2181 (1969) by an analogous series of transformations starting from a substituted derivative of 5-phenylpentanoic acid 4 as shown in Scheme 2.

Scheme 2

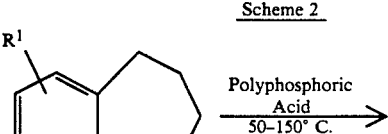

4

5

5    6

As shown in Scheme 3, 3-aminobenzolactam analogs wherein the lactam is a six-membered ring (11) are prepared from a substituted derivative of 2-nitrobenzyl chloride (or bromide) 7 by the method of A. L. Davis, et al, Arch. Biochem. Biophys, 102, 48–51 (1963) and references cited therein.

Scheme 3

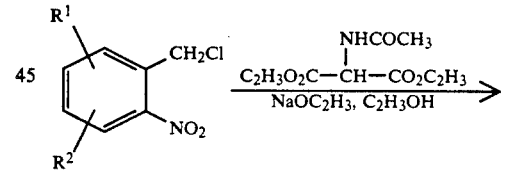

7

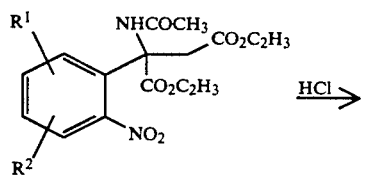

8

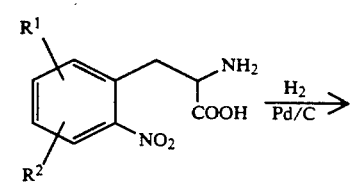

9

-continued
Scheme 3

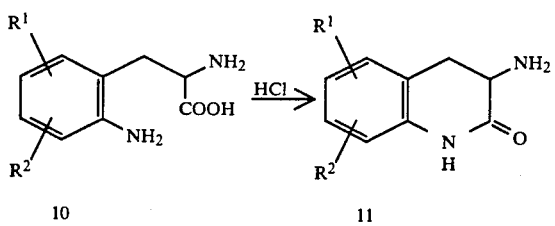

Conversion of substituted benzo-fused lactams to the requisite 3-amino derivatives can be achieved by a number of methods familiar to those skilled in the art, including those described by Watthey, et al, J. Med. Chem., 28 1511-1516 (1985) and references cited therein. One common route proceeds via the intermediacy of a 3-halo (chloro, bromo or iodo) intermediate which is subsequently displaced by a nitrogen nucleophile, typically azide. A useful method of forming the 3-iodobenzolactam intermediates 12 involves treating the benzolactam with two equivalents each of iodotrimethylsilane and iodine at low temperature, as illustrated in Scheme 4 for the seven-membered ring analogs 3.

Scheme 4

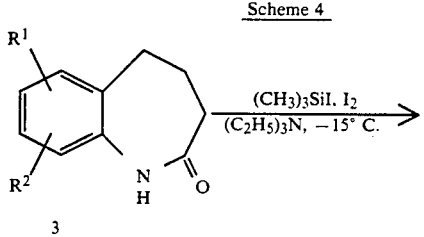

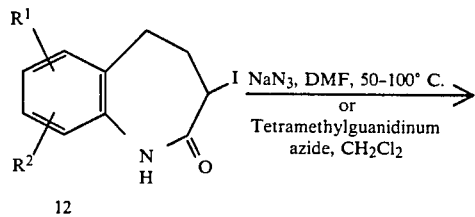

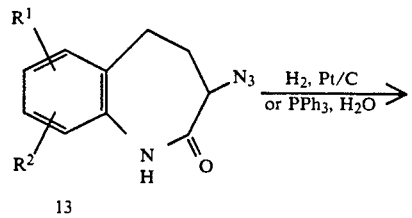

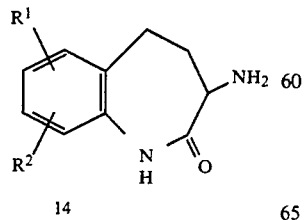

Elaboration of the iodo-benzolactams to the desired aminolactam intermediates II is achieved by a two-step procedure illustrated in Scheme 4. Typically, iodo-benzolactams 12 are treated with sodium azide in N,N-dimethylformamide at 50-100° C. to give the 3-azido derivatives 13. Alternatively, tetramethylguanidinium azide in a solvent such as methylene chloride can be employed to achieve similar results. Hydrogenation with a metal catalyst, such as platinum on carbon, or alternatively, treatment with triphenylphosphine in wet toluene, results in formation of the amine derivative 14. Formation of the analogous derivatives of the eight-membered benzolactams is also achieved by the routes shown in Scheme 4.

Chiral aminobenzolactams are obtained by resolution of the racemates by classical methods familiar to those skilled in the art. For example, resolution can be achieved by formation of diastereomeric salts of the racemic amines with optically active acids such as D- and L-tartaric acid. Determination of absolute sterochemistry can be achieved in a number of ways including X-ray analysis of a suitable crystalline derivative.

Intermediates of Formula II wherein X is a sulfur atom are prepared by methods described in the literature and known to those skilled in the art. As illustrated in Scheme 5, the seven-membered ring analog 22 is prepared from a protected derivative of cysteine 16 by the method of Slade, et al, J. Med. Chem., 28 1517-1521 (1985) and references cited therein (Cbz=benzyloxycarbonyl).

Scheme 5

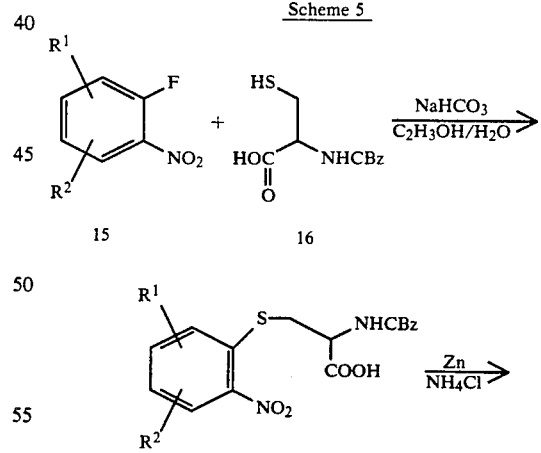

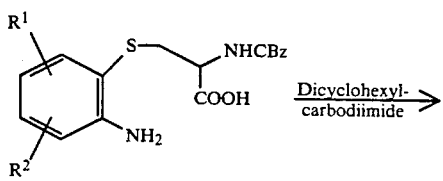

-continued
Scheme 5

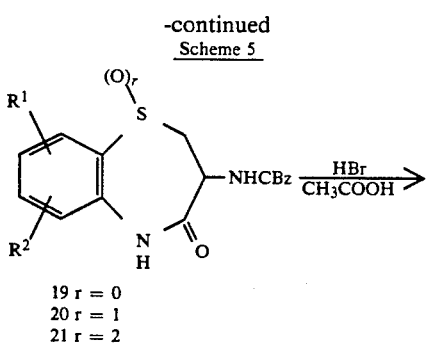

19 r = 0
20 r = 1
21 r = 2

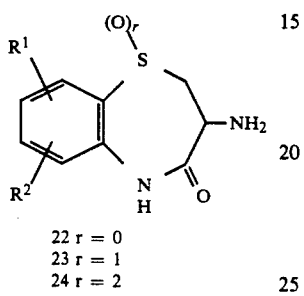

22 r = 0
23 r = 1
24 r = 2

Sulfoxide and sulfone intermediates 23 and 24 are prepared by oxidation of 19 with various oxidants such as sodium periodate or meta-chloro-perbenzoic acid. Eight-membered ring intermediates of Formula II wherein X is sulfur can be prepared by an analogous route starting from derivatives of homo-cysteine.

Intermediates of Formula II wherein X is an oxygen atom are prepared by methods described in the literature and known to those skilled in the art. For example, the seven membered ring analog 26 can be prepared from a substituted derivative of 3-(2-nitro-phenoxy)-butyric acid 25 by the method of J. Ott, Arch. Pharm. (Weinheim, Ger.), 323(9), 601–603 (1990).

Scheme 6

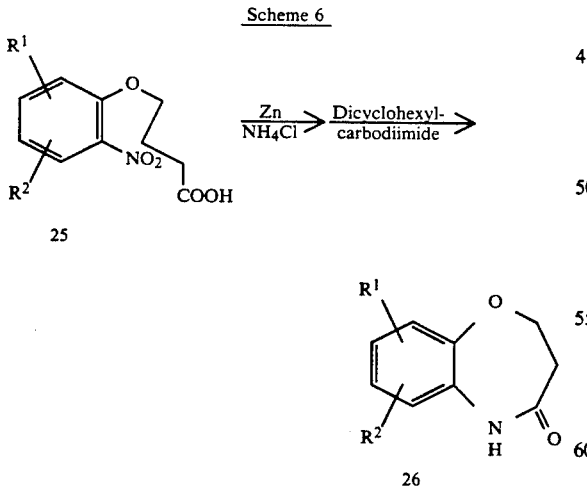

25

26

Six-membered ring analogs wherein X is oxygen (28) may be prepared by reaction of a substituted derivative of 2-aminophenol 27 with chloroacetyl chloride by the method of Huang and Chan, Synthesis, 10, 851 (1984) and references cited therein. Subsequent incorporation of an amino group at the 3 position of either 26 or 28 is achieved by the methods described in Scheme 4.

Scheme 7

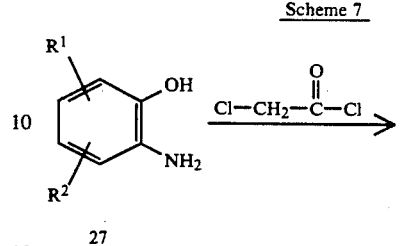

27

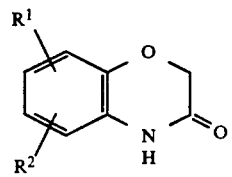

28

Seven-membered ring analogs of Formula II wherein X is C=O can be prepared from derivatives of tryptophan as described in the Australian Journal of Chemistry, 33, 633–640 (1980). Seven-membered ring analogs of Formula II wherein X is CH=CH can be prepared from the aforementioned analogs wherein X is C=O. Treatment of 37 with chemical reducing agents such as sodium borohydride in a polar solvent such as methanol or ethanol results in reduction to give the secondary alcohol derivative 38 (X=CHOH).

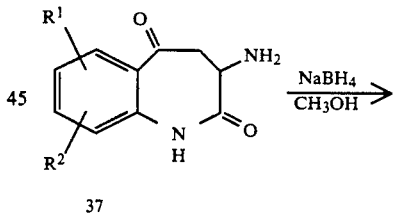

37

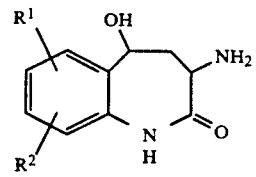

38

Dehydration of 38 can be achieved by several methods described in the literature and familiar to those skilled in the art. For example, treatment of 38 in an inert solvent, such as benzene, with a strong acid such as p-toluenesulfonic acid, will result in dehydration to the unsatured analog 39.

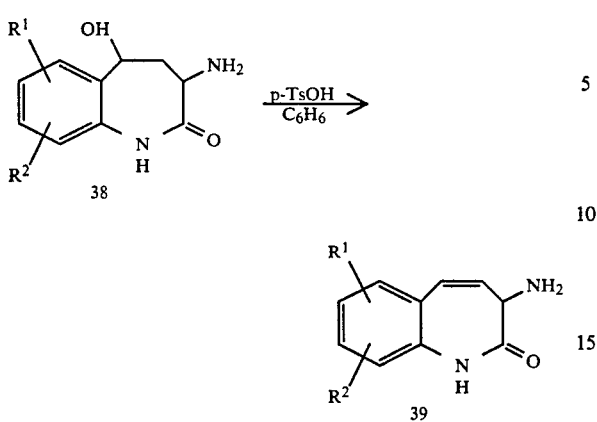

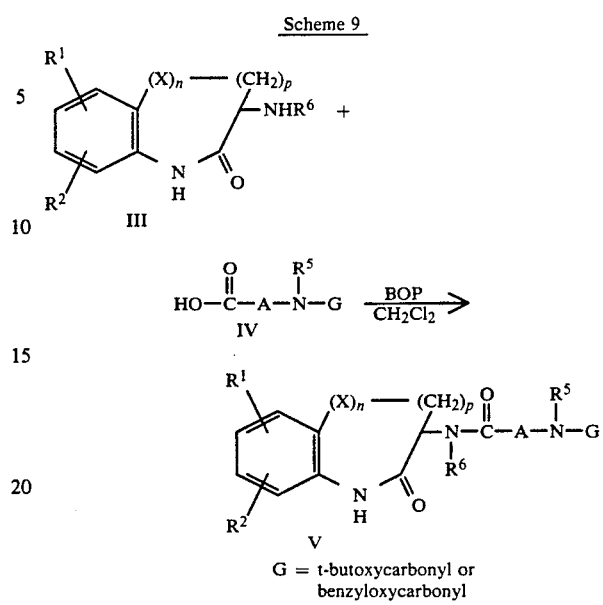

Intermediates of formula II can be further elaborated to new intermediates (formula III) which are substituted on the amino group (Scheme 8). Reductive alkylation of II with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol.

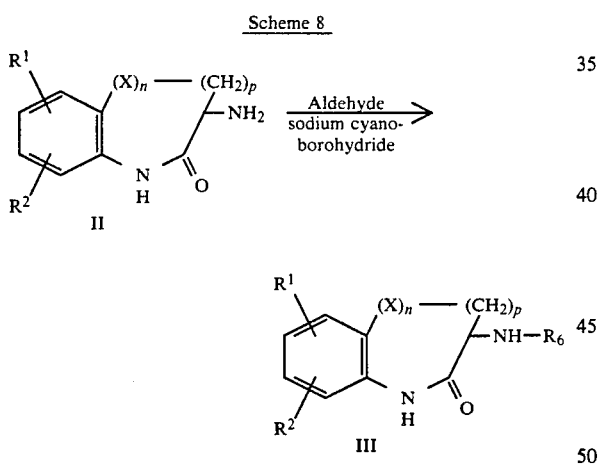

Attachment of the amino acid sidechain to intermediates of formula III is accomplished by the route shown in Scheme 9. Coupling is conveniently carried out by the use of an appropriately protected amino acid derivative, such as that illustrated by formula IV, and a coupling reagent such as benzotriazol-1-yloxytris(dimethylamino)phosphonium hexafluorophosphate ("BOP") in an inert solvent such as methylene chloride. Separation of unwanted side products, and purification of the intermediates is achieved by chromatography on silica gel, employing flash chromatography (W. C. Still, M. Kahn and A. Mitra, J. Org. Chem., 43 2923 (1978)) or by medium pressure liquid chromatography.

The protected amino acid derivatives IV are, in many cases, commercially available in t-butoxycarbonyl (BOC) or benzyloxycarbonyl (CBz) forms. A useful method to prepare the preferred sidechain 31 is shown in Scheme 10.

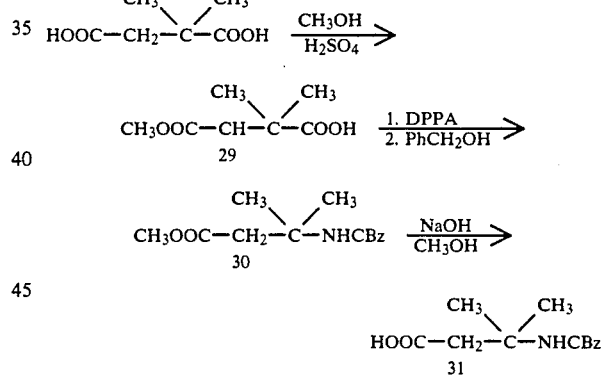

Formation of the monomethyl ester 29 of 2,2-dimethylsuccinic acid is achieved by treatment of a methanolic solution with a catalytic amount of a strong acid, such as sulfuric acid. Treatment of 29 with diphenylphosphoryl azide (DPPA) followed by benzyl alcohol results in formation of the benzyloxycarbonyl (CBz) compound 30. Alkaline hydrolysis with sodium hydroxide in methanol affords the product 31.

Intermediates of formula VII can be prepared as shown in Scheme 11 by treatment of the desired lactam intermediate V with an alkylating agent VI, wherein L is a good leaving group such as Cl, Br, I, O-methanesulfonyl or O-(p-toluenesulfonyl). Alkylation of intermediates of formula V is conveniently carried out in anhydrous dimentyl formamide (DMF) in the presence of bases such as sodium hydride or potassium t-butoxide for a period of 0.5 to 24 hours at temperatures of 20-100° C. Substituents on the alkylating agent VI may need to be protected during alkylation. A description of such protecting groups may be found in: *Protective Groups in Organic Synthesis*, T. W. Greene, John Wiley and Sons, New York, 1981.

references cited therein. A useful method to prepare the preferred alkylating agent 36 is shown in reaction Scheme 12, and in U.S. Pat. No. 5,039,814.

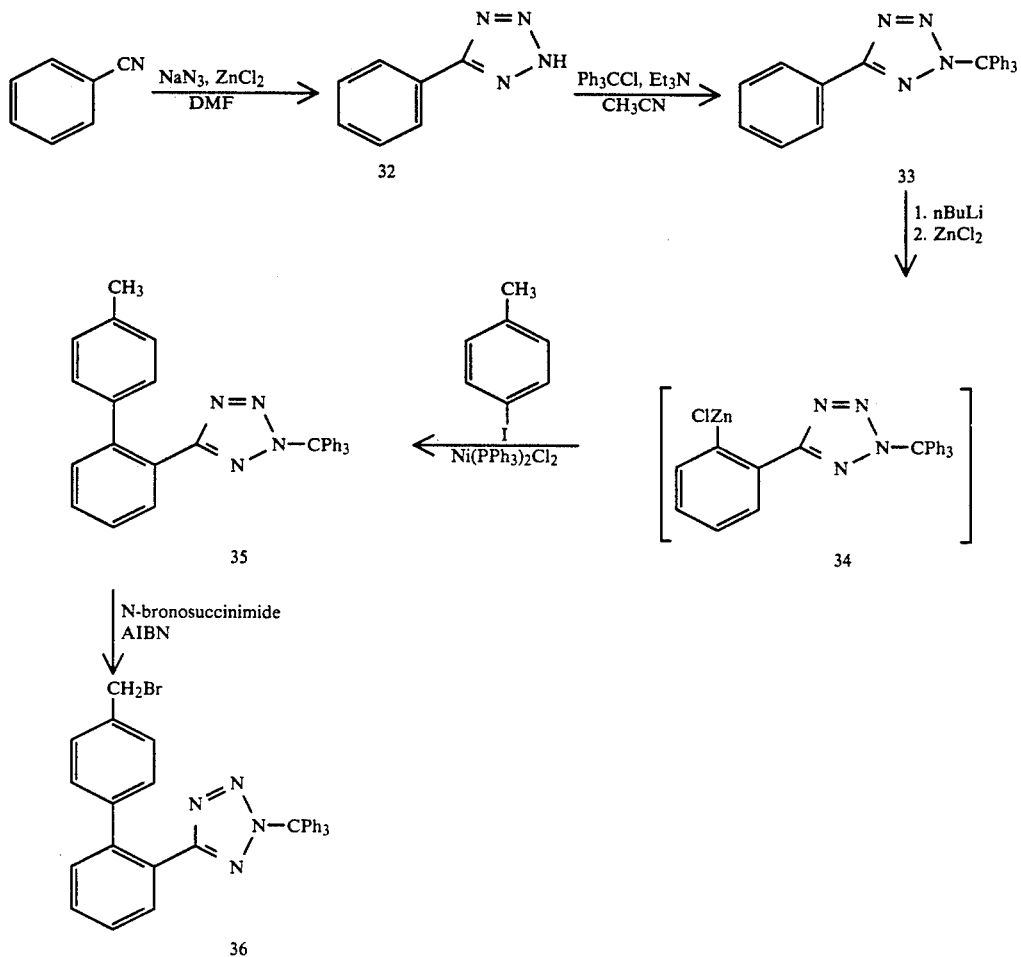

As outlined in Scheme 12, benzonitrile is treated with sodium azide and zinc chloride to give 5-phenyltetrazole 32 which is converted to the N-trityl derivative

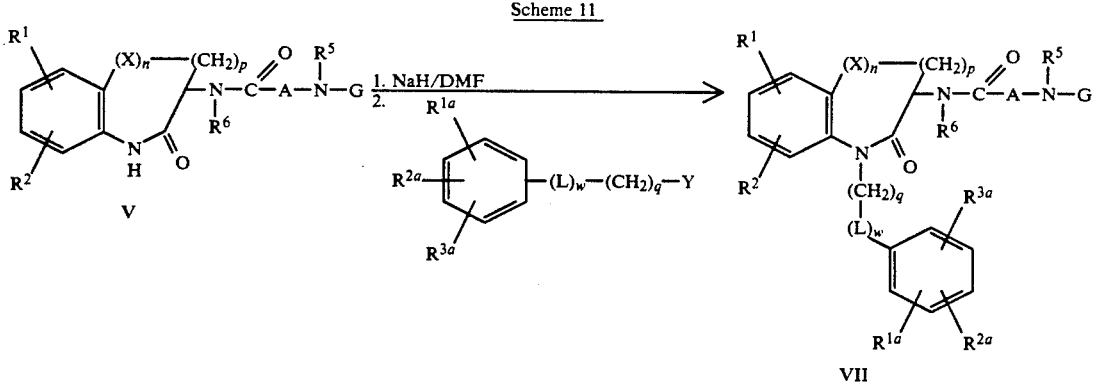

Y is a leaving group
G is t-butoxycarbonyl or benzyloxycarbonyl

Alkylating agents VI are, in some cases commercially available compounds or may be prepared as described in EPO publications 253,310; 291,969; 324,377 and the 33 by treatment with triphenylmethyl chloride and triethylamine. The zinc reagent 34 was prepared by treatment with n-butyl lithium followed by zinc chloride. Coupling with 4-iodotoluene using the catalyst bis(triphenyl-phosphine)-nickel(II) dichloride gives the biphenyl product 35 in high yield. Reaction with N-bromosuccinimide and AIBN gives bromide 36.

Conversion to the final products of formula I wherein $R^4$ is hydrogen, is carried out by simultaneous or sequential removal of all protecting groups from intermediate VII as illustrated in Scheme 13. Removal of benzyloxycarbonyl groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Catalytic hydrogenation is also employed in the removal of N-triphenylmethyl (trityl) protecting groups. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis*.

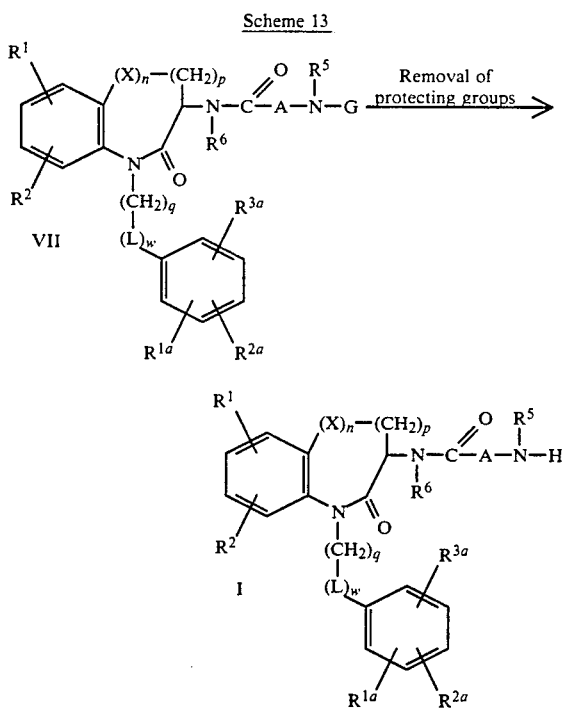

Compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatography (HPLC) or by recrystallization.

Compounds of Formula I wherein $R^{3a}$ or $R^{3b}$ are taken as $R^4R^5NCO(CH_2)_v$ and v is 0 can be prepared by several methods. For example, as shown in Scheme 14, compound 41 wherein $R^4$ and $R^5$ are both hydrogen is conveniently prepared by hydrolysis of a nitrile precursor 40.

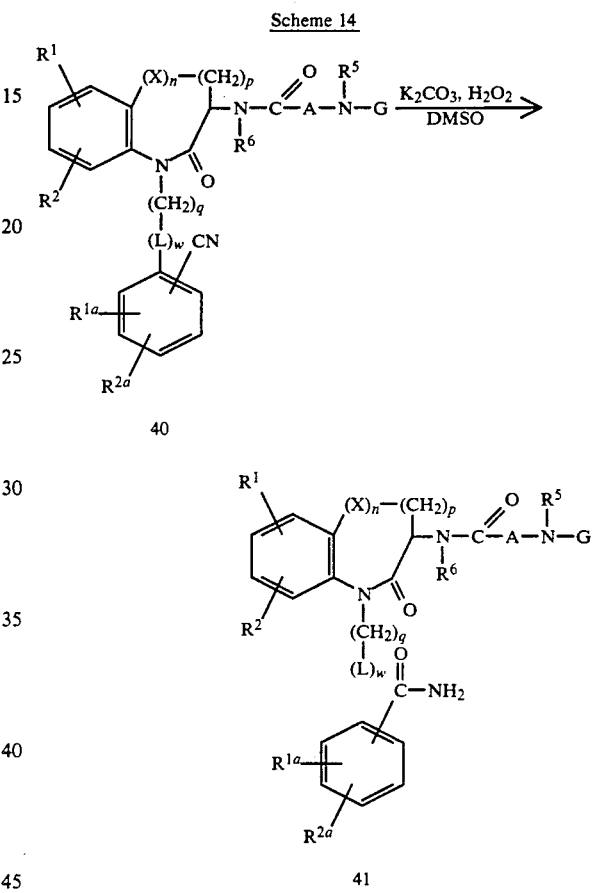

Thus, treatment of the nitrile 40 with hydrogen peroxide and a strong base, such as potassium carbonate, in a polar solvent, such as dimethylsulfoxide at temperatures of 25° C. to 150° C. results in formation of the amide derivative 41. The precursor 40 can be prepared from an appropriate alkylating agent VI, where $R^{3a}$ is cyano, as described in Scheme 11.

A useful method of preparing the alkylating agent 44 is outlined in Scheme 15.

-continued
Scheme 15

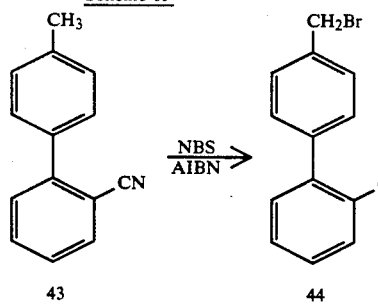

Thus, treatment of 4-(methylphenyl)trimethyl stannane 42 with 2-bromobenzonitrile in dimethylformamide at 100° C. in the presence of bis-triphenylphosphine palladium (II) chloride results in coupling to form the biphenyl nitrile 43 in high yield. Conversion to bromide 44 is achieved by treatment with N-bromosuccinimide and a radical initiator, such as azobisisobutyronitrile (AIBN), in refluxing carbon tetrachloride.

Compounds of Formula I wherein $R^{3a}$ or $R^{3b}$ are taken as $R^4R^5NCO(CH_2)_v$ and v is 0 and $R^4$ and/or $R^5$ are not hydrogen are prepared from the corresponding carboxylic acid derivatives 45 as shown in Scheme 16.

Scheme 16

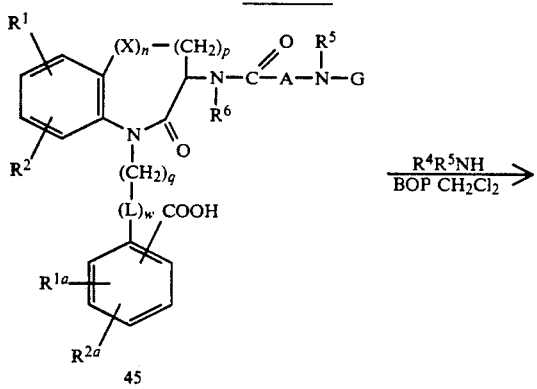

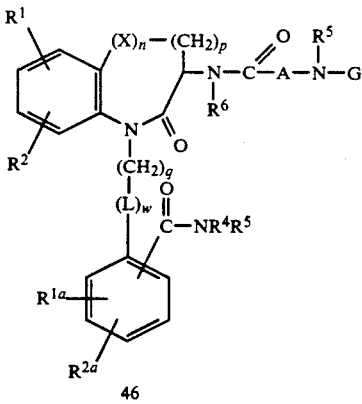

Coupling of the carboxylic acid derivative 45 with $R^4R^5NH$ is conveniently carried out by the use of a coupling reagent such as benzotriazol-1-yloxytris(dimethylamino)phosphonium hexafluoro-phosphate ("BOP") in an inert solvent such as methylene chloride. The requisite carboxylic acid precursors can be prepared as illustrated in Scheme 17 for the biphenyl compound 49.

Scheme 17

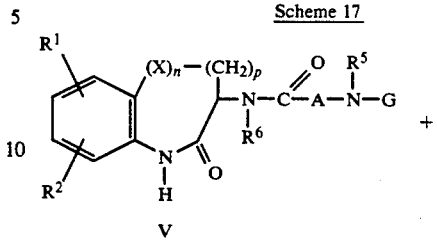

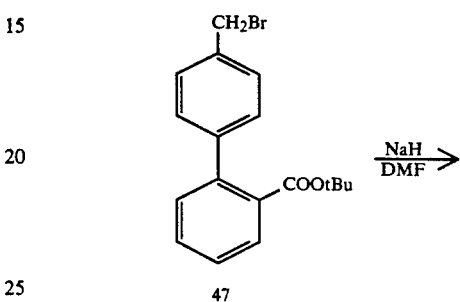

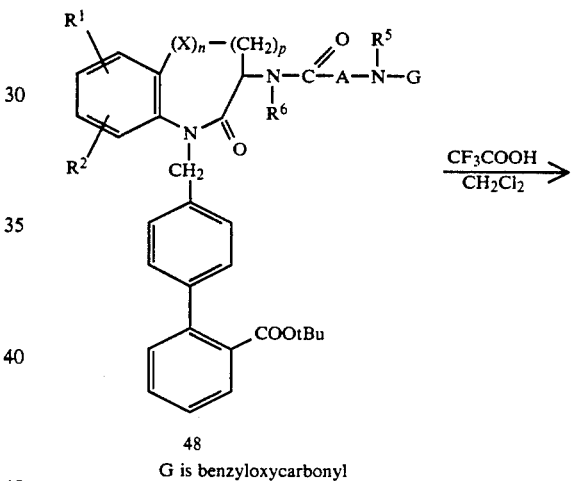

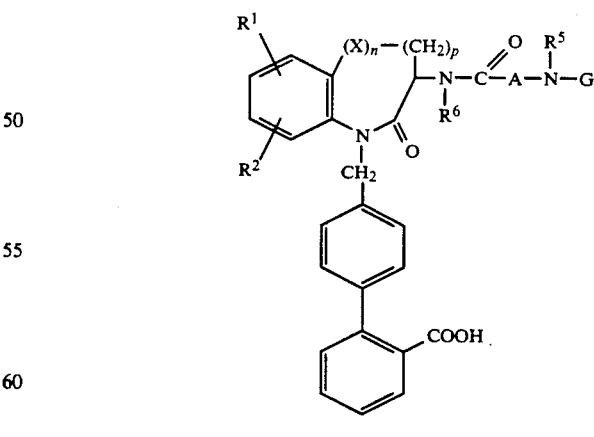

G is benzyloxycarbonyl

Alkylation of V with t-butyl 4'-bromomethyl-biphenyl-2-carboxylate 47 (prepared as described in EPO Publication 324,377) in the presence of sodium hydride as previously described in Scheme 11 gives the adduct 48 in high yield. Hydrolysis of the t-butyl ester is conveniently achieved by treatment with a strong acid, such as trifluoroacetic, in an inert solvent such as methylene chloride. It is noted that the protecting group G in this instance must be inert to strongly acidic conditions, for example G is benzyloxycarbonyl (CBz). A useful preparation of the chiral intermediate 54 is shown in Scheme 18.

with potassium carbonate followed by extractive isolation.

An improved route to compounds containing the 3-amino-3-methylbutanamide sidechain is presented in Scheme 19.

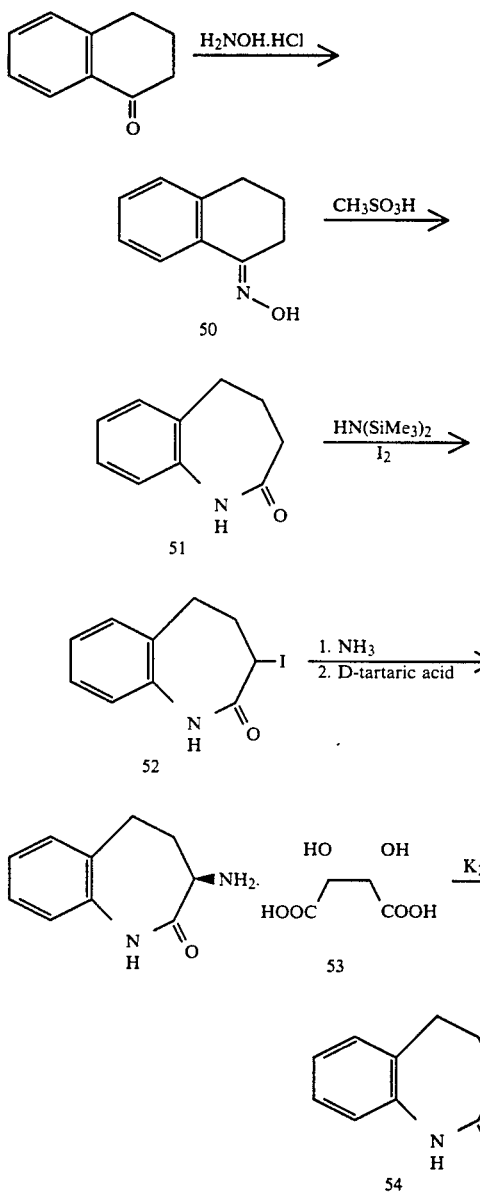

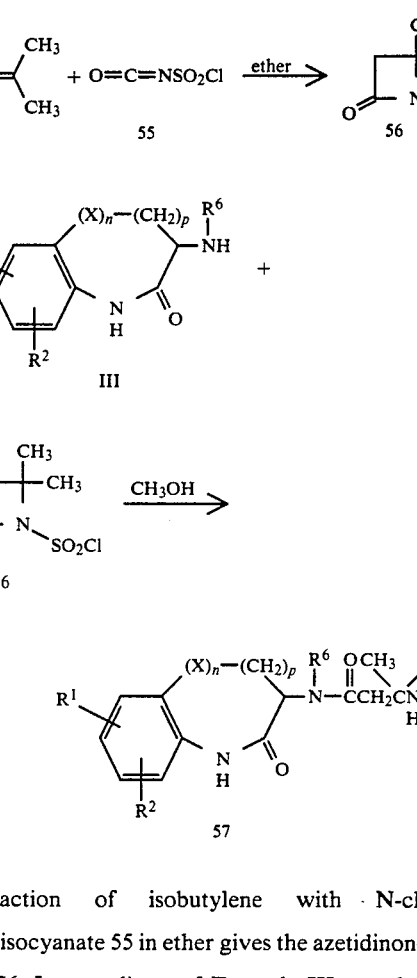

Conversion of 1-tetralone to the seven-membered benzolactam 51 is achieved by Beckman rearrangement of the intermediate oxime 50. Treatment of 51 with iodine and hexamethyldisilazane gives the 3-iodo derivative 52 which is sequentially treated with ammonic and D-tartaric acid to give the diastereomeric D-tartrate salt 53 after recrystallization. Liberation of the free amine 54 is achieved by neutralization of the D-tartrate salt Reaction of isobutylene with N-chlorosulfonylisocyanate 55 in ether gives the azetidinone derivative 56. Intermediates of Formula III can then be reacted with 56 to give the 3-methyl-3-amino-butanamide intermediates 57 directly. Removal of the methoxysulfonyl auxilliary is conveniently achieved by treatment with aqueous acid, for example, 6N hydrochloric acid. The methoxysulfonyl group also functions as a protection group G which is inert to the basic conditions employed in the subsequent alkylation step as illustrated in Scheme 11.

An alternate route to the sub-class of compounds of Formula I that can be described by Formula IX is shown in Scheme 20.

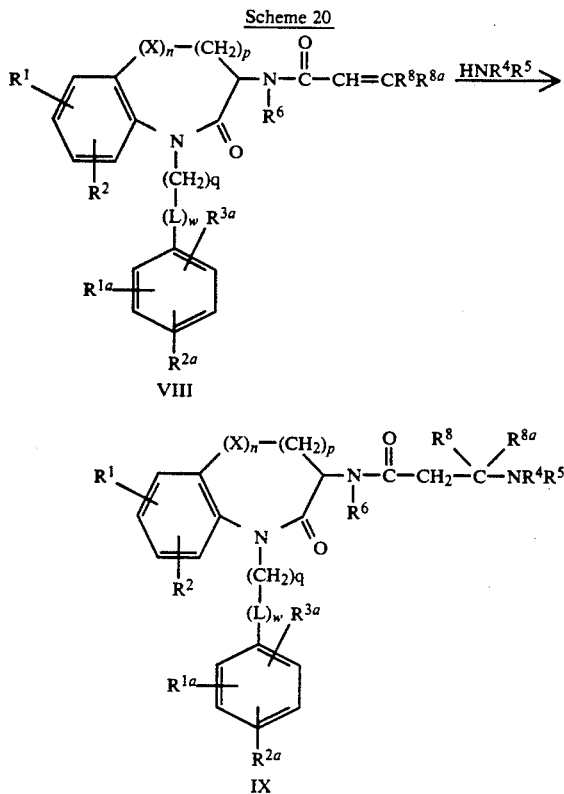

Scheme 20

VIII

IX

Thus, reaction of intermediates of Formula VIII with HNR⁴R⁵ heat or in a polar solvent such as dimethylsulfoxide at temperatures of 50° C. to 200° C., results in a Michael addition to give compounds of Formula IX. Compounds of Formula VIII may themselves be prepared by the transformations illustrated in Schemes 9 and 11.

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors through or known to influence grown hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., sinsulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but ar not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. NO. 4,036,979, e.g., sulbenox or peptides disclosed in U.S. Pat. No. 4,411,890.

A still further use of the disclosed novel benzo-fused lactam growth hormone secretagogues is in combination with other growth hormone secretagogues such as GHRP-6, GHRP-1 as described in U.S. Pat. Nos. 4,411,890; and publications WO 89/07110 and WO 89/07111 and B-HT920 or growth hormone releasing factor and its analogs or growth hormone and its analogs or somatomedins including IGF-1 and IGF-2.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; Prevention of catabolic side effects of glucocorticoids, treatment of osteoporosis, stimulation of the immune system, treatment of retardation, acceleration of wound healing, accelerating bone fracture repair, treatment of growth retardation, treating renal failure or insufficiency resulting in growth retardation, treatment of physiological short stature, including growth hormone deficient children, treating short stature associated with chronic illness, treatment of obesity and growth retardation associated with obesity, treating growth retardation associated with Prader-Willi syndrome and Turner's syndrome; Accelerating the recovery and reducing hospitalization of burn patients; treatment of intrauterine growth retardation, skeletal dysplasia, hypercortisolism and Cushings syndrome; Induction of pulsatile growth hormone release; Replacement of growth hormone in stressed patients; Treatment of osteochondrodysplasias, Noonans syndrome, schizophrenia, depression, Alzheimer's disease, delayed wound healing, and psychosocial deprivation; treatment of pulmonary dysfunction and ventilator dependency; Attenuation of protein catabolic response after a major operation; reducing cachexia and protein loss due to chronic illness such as cancer or AIDS. Treatment of hyperinsulinemia including nesidioblastosis; Adjuvant treatment for ovulation induction; To stimulate thymic development and prevent the age-related decline of thymic function; Treatment of immunosuppressed patients; Improvement in muscle strength, mobility, maintenance of skin thickness, metabolic homeostasis, renal hemeostasis in the frail elderly; Stimulation of osteoblasts, bone remodelling, and cartilage growth; Stimulation of the immune system in companion animals and treatment of disorders of aging in companion animals; Growth promotant in livestock; and stimulation of wool growth in sheep.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the disclosed invention.

EXAMPLE 1

3-Amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate Step A:
3-Amino-2,3,4,5-tetrahydro-1H-1-benzazepin-2-one A solution of 9.22 g (45.6 mmol) of 3-azido-2,3,4,5-tetrahydro-1H-1-benzazepin-2-one (prepared by the method of Watthey, et al., J. Med. Chem., 28, 1511–1516 (1985) in 30 mL methanol was hydrogenated at 40 psi in the presence of 1.0 g of 5% Pt/C for 4.5 hours. Celite was added and the mixture filtered through a pad of Celite. The filtrate was concentrated and allowed to stand for 16 hours at room temperature which resulted in formation of crystals. The material was isolated by filtration and dried under vacuum to afford 4.18 g (23.7 mmol, 52%) of the product. The mother liquors were diluted to 100 mL with methanol, treated with 2 g of charcoal, filtered through Celite and the filtrate concentrated under vacuum to approximately 15 mL. A second crop formed yielding 2.02 g of product (11.5 mmol, 25%). Another recycling of the mother liquors afforded a third crop of 0.88 g (5.0, 11%). A total of 7.08 g (40.2 mmol, 88%) of the product was thus obtained. $^1$H NMR (200 MHz, CDCl$_3$); 1.6 (br s,2 H), 1.80 (m,1 H), 2.55 (m,2 H), 2.88 (m,1 H), 3.42 (dd;7 Hz,11 Hz;1 H), 6.98 (d,8 Hz,1 H), 7.2 (m,3 H), 8.3 (br s,1 H). FAB-MS: calculated for $C_{10}H_{12}N_2O$ 176; found 177 (M+H,100%).

Step B:
3(R)-Amino-2,3,4,5-tetrahydro-1H-1-benzazepin-2-one 2.37 g (13.5 mmol) of 3-amino-2,3,4,5-tetrahydro-1H-1-benzazepin-2-one (Step A) and 2.02 g (13.5 mmol) of L-tartaric acid were suspended in 40 mL of ethanol. The mixture was gently heated and complete dissolution achieved by dropwise addition of 5 mL of distilled water. The solution was cooled to room temperature and aged overnight. The solid that formed was removed by filtration, washed with ethanol/diethyl ether (1:1) and dried under vacuum to afford 1.75 g of crude L-tartrate salt. The mother liquors were evaporated to dryness under vacuum, redissolved in 40 mL of water and the pH adjusted to 10-11 by the addition of solid potassium carbonate. The mixture was extracted with chloroform (6×20 mL) and the combined extracts washed with water (1×) and brine (1×), dried over potassium carbonate, filtered and solvents removed under vacuum to afford 1.29 g (7.33 mmol) of partially enriched 3(R) amine.

The original 1.75 g batch of L-tartrate salt was recrystallized twice from aqueous ethanol to afford 1.03 g (3.17 mmol,24%) of purified L-tartrate salt with $[\alpha]_D = -212°$ (c=1, $H_2O$). The purified L-tartrate salt was dissolved in 20 mL of water and the pH adjusted to 10-11 by the addition of solid potassium carbonate. The mixture was extracted with chloroform (5×10 mL); combined extracts were washed with water and brine then dried over potassium carbonate, filtered and solvents removed under vacuum to afford 522 mg (2.96 mmol,22% overall) of the 3(S) amine, $[\alpha]_D = -446°$ (c=1,$CH_3OH$).

The remaining 1.29 g (7.33 mmol) of partially enriched 3(R) amine was treated with 1.10 g (7.33 mmol) of D-tartaric acid as described above and the resulting salt recrystallized twice from aqueous ethanol to afford 1.20 g of purified D-tartrate salt, $[\alpha]_D = -214°$ (c=1,$H_2O$). The purified D-tartrate salt was dissolved in 20 mL of water and the free base isolated as described above to give 629 mg (3.57 mmol,26% overall) of the 3(R) amine, $[\alpha]_D = -455°$ (c=1,$CH_3OH$).

Step C: 2,2-Dimethylbutanedioic acid, 4-methyl ester 2,2-dimethylsuccinic acid (20 g, 137 mmol) dissolved in 200 mL absolute methanol at 0°0 was treated dropwise with 2 mL concentrated sulfuric acid. After the addition was complete, the mixture was allowed to warm to room temperature and stirred for 16 hours.

The mixture was concentrated in vacuo to 50 mL and slowly treated with 200 mL of saturated aqueous sodium bicarbonate. The mixture was washed with hexane (3×) and the aqueous layer removed and cooled in an ice bath. The mixture was acidified to pH 2 by slow addition of 6N HCl then extracted with ether (8×). The combined extracts were washed with brine, dried over magnesium sulfate, filtered and solvents removed in vacuo. The residue was dried at room temperature under vacuum to afford 14.7 g (91.8 mmol, 67%) of a viscous oil that slowly solidified upon standing. $^1H$ NMR analysis indicates the product is a mixture of the title compound and 15% of the isomeric 2,2-dimethylbutanedioic acid, 1-methyl ester. NMR (200 MHz, $CDCl_3$) of title compound: 1.29 (s,6 H), 2.60 (s,2 H), 3.66 (s,3 H). NMR (200 MHz, $CDCl_3$) of isomer: 1.28 (s,6 H), 2.63 (s,2 H), 3.68 (s,3 H).

Step D: 3-[Benzyloxycarbonylamino]-3-methylbutanoic acid, methyl ester

To 14.7 g (91.8 mmol) of 2,2-dimethylbutanedioic acid-4-methyl ester (Step C), containing 15% of the isomeric 1-methyl ester compound, in 150 mL benzene was added 13 mL of triethylamine (9.4 g, 93 mmol, 1.01 eq) followed by 21.8 mL diphenylphosphoryl azide (27.8 g, 101 mmol, 1.1 eq). The mixture was heated under nitrogen at reflux for 45 minutes then 19 mL (19.9 g, 184 mmol, 2 eq) of benzyl alcohol was added and refluxing continued for 16 hours.

The mixture was cooled, filtered and the filtrate concentrated to a minimum volume under vacuum. The residue was redissolved in 250 mL ethyl acetate, washed with water (1×), saturated aqueous sodium bicarbonate (2×) and brine (1×). The organic layer was removed, dried over magnesium sulfate, filtered and the filtrate concentrated to a minimum volume in vacuo. The crude product was purified by medium pressure liquid chromatography on silica, eluting with hexane/ethyl acetate (4:1), to afford 18.27 g (68.9 mmol, 75%) of the title compound as a pale yellow liquid in addition to a small amount of pure 3-[benzyloxycarbonylamino]-2,2-dimethylpropanoic acid, methyl ester. $^1H$ NMR (200 MHz, $CDCl_3$) of title compound: 1.40 (s,6 H), 2.69 (s,2 H), 3.63 (s,3 H), 5.05 (s,2 H), 5.22 (br s,1 H), 7.32 (s,5 H). $^1H$ NMR (200 MHz, $CDCl_3$) of 3-[benzyloxycarbonylamino]-2,2-dimethylpropanoic acid, methyl ester (200 MHz, $CDCl_3$): 1.19 (s,6 H), 3.30 (d,7 Hz,2 H; resonance collapses to singlet in $CD_3OD$), 3.67 (s,3 H), 5.09 (s,2 H), 5.22 (br s,1 H; resonance not observed in $CD_3OD$), 7.3 (br s,5 H).

Step E: 3-Benzyloxycarbonylamino-3-methylbutanoic acid

A solution of 18.27 g (68.9 mmol) of methyl 3-benzyloxycarbonylamino-3-methylbutanoate (Step D) in 20 mL of methanol at room temperature was treated dropwise wit 51 mL of 2N NaOH (102 mmol, 1.5 eq). The mixture was stirred at room temperature for 16 hours then transferred to a separatory funnel and washed with hexane (3×). The aqueous layer was removed, cooled to 0° and slowly acidified to pH 2 (paper) by dropwise addition of 6N HCl. This mixture was extracted with ether (6×); combined extracts were washed with 1N HCl and brine, then dried over magnesium sulfate, filtered and solvent removed under vacuum to afford 17.26 g (68.7 mmol, 99%) of the product. $^1H$ NMR (200 MHz,$CDCl_3$): 1.42 (s,6 H), 2.77 (s,2 H), 5.06 (s,2 H), 5.2 (br s,1 H), 7.3 (s,5 H).

Step F:
3-Benzyloxycarbonylamino-3-methyl-N-[2,3,4,5-tetrahydro-2-oxo-1H-1-benzazepin-3(R)-yl]-butanamide To a solution of 252 mg (1.43 mmol) of 5(R)-amino-2,3,4,5-tetrahydro-1H-[1]benzazepin-2-one (Step B) in 4 mL of methylene chloride at room temperature was added 400 mg (1.60 mmol, 1.1 eq) of 3-benzyloxycarbonylamino-3-methylbutanoic acid (Step E) followed by 760 mg (1.7 mmol, 1.2 eq) benzotriazol-1-yloxytris(-dimethylamino)phosphonium hexafluorophosphate and 0.50 mL of diisopropylethylamine (380 mg, 2.9 mmol, 2 eq). After 3 hours at room temperature, the mixture was diluted into 30 mL of ethyl acetate and washed with 5% aqueous citric acid, saturated aqueous sodium bicarbonate (2×) and brine. The organic layer was removed, dried over magnesium sulfate, filtered and solvents removed under vacuum. The residue was purified by medium pressure liquid chromatography on silica, eluting with ethyl acetate to afford 586 mg (1.43 mmol, 100%) of the product. $^1$H NMR (200 MHz, CDCl$_3$): 1.38 (s,3 H), 1.39 (s,3 H), 1.82 (m,1 H), 2.52 (s,2 H), 2.5-3.0 (m,3 H), 4.51 (m,1 H), 5.07 (br s,2 H), 5.57 (br s,1 H), 6.68 (d,7 Hz,1 H), 6.97 (d,8 Hz,1 H), 7.1-7.4 (m,8 H), 7.61 (br s,1 H). FAB-MS: calculated for $C_{23}H_{27}N_3O_4$ 409; found 410 (M+H,100%); [a]$_D$=−137° (c=1, CHCl$_3$).

Step G: 5-Phenyltetrazole

Zinc chloride (3.3 g, 24.3 mmol, 0.5 eq) was added to 15 mL of N,N-dimethylformamide in small portions while maintaining the temperature below 60° C. The suspension of zinc chloride was cooled to room temperature and treated with 5.0 g of benzonitrile (48.5 mmol, 1.0 eq) followed by 3.2 g of sodium azide (48.5 mmol, 1.0 eq). The heterogeneous mixture was heated at 115° C. with agitation for 18 hours. The mixture was cooled to room temperature, water (30 mL) was added and the mixture acidified by the addition of 5.1 mL of concentrated hydrochloric acid. The mixture was cooled to 0° C. and aged for one hour, then filtered and the filter cake washed with 15 mL of cold 0.1N HCl then dried at 60° C. under vacuum to afford 6.38 g (43.7 mmol, 90%) of the product.

Step H: 5-Phenyl-2-trityltetrazole

To a suspension of 5.0 g (34.2 mmol) of 5-phenyltetrazole in 55 mL of acetone was added 5.0 mL of triethylamine (3.6 g, 35.6 mmol, 1.04 eq). After 15 minutes, a solution of 10.0 g of triphenylmethyl chloride (35.9 mmol, 1.05 eq) in 20 mL of tetrahydrofuran was added and the mixture stirred at room temperature for one hour. Water (75 mL) was slowly added and the mixture stirred for one hour at room temperature. The product was collected by filtration, washed with 75 mL of water and dried at 60° C. under vacuum to give 13.3 g (34.2 mmol, 100%) of the product.

Step I: N-Triphenylmethyl-5-[2-(4'-methylbiphen-4-yl)]tetrazole

A solution of zinc chloride (6.3 g, 46.2 mmol, 0.6 eq) in 35 mL of tetrahydrofuran was dried over molecular sieves. 5-Phenyl-2-trityltetrazole (30.0 g, 77.3 mmol, 1.0 eq) was dissolved in 300 mL of dry tetrahydrofuran and the solution gently stirred while being degassed three times by alternating vacuum and nitrogen purges. The stirred solution was cooled to −15° C. and treated slowly with 50.5 mL of 1.6M n-butyllithium in hexane (80.0 mmol, 1.05 eq) so as to maintain the temperature below −5° C. The solution was maintained at −5° to −15° C. for 1.5 hours then treated with the dried zinc chloride solution and allowed to warm to room temperature.

In a separate flask, 4-iodotoluene (20.17 g, 92.5 mmol, 1.2 eq) and bis-(triphenylphosphine)nickel(II) dichloride (1.5 g, 2.3 mmol, 0.03 eq) were dissolved in 60 mL of tetrahydrofuran, then degassed and left under an atmosphere of nitrogen. The mixture was cooled to 5° C. and treated with 1.5 mL of 3.0M solution of methylmagnesium chloride in tetrahydrofuran (4.5 mmol, 0.06 eq) so as to keep the temperature below 10° C. The solution was warmed to room temperature and added, under nitrogen purge, to the arylzinc solution. The reaction mixture was stirred vigorously for 8 hours at room temperature then quenched by the slow addition of a solution of 10 mL of glacial acetic acid (1.6 mmol, 0.02 eq) in 60 mL of tetrahydrofuran at a rate so that the temperature was maintained below 40° C. The mixture was stirred for 30 minutes and 150 mL of 80% saturated aqueous sodium chloride was added; the reaction mixture was extracted for 30 minutes and the layers allowed to separate. The organic layer was removed and washed with 150 mL of 80% saturated aqueous sodium chloride buffered to pH>10 by the addition of ammonium hydroxide. The organic phase was removed and concentrated under vacuum to approximately 50 mL then 250 mL of acetonitrile was added. The mixture was again concentrated under vacuum to 50 mL and acetonitrile added to make the final volume 150 mL. The resulting slurry was cooled at 5° C. for 1 hour then filtered and washed with 50 mL of cold acetonitrile followed by 150 mL of distilled water. The filter cake was air dried to a free flowing solid then further dried under vacuum at 50° C. for 12 hours to afford 30.0 g (62.8 mmol, 81%) of the product. $^1$H NMR (200 MHz, CDCl$_3$): 2.28 (s,3 H), 6.9-7.05 (m,10 H), 7.2-7.5 (m,12 H), 7.9 (m,1 H).

Step J: N-Triphenylmethyl-5-[2-(4'-bromomethylbiphen-4-yl)]tetrazole

A solution of 3.15 g (6.6 mmol) of N-triphenylmethyl-5-[2-(4'-methylbiphen-4-yl)] tetrazole (Step I) in 25 mL of methylene chloride was treated with 1.29 g (7.25 mmol, 1.1 eq) of N-bromosuccinimide, 80 mg (0.5 mmol, 0.07 eq) of AIBN, 200 mg of sodium acetate and 200 mg of acetic acid. The mixture was heated at reflux for 2 to 16 hours then cooled and washed with saturated aqueous sodium bicarbonate. The organic layer was removed, dried over sodium sulfate, filtered and concentrated to a minimum volume by atmospheric distillation. Methyl t-butyl ether was added and distillation continued until almost all the methylene chloride was removed the the total volume reduce to approximately 12 mL and 12 mL of hexanes was then added. The mixture was kept at room temperature for 2 hours and the product isolated by filtration, washed with hexanes then dried under vacuum at 50° C. to give 2.81 g (5.04 mmol, 76%) of the product. $^1$H NMR (200 MHz, CDCl$_3$): 4.38 (s,2H), 6.9-8.0 (m,23 H). NMR indicates presence of approximately 1% of the starting material and 7% of the dibromo derivative.

Step K:
3-Benzyloxycarbonylamino-3-methyl-N-[2,3,4,5-tetrahydro-2-oxo-1-[[2'-(N-triphenylmethyl)-tetrazol-5yl][1,1'-biphenyl]-4-yl]methyl-1H-1-benzazepin-3(R)-yl]-butanamide To a solution of 437 mg (1.07 mmol) of the intermediate obtained in Step F in 2 mL of dry dimethylformamide at room temperature under nitrogen was added 55 mg of 60% sodium hydride oil dispersion (33 mg NaH, 1.38 mmol, 1.3 eq). After 15 minutes, a solution of 715 mg (1.28 mmol, 1.2 eq) N-triphenyl-methyl-5-[2-(4'-bromomethylbiphen-4-yl)] tetrazole (Step J) in 1.5 mL of dry dimethylformamide was added and the mixture stirred for 90 minutes.

The reaction mixture was added to 100 mL of ethyl acetate and washed with water (2×) and brine. The organic layer was removed, dried over magnesium sulfate, filtered and solvents removed under vacuum. Purification by medium pressure liquid chromatography on silica, eluting with ethyl acetate/hexane (1:1), afforded 902 mg (1.02 mmol, 95%) of the product. $^1$H NMR (200 MHz,CDCl$_3$): 1.38 (s,3 H), 1.39 (s,3 H), 1.68 (m,1 H), 2.2–2.5 (m,5 H), 4.44 (m,1 H), 4.67 (d,14 Hz,1 H), 5.06 (s,2 H), 5.12 (d,14 Hz,1 H), 5.63 (br 1,1 H), 6.65 (d,8 Hz,1 H), 6.9–7.5 (m,31 H), 7.85 (m,1 H).

Step L:
3-Amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide,trifluoroacetate A solution of 902 mg (1.02 mmol) of the intermediate obtained in Step H in 5 mL methanol was hydrogenated at room temperature and one atmosphere over 160 mg of 20% Pd(OH)$_c$/C for 14 hours. The mixture was filtered through Celite and concentrated under vacuum. The residue was purified by reverse phase HPLC on C-18, eluting with methanol/0.1% aqueous trifluoroacetic acid (linear gradient: 60% methanol increased to 80% methanol over 10 minutes) to afford 568 mg (0.91 mmol, 89%) of the title compound. $^1$H NMR (200 MHz,CD$_3$OD): 1.33 (s,3 H), 1.37 (s,3 H), 2.0–2.6 (m,6 H), 4.35 (dd;7,11 Hz;1 H), 4.86 (d,15 Hz,1 H), 5.20 (d,15 Hz,1 H), 7.00 (d,8 Hz,2 H), 7.15–7.35 (m,6 H), 7.45–7.70 (m,4 H). FAB-MS: calculated for C$_{29}$H$_{31}$N$_7$O$_2$ 509; found 510 (M+H,100%).

EXAMPLE 2

3-Amino-N-[2,3,4,5-tetrahydro-2-oxo-1-[[2'-(1H-tetrazol-5-yl)[1,1'-biphenyl]-4-yl]methyl]-1H-1-benzazepin-3-yl]-propanamide, mono(hydrochloride)

Step A
3-t-Butoxycarbonylamino-N-[2,3,4,5-tetrahydro-2-oxo-1H-1-benzazepin-3-yl]-propanamide To a solution of 50 mg (0.28 mmol) 3-amino-2,3,4,5-tetrahydro-1H-1-benzazepin-2-one (Example 1; Step A) in 2 mL methylene chloride at room temperature was added 56 mg (0.30 mmol, 1.05 eq) 3-(t-butoxycarbonylamino)propanoic acid followed by 1.0 mL diisopropylethylamine (74 mg, 0.57 mmol, 2 eq) and 190 mg (0.43 mmol, 1.5 eq) benzotriazol-1-yloxytris(dimethylamino) phosphonium hexafluorophosphate. After 1 hour at room temperature, the mixture was added to 20 mL ethyl acetate and washed with 1M aqueous citric acid, saturated aqueous sodium bicarbonate and brine. The organic layer was removed, dried over magnesium sulfate, filtered and solvents removed in vacuo. The residue was purified by medium pressure liquid chromatography on silica, eluting with ethyl acetate/hexane (2:1) to afford 76 mg (0.22 mmol, 77%) of product as a white solid. $^1$H NMR (200 MHz, CDCl$_3$): 1.40 (s,9 H), 1.95 (m,1 H), 2.40 (t,6 Hz,2 H), 2.6–3.0 (m,3 H), 3.36 (q,6 Hz,2 H), 4.52 (m,1 H), 5.15 (br t,1 H), 6.58 (br d,1 H), 7.0–7.3 (m,4 H), 7.6 (br s,1 H). FAB-MS: calc. for C$_{18}$H$_{25}$N$_3$O$_4$ 347; found 348 (M+H,35%).

Step B
3-t-Butoxycarbonylamino-N-[2,3,4,5-tetrahydro-2-oxo-1-[[2'-biphenyl]-4-yl]methyl]-1H-1-benzazepin-3(R)-yl]-propanamide To a solution of 68 mg (0.20 mmol) of the intermediate obtained in Step A in 0.5 mL dry dimethylformamide under nitrogen was added 10 mg of 60% sodium hydride oil dispersion (6 mg NaH, 0.25 mmol, 1.3 eq). After 15 min., a solution of 142 mg (0.26 mmol, 1.3 eq) N-triphenylmethyl-5-(4'-bromomethylbiphen-2 -yl)tetrazole (Example 1, Step J) in 0.5 mL dimethylformamide was added and the mixture stirred at room temperature for 4 hours. The mixture was added to 30 mL ethyl acetate and washed twice with pH 7.0 phosphate buffer and once with brine. The organic layer was removed, dried over magnesium sulfate filtered and solvents removed in vacuo. The residue was purified by medium pressure liquid chromatography on silica, eluting with ethyl acetate to afford 152 mg (0.18 mmol, 94%) of the product as a white foam. $^1$H NMR (200 MHz, CDCl$_3$): 1.40 (s,9 H), 1.77 (m,1 H), 2.3–2.6 (m,5 H), 3.35 (q,6 Hz,2 H), 4.45 (m,1 H), 4.70 (d,15 Hz,1 H), 5.12 (d,15 Hz,1 H), 6.53 (d,7 Hz,1 H), 6.9–7.5 (m, approx. 25 H), 7.85 (m,1 H).

Step C
3-t-Butoxycarbonylamino-N-[2,3,4,5-tetrahydro-2-oxo-1-[[2'-(1H-tetrazol-5-yl)[1,1'-biphenyl[-4-yl]methyl]-1H-1-benzazepin-3-yl]-propanamide The intermediate obtained in Step B (150 mg, 0.18 mmol) dissolved in 5 mL methanol was hydrogenated over 30 mg of Pd(OH)$_2$ on carbon at one atmosphere for 2 hours. The mixture was filtered through Celite and the filtrate concentrated under vacuum. The residue was purified by medium pressure liquid chromatography on silica, eluting with ethyl acetate/acetonitrile/methanol (9:1:1) to afford 62 mg (0.11 mmol, 59%) of the product as a colorless glass. $^1$H NMR (200 MHz, CD$_3$OD): 1.39 (s,9 H), 2.0–2.5 (m,6 H), 3.26 (t,7 Hz,2 H), 4.31 (dd;7,12 Hz;1 H), 4.83 (d,16 Hz,1 H), 5.20 (d,16 Hz,1 H), 6.98 (d,8 Hz,2 H), 7.1–7.6 (m,10 H). FAB-MS: calc. for C$_{32}$H$_{35}$N$_7$O$_4$ 581; found 582 (M+H,19%).

Step D
3-Amino-N-[2,3,4,5-tetrahydro-2-oxo-1-[[2'-(1H-tetrazol-5-yl)[1,1'-biphenyl]-4-yl]methyl]-1H-1-benzazepin-3-yl]-propanamide, mono(hydrochloride)

To a solution of 40 mg (0.07 mmol) of the intermediate obtained in Step C in 2 mL methanol at room temperature was added 0.5 mL of concentrated hydrochloric acid and the mixture stirred for 16 hours. All volatiles were removed under vacuum and the residue further dried under high vacuum to afford 35 mg (0.07 mmol, 100%) of the title compound as a pale yellow glass. $^1$H NMR (200 MHz, CD$_3$OD): 2.0-2.8 (m,6 H), 3.22 (t,6 Hz,2 H), 4.30 (dd;7,10 Hz;1 H), 4.83 (d,16 Hz,1 H), 5.17 (d,16 Hz,1 H), 6.97 (d,8 Hz,2 H), 7.1-7.6 (m,10 H). FAB-MS: calc. for C$_{27}$H$_{27}$N$_7$O$_2$ 481; found 482 (M+H,100%).

EXAMPLE 3

3-Amino-3-methyl-N-[2,3,4,5-tetrahydro-2-oxo-1-phenylmethyl)-1H-1-benzazepin-3(R)-yl]-butanamide, trifluoroacetate

Step A:
3-Benzyloxycarbonylamino-3-methyl-N-[2,3,4,5-tetrahydro-2-oxo-1-(phenylmethyl)-1H-1-benzazepin-3(R)-yl]-butanamide To a solution of 40 mg (0.098 mmol) of 3-benzyloxycarbonylamino-3-methyl-N-[2,3,4,5-tetrahydro- 2-oxo-1H-1-benzazepin-3(R)-yl]-butanamide (Example 1, Step F) in 0.5 mL of dry dimethylformamide at room temperature under nitrogen was added 5 mg of 60% sodium hydride oil dispersion (3 mg NaH, 0.13 mmol, 1.3 eq). After 5 minutes, 0.013 mL of benzyl bromide (19 mg, 0.11 mmol, 1.1 eq) was added and the mixture stirred for 1 hour at room temperature, then added to 20 mL of ethyl acetate and washed with water (2×) and brine. The organic layer was removed, dried over magnesium sulfate, filtered and solvents removed under vacuum. The residue was purified by medium pressure liquid chromatography on silica, eluting with ethyl acetate/hexane (1:1) to afford 44 mg (0.88 mmol, 90%) of product. $^1$H NMR (200 MHz, CDCl$_3$): 1.37 (s,3 H), 1.38 (s,3 H), 1.73 (m,1 H), 2.3-2.6 (m,5 H), 4.48 (m,1 H), 4.80 (d,15 Hz,1 H), 5.07 (br s,2 H), 5.23 (d,15 Hz,1 H), 5.62 (br s,1 H), 6.67 (br d,7 Hz,1H), 7.1-7.4 (m,14 H). FAB-MS: calculated for C$_{30}$H$_{33}$N$_3$O$_4$ 499; found 500 (M+H,100%).

Step B:
3-Amino3-methyl-N-[2,3,4,5-tetrahydro-2-oxo-1-(phenylmethyl)-1H-1-benzazepin-3(R)-yl]-butanamide, trifluoroacetate The intermediate obtained in Step A (17 mg, 0.034 mmol) dissolved in 2 mL of methanol was hydrogenated for 6 hours at room temperature and one atmosphere over 5 mg of Pd(OH)$_2$ on carbon. The mixture was filtered through Celite and the filtrate concentrated under vacuum. The residue was purified by reverse phase HPLC on C-18, eluting with methanol/0.1% aqueous trifluoroacetic acid (linear gradient: 60% methanol to 80% methanol over 10 minutes) to afford 13 mg (0.27 mmol, 80%) of the title compound. $^1$H NMR (200 MHz, CD$_3$OD): 1.32 (s,3 H), 1.35 (s,3 H), 2.0-2.6 (m,6 H), 4.35 (dd;7,11 Hz;1 H), 4.82 (d,15 Hz,1 H), 5.13 (d,15 Hz,1 H), 7.1-7.4 (m,9 H). FAB-MS: calculated for C$_{22}$H$_{27}$N$_3$O$_2$ 365; found 366 (M+H,100%).

EXAMPLE 4

2(R)-Amino-3-hydroxy-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate)

Step A
3(R)-t-Butoxycarbonylamino-2,3,4,5-tetrahydro-1H-1-benzazepion-2-one

To a solution of 400 mg (2.27 mmol) 3(R)-amino-2,3,4,5-tetrahydro-1H-1-benzazepin-2-one (Example 1, Step B) in 5 mL methylene chloride at room temperature was added 0.57 mL (540 mg, 2.48 mmol, 1.1 eq) of di-t-butyl dicarbonate. The mixture was stirred for 3 hours at room temperature then all volatiles were removed under vacuum to give 625 mg (2.26 mmol, 100%) of an oil that slowly solidified upon standing. $^1$H NMR (200 MHz, CDCl$_3$): 1.40 (s,9 H), 2.00 (m,1 H), 2.65 (m,2 H), 2.95 (m,1 H), 4.29 (m,1 H), 5.42 (br d,8 Hz,1 H), 6.97 (d,7 Hz,1 H), 7.2 (m,3 H), 7.50 (br s,1 H).

Step B
3(R)-t-Butoxycarbonylamino-2,3,4,5-tetrahydro-1-[[2'-[N-(triphenylmethyl)-1H-tetrazol-5-yl][1,1'-biphenyl]-4-yl]methyl]-1H-1-benzazepin-2-one To a solution of 310 mg (1.12 mmol) of the intermediate obtained in Step A in 2 mL dry dimethylformamide at room temperature under nitrogen was added 54 mg of 60% sodium hydride oil dispersion (32 mg NaH, 1.3 mmol, 1.2 eq). After 15 minutes, a solution of 750 mg (1.34 mmol, 1.2 eq) N-triphenylmethyl-5-[2-(4'-bromomethylbiphen-4-yl)] tetrazole in 2 mL dry dimethylformamide was added and the mixture stirred for 2 hours. The reaction mixture was added to 50 mL of ethyl acetate and washed with pH 7.0 phosphate buffer (2×) and brine. The organic layer was removed, dried over magnesium sulfate, filtered and solvents removed under vacuum. Purification by medium pressure liquid chromatography on silica, eluting with hexane/ethyl acetate (2:1), afforded 815 mg (1.08 mmol, 96%) of product. $^1$H NMR (200 MHz, CDCl$_3$): 1.40 (s,9 H), 1.80 (m,1 H), 2.40 (m,3 H), 4.24 (m,1 H), 4.65 (d,15 Hz,1 H), 5.08 (d,15 Hz,1 H), 5.45 (br d,7 Hz,1 H), 6.9-7.5 (m,26 H), 7.8 (m,1 H).

Step C
3(R)-Amino-1,3,4,5-tetrahydro-1-[[2'-(1H-tetrazol-5-yl)[1,1'-biphenyl[-4-yl]methyl]-2H-1-benzazepin-2-one, mono(hydrochloride)

A solution of 407 mg (0.54 mmol) of the intermediate obtained in Step B in 5 mL methanol was hydrogenated at room temperature and 1 atmosphere over 40 mg of 20% Pd(OH)$_2$ on carbon for 3 hours. The mixture was filtered through Celite and concentrated under vacuum to give a residue that was purified by medium pressure liquid chromatography on silica eluting with 2% methanol/ethyl acetate. The intermediate thus obtained (260 mg) was dissolved in 5 mL of methanol and treated with 1 mL concentrated hydrochloric acid. After 16 hours, all volatiles were removed under vacuum to afford 226 mg (0.51 mmol, 94%) of product.

Step D
2(R)-(t-Butoxycarbonyl)amino-3-(t-butoxy)-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide To a suspension of 60 mg (0.13 mmol) of the intermediate obtained in Step C in 2 mL of methylene chloride at room temperature was added 65 mg (0.15 mmol, 1.1 eq) of BOC-D-serine t-butyl ether dicyclohexylamine salt, followed by 0.037 mL of triethylamine (27 mg, 0.26 mmol, 2 eq) and 89 mg of benzotriazol-1-yloxytris(dimethylamino)phosphonium hexafluorophosphate (0.20 mmol, 1.5 eq). After 1 hour at room temperature, all volatiles were removed under vacuum. The residue was purified by medium pressure liquid chromatography on silica, eluting with 2% methanol/ethyl acetate to afford 68 mg (0.10 mmol, 77%) of product. $^1$H NMR (200 MHz, CDCl$_3$): 1.15 (s,9 H), 1.32 (s,9 H), 1.88 (m,1 H), 2.54 (m,3 H), 3.36 (dd;6,9 Hz;1 H), 3.72 (m,1 H), 4.10 (m,1 H), 4.45 (m,1 H), 4.89 (d,15 Hz,1 H), 5.05 (d,15 Hz,1 H), 5.38 (br d,7 Hz,1 H), 7.00 (d,8 Hz,2 H), 7.1–7.6 (m,9 H), 7.90 (m,1 H). FAB-MS: calc. for C$_{36}$H$_{43}$N$_7$O$_5$ 653; found 654 (M+H,8%).

Step E
2(R)-Amino-3-hydroxy-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate)

A solution of 65 mg (0.099 mmol) of the intermediate obtained in Step D in 2 mL methylene chloride at room temperature was treated wit 0.1 mL of anisole followed by 1 mL anhydrous trifluoroacetic acid. After 2 hours, all volatiles were removed under vacuum and the residue purified by reverse phase HPLC on C-18 eluting with methanol/0.1% aqueous trifluoroacetic acid (linear gradient: 55% methanol to 75% methanol over 10 minutes). to afford 54 mg (0.088 mmol, 89%) of the title compound. $^1$H NMR (200 MHz, CD$_3$OD): 2.10 (m,1 H), 2.2–2.7 (m,3 H), 3.93 (m,2 H), 4.38 (dd;8,12 Hz;1 H), 4.85 (d,14 Hz,1 H), 5.29 (d,14 Hz,1 H), 7.01 (d,8 Hz,2 H), 7.1–7.4 (m,6 H), 7.5–7.7 (m,4 H). FAB-MS: calc. for C$_{27}$H$_{27}$N$_7$O$_3$ 497; found 498 (M+H,100%).

EXAMPLE 5
2(R)-Amino-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-pentanamide, mono(trifluoroacetate)

Step A N-(t-butoxycarbonyl)-D-norvaline

D-Norvaline (2.0 g, 17.0 mmol) suspended in 5 mL methylene chloride was treated with 4.3 mL of di-ti-butyl-dicarbonate (4.1 g, 18.7 mmol, 1.1 eq) followed by 4.8 mL of triethylamine (3.5 g, 34 mmol, 2 eq). The mixture was stirred at room temperature for 20 hours then added to 100 mL ethyl acetate and washed with 5% citric acid (2×) and brine. The organic layer was removed, dried over magnesium sulfate, filtered and solvent removed under vacuum to afford 3.55 g of the product as a clear, viscous gum. $^1$H NMR (200 MHz, CDCl$_3$): 1.00 (t,7 Hz,3 H), 1.51 (s,9 H), 1.5–2.0 (m,4 H), 4.35 (m,1 H), 5.08 (m,1 H).

Step B
2(R)-Amino-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-pentanamide, mono(trifluoroacetate)

The title compound was prepared from N-(t-butoxycarbonyl)-D-norvaline and 3(R)-amino-1,3,4,5-tetrahydro-1-[[2'-(1H-tetrazol-5-yl)[1,1'-biphenyl]-4-yl]methyl]-2H-1-benzazepin-2-one hydrochloride (Example 4, Step C), using the procedures described in Example 4, Steps D and E. $^1$H NMR (200 MHz, CD$_3$OD): 0.96 (t,7 Hz,3 H), 1.45 (m,2 H), 1.80 (m,2 H), 2.0–2.6 (m,4 H), 3.81 (t,7 Hz,1 H), 4.36 (dd;7,11 Hz;1 H), 4.8 (d,15 Hz,1 H), 5.22 (d,15 Hz,1 H), 6.96 (d,8 Hz,2 H), 7.1–7.3 (m,6 H), 7.4–7.7 (m,4 H). FAB-MS: calc. for C$_{29}$H$_{31}$N$_7$O$_2$ 509; found 510 (M+H,100%).

EXAMPLE 6
2(R)-Amino-3-methyl-N-[2,3,4,5-tetrahydro-2-oxo-1-[[2'-tetrazol-5-yl)[1,1'-biphenyl]-4-yl]methyl]-1H-1-benzazepin-3(R)-yl]-butanamide, mono(trifluoroacetate)

The title compound was prepared from N-(t-butoxycarbonyl)-D-valine and 3(R)-amino-1,3,4,5-tetrahydro-1-[[2'-(1H-tetrazol-5-yl)[1,1'-biphenyl]-4-yl]methyl]-2H-1-benzazepin-2-one hydrochloride (Example 4, Step C), using the procedures described in Example 4, Steps D and E. $^1$H NMR (200 MHz, CD$_3$OD): 1.05 (d,7 Hz,3 H), 1.09 (d,7 Hz,3 H), 2.0–2.6 (m,5 H), 3.68 (d,5 Hz,1 H), 4.40 (dd;7,11 Hz,1 H), 4.8 (d,15 Hz,1 H), 5.23 (d,15 Hz,1 H), 6.98 (d,8 Hz,2 H), 7.1–7.3 (m,6 H), 7.4–7.7 (m,4 H). FAB-MS: calc. for C$_{29}$H$_{31}$N$_7$O$_2$ 509; found 510 (M+H,100%).

EXAMPLE 7
2(R)-Amino-3-phenyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate

Step A
2(R)-t-Butoxycarbonylamino-3-phenyl-N-[2,3,4,5-tetrahydro-2-oxo-1H-1-benzazepin-3(R)-yl]-propanamide To a solution of 30 mg (0.17 mmol) 3(R)-amino-2,3,4,5-tetrahydro-1H-1-benzazepin-2-one (Example 1; Step B) in 2 mL methylene chloride at room temperature was added 50 mg (0.19 mmol, 1.1 eq) N-(t-butoxycarbonyl)-D-phenylalanine followed by 0.047 mL (34 mg, 0.34 mmol, 2 eq) of triethylamine and 113 mg (0.26 mmol, 1.5 eq) benzotriazol-1-yloxytris(dimethylamino)-phosphonium hexafluorophosphate. After 2 hours at room temperature, the mixture was added to 30 mL of ethyl acetate and washed with 5% citric acid (2×), saturated aqueous sodium bicarbonate and brine. The organic layer was removed, dried over magnesium sulfate, filtered and solvents removed under vacuum. The residue was purified by medium pressure liquid chromatography on silica, eluting with ethyl acetate to afford 71 mg (0.17 mmol, 100%) of the product. $^1$H NMR (200 MHz, CDCl$_3$): 1.38 (s,9 H), 1.9 (m,1 H), 2.6–3.1 (m,5 H), 4.44 (m,2 H), 5.10 (br d,7 Hz,1 H), 6.95 (d,8 Hz,1 H), 7.1–7.3 (m,8 H), 8.33 (br s,1 H). FAB-MS: calc. for C$_{24}$H$_{29}$N$_3$O$_4$ 423; found 424 (M+H,65%).

Step B 2(R)-t-Butoxycarbonylamino-3-phenyl-N-2,3,4,5-tetrahydro-2-oxo-1-[[2'-[N-(triphenylmethyl)-1H-tetrazol-5-yl][1,1'-biphenyl]-4-yl]methyl]-1H-1-benzazepin-3(R)-yl]-propanamide To a solution of 70 mg (0.17 mmol) of the intermediate obtained in Step A in 0.5 mL dry dimethylformamide at room temperature under nitrogen was added 8 mg of 60% sodium hydride oil dispersion (5 mg NaH, 0.2 mmol, 1.2 eq). After 10 min., a solution of 120 mg (0.21 mmol, 1.3 eq) N-triphenylmethyl-5-(4'-bromomethylbiphen-2-yl)tetrazole in 0.5 mL dimethylformamide was added and the mixture stirred at room temperature for 1 hour. The reaction mixture was added to 30 mL of ethyl acetate/hexane (1:1) and washed with pH 7.0 phosphate buffer and once with brine. The organic layer was removed, dried over magnesium sulfate filtered and solvents removed under vacuum. The residue was purified by medium pressure liquid chromatography on silica, eluting with ethyl acetate/hexane (2:1) to afford 139 mg (0.15 mmol, 93%) of the product. $^1$H NMR (200 MHz, CDCl$_3$): 1.40 (s,9 H), 1.67 (m,1 H), 2.3–2.7 (m,3 H), 3.02 (d,6 Hz,2 H), 4.37 (m,2 H), 4.72 (d,15 Hz,1 H), 4.90 (br d,1 H), 5.05 (d,15 Hz,1 H), 6.9–7.5 (m, approx. 30 H), 7.86 (m,1 H).

Step C
2(R)-Amino-3-phenyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate)

A solution of 139 mg (0.15 mmol) of the intermediate obtained in Step B in 5 mL methanol was hydrogenated over 30 mg of 20% Pd(OH)$_2$ on carbon at one atmosphere for 3 hours. The mixture was filtered through Celite and the filtrate concentrated under vacuum. The residue was redissolved in 2 mL methylene chloride and the solution treated with 0.1 mL of anisole followed by 1 mL trifluoroacetic acid. After 2 hours at room temperature, all volatiles were removed under vacuum and the residue purified by reverse phase HPLC on C-18, eluting with methanol/0.1% aqueous trifluoroacetic acid (linear gradient: 60% methanol increased to 80% methanol over 10 minutes) affording 82 mg (0.12 mmol, 79%) of the title compound. $^1$H NMR (200 MHz, CD$_3$OD): 2.1 (m,1 H), 2.3–2.6 (m,3 H), 3.00 (dd;9,14 Hz;1 H), 3.33 (dd;5,14 Hz;1 H), 4.13 (dd;5,9 Hz;1 H), 4.38 (dd;7,11 Hz;1 H), 4.89 (d,15 Hz,1 H), 5.18 (d,15 Hz,1 H), 7.00 (d,8 Hz,2 H), 7.1–7.4 (m,11 H), 7.45–7.70 (m,4 H). FAB-MS: calc. for C$_{33}$H$_{31}$N$_7$O$_2$ 557; found 558 (M+H,100%).

EXAMPLE 8
2(R)-Amino-4-phenyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, mono(trifluoroacetate)

The title compound was prepared from 3(R)-amino-2,3,4,5-tetrahydro-1H-1-benzazepin-2-one (Example 1; Step B) and N-(t-butoxycarbonyl)-D-homophenylalanine by the procedures described in (Example 7. $^1$H NMR (200 MHz, CD$_3$OD); 2.1 (m,3 H ), 2.2–2.6 (m,3 H), 2.75 (m,2 H), 3.94 (t,7 Hz,1 H), 4.30 (dd;7,11 Hz;1 H), 4.84 (d,15 Hz,1 H), 5.22 (d,15 Hz,1 H), 6.97 (d,8 Hz,2 H), 7.1–7.7 (m,15 H). FAB-MS: calc. for C$_{34}$H$_{33}$N$_7$O$_2$ 571; found 572 (M+H,100%).

EXAMPLE 9
2(R)-Amino-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate)

The title compound was prepared from 3(R)-amino-2,3,4,5-tetrahydro-1H-1-benzazepin-2-one (Example 1; Step B) and N-(t-butoxycarbonyl)-D-alanine by the procedures described in Example 7. $^1$H NMR (200 MHz, CD$_3$OD): 1.51 (d,7 Hz,3 H), 2.0–2.6 (m,4 H), 3.90 (q,7 Hz,1 H), 4.36 (dd;7,12 Hz;1 H), 4.82 (d,15 Hz,1 H), 5.23 (d,15 Hz,1 H), 6.98 (d,8 Hz,2 H), 7.10–7.35 (m,6 H), 7.45–7.70 (m,4 H). FAB-MS: calc. for C$_{27}$H$_{27}$N$_7$O$_2$ 481; found 482 (M+H,100%).

EXAMPLE 10
2(S)-Amino-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate)

The title compound was prepared from 3(R)-amino-2,3,4,5-tetrahydro-1H-1-benzazepin-2-one (Example 1; Step B) and N-(t-butoxycarbonyl)-L-alanine by the procedures described in Example 7. $^1$H NMR (200 MHz, CD$_3$OD): 1.42 (d,7 Hz,3 H), 2.0–2.6 (m,4 H), 3.92 (q,7 Hz,1 H), 4.31 (dd;7,12 Hz;1 H), 4.88 (d,15 Hz,1 H), 5.19 (d,15 Hz,1 H), 7.00 (d,8 Hz,2 H), 7.10–7.35 (m,6 H), 7.45–7.70 (m,4 H). FAB-MS: calc. for C$_{27}$H$_{27}$N$_7$O$_2$ 481; found 482 (M+H,100%).

EXAMPLE 11
2(R)-Methylamino-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate)

The title compound was prepared from 3(R)-amino-2,3,4,5-tetrahydro-1H-1-benzazepin-2-one (Example 1; Step B) and N-methyl-N-(t-butoxycarbonyl)D-alanine by the procedures described in Example 7 $^1$H NMR (200 MHz, CD$_3$OD): 1.52 (d, 7 Hz, 3 H,), 2.0–2.6 (m,4 H), 2.60 (s,3 H), 3.81 (q,7 Hz,1 H), 4.36 (dd;8,12 Hz;1 H), 4.85 (d,15 Hz,1 H), 5.22 (d,15 Hz,1 H), 6.98 (d,8 Hz,2 H), 7.10–7.35 (m,6 H), 7.45–7.70 (m,4 H). FAB-MS: calc. for C$_{28}$H$_{29}$N$_7$O$_2$ 495; found 496 (M+H, 100%).

EXAMPLE 12
2(R)-Amino-N-[2,3,4,5-tetrahydro-2-oxo-1-[[2'-(1H-tatrazol-5-yl)[1,1'-biphenyl]-4-yl]methyl]-1H-1-benzazepin-3(R)-yl]-butanamide, mono(trifluoroacetate)

Step A: 2(R)-(t-Butoxycarbonylamino)butanoic acid (R)-2-Aminobutanoic acid (1.03 g, 10.0 mmol) suspended in 5 mL methylene chloride was treated with 2.3 mL of di-t-butyl-dicarbonate (2.18 g, 10.0 mmol, 1 eq) and 4 mL of diisopropylethylamine (2.83 g, 23 mmol, 2.3 eq). The mixture was stirred at room temperature for 16 hours then extracted with 30 mL saturated aqueous sodium bicarbonate. The aqueous layer was washed with 20 mL of methylene chloride then removed and acidified to pH 2 by dropwise addition of saturated aqueous potassium hydrogen sulfate. The mixture was extracted with ethyl acetate (2×20 mL); the combined extracts were dried over magnesium sulfate, filtered and solvents removed under vacuum to afford 451 mg (2.2 mmol, 22%) of product. $^1$H NMR (200 MHz, CDCl$_3$): 0.93 (t,8 Hz,3 H), 1.40 (s,9H), 1.6–2.0 (m,2 H), 4.25 (m,1 H), 5.10 (br d,7Hz,1 H), 6.45 (br s,1 H). Step B: The title compound was prepared from the intermediate obtained in Step A and 3(R)-amino-2,3,4,5-tetrahydro-1H-1-benzazepin-2-one (Example 1; Step B) by the procedures described in Example 7. $^1$H NMR (200 MHz, CD$_3$OD): 1.05 (t,7 Hz,3 H), 1.8–2.6 (m,6 H), 3.78 (t,6 Hz,1 H), 4.38 (m, 1 H), 4.82 (d,15 Hz,1 H), 5.23 (d,15 Hz,1 H), 6.98 (d,8 Hz,2 H), 7.10–7.35 (m,6 H), 7.45–7.70 (m,4 H). FAB-MS: calc. for C$_{28}$H$_{29}$N$_7$O$_2$ 495; found 496 (M+H,77%).

EXAMPLE 13

2(R)-Amino-3-[indol-3-yl]-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoro acetate)

Step A
2(R)-t-Butoxycarbonylamino-3-[N-formyl(indol-3-yl)]-N-[2,3,4,5-tetrahydro-2-oxo-1-[[2'-[N-(triphenylmethyl)-1H-tetrazol-5-yl]-[1,1'-biphenyl]-4-yl]methyl]-1H-1-benzazepin-3(R)-yl]propanamide This intermediate was prepared from N$_a$-t-butoxycarbonyl-N'-formyl-D-tryptophan and 3(R)-amino-2,3,4,5-tetrahydro-1H-1-benzazepin-2-one (Example 1; Step B) by the procedures described in Example 7, Steps A and B. $^1$H NMR (200 MHZ, CDCl$_3$): 1.43 (s,9 H), 2.3–2.5 (m,4 H), 3.09 (dd;8,13 Hz;1 H), 3.28 (m,1 H), 4.4 (m,2 H), 4.73 (d,15 Hz,1 H), 4.94 (d,15 Hz,1 H), 5.2 (br s,1 H), 6.65 (d,7 Hz,1 H), 6.9–7.5 (m, approx. 30 H), 7.56 (d,8 Hz,1 H), 7.84 (m,1 H), 8.18 (br s,1 H).

Step B:
2(R)-Amino-3-[indol-3-yl]-N-2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate)

A solution of 125 mg (0.13 mmol) of the intermediate obtained in Step A in 2 mL of methanol was hydrogenated at room temperature and one atmosphere over 30 mg of 20% (Pd(OH)$_2$ on carbon for 3 hours. The mixture was filtered through Celite and solvent removed under vacuum. The residue was redissolved in 2 mL of methylene chloride and treated with 0.1 mL of anisole followed by 1 mL of trifluoroacetic acid. After 1 hour at room temperature, all volatiles were removed under vacuum and the residue redissolved in 2 mL of methanol and treated with 0.5 mL of concentrated hydrochloric acid. The mixture was heated at 60° C. for 2 hours then all volatiles were removed under vacuum. The residue was purified by reverse-phase HPLC on C-18, eluting with methanol/0.1% aqueous trifluoroacetic acid (linear gradient: 55% methanol increased to 75% methanol over 10 minutes) to afford 68 mg (0.096 mmol, 74%) of the title compound. $^1$H NMR (200 MHz, CD$_3$OD): 2.0 (m,1 H), 2.2–2.6 (m,3 H), 3.20 (dd;8,13 Hz;1 H), 3.44 (dd;6,13 Hz;1 H), 4.14 (dd;6,8 Hz;1 H) 4.29 (dd;6,11 Hz;1 H), 4.76 (d,15 Hz,1 H), 5.22 (d,15 Hz,1 H), 6.9–7.7 (m,17 H). FAB-MS: calc. for C$_{35}$H$_{32}$N$_8$O$_2$ 596; found 597 (M+H,100%).

EXAMPLE 14

2(R)-Amino-3-[imidazol-4-yl]-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate)

Step A
2(R)-t-Butoxycarbonylamino-3-[N-tosyl(imidazol-4-yl)]-N-[2,3,4,5-tetrahydro-2-oxo-1H-1-benzazepin-3(R)-yl]-propanamide Prepared from N$_a$-t-butoxycarbonyl-N$_{im}$-tosyl-D-histidine and 3(R)-amino-2,3,4,5-tetrahydro-1H-1-benzazepin-2-one (Example 1; Step B) by the procedure described in Example 7, Step A. $^1$H NMR (200 MHz, CDCl$_3$): 1.38 (s,9 H), 1.70 (m,1 H), 2.42 (s,3 H), 2.5–2.9 (m,5 H), 4.42 (m,2 H), 5.77 (br s,1 H), 6.96 (d,7 Hz,1 H), 7.05 (s,1 H), 7.1–7.3 (m,3 H), 7.33 (d,8 Hz,2 H), 7.58 (br d,7 Hz,1 H), 7.79 (d,8 Hz,2 H), 7.90 (s,1 H), 8.40 (br s,1 H). FAB-MS: calc. for C$_{28}$H$_{33}$N$_5$O$_6$S 567; found 568 (M+H,100%).

Step B
2(R)-t-Butoxycarbonylamino-3-[N-tosyl(imidazol-4-yl)]-N-[2,3,4,5-tetrahydro-2-oxo-1-[[2'-[N-(triphenylmethyl)-1H-tetrazol-5-yl][1,1'-biphenyl]-4-yl]methyl]-1H-1-benzazepin-3-(R)-yl]-propanamide Prepared from the product obtained in Step A and N-triphenylmethyl-5-[2-(4'-bromomethylbiphen-4-yl)] tetrazole by the procedure described in Example 7, Step B. $^1$H NMR (200 MHz, CDCl$_3$): 1.43 (s,9 H), 2.2–2.4 (m,4 H), 2.40 (s,3 H), 2.83 (dd;5,14 Hz;1 H), 3.05 (dd;6,14 Hz;1H), 4.35 (m,2 H), 4.63 (d,14 Hz,1 H). 5.12 (d,14 Hz,1 H), 5.88 (br s,1 H), 6.9–7.5 (m,approx. 28 H), 7.75–7.95 (m,4 H).

Step C:
2(R)-Amino-3-[imidazol-4-yl]-N-[2,3,4,5-tetrahydro-2-oxo-1-[[2'-(1H-tetrazol-5-yl)[1,1'-biphenyl]-4-yl]methyl]-1H-1-benzazepin-3-(R)-yl]-propanamide, mono(trifluoroacetate)

A solution of 104 mg (0.10 mmol) of the intermediate obtained in Step B in 2 mL of chloroform at room temperature was treated with 27 mg (0.20 mmol, 2 eq) of 1-hydroxybenzotriazole hydrate. After 14 hours, the solvent was removed under vacuum and the residue redissolved in 2 mL of methanol and hydrogenated at one atmosphere over 20 mg of 20% Pd(OH)$_2$/C for 3 hours. The mixture was filtered through Celite and solvent removed under vacuum. The residue was redissolved in 2 mL of methylene chloride and treated with 0.1 mL of anisole followed by 1 mL of trifluoroacetic acid. After 2 hours at room temperature, all volatiles were removed under vacuum and the residue purified by reverse-phase HPLC on C-18, eluting with methanol/0.1% aqueous trifluoroacetic acid (linear gradient: 45% methanol increased to 65% methanol over 10 minutes) to afford 56 mg (0.085 mmol, 85%) of the title compound. $^1$H NMR (200 MHz, CD$_3$OD): 2.15–2.50 (m,4H), 3.38 (dd;6,12 Hz;1H), 3.15 (dd;4,12 Hz;1 H), 424 (dd;4,6 Hz;1 H), 4.38 (dd;8,12 Hz,1), 5.12 (s,2 H), 7.03 (d,8 Hz,2 H), 7.2–7.4 (m6 H), 7.4–7.7 (m,5 H), 8.61 (s,1 H). FAB-MS: calc. for $C_{30}H_{29}N_9O_2$ 547; found 548 (M+H,77%).

EXAMPLE 15

2(S)-Amino-3-[imidazol-4-yl]-N-[2,3,4,5-tetrahydro-2-oxo-1-[[2'-(1H-tetrazol-5-yl)-[1,1'-biphenyl]-4-yl]methyl]-1H-1-benzazepin-3(R)-yl]-propanamide, mono(trifluoroacetate)

The title compound was prepared from $N_\alpha$-t-butoxycarbonyl-N-$_{im}$-tosyl-L-histidine, dicyclohexylamine salt and 3(R)-amino-2,3,4,5-tetrahydro-1H-1-benzazepin-2-one (Example 1; Step B) by the procedures described in Example 14. $^1$H NMR (200 MHz, CD$_3$OD): 1.9–2.6 (m,4 H), 3.25 (m,2 H), 4.16 (t,7 Hz,1 H), 4.31 (dd;7,11 Hz;1 H), 4.88 (d,15 Hz,1 H), 5.17 (d,15 Hz,1H), 6.99 (d,8 Hz,2 H), 7.1–7.6 (m,11 H), 8.82 (s,1 H). FAB-MS: calc. for $C_{30}H_{29}N_9O_2$ 547; found 548 (M+H,81%).

EXAMPLE 16

3-Amino-3-methyl-N-[2,3,4,5-tetrahydro-2-oxo-1-[[2'-(1-methyltetrazol-5-yl)[1,1'-biphenyl]-4-yl]methyl]-1H-1-benzazepin-3(R)-yl]-butanamide, mono(trifluoroacetate)

Step A:
3-(t-Butoxycarbonylamino)-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide A solution of 50 mg (0.080 mmol) of 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) in 2 mL of methylene chloride at room temperature was treated with 0.017 mL of triethylamine (12 mg, 0.12 mmol, 1.5 eq) followed by 0.021 mL of di-t-butyl-dicarbonate (20 mg, 0.091 mmol, 1.1 eq). The mixture was stirred for 14 hours then all volatiles were removed under vacuum. The residue was purified by medium pressure liquid chromatography on silica, eluting with ethyl acetate/acetonitrile/methanol (9:1:.5) to afford 42 mg of product (0.069 mmol, 86%). $^1$ NMR (200 MHz, CD$_3$OD): 1.25 (s,6 H), 1.45 (s,9 H), 2.0 (m,1 H), 2.2–2.6 (m,5 H), 4.32 (m,1 H), 4.78 (d,14 Hz,1 H), 5.26 (d,14 Hz,1 H), 6.97 (d,8 Hz,2 H), 7.0–7.35 (m,6 H), 7.40–7.60 (m,4 H). FAB-MS: calculated for $C_{34}H_{39}N_7O_4$ 609; found 610 (M+H, 22%).

Step B:
3-Amino-3-methyl-N-[2,3,4,5-tetrahydro-2-oxo-1-[[2'-(1-methyltetrazol-5-yl)[1,1'-biphenyl]-4-yl]methyl]-1H-1-benzazepin-3(R)-yl]-butanamide, mono(trifluoroacetate)

A solution of 42 mg (0.070 mmol) of the intermediate obtained in Step A in 2 mL of methylene chloride at room temperature was treated with a diethyl ether solution of diazomethane until a yellow color persisted. Glacial acetic acid (0.2 mL) was added and all volatiles removed under vacuum. The residue was redissolved in 2 mL of methylene chloride and treated with 0.1 mL of anisole followed by 0.5 mL of trifluoroacetic acid. After two hours at room temperature, all volatiles were removed under vacuum and the residue purified by reverse phase HPLC on C-18, eluting with methanol/0.1% aqueous trifluoroacetic acid (linear gradient; 75% methanol increased to 85% methanol over ten minutes). Two components were isolated: the title compound elutes first and 26 mg (0.041 mmol, 59%) was thus obtained. This was followed by the N$_2$ isomer (8 mg, 0.013 mmol, 18%) described in Example 17. $^1$H NMR (200 MHz, CD$_3$OD): 1.33 (s,3 H), 1.37 (s,3 H), 2.0–2.6 (m6 H), 3.13 (s,3 H), 4.34 (dd;7,11 Hz;1 H), 4.77 (d,14 Hz,1 H), 5.37 (d,14 Hz,1 H), 6.98 (d,8 Hz,2 H), 7.1–7.4 (m,6 H), 7.5–7.8 (m,4 H). FAB-MS: calc. for $C_{30}H_{33}N_7O_2$ 523; found 524 (M+H,100%).

EXAMPLE 17

3-Amino-3-methyl-N-[2,3,4,5-tetrahydro-2-oxo-1-[[2'-(2-methyltetrazol-5-yl)[1,1'-biphenyl]-4-yl]methyl]-1H-1-benzazepin-3(R)-yl]-butanamide, mono(trifluoroacetate)

The title compound was obtained from 3-amino-3-methyl-N-]2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) by the procedures described in Example 16. $^1$H NMR (200 MHz, CD$_3$OD): 1.32 (s,3 H), 1.36 (s,3 H), 2.0–2.6 (m,6 H), 4.21 (s,3 H), 4.37 (dd;8,12 Hz;1 H), 4.87 (d,15 Hz,1 H), 5.22 (d,15 Hz,1 H), 7.00 (d,8 Hz,2 H), 7.1–7.6 (m,9 H), 7.69 (d,8 Hz,1 H). FAB-MS: calc. for $C_{30}H_{33}N_7O_2$ 523; found 524 (M+H,100%).

EXAMPLE 18

3-(2-Benzyloxyethyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, mono(trifluoroacetate)

To a stirred solution of 50 mg (0.080 mmol) 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) in 3 mL of absolute methanol was added 0.022 mL (16 mg, 0.16 mmol, 2 eq) of triethylamine followed by 120 mg of powdered 3A molecular sieves. To this stirred mixture was added a solution of 0.012 mL (12 mg. 0.08 mmol, 1 eq) of benzyloxyacetaldehyde (prepared from 2,3-Q-isopropylideneglycerol by the method of Shiao, et al. Synth. Comm., 18, 359 (1988)) ion 2 mL dry methanol. The pH of the reaction mixture was adjusted to 7.5 (paper) by the addition of triethylamine and trifluoroacetic acid and was stirred for two hours. To this was added 0.48 mL of a 1M solution of sodium cyanoborohydride in tetrahydrofuran (0.48 mmol, 6 eq). The reaction mixture was stirred at room temperature for 24 hours then filtered and the filtrate treated with 2 mL of glacial acetic acid. After concentration under vacuum, the residue was purified by reverse phase HPLC on C-18, eluting with methanol/0.1% aqueous trifluoroacetic acid (linear gradient: 60% methanol increased to 80% methanol in 10 minutes) to afford 35 mg (0.046 mmol, 58%) of the title compound. $^1$ NMR (200 MHz, CD$_3$OD): 1.34 (s,3 H), 1.36 (s,3 H), 2.0–2.6 (m6 H), 3.20 (t,5 Hz,2 H), 3.70 (t,5 Hz,2 H) 4.38 (dd,7,11 Hz,1 H), 4.52 (s,2 H), 4.93 (d,15 Hz,1 H), 5.11 (d,15 Hz,1 H), 6.98 (d,8 Hz,2 H), 7.1–7.3 (m,11 H), 7.4–7.6 (m4 H). FAB- MS: calc. for $C_{38}H_{41}N_7O_3$ 643; found 644 (M+H,100%).

EXAMPLE 19

3-(2-hydroxyethyl)amino-3-methyl-N-[2,3,4,5-tetrahydro-2-oxo-1-[[2'-(1H-tetrazol-5yl)[1,1'-biphenyl]-4yl]-methyl]-1H-1-benzazepin-3(R)-yl]-butanamide, trifluoroacetate A solution of 12 mg (0.016 mmol) of 3-(2-benzyloxyethyl)amino-3-methyl-N-[2,3,4,5-tetrahydro-2-oxo-1-[[2'-(1Htetrazol-5-yl)[1,1'-biphenyl]-4-yl]-methyl]-1H-1-benzazepin-3(R)-yl]-butanamide trifluoroacetate (Example 18) in 12 mL of absolute methanol was hydrogenated at room temperature and 40 psi over 30% Pd/C for 24 hours. The mixture was filtered through Celite and the filtrate concentrated under vacuum. The residue was purified by reverse phase HPLC on C-18, eluting with methanol/0.1% aqueous trifluoroacetic acid (linear gradient: 60% methanol increased to 80% methanol in 10 minutes) to afford 6.3 mg (0.0094 mmol, 59%) of the title compound. $^1$H NMR (200 MHz, CD$_3$OD): 1.35 (s,3 H), 1.38 (s,3 H), 2.0–2.6 (m6 H), 3.09 (t,5 Hz,2 H), 3.73 (t,5 Hz,2 H), 4.33 (dd;7,11 Hz;1 H), 4.90 (d,15 Hz,1H), 5.13 (d,15 Hz,1H), 7.00 (d,8 Hz,2 H), 7.1–7.4 (m,6 H), 7.5–7.7 (m,4 H). FAB-MS: calculated for $C_{31}H_{35}N_7O_3$ 553; found 554 (M+H,100%).

EXAMPLE 20

3(2-Hydroxyethyl)amino-3-methyl-N-[2,3,4,5-tetrahydro-2-oxo-1-[[2'-[1-(2-hydroxyethyl)-tetrazol-5-yl][1,1'-biphenyl]-4-yl]methyl]-1H-1-benzazepin-3(R)-yl]-butanamide, mono(trifluoroacetate)

Step A:

3(2-Benzyloxyethyl)amino-3-methyl-N-[2,3,4,5-tetrahydro-2-oxo-1-[[2'-[1-(2-hydroxyethyl)-tetrazol-5-yl][1,1'-biphenyl]-4-yl]methyl]-1H-1-benzazepin-3(R)-yl]-butanamide, mono(trifluoroacetate) and 3-(2-Benzyloxyethyl)amino-3-methyl-N-[2,3,4,5-tetrahydro-2-oxo-1-[[2'-[2-(2-hydroxyethyl)-tetrazol-5-yl][1,1'-biphenyl]-4-yl]methyl]-1H-1-benzazepin-3(R)-yl]-butanamide, mono(trifluoroacetate)

To a solution of 40 mg (0.053 mmol) of 3(2-benzyloxyethyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide mono(trifluoroacetate) (Example 18) in 3 mL of methanol was added a catalytic amount of pyridinium p-toluenesulfonate. Ethylene oxide was bubbled through the solution for five minutes; the flask was capped tightly and the solution stirred at room temperature for 24 hours. All volatiles were removed under vacuum and the residue purified by reverse phase HPLC on C-18, eluting with methanol/0.1% aqueous trifluoroacetic acid (linear gradient; 60% methanol increased to 85% methanol in 10 minutes) to afford 18 mg (0.022 mmol, 43%) of the N$_1$ product followed by 6 mg (0.0075 mmol, 14%) of the N$_2$ product. $^1$H NMR (200 MHz, CD$_3$OD): 1.35 (s,3 H), 1.38 (s,3 H), 2.0–2.6 (n,6 H), 3.22 (t,5 Hz,2 H), 54 (m4 H), 3.71 (t,5 Hz,2 H), 4.37 (dd;7,11 Hz;1 H), 4.55 (s,2 H), 4.86 (d,15 Hz,1 H), 5.22 (d,15 Hz,1 H), 6.95 (d,8 Hz,2 H), 7.1–7.4 (m,11 H), 7.5–7.8 (m,4 H). FAB-MS: calc. for $C_{40}H_{45}N_7O_4$ 687; found 688 (M+H,100%).

Step B:

3-(2-Hydroxyethyl)amino-3-methyl-N-[2,3,4,5-tetrahydro-2-oxo-1-[[2'-[1-(2-hydroxyethyl)tetrazol-5-yl][1,1'-biphenyl]-4-yl]methyl]-1H-1-benzazepin-3(R)-yl]-butanamide, mono(trifluoroacetate)

A solution of 18 mg (0.022 mmol) of the N1 intermediate obtained in Step A in methanol was hydrogenated at room temperature and 40 psi over 30% Pd/C for 24 hours. The mixture was filtered and concentrated under vacuum. The residue was purified by reverse phase HPLC on C-18, eluting with methanol/0.1% aqueous trifluoroacetic acid (linear gradient: 55% methanol increased to 85% methanol in 10 minutes) to afford 12 mg (0.017 mmol, 75%) of the title compound. $^1$ NMR (200 MHz, CD$_3$OD): 1.35 (s,3 H), 1.38 (s,3 H), 2.0–2.6 (m,6 H), 3.09 (t,5 Hz,2 H), 3.56 (br, s, 4H), 3.73 (t,5 Hz,2 H), 4.32 (dd;8,12 Hz;1 H), 4.84 (d,15 Hz,1 H), 5.28 (d,15 Hz,1 H), 7.00 (d,8 Hz,2 H), 7.1–7.3 (m,6 H), 7.–7.7 (m,4 H). FAB-MS: calc. for $C_{33}H_{39}N_7O_4$ 597; found 598 (M+H,100%).

EXAMPLE 21

3-(2-Hydroxyethyl)amino-3-methyl-N-[2,3,4,5-tetrahydro-2-oxo-1-[[2'-[2-(2-hydroxyethyl)-tetrazol-5-yl][1,1'-biphenyl]-4-yl]methyl]-1H-1-benzazepin-3-(R)-yl]-butanamide, mono(trifluoroacetate)

Step A:

3-(2-Benzyloxyethyl)amino-3-methyl-N-[2,3,4,5-tetrahydro-2-oxo-1-[[2'-[2-(2-hydroxyethyl)-tetrazol-5-yl][1,1'-biphenyl]-4-yl]methyl]-1H-1-benzazepin-3(R)-yl]-butanamide, mono(trifluoroacetate)

Prepared from 3-(2-Benzyloxyethyl)amino-3-methyl-N-[2,3,4,5-tetrahydro-2-oxo-1-[[2'-[1H-tetrazol-5-yl][1,1'-biphenyl]-4-yl]methyl]-1H-1-benzazepin-3(R)-yl]-butanamide, mono(trifluoroacetate) Example 18) by the procedures described in Example 20, Step A. $^1$H NMR (200 MHz, CD$_3$OD): 1.32 (s,3 H), 1.36 (s,3 H), 2.0–2.7 (m,6 H), 3.19 (t,5 Hz,2 H), 3.66 (t,5 Hz,2 H), 3.88 (t,5 Hz,2 H), 4.40 (dd;8,12 Hz;1 H), 4.50 (s,2 H), 4.56 (t,5 Hz,2 H), 5.02 (br s,2 H), 6.99 (d,8 Hz,2 H), 7.1–7.6 (m,15 H). FAB-MS: calc. for $C_{40}H_{45}N_7O_4$ 687; found 688 (M+H,100%).

Step B:

3-(2-Hydroxyethyl)amino-3-methyl-N-[2,3,4,5-tetrahydro-2-oxo-1-[[2'-[2-(2-hydroxyethyl)tetrazol-5-yl][1,1'-biphenyl]-4-yl]methyl]-1H-1-benzazepin-3(R)-yl]-butanamide, mono(trifluoroacetate)

The title compound was prepared from the intermediate obtained in Step A by the procedure described in Example 20, Step B. $^1$H NMR (200 MHz, CD$_3$OD): 1.34 (s,3 H), 1.37 (s,3 H), 2.0–2.7 (m,6 H), 3.08 (t,5 Hz,2 H), 3.72 (t,5 Hz,2 H), 3.90 (t,5 hz,2 H), 4.35 (dd;8,12 Hz;1 H), 4.59 (t,5 Hz,2 H), 4.96 (d,15 Hz,1 H), 5.10 (d,15 Hz,1 H), 7.02 (d,8 Hz,2 H), 7.1–7.7 (m,10 H). FAB-MS: Calc. for $C_{33}H_{39}N_7O_4$ 597; found 598 (M+H,67%).

EXAMPLE 22

3-(2-Hydroxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, mono(trifluoroacetate)

Step A:

3-(2-Benzyloxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, mono(trifluoroacetate)

This intermediate was prepared as a mixture of diastereomers (at the carbinol carbon) from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) and (+/−) 2-benzyloxypropionaldehyde [prepared from 3-buten-2-ol by the method of Shiao, et al, Synth. Comm., 18, 359 (1988)] by the procedure described in Example 18, Step A. $^1$H NMR (200 MHz, CD$_3$OD): 1.24 (m,3 H), 1.34 (m6 H), 2.0–2.6 (m,6 H), 2.93 (dd,9,12 Hz;1 H), 3.16 (dd;3,12 Hz;1 H), 3.80 (m,1 H), 4.40 (m,2 H), 4.62 (m,2 H), 4.8–5.2 (m,2 H), 6.9–7.6 (m,17 H). FAB-MS: calc. for C$_{39}$H$_{43}$N$_7$O$_3$ 657; found 658 (M+H,100%).

Step B:

3(2-Hydroxypropyl)amino-3-methyl-N-[2,3,4,5-tetrahydro-2oxo-1-[[2'-(1H-tetrazol-5-yl)-[1,1'-biphenyl]-4-yl]methyl]-1H-1-benzazepin-3(R)-yl]-butanamide, mono(trifluoroacetate)

The title compound was prepared from the intermediate obtained in Step A by the procedure described in Example 19. $^1$H NMR (200 MHz, CD$_3$OD): 1.20 (d,7 Hz,3H), 1.35 (m,6 H), 2.0–2.7 (m,6 H), 2.75 (m,1 H), 3.07 (dd;3,12 Hz,1 H), 391 (m, 1 H),4.33 (dd;8,12 Hz;1 H), 4.9 (m,1 H), 5.2 (m,1 H), 7.02 (d,8 Hz,2 H), 6.9–7.6 (m,12 H), FAB-MS: calc. for C$_{32}$H$_{37}$N$_{73}$ 567; found 568 (M+H,100%).

EXAMPLE 23

3-Amino-3-methyl-N-[2,3,4,5-tetrahydro-2-oxo-1-[[2'-[1-(2-hydroxyethyl)-tetrazol-5-yl][1,1'-biphenyl]-4-yl]methyl]-1H-1-benzazepin-3(R)-yl]-butanamide, mono(trifluoroacetate)

Step A:

3-Amino-3-methyl-N-[2,3,4,5-tetrahydro-2-oxo-1-[[2'-[1(2-hydroxyethyl)-tetrazol-5-yl]-[1,1'-biphenyl]-4-yl]methyl]-1H-1-benzazepin-3(R)-yl]-butanamide, mono(trifluoroacetate)

To a solution of 54 mg (0.099 mmol) of 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide mono(trifluoroacetate) (Example 1) in 2 mL of methylene chloride was added a catalytic amount of pyridinium p-toluenesulfonate. Ethylene oxide was bubbled through the solution for five minutes; the flask was capped tightly and the solution stirred at room temperature for 24 hours. All volatiles were removed under vacuum and the residue purified by reverse phase HPLC on C-18, eluting with methanol/0.1% aqueous trifluoroacetic acid (linear gradient: 60% methanol increased to 80% methanol in 10 minutes) to afford 37 mg (0.055 mmol, 56%) of the title compound followed by 15 mg (0.022 mmol, 22%) of the N2 product. $^1$H NMR (200 MHz, CD$_3$OD): 1.32 (s,3 H), 1.36 (s,3 H), 2.0–2.6 (m,6 H), 3.55 (m,4 H), 4.33 (dd;7,11 Hz;1 H), 4.79 (d,14 Hz,1 H), 5.31 (d,14 Hz,1 H), 6.99 (d,8 Hz,2 H), 7.1–7.3 (m,6 H), 7.5–7.8 (m,4 H). FAB-MS: calc. for C$_{31}$H$_{35}$N$_7$O$_3$ 553; found 554 (M+H,100%).

EXAMPLE 24

3-Amino-3-methyl-N-[2,3,4,5-tetrahydro-2-oxo-1-[[2'-[2-(2-hydroxyethyl)-tetrazol-5-yl][1,1'-biphenyl]-4-yl]methyl]-1H-1-benzazepin-3(R)-yl]-butanamide, mono(trifluoroacetate)

The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide mono(trifluoroacetate) (Example 1) by the procedure described in Example 23. $^1$H NMR (200 MHz, CD$_3$OD): 1.33 (s,3 H), 1.36 (s,3 H), 2.0–2.6 (m,6 H), 3.90 (t,5 Hz,2 H), 4.37 (dd;8,12 Hz;1 H), 4.60 (d,5 Hz,2 H), 4.91 (d,15 Hz,1 H), 5.17 (d,15 Hz,1 H), 7.01 (d,8 Hz,2 H), 7.1–7.6 (m,9 H), 7.75 (d,7 Hz,2 H). FAB-MS: calc. for C$_{31}$H$_{35}$N$_7$O$_3$ 553; found 554 (M+H,100%).

EXAMPLE 25

2-Amino-N-[2,3,4,5-tetrahydro-2-oxo-1-[[2'-(1H-tetrazol-5-yl)[1,1'-biphenyl]-4-yl]methyl]-1H-1-benzazepin-3-yl]-acetamide, hydrochloride

Step A:

3-t-Butoxycarbonylamino-N-[2,3,4,5-tetrahydro-2-oxo-1H-1-benzazepin-3-yl]-acetamide To a solution of 169 mg (0.965 mmol) of N-(t-butoxycarbonyl) glycine in 2 mL of methylene chloride at room temperature was added 222 mg (1.158 mmol, 1.2 eq) of 1-(3-dimethylaminopropyl)-3-ethylcarbodiimide hydrochloride, 11 mg (0.09 mmol, 0.1 eq) of 4-dimethylaminopyridine and 170 mg (0.97 mmol, 1 eq) of 3-amino-2,3,4,5-tetrahydro-1H-[1]benzazepin-2-one (Example 1, Step A). The reaction was stirred at room temperature for 3 hours. The reaction was then quenched by the addition of 5 mL of 1M aqueous hydrochloric acid, and the aqueous phase extracted with methylene chloride (2×5 mL). The combined organic phases were dried over magnesium sulfate, filtered and the solvent removed under vacuum. The residue was purified by flash chromatography on silica gel, eluting with ethyl acetate, to afford 218 mg (0.65 mmol, 68%) of the product. $^1$H NMR (200 MHZ, CDCl$_3$): 1.43 (s,9 H), 1.96 (m,1 H), 2.83 (m,3 H), 3.81 (dq;2,8 Hz;2 H), 4.54 (m,1 H), 5.21 (t,3 Hz,1 H), 7.15 (m,4 H), 7.84 (br s,1 H). FAB-MS: calculated for C$_{17}$H$_{23}$N$_3$O$_4$ 333; found 334 (M+H,43%).

Step B:

2-t-Butoxycarbonylamino-N-[2,3,4,5-tetrahydro-2-oxo-1-[[2'-[N-(triphenylmethyl)tetrazol-5-yl][1,1'-biphenyl]-4-yl]methyl]-1H-1-benzazepin-3-yl]-acetamide Prepared from the intermediate obtained in Step A and N-triphenylmethyl-5-[2-(4'-bromomethylbiphen-4-yl)] tetrazole by the procedure described in Example 1, Step K. ¹H NMR (200 MHz, CDCl₃): 1.26 (s,9 H), 1.82 (m,1 H), 2.48 (m,3 H), 3.80 (dq;3,9 Hz;2 H), 4.50 (m,1 H), 4.72 (d,7 Hz,1 H), 5.10 (d,7 Hz,1 H), 6.9–7.6 (m,26 H), 7.96 (m,1 H).

Step C:
2-t-Butoxycarbonylamino-N-[2,3,4,5-tetrahydro-2-oxo-1-[[2′-(1H-tetrazol-5-yl)[1,1′-biphenyl]-4-yl]methyl]-1H-1-benzazepin-3-yl]acetamide 323 mg (0.43 mmol) of the intermediate obtained in Step B was dissolved in 1 mL of glacial acetic acid and 1 mL of water was added dropwise with stirring. The reaction mixture was stirred at room temperature for 16 hours then solvents were removed under vacuum and the residue purified by flash chromatography on a silica gel column, eluting with ethyl acetate to afford 109 mg (0.196 mmol, 46%) of the product. ¹H NMR (200 MHz, CDCl₃): 1.38 (s,9 H), 1.97 (m,1 H), 2.55 (m,3 H), 3.65 (m,2 H), 4.50 (m,1 H), 4.85 (d,15 Hz,1 H), 5.05 (d,16 Hz,1 H), 5.51 (br s,1 H) 6.95–7.95 (m,11 H), 7.83 (d,3 Hz,1 H).

Step D:
2-Amino-N-[2,3,4,5-tetrahydro-2-oxo-1-[[2′-(1H-tetrazol-5-yl)[1,1′-biphenyl]-4-yl]methyl]-1H-1-benzazepin-3-yl]-acetamide, hydrochloride The intermediate obtained in Step C (109 mg, 0.196 mmol) was dissolved in 2 mL of methanol and treated with 0.1 mL of concentrated hydrochloric acid. The reaction mixture was stirred at room temperature for 16 hours then solvents were removed under vacuum and the residue redissolved in water and washed with ethyl acetate. The aqueous layer was separated and the solvent removed under vacuum to yield 87 mg (0.17 mmol, 88%) of the title compound. ¹H NMR (200 MHz, CD₃OD): 2.10 (m, 1 H), 2.48 (m, 3 H), 3.68 (s,2 H), 4.37 (m,1 H), 4.84 (d,14 Hz,1 H), 5.22 (d,14 Hz,1 H), 6.9–7.7 (m,12 H). FAB-MS: calculated for C₂₆H₂₅N₇O₂ 467; found 468 (M+H,100%).

EXAMPLE 26

4-Amino-N-[2,3,4,5-tetrahydro-2-oxo-1-[[2′-(1H-tetrazol-5-yl)[1,1′-biphenyl]-4-yl]methyl]-1H-1-benzazepin-3yl]-butanamide, hydrochloride Step A:
4-t-Butoxycarbonylamino-N-[2,3,4,5-tetrahydro-2-oxo-1H-1-benzazepin-3-yl]-butanamide Prepared from 3-amino-2,3,4,5-tetrahydro-1H-[1]benzazepin-2-one (Example 1, Step A) and 4-(t-butoxycarbonylamino)butyric acid by the procedure described in Example 25, Step A. ¹H NMR (200 MHz, CDCl₃); 1.42 (s,9 H), 1.7–2.1 (m,3 H), 2.24 (t,5 Hz,2 H), 2.58–3.29 (m,5 H), 4.57 (m,1 H), 4.86 (br s,1 H), 7.0–7.3 (m,4 H), 8.32 (s,1 H), FAB-MS: calculated for C₁₉H₂₇N₃O₄ 361; found 362 (M+H,60%).

Step B
4-t-Butoxycarbonylamino-N-[2,3,4,5-tetrahydro-2-oxo-1-[[2′-[N-(triphenylmethyl)tetrazol-5-yl][1,1′-biphenyl]-4-yl]methyl]-1H-1-benzazepin-3-yl]-butanamide Prepared from the intermediate obtained in Step A and N-triphenylmethyl-5-[2(4′-bromomethylbiphen-4-yl)] tetrazole by the procedure described in Example 1, Step K. ¹H NMR (200 MHz, CDCl₃): 1.42 (s,9 H), 1.78 (m,3 H), 2.20 (t,5 Hz,2 H), 2.2–2.7 (m,2 H), 3.13 (m,2 H), 4.46 (m,1 H), 4.70 (d,14 Hz,1 H), 5.10 (d,14 Hz,1 H), 6.64 (d,7 Hz,1 H), 6.8–7.5 (m,26 H), 7.85 (m,1 H).

Step C:
4-t-Butoxycarbonylamino-N-]2,3,4,5-tetrahydro-2-oxo-1-[[2′-(1H-tetrazol-5-yl)[1,1′-biphenyl]-4-yl]methyl]-1H-1-benzazepin-3-yl]butanamide The intermediate obtained in Step B (349 mg, 0.40 mmol) was dissolved in 5 mL of methanol and hydrogenated to room temperature and one atmosphere over 70 mg of 20% Pd(OH)₂/C for 16 hours. The reaction mixture was filtered through Celite and solvent removed under vacuum. The crude product was purified by flash chromatography on silica, eluting with 10% methanol/ethyl acetate to afford 168 mg (0.28 mmol, 71%) of product. ¹H NMR (200 MHz, CD₃OD): 1.41 (s,9 H), 1.72 (m,2 H), 2.0–2.6 (m,6 H), 3.24 (t,7 Hz,2 H), 4.32 (m,1 H), 4.85 (d,14 Hz,1 H), 5.20 (d,14 Hz,1 H), 6.9–7.7 (m,12 H).

Step D:
4-Amino-N-[2,3,4,5-tetrahydro-2-oxo-1-[[2′-(1H-tetrazol-5-yl)[1,1′-biphenyl]-4-yl]methyl]-1H-1-benzazepin-3-yl]-butanamide, hydrochloride The title compound was prepared from the intermediate obtained in Step C by the procedure described in Example 25, Step D. ¹H NMR (200 MHz, CD₃OD): 1.8–2.6 (m, H), 2.96 (t,6 Hz,2 H), 4.30 (m,1 H), 4.88 (d,15 Hz,1 H), 5.25 (d,15 Hz,1 H), 6.9–7.4 (m,8 H), 7.5–7.7 (m,4 H). FAB-MS: calculated for C₂₈H₂₉N₇O₂ 495; found 496 (M+H,100%).

EXAMPLE 27

2-Amino-2-methyl-N-[2,3,4,5-tetrahydro-2-oxo-1-[[2′-(1H-tetrazol-5yl)[1,1′-biphenyl]-4-yl]methyl]-1H-1-benzazepin-3-yl]-propanamide, hydrochloride Step A:
2-(t-Butoxycarbonylamino)-2-methyl-N-[2,3,4,5-5-tetrahydro-2-oxo-2H-1-benzazepin-3-yl]propanamide Prepared from 2-(t-butoxycarbonylamino)-2-methylpropanoic acid and 3-amino-2,3,4,5-tetrahydro-1H-[1]benzazepin-2-one (Example 1, Step A) by the procedure described in Example 25, Step A. ¹H NMR (200 MHz, CDCl₃): 1.38 (s,12 H), 144 (s,3 H), 1.90 (m,1 H), 2.5–3.0 (m,3 H), 4.45 (m,1 H), 5.10 (s,1 H), 6.97 (m,1 H), 7.20 (m,3 H), 8.45 (s,1 H).

Step B:
2-(t-Butoxycarbonylamino)-2-methyl-N-[2,3,4,5-tetrahydro-2-oxo-1-[[2′-(N-(triphenylmethyl)-tetrazol-5-yl][1,1′-biphenyl]-4-yl]methyl]-1H-1-benzazepin-3-yl]-propanamide Prepared from the intermediate obtained in Step A and N-triphenylmethyl-5-[2-(4′-bromomethylbiphen-4-yl)] Tetrazole by the procedure described in Example 1, Step K. ¹H NMR (200 MHz, CDCl₃): 1.42 (s,9 H), 1.43 (s,3 H), 1.47 (s,3 H), 1.75 (m,1 H), 2.2–2.7 (m,3 H), 4.45 (m,1 H), 4.71 (d,14 Hz,1 H), 5.10 (d,14 Hz,1 H), 6.9–7.5 (m,26 H), 7.87 (m,1 H).

Step C:
2-(t-butoxycarbonylamino)-2-methyl-N-[2,3,4,5-tetrahydro-2-oxo-1-[[2'-(1H-tetrazol-5-yl)-[1,1'-biphenyl]-4-yl]methyl]-1H-1-benzazepin-3-yl]-propanamide Prepared from the intermediate obtained in Step B by the procedure described in Example 26, Step C. $^1$H NMR (200 MHz, CD$_3$OD): 1.34 (s,6 H), 1.40 (S,9 H), 1.95 (m,1 H), 2.44 (m,3 H), 4.30 (m,1 H), 4.77 (d,14 Hz,1 H), 5.26 (d,14 Hz,1 H), 6.9–7.7 (m,12 H). FAB-MS: calculated for C$_{33}$H$_{37}$N$_7$O$_4$ 595; found 596 (M+H,40%).

Step D:
2-Amino-2-methyl-N-[2,3,4,5-tetrahydro-2-oxo-1-[[2'-(1H-tetrazol-5-yl)[1,1'-biphenyl]-4-yl]methyl]-1H-1-benzazepin-3-yl]-propanamide, hydrochloride The title compound was prepared from the intermediate obtained in Step C by the procedure described in Example 25, Step D. $^1$H-NMR (200 MHz, CD$_3$OD): 1.50 (s,3 H), 1.62 (s,3 H), 2.2–2.7 (m,4 H), 4.32 (m,1 H), 4.85 (d,14 Hz,1 H), 5.17 (d,14 Hz,1 H), 6.9–7.7 (m,12 H). FAB-MS: calculated for C$_{28}$H$_{29}$N$_7$O$_2$ 495; found 496 (M+H,100%).

EXAMPLE 28

6-Amino-N-[2,3,4,5-tetrahydro-2-oxo-1-[[2'-(1H-tetrazol-5-yl)[1,1'-biphenyl]-4-yl]methyl]-1H-1-benzazepin-3-yl]-hexanamide, hydrochloride

Step A:
6-t-Butoxycarbonylamino-N-[2,3,4,5-tetrahydro-2-oxo-1H-1-benzazepin-3-yl]-hexanamide Prepared from 6-(t-butoxycarbonylamino)hexanoic acid and 3-amino-2,3,4,5-tetrahydro-1H-[1]benzazepin-2-one (Example 1, Step A) by the procedure described in Example 25, Step A. $^1$H NMR (200 MHz, CDCl$_3$): 1.2–1.7 (m,14 H), 1.92 (m,2 H), 2.16 (t,5 Hz,1 H), 2.5–3.1 (m,6 H), 4.53 (m,2 H), 6.54 (d,7 Hz,1 H), 6.96 (m,1 H), 7.18 (m,3 H), 8.00 (s,1 H). FAB-MS: calculated for C$_{21}$H$_{31}$N$_3$O$_4$ 389; found 390 (M+H,18%).

Step B:
2-t-Butoxycarbonylamino-N-[2,3,4,5-tetrahydro-2-oxo-1-[[2'-[N-(triphenylmethyl)tetrazol-5-yl][1,1'-biphenyl]-4-yl]methyl]-1H-1-benzazepin-3-yl]-hexanamide Prepared from the intermediate obtained in Step A and N-triphenylmethyl-5-[2-(4'-bromomethylbiphen-4-yl)] tetrazole by the procedure described in Example 1, Step K. $^1$H NMR (200 MHz, CDCl$_3$): 1.1–1.9 (m,16 H), 2.15 (t,5 Hz,2 H), 2.2–2.7 (m,3 H), 3.07 (q,6 Hz,2 H), 4.49 (m,2 H), 4.70 (d,14 Hz,1 H), 5.11 (d,14 Hz,1 H), 6.49 (d,8 Hz,1 H), 6.8–7.5 (m,26 H), 7.86 (m,1 H).

Step C:
2-t-Butoxycarbonylamino-N-[2,3,4,5-tetrahydro-2-oxo-1-[[2'-(1H-tetrazol-5-yl)[1,1'-biphenyl]-4-yl]methyl]-1H-1-benzazepin-3-yl]hexanamide Prepared from the intermediate obtained in Step B by the procedure described in Example 26, Step C. $^1$H NMR (200 MHz, CD$_3$OD): 1.1–1.7 (m,16 H), 2.2–2.6 (m,5 H), 2.98 (t,2 H), 4.32 (m,1 H), 4.81 (d,16 Hz,1 H), 5.22 (d,16 Hz,1 H), 6.95 (m,2 H), 7.23 (m,6 H), 7.52 (m,4 H). FAB-MS: calculated for C$_{35}$H$_{41}$N$_7$O$_4$ 623; found 646 (M+Na,45%).

Step D:
2-Amino-N-[2,3,4,5-tetrahydro-2-oxo-1-[[2'-(1H-tetrazol-5-yl)[1,1'-biphenyl]-4-yl]methyl]-1H-1-benzazepin-3-yl]-hexanamide, hydrochloride The title compound was prepared from the intermediate obtained in Step C by the procedure described in Example 25, Step D. $^1$H NMR (200 MHz, CD$_3$OD): 1.88 (m,2H), 1.63 (m,4 H), 2.0–2.7 (m,6 H), 290 (br s,2 H), 4.31 (m,1 H), 4.86 (d,14 Hz,1 H), 5.17 (d,14 Hz,1 H), 6.98 (d,8 Hz,2 H), 7.22 (m, 6 H), 7.56 (m,4 H). FAB-MS: calculated for C$_{30}$H$_{33}$N$_7$O$_2$ 523; found 524 (M+H,100%).

EXAMPLE 29

1-Amino-N-[2,3,4,5-tetrahydro-2-oxo-1-[[2'-(1H-tetrazol-5-yl)[1,1'biphenyl]-4-yl]methyl]-1H-1-benzazepin-3-yl]-cyclohexanecarboxamide, hydrochloride

Step A:
1-t-Butoxycarbonylamino-N-[2,3,4,5-tetrahydro-2-oxo-1H-1-benzazepin-3-yl]-cyclohexanecarboxamide Prepared from 1(t-butoxycarbonylamino)cyclohexanecarboxylic acid and 3-amino-2,3,4,5-tetrahydro-1H-[1]benzazepin-2-one (Example 1, Step A) by the procedure described in Example 25, Step A. $^1$H NMR (200 MHz, CDCl$_3$): 1.1–2.2 (m,19 H), 2.00 (m,2 H), 2.50 (m,2 H), 4.55 (m,1 H), 6.9–7.2 (m,4 H). FAB-MS: calculated for C$_{22}$H$_{31}$N$_3$O$_4$ 401; found 402 (M+H,40%).

Step B:
1-t-Butoxycarbonylamino-N-[2,3,4,5-tetrahydro-2-oxo-1-[[2'-[N-(triphenylmethyl)tetrazol-5-yl][1,1'-biphenyl]-4-yl]methyl]-1H-1-benzazepin-3-yl]-cyclohexanecarboxamide Prepared from the intermediate obtained in Step A and N-triphenylmethyl-5-[2-(4'-bromomethylbiphen-4-yl)] tetrazole by the procedure described in Example 1, Step K. $^1$H NMR (200 MHz, CDCl$_3$): 1.1–2.1 (m,19 H), 2.20 (m,4 H), 4.45 (m,1 H), 4.67 (s,1 H), 4.72 (d,13 Hz,1 H), 5.06 (d,13 Hz,1 H), 6.8–7.5 (m,26 H), 7.86 (m,1 H).

Step C:
1-t-Butoxycarbonylamino-N-[2,3,4,5-tetrahydro-2-oxo-1-[[2'-(1H-tetrazol-5-yl)[1,1'-biphenyl]-4-yl]methyl]-1H-1-benzazepin-3-yl]cyclohexanecarboxamide Prepared from the intermediate obtained in Step B by the procedure described in Example 26, Step C. $^1$H NMR (200 MHz, CD$_3$OD): 1.2–1.9 (m,19 H), 2.20 (br s,2 H), 2.53 (m,3 H), 4.40 (m,1 H), 4.86 (d,14 Hz,1 H), 5.34 (d,14 Hz,1 H), 6.81 (br s,1 H), 7.0–7.5 (m,8 H), 7.60 (m,4 H). FAB-MS: calculated for C$_{36}$H$_{41}$N$_7$O$_4$ 635; found 636 (M+H,20%).

Step D:
1-Amino-N-[2,3,4,5-tetrahydro-2-oxo-1-[[2'-(1H-tetrazol-5-yl)[1,1'-biphenyl]-4-yl]methyl]-1H-1-benzazepin-3-yl]-cyclohexanecarboxamide, hydrochloride The title compound was prepared from the intermediate obtained in Step C by the procedure described in Example 25, Step D. $^1$H NMR (200 MHz, CD$_3$OD): 1.6–2.4 (m,8 H), 2.28 (m,4 H), 2.62 (m,2 H), 4.42 (m,1

H), 4.96 (d,15 Hz,1 H), 5.26 (d,15 Hz,1 H), 7.0-7.5 (m,8 H), 7.64 (m,4 H). FAB-MS: calculated for C₃₁H₃₃N₇O₂ 535; found 536 (M+H,100%).

EXAMPLE 30

2(S),6-Diamino-N-[2,3,4,5-tetrahydro-2-oxo-1-[[2'-(1H-tetrazol-5-yl)[1,1'-biphenyl]-4-yl]methyl]-1H-1-benzazepin-3-yl]-hexanamide, dihydrochloride Step A:
2(S),6-Di-(t-butoxycarbonylamino)-N-[2,3,4,5-tetrahydro-2-oxo-1H-1-benzazepin-3-yl]-hexanamide Prepared from N$_a$, N$_e$-di(t-butoxycarbonyl)L-lysine and 3-amino-2,3,4,5-tetrahydro-1H-[1]benzazepin-2-one (Example 1, Step A) by the procedure described in Example 25, Step A. ¹H NMR (200 MHz, CDCl₃): 1.2-2.1 (m,24 H), 2.6-3.3 (m,6 H), 4.20 (m,1 H), 4.62 (m,2H), 5.26 (m,1H), 7.0-7.4 (m,4 H). FAB-MS: calculated for C₂₆H₄₀N₄O₆ 504; found 505 (M+H,20%).

Step B:
2(S),6-Di-(t-butoxycarbonylamino)-N-[2,3,4,5-tetrahydro-2-oxo-1-[[2'-[N-(triphenylmethyl)tetrazol-5-yl][1,1'-biphenyl]-4yl]methyl]-1H-1-benzazepin-3-yl]-hexanamide Prepared from the intermediate obtained in Step A and N-triphenylmethyl-5-[2-(4'-bromomethylbiphen-4-yl)] tetrazole by the procedure described in Example 1, Step K. ¹H NMR (200 MHz, CDCl₃): 1.42 (s,18 H), 1.60 (m,2 H), 1.79 (m,2 H), 2.42 (m,4 H), 3.10 (m,4 H), 4.09 (m,1 H), 4.42 (m,1 H), 4.60 (d,13 Hz,1 H), 5.17 (d,13 Hz,1 H), 6.8-7.5 (m,26 H), 7.85 (m,1 H).

Step C:
2(S),6-Di-(t-butoxycarbonylamino-N-[2,3,4,5-tetrahydro-2-oxo-1-[[2'-(1H-tetrazol-5-yl)-[1,1'-biphenyl]-4-yl]methyl]-1H-1-benzazepin-3-yl]-hexanamide Prepared from the intermediate obtained in Step B by the procedure described in Example 26, Step C. ¹H NMR (200 MHz, CD₃OD): 1.0-1.8 (m,20 H), 2.00 (m,2 H), 3.00 (m,2 H), 3.96 (m,1 H), 4.32 (m,1 H), 4.76 (d,13 Hz,1 H), 5.26 (d,13 Hz,1 H), 6.9-7.4 (m,8 H), 7.4-7.6 (m,4 H). FAB-MS: calculated for C₄₀H₅₀N₈O₆ 738; found 739 (M+H,10%).

Step D:
2(S),6-diamino-N-[2,3,4,5-tetrahydro-2-oxo-1-[[2'-(1 H-tetrazol-5-yl)[1,1'-biphenyl]-4-yl]methyl]-1H-1-benzazepin-3-yl]-hexanamide, dihydrochloride The title compound was prepared from the intermediate obtained in Step C by the procedure described in Example 25, Step D. ¹H NMR (200 MHz, CD₃OD): 1.3-2.0 (m,6 H), 2.0-2.7 (m,4 H), 2.95 (m,2 H), 3.95 (m,1 H), 4.37 (m,1 H), 4.89 (d,15 Hz,1 H), 5.19 (dd;4,15 Hz,1 H), 6.9-7.4 (m,8 H), 7.5-7.7 (m,4 H). FAB-MS: calculated for C₃₀H₃₄N₈O₂ 538; found 539 (M+H,100%).

EXAMPLE 31

3-amino-3-methyl-N-[7-fluoro-2,3,4,5-tetrahydro-2-oxo-1-[[2'-(1H-tetrazol-5-yl)[1,1'-biphenyl]-4-yl]methyl]-1H-1-benzazepin-3-yl]-butanamide, trifluoroacetate Step A:
7-fluoro-2,3,4,5-tetrahydro-1H-1-benzazepin-2-one Sodium azide 1.1 g (16.92 mmol) was added to a mixture of 6.0 mL of chloroform and 1.1 mL of water at 0° C. Concentrated sulfuric acid (0.44 mL) was added dropwise and the mixture stirred at 0° C. for two hours then filtered. The chloroform layer containing hydrazoic acid was added to a solution of 1.3 g (7.92 mmol) of 6-fluoro-1-tetralone (prepared by the method of Allinger and Jones, J. Org. Chem., 27, 70–76 (1962)) in 4.8 mL of chloroform. Additional sulfuric acid (2.16 mL) was added dropwise with stirring while maintaining the temperature below 40° C. The mixture was stirred at 40° C. for two hours then at room temperature for 16 hours. The mixture was transferred to a separatory funnel and the layers were separated. The aqueous layer was added to ice; the resulting recipitate was extracted with methylene chloride (5x). The combined extracts were washed with brine, dried over magnesium sulfate and filtered through a silica plug. Solvents were removed under vacuum to afford 162 mg (0.92 mmol, 11%) of the product. ¹H NMR (300MHz, CDCl₃): 2.21 (m,2H), 2.32 (t,7Hz,2H), 2.7 (t,7Hz,2H), 6.93 (m,3H), 7.8 (br s,1H). FAB-MS: calculated for C₁₀H₁₀FNO 179; found 180 (M+H,100%).

Step B:
3-iodo-7-fluoro-2,3,4,5-tetrahydro-1H-1-benzazepin-2-one 7-fluoro-2,3,4,5-tetrahydro-1H-1-benzazepin-2-one (411 mg, 2.3 mmol) (Step A) dissolved in a mixture of 7.9 mL of dry methylene chloride and 1.0 mL of dry tetrahydrofuran was treated with 1.62 mL (1.18 g, 11.6 mmol, 5 eq) of triethylamine and the resulting solution cooled to −15° C. Iodotrimethylsilane (0.66 mL, 932 mg, 4.7 mmol, 2 eq) was added followed by 1.183 g of iodine (4.7 mmol, 2 eq) added in small portions over 5 minutes. The mixture was warmed to room temperature over 5 minutes at which time 15 mL of methylene chloride was added followed by 20 mL of 10% aqueous sodium sulfite. The layers were separated and the organic layer washed with 10% sodium sulfite (3×20 mL). The aqueous layer was further extracted with 20 mL of methylene chloride. The combined extracts were washed with brine, dried over magnesium sulfate, filtered and concentrated to dryness under vacuum. The crude product was chromatographed on silica gel, eluting with methylene chloride/methanol (99:1) to afford 511 mg (1.68 mmol, 73%) of the product. ¹H NMR (300MHz, CDCl₃): 2.70 (m,3H), 2.93 (m,1H), 4.62 (t,9Hz,1H), 6.95 (m,3H), 7.86 (br s,1H). FAB-MS: calculated for C₁₀H₉FINO 305; found 306 (M+H,100%).

Step C:
3-Azido-7-fluoro-2,3,4,5-tetrahydro-1H-1-benzazepin-2-one 101 mg (0.33 mmol) of 3-iodo-7-fluoro-2,3,4,5-tetrahydro-1H-1-benzazepin-2-one (Step B) was dissolved in 8.3 mL of methylene chloride and 105 mg (0.66 mmol, 2 eq) of tetramethylguanidinium azide was added. The mixture was stirred at room temperature for 16 hours then water was added and the layers allowed to separate. The organic layer was removed, washed with water and brine, then dried over magnesium sulfate, filtered and solvents removed under vacuum to afford 66 mg (0.30 mmol, 90%) of the product. ¹H NMR (200MHz, CDCl$_3$): 2.28 (m,1H), 2.45 (m,1H), 2.73 (m,1H), 2.93 (m,1H), 3.86 (dd;8,11 Hz;1H), 7.0 (m,3H), 8.15 (br s,1H). FAB-MS: calculated for C$_{10}$H$_9$FN$_4$O 220: found 221 (M+H,100%).

Step D:
3-Amino-7-fluoro-2,3,4,5-tetrahydro-1H-1-benzazepin-2-one

3-Azido-7-fluoro-2,3,4,5-tetrahydro-1H-1-benzazepin-2-one (3.36 g, 15.3 mmol) (Step C) dissolved in dry tetrahydrofuran was treated with 4.00 g (15.3 mmol; 1eq) of triphenylphosphine and the resulting solution stirred at room temperature under nitrogen for 2 hours. Water (0.48 mL, 2eq) was added and the mixtured stirred at room temperature for 16 hours. Solvents were removed under vacuum and the residue purified by preparative HPLC on silica, eluting with methylene chloride/methanol (9:1) to afford 2.39 g (12.3 mmol, 81%) of product. $^1$H NMR (200MHz, CD$_3$OD): 1.87 (m,1H), 2.41 (m,1H), 2.6–2.9 (m,2H), 3.30 (dd;8,12 Hz;1H), 7.0 (m,3H). FAB-MS: calculated for C$_{10}$H$_{11}$FN$_2$O 194; found 195 (M+H,100%).

Step E: 3-t-Butoxycarbonylamino3-methylbutanoic acid

A solution of 4.65 g (17.5 mmol) of methyl 3-benzyloxycarbonylamino-3-methylbutanoate (Example 1, Step D) in 100 mL absolute methanol at room temperature was treated with 3 mL concentrated hydrochlorid acid and hydrogenated at one atmosphere over 0.92 g of 20% Pd(OH)$_2$/C. After 16 hours, an additional 0.4 g of catalyst was added and hydrogenation continued for 8 hours. The catalyst was removed by filtration through Celite and the filtrate concentrated under vacuum. The residue was redissolved in 50 mL methylene chloride and treated with 6.0 mL (5.7 g, 26 mol, 1.5 eq) di-t-butyldicarbonate followed by 7.3 mL triethylamine (5.3 g, 52 mmol, 3 eq). The mixture was stirred at room temperature for 14 hours then diluted into 300 mL of hexane/ethyl acetate (1:1) and washed with water (2x), saturated aqueous sodium bicarbonate and brine. The organic layer was removed, dried over magnesium sulfate, filtered and the solvents removed under vacuum. Purification by preparative HPLC on silica, eluting with hexane/ethyl acetate (6:1), afforded 3.40 g (14.7 mmol, 84%) of the intermediate BOC-methyl ester as a colorless liquid.

This intermediate (3.40 g, 14.7 mmol) in 5 mL methanol at room temperature was treated with 11 mL of 2.0N NaOH (22 mmol, 1.5 eq) and the resulting mixture stirred at room temperature for 24 hours. The mixture was diluted with 15 mL water and washed with hexane. The aqueous layer was removed, cooled to 0°, and acidified by dropwise addition of saturated aqueous potassium hydrogen sulfate to a pH of 2-3. The mixture was extracted with ether (6×25 mL); the combined extracts washed with brine, dried over magnesium sulfate, filtered and solvents removed under vacuum. The residue solidified upon standing to afford 3.11 g (14.3 mmol, 97%) of the product. $^1$H NMR (200MHz, CDCl$_3$): 1.39 (s,6H), 1.44 (s,9H), 2.72 (s,2H). FAB-MS: calculated for C$_{10}$H$_{19}$NO$_4$ 217; found 218 (M+H,54%).

Step F:
3-t-Butoxycarbonylamino-3-methyl-N-[7-fluoro-2,3,4,5-tetrahydro-2-oxo-1H-1-benzazepin -3-yl]-butanamide Prepared from 3-t-butoxycarbonylamino-3-methylbutanoic acid (Step E) and the amine obtained in Step D by the procedure described in Example 1, Step F. $^1$H NMR (200MHz, CDCl$_3$): 1.33 (s,6H), 1.40 (s,9H), 1.90 (m,1H), 2.45 (d,15Hz,1H), 2.56 (d,15Hz, 1H), 2.60 (m,1H), 2.73 (m,1H), 2.91 (m,1H), 4.50 (m,1H), 5.16 (br s,1H), 6.66 (d,7Hz,1H), 6.94 (m,3H), 7.51 (br s,1H). FAB-MS: calculated for C$_{20}$H$_{28}$FN$_3$O$_4$ 393; found 394 (M+H,42%).

Step G:
3-t-Butoxycarbonylamino-3-methyl-N-[7-fluoro-2,3,4,5-tetrahydro-2-oxo-1-[[2'-(N-triphenylmethyl)-tetrazol-5-yl][1,1'-biphenyl]-4-yl]-methyl-1H-1-benzazepin-3-yl]-butanamide Prepared from the intermediate obtained in Step F and N-triphenylmethyl-5-[2-(4'-bromomethylbiphen-4-yl)] tetrazole by the procedure described in Example 1, Step K. $^1$H NMR (200MHz, CDCl$_3$): 1.34 (s,6H), 1.40 (s,9H), 1.74 (m,1H), 2.2–2.6 (m,3H), 2.43 (d,15Hz,1H), 2.53 (d,15Hz,1H), 4.43 (m,1H), 4.61 (d,14Hz,1H), 5.12 (d,14Hz,1H), 5.28 (br s,1H), 6.6–6.9 (m,3H), 6.9–7.5 (m,22H), 7.84 (m,1H).

Step H:
3-Amino-3-methyl-N-[7-fluoro-2,3,4,5-tetrahydro-3-oxo-1-[[2'-(1H-tetrazol -5-yl)[1,1'-biphenyl]-4-yl]methyl]-1H-1-benzazepin-3-yl]-butanamide, trifluoroacetate The intermediate obtained in Step G (360 mg, 0.41 mmol) was dissolved in 1 mL of methanol and treated dropwise with 1 mL of 9N HCl. The mixture was stirred at room temperature for 16 hours then all volatiles were removed under vacuum and the residue purified by reverse phase HPLC on C-18, eluting with methanol/0.1% aqueous trifluoroacetic acid (linear gradient; 60% methanol increased to 80% over 10 minutes) to afford 222 mg (0.35 mmol, 84%) of the title compound. $^1$H NMR (300MHz, CD$_3$OD): 1.39 (s,3H), 1.42 (s,3H), 2.12 (m,1H), 2.3–2.7 (m,5H), 4.40 (dd;7,12Hz;1H), 4.85 (d,15Hz,1H), 5.30 (d,15Hz,1H), 7.0–7.3 (m,6H), 7.40 (m,1H), 7.60 (m,2H), 7.70 (m,2H). FAB-MS: calculated for C$_{29}$E$_{30}$FN$_7$O$_2$ 527; found 528 (M+H,100%).

EXAMPLE 32

3-Amino-3-methyl-N-[8-iodo-2,3,4,5-tetrahydro-2-oxo-1-[[2'-(1H-tetrazol-5-yl)[1,1'-biphenyl]-4-yl]methyl]-1H-1-benzazepin-3-yl]-butanamide, trifluoroacetate

Step A: 7-iodo-1-tetralone 4-(p-Iodophenyl)butyric acid (5.00 g, 17.2 mmol) was added to 48 g of polyphosphoric acid and the mixture heated at 95°–105° C. for 1 hour, then stirred at room temperature for 16 hours. The reaction mixture was added to 500 mL of ice/water and extracted with ether (3×200 mL). The combined extracts were dried over magnesium sulfate and the solvent removed under vacuum. The residue was purified by medium pressure liquid chromatography on silica, eluting with chloroform to yield 3.63 g (13.4 mmol, 77%) of the product. $^1$H NMR (200MHz, CDCl$_3$): 2.11 (m,2H), 2.62 (t,5Hz,2H), 2.90 (t,5Hz,2H), 6.99 (d,8Hz,1H), 7.74 (dd;2,8Hz;1H), 8.30 (d,2Hz,1H). FAB-MS: calculated for C$_{10}$H$_9$IO 272; found 273 (M+H,100%).

Step B:
8-iodo-2,3,4,5-tetrahydro-1H-1-benzazepin-2-one

Prepared from 7-iodo-1-tetralone by the procedure described in Example 31, Step A. $^1$H NMR (200MHz, CDCl$_3$): 2.32 (m,2H), 2.42 (m,2H), 2.85 (t,6Hz,2H), 7.05 (d,8Hz,1H), 7.44 (d,2Hz 1H) 7.56 (dd;2,8Hz;1H). FAB-MS: calculated for C$_{10-10}$INO 287; found 288 (M+H,100%).

Step C:
3,8-diiodo-2,3,4,5-tetrahydro-1H-1-benzazepin-2-one

Prepared from 8-iodo-2,3,4,5-tetrahydro-1H-1-benzazepin-2-one by the procedure described in Example 31, Step B. $^1$H NMR (200MHz, CDCl$_3$): 2.56 (m,4H), 4.48 (t,6Hz,1H), 6.80 (d,8Hz,1H), 7.22 (d,2Hz,1H), 7.32 (dd;2,8Hz;1H). FAB-MS: calculated for C$_{10}$H$_9$I$_2$NO 413; found 414 (M+H,58%).

Step D:
3-Azido-8-iodo-2,3,4,5-tetrahydro-1H-1-benzazepin-2-one

Prepared from 3.8-diiodo-2,3,4,5-tetrahydro-1H-1-benzazepin-2-one by the procedure described in Example 31, Step C. $^1$H NMR (200MHz, CDCl$_3$): 2.3–3.2 (m,4H), 3.99 (m,1H), 7.10 (d,8Hz,1H), 7.58 (m,2H). FAB-MS: calculated for C$_{10}$H$_9$IN$_4$O 328; found 329 (M+H,100%).

Step E:
3-Amino-8-iodo-2,3,4,5-tetrahydro-1H-1-benzazepin-2-one

Prepared from 3-azido-8-iodo-2,3,4,5-tetrahydro-1H-1-benzazepin-2-one by the procedure described in Example 31, Step D. $^1$H NMR (200MHz, CDCl$_3$): 1.92 (m,1H), 2.56 (m,2H), 2.82 (m,1H), 3.40 (m,1H), 6.98 (d,8Hz,1H), 7.32 (d,2Hz,1H), 7.45 (dd;2,8Hz;1H), 7.60 (br s,1H). FAB-MS: calculated for C$_{10}$H$_{11}$IN$_2$O 302; found 303 (M+H,62%).

Step F:
3-t-Butoxycarbonylamino-3-methyl-N-[8-iodo-2,3,4,5-tetrahydro-2-oxo-1H-1-benzazepin-3-yl]-butanamide Prepared from 3-t-butoxycarbonylamino-3-methylbutanoic acid (Example 31, Step E) and the amine obtained in Step E by the procedure described in Example 1, Step F. $^1$H NMR (200MHz, CDCl$_3$): 1.33 (s,6H), 1.42 (s,9H), 1.80(m,1H), 2.24 (m,2H), 2.50 (m,3H), 4.45 (m,1H), 6.98 (d,8Hz,1H), 7.35 (d,2Hz,1H), 7.43 (dd;2,8Hz;1H). FAB-MS: calculated for C$_{20}$H$_{28}$IN$_3$O$_4$ 501; found 502 (M+H,20%).

Step G:
3-t-Butoxycarbonylamino-3-methyl-N-[8-iodo-2,3,4,5-tetrahydro-2-oxo-1-[[2'-(N-triphenylmethyl)-tetrazol-5yl][1,1'-biphenyl]-4-yl]methyl-1H-1-benzazepin-3-yl]-butanamide Prepared from the intermediate obtained in Step F and N-triphenylmethyl-5-[2-(4'-bromomethylbiphen-4-yl)] tetrazole by the procedure described in Example 1, Step K. $^1$H NMR (200MHz, CD$_3$OD): 1.35 (s,6H), 1.42 (s,9H), 1.70 (m,1H), 2.22 (m,2H), 2.48 (m,3H), 4.40 (m,1H), 4.39 (d,14Hz,1H), 5.28 (d,14Hz,1H), 6.74 (m,2H), 6.8–7.6 (m,23H), 7.88 (m,1H).

Step H:
3-Amino-3-methyl-N-[8-iodo-2,3,4,5-tetrahydro-2-oxo-1-[[2'-(1H-tetrazol -5-yl)[1,1'-biphenyl]-4-yl]methyl]-1H-1-benzazepin-3-yl]butanamide, trifluoroacetate The title compound was prepared from the intermediate obtained in Step G by the procedure described in Example 31, Step H. $^1$H NMR (200MHz, CD$_3$OD): 1.32 (s,3H), 1.37 (s,3H), 2.04 (m,1H), 2.1–2.6 (m,3H), 2.50 (d,4Hz,2H), 4.30 (m,1H), 4.76 (d,14Hz,1H), 5.24 (d,14Hz,1H), 6.96 (m,3H), 7.15 (m,2H), 7.60 (m,6H). FAB-MS: calculated for C$_{29}$H$_{30}$IN$_7$O$_2$ 635; found 636 (M+H,100%).

EXAMPLE 33
3-Amino-3-methyl-N-[8-methoxy-2,3,4,5-tetrahydro-2-oxo-1-[[2'-(1H-tetrazol-5 -yl)[1,1'-biphenyl]-4-yl]methyl]-1H-1-benzazepin-3-yl]-butanamide, trifluoroacetate

Step A:
8-Methoxy-2,3,4,5-tetrahydro-1H-1-benzazepin-2-one

Prepared from 7-methoxy-1-tetralone by the procedure described in Example 31, Step A. $^1$H NMR (200MHz, CDCl$_3$): 2.19 (m,2H), 2.32 (m,2H), 2.70 (t,6Hz,2H), 3.76 (s,3H), 6.57 (d,2Hz, 1H), 6.66 (dd;2,8Hz;1H), 7.09 (d,8Hz,1H). FAB-MS: calculated for C$_{11}$H$_{13}$NO$_2$ 191; found 192 (M+H,100%).

Step B:
3-Iodo-8-methoxy-2,3,4,5-tetrahydro-1H-1-benzazepin-2-one

Prepared from 8-methoxy-2,3,4,5-tetrahydro-1H-1-benzazepin-2-one by the procedure described in Example 31, Step B. $^1$H NMR (200MHz, CDCL$_3$): 2.6–3.1 (m,4H), 3.88 (s,3H), 4.76 (t,6Hz,1H), 6.68 (d,2Hz,1H), 6.81 (dd;2,8Hz;1H), 7.20 (d,2Hz,1H). FAB-MS: calculated for C$_{11}$H$_{12}$INO$_2$ 317; found 318 (M+H,44%).

Step C:
3-Azido-8-methoxy-2,3,4,5-tetrahydro-1H-1-benzazepin-2-one

Prepared from 3-iodo-8-methoxy-2,3,4,5-tetrahydro-1H-1-benzazepin-2-one by the procedure described in Example 31, Step C. $^1$H NMR (200MHz, CDCl$_3$): 2.3–3.2 (m,4H), 3.90 (s,3H), 4.01 (m,1H), 6.74 (d,2Hz,1H), 6.82 (dd;2,8Hz;1H), 7.22 (d,8Hz,1H). FAB-MS: calculated for C$_{11}$H$_{12}$N$_4$O$_2$ 232; found 233 (M+H,100%).

Step D:
3-Amino-8-methoxy-2,3,4,5-tetrahydro-1H-1-benzazepin-2-one

Prepared from 3-azido-8-methoxy-2,3,4,5-tetrahydro-1H-1-benzazepin-2-one by the procedure described in Example 31, Step D. $^1$H NMR (200MHz, CDCl$_3$): 2.02 (m,1H), 2.68 (m,2H), 2.90 (m,1H), 3.59 (m,1H), 3.92 (s,3H), 6.74 (d,2Hz,1H), 6.82 (dd;2,8Hz;1H), 7.22

(d,8Hz,1H), 8.25 (br s,1H). FAB-MS: calculated for C$_{11}$H$_{14}$N$_2$O$_2$ 206; found 207 (M+H,40%).

Step E:
3-t-Butoxycarbonylamino-3-methyl-N-[8-methoxy-2,3,4,5-tetrahydro-2-oxo-1H-1-benzazepin-3-yl]-butanamide Prepared from 3-t-butoxycarbonylamino-3-methyl-butanoic acid (Example 31, Step E) and the amine obtained in Step D by the procedure described in Example 1, Step F. $^1$H NMR (200MHz, CDCl$_3$): 1.44 (s,6H), 1.50 (s,9H), 1.80 (m,1H), 2.80 (m,5H), 3.86 (2,3H), 4.62 (m,1H), 6.62 (d,2Hz,1H), 6.76 (dd;2,8Hz;1H), 7.20 (d,8Hz,1H). FAB-MS: calculated for C$_{21}$H$_{31}$N$_3$O$_5$ 405; found 406 (M+H,42%).

Step F:
3-t-Butoxycarbonylamino-3-methyl-N-[8-methoxy-2,3,4,5-tetrahydro-2-oxo-1-[[2'-(N-triphenylmethyl)-tetrazol-5-yl][1,1'-biphenyl]-4-yl]methyl-1H-1-benzazepin-3-yl]butanamide Prepared from the intermediate obtained in Step E and N-triphenylmethyl-5-[2-(4'- bromomethylbipheny-4-yl)] tetrazole by the procedure described in Example 1, Step K. $^1$H NMR (200MHz, CD$_3$OD): 1.47 (s,6H), 1.55 (s,9H), 1.80 (m,1H), 2.42 (m,2H), 2.60 (m,3H), 3.84 (s,3H), 4.62 (m,1H), 4.78 (d,14Hz, 1H), 5.30 (d,14Hz,1H), 6.79 (m,2H), 7.08 (m,12H), 7.42 (m,11H), 7.98 (m,1H).

Step G:
3-t-Butoxycarbonylamino-3-methyl-N-[8-methoxy-2,3,4,5-tetrahydro-2-oxo-1-[[2'-(1H-tetrazol-5-yl)[1,1'-biphenyl]-4-yl]methyl]-1H-1-benzazepin-3-yl]-butanamide Prepared from the intermediate obtained in Step F by the procedure described in Example 2, Step C. $^1$H NMR (200MHz, CD$_3$OD): 1.42 (s,6H), 1.50 (s,9H), 2.10 (m,1H), 2.56 (m,5H), 3.82 (s,3H), 4.43 (m,1H), 4.92 (d,15Hz,1H), 5.31 (d,15Hz,1H), 6.86 (m,1H), 6.97 (m,2H), 7.0–7.3 (m,4H), 7.64 (m,3H), 8.05 (m,1H). FAB-MS: calculated for C$_{35}$H$_{41}$N$_7$O$_5$ 639; found 640 (M+H,20%).

Step H:
3-Amino-3-methyl-N-[8-methoxy-2,3,4,5-tetrahydro-2-oxo-1-[[2'-(1H-tetrazol-5-yl)[1,1'-biphenyl]-4-yl]methyl]-1H-1-benzazepin-3yl]-butanamide, mono(trifluoroacetate)

The title compound was prepared from the intermediate obtained in step G by the procedure described in Example 31, Step H. $^1$H NMR (200MHz, CD$_3$OD): 1.43 (s,3H), 1.49 (s,3H), 2.15 (m,1H), 2.2–2.7 (m,5H), 3.85 (s,3H), 4.48 (m,1H), 5.04 (d,14Hz,1H), 5.28 (d,14Hz,1H), 6.92 (m,2H), 7.1–7.4 (m,4H), 7.65 (m,5H). FAB-MS: calculated for C$_{30}$H$_{33}$N$_7$O$_3$ 539; found 540 (M+H,100%).

EXAMPLE 34
3-Amino-3-methyl-N-[7-trifluoromethyl-2,3,4,5-tetrahydro-2-oxo-1-[[2'-(1H-tetrazol-5-yl)[1,1'-biphenyl]-4-yl]methyl]-1H-1-benzazepin-3-yl-butanamide, hydrochloride

Step A: 3-(Trifluoromethyl)phenethyl tosylate

A solution of 10.0 g (52.6 mmol) of 3-(trifluoromethyl)phenethyl alcohol in 75 mL of ether under nitrogen was treated with 10.53 g (55.2 mmol, 1.05 eq) p-toluenesulfonyl chloride. The solution was cooled to 0° and treated with 7.67 mL (5.57 g, 55.0 mmol, 1.05 eq) of triethylamine. The mixture was stirred at 0° for 30 minutes then warmed to room temperature and stirred for 16 hours. The precipitate was removed by filtration and washed with ether. The combined filtrate and ether was were evaporated under vacuum. The residue was redissolved in ethyl acetate and washed with 0.5N HCl and brine; the organic layer was removed, dried over sodium sulfate, filtered and concentrated under vacuum. Purification by flash chromatography on silica, eluting with 30% ethyl acetate/hexane, afforded 15.14 g (44.0 mmol, 84%) of the product. $^1$H NMR (200MHz, CDCl$_3$): 2.44 (s,3H), 3.03 (t,7Hz,2H), 4.26 (t,7Hz,2H), 7.2–7.5 (m,6H), 7.66 (d,8Hz,2H). FAB-MS: calculated for C$_{16}$H$_{15}$F$_3$SO$_3$ 344; found 345 (M+H,8%).

Step B:
2-[2-(3-Trifluoromethylphenyl)-ethyl]propane-1,3-dioic acid, dimethyl ester A suspension of 1.4 g of 60% sodium hydrode oil dispersion (0.84 g, 35 mmol, 1.1 eq) in 30 mL of tetrahydrofuran at room temperature under nitrogen was treated dropwise over 15 minutes with a solution of 4.0 mL of dimethyl malonate (4.62 g, 35 mmol, 1.1 eq) in 30 mL of tetrahydrofuran. After evolution of hydrogen ceased, a solution of 11.03 g (32.0 mmol, 1.0 eq) of 3-(trifluoromethyl)phenethyl tosylate (Step A) in 30 mL of tetrahydrofuran was added over 15 minutes. The mixture was heated at reflux for a total of 21 hours. The mixture was filtered; the filtrate was dried over magnesium sulfate, filtered and concentrated under vacuum to afford 10.89 g of product which contained approximately 5% of unreacted tosylate and was used without purification. $^1$H NMR (200MHz, CDCl$_3$): 2.24 (m,2H), 2.70 (t,8Hz,2H), 3.37 (t,8Hz,1H), 3.74 (s,6H), 7.3–7.5 (m,4H).

Step C: 4-(3-Trifluoromethylphenyl)-butanoic acid

The intermediate obtained in Step B (2.15 g, 7.07 mmol) was treated with 3.5 mL of a 4.53M solution of methanolic potassium hydroxide (15.9 mmol, 2.2 eq) and the resulting mixture stirred at room temperature for 72 hours. The mixture was concentrated under vacuum and the solid residue redissolved in 4mL of concentrated hydrochloric acid and heated at reflux for 3 hours. The mixture was cooled, then extracted with methylene chloride (3×6mL); the combined extracts were washed with brine, dried over magnesium sulfate, filtered and concentrated under vacuum. The residue was suspended in 20 mL of water and treated with 700 mg (8.3 mmol) of sodium bicarbonate. The solution was washed with ether (2×20 mL); the aqueous phase was removed and acidified (pH 1-2) with 2N HCl. The mixture was extracted with methylene chloride and the combined extracts dried over sodium sulfate, filtered and concentrated under vacuum. The residue was treated with 30 mL of concentrated hydrochloric acid and the mixture heated at reflux for 20 hours. All volatiles were removed under vacuum to afford 1.12 g (4.82 mmol, 68%) of product. $^1$H NMR (200MHz, CDCl$_3$): 1.98 (m,2H), 2.40 (t,8Hz,2H), 2.74 (t,8Hz,2H), 7.3–7.5 (m,4H).

Step D: 7-Trifluoromethyl-1-tetralone

Prepared from 4-(3-trifluoromethylphenyl)butanoic acid by the procedure described in Example 32, Step A. $^1$H NMR (200MHz, CDCl$_3$): 2.16 (m,2H), 2.69 (t,6Hz,2H), 3.01 (t,6Hz,2H), 7.5 (m,2H), 8.12 (d,8Hz,1H). EI-MS: calculated for C$_{11}$H$_9$F$_3$O 214; found 214 (M+,40%).

Step E:
7-Trifluoromethyl-2,3,4,5-tetrahydro-1H-1-benzazepin-2-one

Prepared from 7-trifluoromethyl-1tetralone by the procedure described in Example 31, Step A. $^1$H NMR (200MHz, CDCl$_3$): 2.3 (m,4H), 2.86 (t,7Hz,2H), 7.08 (d,8Hz,1H), 7.48 (m,2H), 8.3 (br s,1H). FAB-MS: calculated for C$_{11}$H$_{10}$F$_3$NO 229; found 230 (M+H,100%).

Step F:
3-Iodo-7-trifluoromethyl-2,3,4,5-tetrahydro-1H-1-benzazepin-2-one

Prepared from 7-trifluoromethyl-2,3,4,5-tetrahydro-1H-1-benzazepin-2-one by the procedure described in Example 31, Step B. $^1$H NMR (200MHz, CDCl$_3$): 2.8 (m,4H), 4.68 (t,8Hz,1H), 7.11 (d,8Hz,1H), 7.52 (m,2H), 7.95 (br s,1H). FAB-MS: calculated for C$_{11}$H$_9$F$_3$INO 355; found 356 (M+H,100%).

Step G:
3-Azido-7-trifluoromethyl-2,3,4,5-tetrahydro-1H-1-benzazepin-2-one

Prepared from 3-iodo-7-trifluoromethyl-2,3,4,5-tetrahydro-1H-1-benzazepin-2-one by the procedure described in example 31, Step C. $^1$H NMR (200MHz, CDCl$_3$): 2.32 (m,1H), 2.55 (m,1H), 2.81 (m,1H), 3.00 (m,1H), 3.88 (dd;8,12Hz;1H), 7.14 (d,7Hz,1H), 7.52 (m,2H, 8.34 (br s,1H). FAB-MS: calculated for C$_{11}$H$_9$F$_3$N$_4$O 270; found 271 (M+H,100%).

Step H:
3-Amino-7-trifluoromethyl-2,3,4,5-tetrahydro-1H-1-benzazepin-2-one

Prepared from 3-azido-7-trifluoromethyl-2,3,4,5-tetrahydro-1H-1-benzazepin-2-one by the procedure described in Example 31, Step D. $^1$H NMR (200MHz, (D$_3$OD): 1.95 (m,1H), 2.46 (m,1H), 2.80 (m,2H), 3.35 (dd;8,12Hz;1H), 7.15 (d,8Hz,1H), 7.63 (m,2H). FAB-MS: calculated for C$_{11}$H$_{11}$F$_3$N$_2$O 244; found 245 (M+H,100%).

Step I:
3-t-Butoxycarbonylamino-3-methyl-N-[7-trifluoromethyl-2,3,4,5-tetrahydro-2-oxo-1H-1-benzazepin-3-yl]-butanamide Prepared from 3-t-butoxycarbonylamino-3-methylbutanoic acid (Example 31, Step E) and the amine obtained in Step H by the procedure described in Example 1, Step F. $^1$H NMR (200MHz, CDCl$_3$): 1.34 (s,6H), 1.42 (s,9H), 1.98 (m,1H), 2.50 (d,14Hz,1H), 2.63 (d,14Hz,1H), 2.7–3.0 (m,3H), 4.50 (m,1H), 6.75 (d,7Hz,1H), 7.10 (d,8Hz,1H), 7.51 (br s,2H), 7.94 (br s,1H). FAB-MS: calculated for C$_{21}$H$_{28}$F$_3$N$_3$O$_4$ 443; found 444 (M+H,74%).

Step J:
3-t-Butoxycarbonylamino-3-methyl-N-[7-trifluoromethyl-2,3,4,5-tetrahydro-2-oxo-1-[[2'-(N-triphenylmethyl)-tetrazol-5-yl][1,1'-biphenyl]-4-yl]methyl-1H-1-benzazepin-3-yl]-butanamide Prepared from the intermediate obtained in Step I and N-triphenylmethyl-5-[2-(4'-bromomethylbiphen-4-yl)] tetrazole by the procedure described in Example 1, Step K. $^1$H NMR (200MHz, CDCl$_3$): 1.36 (s,6H), 1.42 (s,9H), 1.71 (m,1H), 2.4–2.6 (m,5H), 4.44 (m,1H), 4.75 (d,15Hz,1H), 5.11 (d,15Hz,1H), 5.19 (br s,1H), 6.64 (d,7Hz,1H), 6.9–7.1 (m,10H), 7.2–7.5 (m,15H), 7.88 (m,1H).

Step K:
3-amino-3-methyl-N-[7-trifluoromethyl-2,3,4,5-tetrahydro-2-oxo-1-[[2'-(1H-tetrazol-5yl)[1,1'-biphenyl]-4-yl]methyl]-1H-1-benzazepin-3-yl]-butanamide, hydrochloride The intermediate prepared in Step J (436 mg, 0.47 mmol) was dissolved in 4 mL of methanol and treated dropwise with 4 mL of 9N HCl. The mixture was stirred at room temperature for 16 hours then evaporated to dryness under vacuum. The dry solid was triturated with benzene (5×5 mL) then with warm benzene (2×5 mL) then dried to constant weight. Thus, 304 mg (0.47 mmol, 100%) of the title compound was obtained. $^1$H NMR (200MHz, CD$_3$OD): 1.33 (s,3H), 1.36 (s,3H), 2.1–2.8 (m,6H), 4.30 (dd;8,12Hz;1H), 4.96 (d,15Hz,1H), 5.33 (d,15Hz,1H), 7.06 (d,8Hz, 2H), 7.2–7.5 (m,3H), 7.5–7.7 (m,6H). FAB-MS: calculated for C$_{30}$H$_{30}$F$_3$N$_7$O$_2$ 577; found 578 (M+H,100%).

EXAMPLE 35

3-amino-3-methyl-N-[8-chloro-2,3,4,5-tetrahydro-2-oxo-1-[[2'-(1H-tetrazol-5yl)[1,1'-biphenyl]-4-yl]methyl]-1H-1-benzazepin-3-yl]-butanamide, trifluoroacetate Step A: 7-Amino-1-tetralone 7-Nitrotetralone (2.5 g, 13 mmol) was suspended in 50 mL of methanol and complete dissolution achieved by the addition of 10 mL of tetrahydrofuran. The solution was hydrogenated at room temperature and 20-30 psi over 100 mg of 10% Pd/C for 2 hours. The mixture was filtered through Celite, washed with methanol and evaporated to dryness under vacuum to afford 2.1 g (13 mmol, 100%) of the product. $^1$H NMR (300MHz, CDCl$_3$): 2.09 (m,2H), 2.60 (t,6Hz,2H), 2.84 (t,6Hz,2H), 6.83 (m,1H), 7.06 (d,8Hz,1H), 7.32 (d,2Hz,1H). FAB- MS: calculated for $C_{10}H_{11}NO$ 161; found 162 (M+H,100%).

Step B: 7-chloro-1-tetralone

7-Amino-1-tetralone (500 mg, 3.1 mmol) was suspended in 3 mL of water and treated with 3 mL of concentrated hydrochloric acid with stirring. The mixture was cooled in an ice bath and treated dropwise with vigorous stirring with a solution of 241 mg of sodium nitrite in 1.5 mL of water (3.5 mmol, 1.1eq). The mixture was stirred at 0°–5° for 15 minutes then added dropwise to a cold solution of 366 mg of CuCl (3.7 mmol, 1.2 eq) in 6 mL of concentrated hydrochloric acid. The mixture was stirred for 5 minutes at 0° and 1 hour at room temperature. The mixture was extracted with methylene chloride (3×15 mL); the combined extracts were washed with brine, dried over magnesium sulfate, filtered and evaporated to dryness under vacuum at room temperature to give 550 mg (3.05 mmol, 98%) of the product, $^1$H NMR (300MHz, CDCl$_3$): 2.16 (m,2H), 2.67 (t,6Hz,2H), 2.95 (t,6Hz,2H), 7.22 (d,8Hz,1H), 7.44 (dd;2,8Hz;1H), 8.01 (d,2Hz,1H). FAB-MS: calculated for $C_{10}H_9ClO$ 180; found 181 (M+H,10%).

Step C: 8-Chloro-2,3,4,5-tetrahydro-1H-1-benzazepin-2-one

Prepared from 7-chloro-1-tetralone by the procedure described in Example 31, Step A. $^1$H NMR (300MHz), CDCl$_3$): 2.23 (m,2H), 2.37 (t,6Hz,2H), 2.80 (t,6Hz,2H) 7.3 (n,3H), 9.08 (br s,1H). FAB-MS: calculated for $C_{10}H_{10}ClNO$ 195; found 195 (M+,30%).

Step D: 3-Iodo-8-chloro-2,3,4,5-tetrahydro-1H-1-benzazepin-2-one

Prepared from the intermediate obtained in Step C by the procedure described in Example 31, Step B. $^1$H NMR (300MHz, CDCl$_3$): 2.72 (m,3H), 2.90 (m,1H), 4.67 (t,8Hz,1H), 7.05 (s,1H), 7.18 (s,2H), 7.71 (br s,1H). FAB-MS: calculated for $C_{10}H_9ClINO$ 320; found 321 (M+H,100%).

Step E: 3-Azido-8-chloro-2,3,4,5-tetrahydro-1H-1-benzazepin-2-one

Prepared from the intermediate obtained in Step D by the procedure described in Example 31, Step C. $^1$H NMR (300MHz, DMF-d$_7$): 2.10 (m,1H), 2.40 (m,1H), 2.76 (m,2H), 4.01 (dd;8,12Hz;1H), 7.10 (d,2Hz,1H), 7.16 (dd;2,8Hz;1H), 7.30 (d,8Hz,1H), 7.95 (br s,1H). FAB-MS: calculated for $C_{10}H_9ClN_4O$ 236; found 237 (M+H,100%).

Step F: 3-Amino-8-chloro-2,3,4,5-tetrahydro-1H-1-benzazepin-2-one

Prepared from the intermediate obtained in Step E by the procedure described in Example 31, Step D. $^1$H NMR (300MHz, CDCl$_3$): 1.94 (m,1H), 2.52 (m,1H), 2.67 (m,1H), 2.89 (m,1H), 3.44 (m,1H), 7.02 (d,2Hz,1H), 7.18 (m,2), 7.70 (br s,2H). FAB-MS: calculated for $C_{10}H_{11}ClN_2O$ 210; found 211 (M+H,84%).

Step G: 3-t-Butoxycarbonylamino-3-methyl-N-[8-chloro-2,3,4,5-tetrahydro-2-oxo-1H-1-benzazepin-3-yl]-butanamide Prepared from 3-t-butoxycarbonylamino-3-methylbutanoic acid (Example 31, Step E) and the amine obtained in Step F by the procedure described in Example 1, Step F. $^1$H NMR (300MHz, CDCl$_3$): 1.35 (s,6H), 1.42 (s,9H), 1.95 (m,1H), 2.4–2.8 (m,5H), 4.51 (m,1H), 5.22 (br s,1H), 6.73 (d,7Hz,1H), 7.02 (s,1H), 7.14 (br s,2H), 8.21 (br s,1H). FAB-MS: calculated for $C_{20}H_{28}ClN_3O_4$ 409; found 410 (M+H,55%).

Step H: 3-t-Butoxycarbonylamino-3-methyl-N-[8-chloro-2,3,4,5-tetrahydro-2-oxo-1-[[2'-(N-triphenylmethyl)-tetrazol-5-yl][1,1'-biphenyl]-4-yl]methyl-1H-1-benzazepin-3-yl]-butanamide Prepared from the intermediate obtained in Step G and N-triphenylmethyl-5-[2-(4'-bromomethylbiphen-4-yl)] tetrazole by the procedure described in Example 1, Step K.

Step I: 3-Amino-3-methyl-N-[8-chloro-2,3,4,5-tetrahydro-2-oxo-1-[[2'-(1H-tetrazol-5-yl)[1,1'-biphenyl]-4-yl]methyl]-1H-1-benzazepin-3-yl]butanamide, trifluoroacetate Prepared from the intermediate obtained in Step H by the procedure described in Example 31, Step H. $^1$H NMR (300MHz, CD$_3$OD): 1.40 (s,3H), 1.43 (s,3H), 2.12 (m,1H), 2.3–2.7 (m,5H), 4.30 (dd;8,12Hz;1H), 4.87 (d,15Hz,1H), 5.34 (d,15Hz,1H), 7.08 (d,8Hz,2H), 7.23 (d,8Hz,2H), 7.28 (s,2H), 7.45 (s,1H), 7.59 (t,8Hz,2H), 7.70 (m,2H). FAB-MS: calculated for $C_{29}H_{30}ClN_7O_2$ 543; found 544 (M+H,43%).

EXAMPLE 36

3-Amino-3-methyl-N-[8-fluoro-2,3,4,5-tetrahydro-2-oxo-1-[[2'-(1H-tetrazol-5-yl)[1,1'-biphenyl]-4-yl]methyl]-1H-1-benzazepin-3-yl]-butanamide, trifluoroacetate

Step A: 7-Fluoro-1-tetralone

In a specially designed Kel-F reactor (cylindrical shape 1.25"od×3"h equipped with a screw cap and N$_2$ inlet-outlet) was placed hydrogen fluoride-pyridine 6:4 solution (10 mL, prepared by diluting commercially available hydrogen fluoride-pyridine 7:3 solution with dry pyridine). 7-amino-tetralone (644 mg, 4.0 mmol), (Example 35, Step A) was added under N$_2$ and the solution was cooled to 0°. Sodium nitrite (304 mg, 4.4 mol, 1.1 eq) was added in portions and the mixture was stirred for 30 minutes. The mixture was then heated at 90° C. for 1 hour with stirring. The reaction mixture was quenched with approx. 60 mL of ice/water and the solid that separated extracted with methylene chloride (3×30 mL). The combined extracts were washed with water and brine, dried over magnesium sulfate, filtered and evaporated to dryness under vacuum at room temperature. Purification by flash chromatography on silica, eluting with ethyl acetate/hexane (5:95), afforded pure 7-fluoro-1-tetralone (367 mg, 2.2 mmol, 56%). $^1$H NMR (300MHz, CDCl₃): 2.13 (m,2H), 2.65 (t,7Hz,2H), 2.94 (t,7Hz,2H), 7.1–7.3 (m,2H), 7.69 (dd;2,8Hz;1H). FAB-MS: calculated for C₁₀H₉FO 164; found 164 (M+,71%).

Step B:
8-fluoro-2,3,4,5-tetrahydro-1H-1-benzazepin-2-one

Prepared from 7-fluoro-1-tetralone by the procedure described in Example 31, Step A. ¹H NMR (300MHz, CDCl₃): 2.22 (m,2H), 2.38 (t,6Hz,2H), 2.78 (t,6Hz,2H), 6.75 (dd;2,8Hz;1H), 6.84 (dt;2,8Hz;1H), 7.16 (t,8Hz,1H), 8.35 (br s,1H).

Step C:
3-Iodo-8-fluoro-2,3,4,5-tetrahydro-1H-1-benzazepin-2-one

Prepared from the intermediate obtained in Step B by the procedure described in Example 31, Step B. ¹H NMR (300MHz, CDCl₃): 2.73 (m,3H), 2.92 (m,1H), 4,68 (t,8Hz,1H), 6.79 (dd;2,8Hz;1H), 6.90 (dt;2,8Hz;1H), 7.18 (t,8Hz,1H), 8.14 (br s,1H).

Step D:
3-Azido-8-fluoro-2,3,4,5-tetrahydro-1H-1-benzazepin-2-one

Prepared from the intermediate obtained in Step C by the procedure described in Example 31, Step C. ¹H NMR (300MHz, CDCl₃): 2.30 (m,1H), 2.51 (m,1H), 2.74 (m,1H), 2.93 (m,1H), 3.88 (dd;8,12Hz;1H), 6.80 (dd;2,8Hz;1H), 6.89 (dt;2,8Hz;1H), 7.21 (t,8Hz,1H), 8.10 (br s,1H).

Step E:
3-Amino-8-fluoro-2,3,4,5-tetrahydro-1H-1-benzazepin-2-one

Prepared from the intermediate obtained in Step D by the procedure described in Example 31, Step D. ¹H NMR (300MHz, CDCl₃): 1.92 (m,1H), 2.52 (m,1H), 2.65 (m,1H), 2.86 (m,1H), 3.45 (m,1H), 6.78 (dd;2,8Hz;1H), 6.87 (dt;2,8Hz;1H), 7.20 (t,8Hz,1H), 8.56 (br s,1H). FAB-MS: calculated for C₁₀H₁₁FN₂O 194; found 195 (M+H,100%).

Step F:
3-t-Butoxycarbonylamino-3-methyl-N-[8-fluoro-2,3,4,5-tetrahydro-2-oxo-1H-1-benzazepin -3-yl]-butanamide Prepared from 3-t-butoxycarbonylamino-3-methylbutanoic acid (Example 31, Step E) and the amine obtained in Step E by the procedure described in Example 1, Step F. ¹H NMR (300MHz, CDCl₃): 1.35 (s,6H), 1.41 (s,9H), 1.93 (m,1H), 2.4–2.9 (m,5H), 4.54 (m,1H), 5.19 (br s,1H), 6.73 (m,2H), 6.88 (dt;2,8Hz;1H), 7.19 (dd;6,8Hz;1H), 8.07 (m,1H). FAB-MS: calculated for C₂₀H₂₈FN₃O₄ 393; found 394 (M+H,56%).

Step G:
3-t-Butoxycarbonylamino-3-methyl-N-[8-fluoro-2,3,4,5-tetrahydro-2-oxo-1-[[2'-(N -triphenylmethyl)-tetrazol-5-yl][1,1'-biphenyl]-4-yl]-methyl-1H-1-benzazepin-3-yl]-butanamide Prepared from the intermediate obtained in Step F and N-triphenylmethyl-5-[2-(4'-bromomethylbiphen-4-yl)] tetrazole by the procedure described in Example 1, Step K. ¹H NMR (300MHz, CDCl₃): 1.36 (s,3H), 1.37 (s,3H), 1.42 (s,9H), 1.75 (m,1H), 2.3–2.6 (m,5H), 4.5 (m,2H), 5.25 (m,2H), 6.64 (d,7Hz,1H), 6.8–7.1 (m,11H), 7.2–7.5 (m,13H), 7.85 (m,1H).

Step H:
3-Amino-3-methyl-N-[8-fluoro-2,3,4,5-tetrahydro-2-oxo-1-[[2'-(1H-tetrazol -5-yl)[1,1'-biphenyl]-4-yl]methyl]-1H-1-benzazepin-3-yl]-butanamide, trifluoroacetate Prepared from the intermediate obtained in Step G by the procedure described in Example 31, Step H. ¹H NMR (300MHz, CD₃OD): 1.40 (2,3H), 1.43 (s,3H), 2.12 (m,1H), 2.3–2.7 (m,5H), 4.41 (dd;8,12Hz;1H), 4.88 (d,15Hz,1H), 5.34 (d,15Hz,1H), 7.0–7.2 (m,3H), 7.2–7.4 (m,5H), 7.5–7.8 (m,3H). FAB-MS: calculated for C₂₉H₃₀FN₇O₂ 527; found 528 (M+H,100%).

EXAMPLE 37

3-Amino-3-methyl-N-[6-fluoro-2,3,4,5-tetrahydro-2-oxo-1-[[2'-(1H-tetrazol-5-yl)[1,1'-biphenyl]-4-yl]methyl]-1H-1-benzazepin-3-yl]-butanamide, trifluoroacetate Step A: 4-(2-Fluorophenyl)butyric acid Prepared from 4-(2-aminophenyl)butyric acid by the procedure described in Example 36, Step A. ¹H NMR (300MHz, CDCl₃): 1.95 (m,2H), 2.39 (t,7Hz,2H), 2.70 (t,7Hz,2H), 6.9–7.3 (m,4H). FAB-MS: calculated for C₁₀H₁₁FO₂ 182; found 182 (M+,75%).

Step B: 5-Fluoro-1-tetralone

Prepared from 4-(2-fluorophenyl)butyric acid by the procedure described in Example 32, Step A. ¹H NMR (300MHz, CDCl₃): 2.10 (m,2H), 2.60 (t,7Hz,2H), 2.88 (t,7Hz,2H), 7.1–7.3 (m,2H), 7.78 (d,8Hz,1H). EI-MS: calculated for C₁₀H₉FO 164; found 164 (M+,44%).

Step C:
6-Fluoro-2,3,4,5-tetrahydro-1H-1-benzazepin-2-one

Prepared from 5-fluoro-1-tetralone by the procedure described in Example 31, Step A. ¹H NMR (300MHz, CDCl₃): 2.26 (m,2H), 2.40 (t,6Hz,2H), 2.88 (t,6Hz,2H), 6.83 (d,8Hz,1H), 6.94 (t,8Hz,1H), 7.20 (m,1H), 7.75 (br s,1H). FAB-MS: calculated for C₁₀H₁₀FNO 179; found 180 (M+H,100%).

Step D:
3-Iodo-6-fluoro-2,3,4,5-tetrahydro-1H-1-benzazepin-2-one

Prepared from the intermediate obtained in Step C by the procedure described in Example 31, Step B. ¹H NMR (300MHz, CDCl₃): 2.7–2.9 (m,3H), 2.97 (m,1H), 4.68 (t,8Hz,1H), 6.81 (d,8Hz,1H), 6.94 (t,8Hz,1H), 7.20 (m,1H), 7.83 (br s,1H).

Step E:
3-Azido-6-fluoro-2,3,4,5-tetrahydro-1H-1-benzazepin-2-one

Prepared from the intermediate obtained in Step D by the procedure described in Example 31, Step C. ¹H NMR (300MHz, CD₃OD): 2.22 (m,1H), 2.60 (m,2H), 3.21 (m,1H), 3.85 (dd;8,12Hz;1H), 6.91 (d,8Hz,1H), 7.02 (t,8Hz,1H), 7.30 (m,1H). FAB-MS: calculated for C₁₀H₁₁FN₂O 194; found 195 (M+H,100%).

Step G:
3-t-Butoxycarbonylamino-3-methyl-N-[6-fluoro-2,3,4,5-tetrahydro-2-oxo-1H-1-benzazepin-3-yl]-butanamide Prepared from 3-t-butoxycarbonylamino-3-methyl-butanoic acid (Example 31, Step E) and the amine obtained in Step F by the procedure described in Example 1, Step F. $^1$H NMR (300MHz, CDCl$_3$): 1.36 (s,6H), 1.43 (s,9H), 1.91 (m,1H), 2.4–2.8 (m,3H), 3.18 (m,2H), 4.54 (m,1H), 5.18 (br s,1H), 6.66 (d,7Hz,1H), 6.81 (d,8Hz,1H), 6.94 (t,8Hz,1H), 7.18 (m,1H), 7.71 (br s,1H). FAB-MS: calculated for C$_{20}$H$_{28}$FN$_3$O$_4$ 393; found 394 (M+H,26%).

Step H:
3-t-Butoxycarbonylamino-3-methyl-N-[6-fluoro-2,3,4,5-tetrahydro-2-oxo-1-[[2'-(N-triphenylmethyl)-tetrazol-5-yl][1,1'-biphenyl]-4-yl]methyl-1H-1-benzazepin-3-yl]-butanamide Prepared from the intermediate obtained in Step G and N-triphenylmethyl-5-[2-(4'-bromomethylbiphen-4-yl)] tetrazole by the procedure described in Example 1, Step K. $^1$H NMR (300MHz, CDCl$_3$): 1.38 (s,6H), 1.45 (s,9H), 1.81 (m,1H), 2.18 (m,1H), 2.4–2.7 (m,3H), 2.89 (dd;7,14Hz;1H), 4.52 (m,1H), 4.77 (d,15Hz,1H), 5.09 (d,15Hz,1H), 5.29 (br s,1H), 6.67 (d,7Hz,1H), 6.9–7.2 (m,12H), 7.2–7.5 (m,13H), 7.85 (m,1H).

Step I:
3-Amino-3-methyl-N-[6-fluoro-2,3,4,5-tetrahydro-2-oxo-1-[[2'-(1H-tetrazol-5-yl)[1,1'-biphenyl]-4-yl]methyl]-1H-1-benzazepin-3-yl]-butanamide, trifluoroacetate Prepared from the intermediate obtained in Step H by the procedure described in Example 31, Step H. $^1$H NMR (300MHz, CD$_3$OD): 1.32 (s,3H), 1.36 (s,3H), 2.0–2.3 (m,3H), 2.40 (br s,2H), 3.00 (m,1H), 4.35 (m,1H), 4.87 (d,15Hz,1H), 5.20 (d,15Hz,1H), 7.00 (m,3H), 7.1–7.4 (m,4H), 7.5–7.7 (m,4H). FAB-MS: calculated for C$_{29}$H$_{30}$FN$_7$O$_2$ 527; found 528 (M+H,100%).

EXAMPLE 38

3-Amino-3-methyl-N-[1,2,3,4,5,6-hexahydro-2-oxo-1-[[2'-(1H-tetrazol-5-yl)[1,1'-biphenyl]-4-yl]methyl]-1H-1-benzazocin-3-yl]-butanamide, trifluoroacetate

Step A:
3-benzyloxycarbonylamino-3-methyl-N-[1,2,3,4,5,6-hexahydro-2-oxo-1H-1-benzazocin-3-yl]-butanamide 3-Azido-3,4,5,6-tetrahydro-1-benzazocin-2(1H)-one prepared by the method of Watthey, et al., J. Med Chem., 28, 1511–1516 (1985)) was reduced to 3-amino-3,4,5,6-tetrahydro-1-benzazocin-2(1H)-one by the procedure described in Example 1, Step A, then coupled with 3-benzyloxycarbonylamino-3-methylbutanoic acid (Example 1, Step E) by the procedure described in Example 1, Step F. $^1$H NMR (200MHz, CDCl$_3$): 1.36 (s,6H), 1.75 (m,3H), 2.08 (m,1H), 2.47 (m,3H), 2.80 (m,1H), 4.13 (m,1H), 5.12 (s,2H), 5.79 (s,1H), 6.86 (d,7Hz,1H), 7.0–7.4 (m,8H), 7.90 (s,1H). FAB-MS: calculated for C$_{24}$H$_{29}$N$_3$O$_4$ 423; found 424 (M+H,100%).

Step B:
3-Benzyloxycarbonylamino-3-methyl-N-[1,2,3,4,5,6-hexahydro-2-oxo-1-[[2'-(N-triphenylmethyl)-tetrazol-5-yl][1,1'-biphenyl]-4-yl]-methyl-1H-1-benzazocin-3-yl]-butanamide Prepared from the intermediate obtained in Step A and N-triphenylmethyl-5-[2-(4'-bromomethylbiphen-4-yl)] tetrazole by the procedure described in Example 1, Step K. $^1$H NMR (200MHz, CDCl$_3$): 1.42 (s,6H), 1.72 (m,4H), 2.42 (m,4H), 4.16 (m,1H), 4.49 (d,13Hz,1H), 5.10 (s,2H), 5.30 (d,13Hz,1H), 5.79 (s,1H), 6.80 (d,6Hz,2H), 6.9–7.6 (m,32H), 7.86 (m,1H).

Step C:
3-Amino-3-methyl-N-[1,2,3,4,5,6-hexahydro-2-oxo-1-[[2'-(1H-tetrazol-5-yl)[1,1'-biphenyl]-4-yl]methyl]-1H-1-benzazocin-3-yl]-butan-amide, trifluoroacetate The title compound was prepared from the intermediate obtained in Step B by the procedure described in Example 1, Step L. $^1$H NMR (200MHz, CD$_3$OD): 1.28 (s,3H), 1.32 (s,3H), 1.44 (m,1H), 1.75 (m,3H), 2.05 (m,1H), 2.48 (m,3H), 4.00 (m,1H), 4.64 (d,13Hz,1H), 5.19 (d,13Hz,1H), 6.9–7.4 (m,8H), 7.4–7.7 (m,4H). FAB-MS: calculated for C$_{30}$H$_{33}$N$_7$O$_2$ 523; found 524 (M+H,100%).

EXAMPLE 39

3-Amino-3-methyl-N-[1,2,3,4-tetrahydro-2-oxo-1-[[2'-(1H-tetrazol-5-yl)[1,1'-biphenyl]-4-yl]methyl]-1H-1-quinolin-3-yl]-butanamide, trifluoroacetate

Step A:
3-Benzyloxycarbonylamino-3-methyl-N-[1,2,3,4-tetrahydro-2-oxo-1H-1-quinolin-3-yl]-butanamide Prepared as in Example 1, Step F from 3-amino-1,2,3,4-tetrahydroquinolin-2-one (prepared by the method of Davis, et al; Arch. Biochem. Biophys., 102, 48 (1963)) and 3-benzyloxycarbonylamino-3-methyl-butanoic acid (Example 1, Step E). $^1$H NMR (200 MHz, CDCl$_3$): 1.42 (s,6H), 2.69 (s,2H), 2.86 (t,13 Hz, 1H), 3.00 (m,1H), 4.67 (m,1H), 5.00 (s,2H), 6.9–7.3 (m,9H). FAB-MS: calculated for C$_{22}$H$_{25}$N$_3$O$_4$ 395; found 396 (M+1,100%).

Step B:
3-Benzyloxycarbonylamino-3-methyl-N-[1,2,3,4-tetrahydro-2-oxo-1-[[2'-(N-triphenylmethyl)-tetrazol-5-yl][1,1'-biphenyl]-4-yl]methyl-1H-1-quinolin-3-yl]-butanamide Prepared from 3-benzyloxycarbonylamino-3-methyl-N-[1,2,3,4-tetrahydro-2-oxo-1H-1-quinolin-3-yl]butanamide and N-triphenylmethyl-5-[2-(4'-bromo-methylbiphen-4-yl)] tetrazole by the procedure described in Example 1, Step K. $^1$H NMR (200 MHz, CD$_3$OD): 1.41 (s, 6H, 2.66 (s,2H), 2.85 (t,11 Hz, 1H), 3.11 (m, 1H), 4.15 (m,1H), 4.97 (d,15 Hz, 1H), 5.30 (d,15 Hz, 1H), 6.7–7.6, (m,26H), 7.80 (m,1H).

Step C:
3-Amino-3-methyl-N-[1,2,3,4-tetrahydro-2-oxo-1-[[2'-(1H-tetrazol-5-yl)[1,1'-biphenyl]-4-yl]methyl]-1H-1-quinolin-3-yl]-butanamide, trifluoroacetate The title compound was prepared from the intermediate obtained in Step B by the procedure described in Example 1, Step L. $^1$H NMR (200 MHz, CD$_3$OD): 1.50 (s,3H), 1.52 (s,3H), 2.66 (m,2H), 3.16 (m,2H), 4.84 (m,1H), 5.17 (d,11 Hz, 1H), 5.39 (d,11 Hz, 1H), 7.0–7.4 (m, 8H), 7.57 (m,4H). FAB-MS: calculated for $C_{28}H_{29}N_7O_2$ 495; found 496 (M+H,100%).

EXAMPLE 40

3-Benzylamino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) and benzaldehyde by the procedure described in Example 18. $^1$H NMR (200 MHz, CD$_3$OD): 1.42 (s,3H), 1.46 (s,3H), 2.0–2.6 (m,4H), 2.69 (br s,2H), 4.12 (s,2H), 4.37 (dd;8,12 Hz; 1H), 4.90 (d,15 Hz, 1H), 5.18 (d,15 Hz, 1H), 6.97 (d,8 Hz, 2H), 7.1–7.7 (m,15H). FAB-MS: calculated for $C_{36}H_{37}N_7O_2$ 599; found 600 (M+H,100%).

EXAMPLE 41

3-Benzylamino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) and isobutyraldehyde by the procedure described in Example 18. $^1$H NMR (200 MHz, CD$_3$OD): 0.99 (d,8 Hz, 3H), 1.00 (d,8 Hz, 3H), 1.35 (s,3H), 1.39 (s,3H), 1.8–2.6 (m,7H), 2.81 (d,7 Hz, 2H), 4.32 (dd;8,12 Hz; 1H), 4.92 (d,15 Hz, 1H), 5.14 (d,15 Hz, 1H), 7.00 (d,8 Hz, 2H), 7.1–7.4 (m, 6H), 7.5–7.7 (m,4H). FAB-MS: calculated for $C_{33}H_{39}N_7O_2$ 565; found 566 (M+H,100%).

EXAMPLE 42

3-Propylamino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) and propionaldehyde by the procedure described in Example 18. $^1$H NMR (200 MHz, CD$_3$OD): 0.97 (t,8 Hz, 3H), 1.32 (s,3H), 1.36 (s,3H), 1.65 (m,2H), 2.0–2.6 (m,8H), 2.93 (t,7 Hz, 2H), 4.33 (dd;7,11 Hz; 1H), 4.89 (d,15 Hz, 1H), 5.18 (d,15 Hz, 1H), 6.99 (d,8 Hz, 2H), 7.10–7.35 (m,6H), 7.45–7.65 (m,4H). FAB-MS: calculated for $C_{32}H_{37}N_7O_2$ 551; found 552 (M+H,73%).

EXAMPLE 43

3-(Cyclopropylmethyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) and cyclopropanecarboxaldehyde by the procedure described in Example 18. $^1$H NMR (200 MHz, CD$_3$OD): 0.37 (m,2H), 0.65 (m,2H), 1.00 (m,1H), 1.34 (s,3H), 1.36 (s,3H), 2.0–2.6 (m,6H), 2.88 (d,7 Hz, 2H), 4.33 (dd;7,11 Hz; 1H), 4.89 (d,15 Hz, 1H), 5.18 (d,15 Hz, 1H), 7.01 (d,8 Hz, 2H), 7.15–7.35 (m,6H), 7.45–7.70 (m,4H). FAB-MS: calculated for $C_{33}H_{37}N_7O_2$ 563; found 564 (M+H,100%).

EXAMPLE 44

3-(Cyclohexylmethyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) and cyclohexanecarboxaldehyde by the procedure described in Example 18. $^1$H NMR (200 MHz, CD$_3$OD): 0.8–1.4 (m,6H), 1.33 (s,3H), 1.37 (s,3H), 1.5–1.9 (m,5H), 2.0–2.6 (m,6H), 2.80 (d,7 Hz, 2H), 4.32 (dd;8,12 Hz; 1H), 4.92 (d,15 Hz, 1H), 5.14 (d,15 Hz, 1H), 7.00 (d,8 Hz, 2H), 7.10–7.35 (m,6H), 7.45–7.70 (m,4H). FAB-MS: calculated for $C_{36}H_{43}N_7O_2$ 605; found 606 (M+H,100%).

EXAMPLE 45

3-(4-hydroxybenzyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate Step A:
3-(4-benzyloxybenzyl)amino-3-methyl-N-[2,3,4,5-tetrahydro-2-oxo-1-[[2'-(1H-tetrazol-5-yl)-[1,1'-biphenyl]-4-yl]methyl]-1H-1-benzazepin-3(R)-yl]-butanamide, trifluoroacetate Prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide trifluoroacetate (Example 1) and 4-benzyloxybenzaldehyde by the procedure described in Example 18. $^1$H NMR (200 MHz, CD$_3$OD): 1.32 (s,3H), 1.35 (s,3H), 2.0–2.7 (m,6H), 4.10 (s,2H), 4.36 (dd;8,12 Hz; 1H), 4.91 (d,15 Hz, 1H), 5.02 (s,2H), 5.09 (d,15 Hz, 1H), 6.98 (d,8 Hz, 6H), 7.1–7.6 (m,15H). FAB-MS: calculated for $C_{43}H_{43}N_7O_3$ 705; found 706 (M+H,100%).

Step B:
3-(4-Hydroxybenzyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The intermediate obtained in Step A (14.6 mg, 0.018 mmol) dissolved in 1.5 mL of methanol was hydrogenated at room temperature and one atmosphere over 10 mg of 10% Pd/C for 2 hours. The reaction mixture was filtered through Celite and the filtrate concentrated under vacuum. The residue was purified by reverse phase HPLC on C-18 eluting with methanol/0.1% aqueous trifluoroacetic acid (linear gradient: 60% methanol increased to 75% methanol over 10 minutes) to afford 8.1 mg (0.011 mmol, 62%) of the title compound. $^1$H NMR (200 MHz, CD$_3$OD): 1.40 (s,3H), 1.44 (s,3H), 2.0–2.7 (m,6H), 4.08 (s,2H), 4.36 (m,1H), 4.87 (d,15 Hz, 1H), 5.20 (d,15 Hz, 1H), 6.78 (d,8 Hz, 2H), 6.96 (d,8 Hz, 2H), 7.1–7.7 (m,12H). FAB-MS: calculated for C$_{36}$H$_{37}$N$_7$O$_3$ 615; found 616 (M+H,46%).

EXAMPLE 46

3-Amino-3-methyl-N-[3,4-dihydro-4-oxo-5-[[2'-(1H-tetrazol-5-yl)[1,1'-biphenyl]-4-yl]methyl]-1,5-benzothiazepin-3(S)-yl]-butanamide, trifluoroacetate

Step A:
3-t-Butoxycarbonylamino-3-methyl-N-[3,4-dihydro-4-oxo-1,5-benzothiazepin-3(S)-yl]-butanamide Prepared from 3(S)-amino-3,4-dihydro-1,5-benzothiazepin-4(5H)-one (prepared from D-cysteine (S-cysteine) by the method of Slade, et al, J. Med. Chem., 28, 1517–1521 (1985)) and 3-t-butoxycarbonylamino-3-methylbutanoic acid (Example 31, Step E) by the procedure described in Example 1, Step F. $^1$H NMR (200 MHz, CDCl$_3$): 1.38 (s,6H), 1.45 (s,9H), 2.32 (d,10 Hz, 1H), 2.50 (d,14 Hz, 1H), 2.70 (d,14 Hz, 1H), 2.92 (T,11 Hz, 1H), 3.93 (dd;7,11 Hz; 1H), 4.76 (m,1H), 7.02 (d,8 Hz, 1H), 7.1–7.3 (m,2H), 7.40 (t,8 Hz, 1H), 7.66 (d,7 Hz, 1H), 8.23 (br s,1H). FAB-MS: calculated for C$_{19}$H$_{27}$N$_3$O$_4$S 393; found 394 (M+H,36%).

Step B:
3-t-Butoxycarbonylamino-3-methyl-N-[3,4-dihydro-4-oxo-5-[[2'-(N-triphenylmethyl)-tetrazol-5-yl][1,1'-biphenyl]-4-yl]methyl]-1,5-benzothiazepin-3(S)-yl]-butanamide Prepared from the intermediate obtained in Step A and N-triphenylmethyl-5-[2-(4'-bromomethylbiphen-4-yl)]tetrazole by the procedure described in Example 1, Step K. $^1$H NMR (200 MHz, CD$_3$OD): 1.32 (s,6H), 1.39 (s,9H), 2.26 (d,7 Hz, 1H), 2.47 (d,14 Hz, 1H), 2.63 (d,14 Hz, 1H), 3.01 (t,11 Hz, 1H), 3.60 (dd;7,11 Hz; 1H), 4.76 (dd;7,11 Hz; 1H), 5.05 (br s,2H), 6.9–7.6 (m,26H), 7.80 (m,1H). FAB-MS (Li+ spike): calculated for C$_{52}$H$_{51}$N$_7$O$_4$S 870; found 876 (M+Li,100%).

Step C:
3-Amino-3-methyl-N-[3,4-dihydro-4-oxo-5-[[2'-(1H-tetrazol-5-yl)[1,1'-biphenyl]-4-yl]-methyl]-1,5-benzothiazepin-3(S)-yl]-butanamide, trifluoroacetate The title compound was prepared from the intermediate obtained in Step B by the procedure described in Example 31, Step A. $^1$H NMR (200 MHz, CD$_3$OD): 1.38 (s,3H), 1.40 (s,3H), 2.55 (br s,2H), 3.09 (t,11 Hz, 1H), 3.64 (dd;7,11 Hz; 1H), 4.65 (dd;7,11 Hz; 1H), 5.07 (d,15 Hz, 1H), 5.24 (d,15 Hz, 1H), 7.06 (d,8 Hz, 2H), 7.3–7.7 (m,10H). FAB-MS: calculated for C$_{28}$H$_{29}$N$_7$O$_2$S 527; found 528 (M+H,100%).

EXAMPLE 47

3-Amino-3-methyl-N-[3,4-dihydro-1,1,4-trioxo-5-[[2'-(1H-tetrazol-5-yl)[1,1'-biphenyl]-4-yl]methyl]-1,5-benzothiazepin-3(S)-yl]-butanamide, trifluoroacetate

Step A:
3-t-Butoxycarbonylamino-3-methyl-N-[3,4-dihydro-1,1,4-trioxo-1,5-benzothiazepin-3(S)-yl]-butanamide To a solution of 88 mg (0.22 mmol) of 3-t-butoxycarbonylamino-3-methyl-N-[3,4-dihydro-4-oxo-1,5-benzothiazepin-3(S)-yl]-butanamide (Example 46, Step A) in 2 mL of dry methylene chloride under nitrogen was added 38 mg of solid sodium bicarbonate (0.44 mmol, 2 eq) followed by 106 mg of 80% m-chloroperbenzoic acid (85 mg mCPBA, 0.49 mmol, 2.2 eq). The mixture was stirred at room temperature for 3 hours then concentrated under vacuum. The residue was chromatographed on silica, eluting with ethyl acetate/hexane (7:3). The chromatographed material was redissolved in 50 mL of ethyl acetate, washed with 1:1 saturated aqueous sodium chloride/saturated aqueous potassium carbonate, then brine, dried over magnesium sulfate, filtered and evaporated under vacuum to afford 86 mg (0.20 mmol, 91%) of the product. $^1$H NMR (200 MHz, CDCl$_3$): 1.36 (s,3H), 1.38 (s,3H), 1.45 (s,9H), 2.51 (d,13 Hz, 1H), 2.83 (d,13 Hz, 1H), 3.58 (dd;12,14 Hz, 1H), 4.33 (dd;8,14 Hz; 1H), 4.90 (m,2H), 7.30 (m,2H), 7.46 (t,8 Hz, 1H), 7.70 (t,8 Hz, 1H), 8.07 (d,8 Hz, 1H), 8.70 (br s,1H). FAB-MS: calculated for C$_{19}$H$_{27}$N$_3$O$_6$S 425; found 426 (M+H,32%).

Step B:
3-t-Butoxycarbonylamino-3-methyl-N-[3,4-dihydro-1,1,4-trioxo-5-[[2'-(N-triphenylmethyl)-tetrazol-5-yl][1,1'-biphenyl]-4-yl]-methyl]-1,5-benzothiazepin-3(S)-yl]-butanamide Prepared from the intermediate obtained in Step A and N-triphenylmethyl-5-[2-(4'-bromomethylbiphen-4-yl)]tetrazole by the procedure described in Example 1, Step K. $^1$H NMR (200 MHz, CDCl$_3$): 1.35 (s,3H), 1.37 (s,3H), 1.47 (s,9H), 2.45 (d,13 Hz, 1H), 2.81 (d,13 Hz, 1H), 3.40 (dd;11,14 Hz, 1H), 4.18 (m,3H), 4.80 (m,2H), 5.65 (d,15 Hz, 1H), 6.9–7.6 (m,25H), 7.95 (m,2H). FAB-MS (Li+ spike): calculated for C$_{52}$H$_{51}$N$_7$O$_6$S 902; found 909 (M+Li,100%).

Step C:
3-Amino-3-methyl-N-[3,4-dihydro-1,1,4-trioxo-5-[[2'-(1H-tetrazol-5-yl)[1,1'-biphenyl]-4-yl]methyl]-1,5-benzothiazepin-3(S)-yl]-butanamide, trifluoroacetate Prepared from the intermediate obtained in Step B by the procedure described in Example 31, Step H. $^1$H NMR (200 MHz, CD$_3$OD): 1.32 (br s,6H), 2.51 (br s,2H), 3.64 (dd;12,14 Hz, 1H), 3.98 (dd;8,14;1H), 4.54 (c,16 Hz, 1H), 4.78 (m,1H), 5.43 (d,16 Hz, 1H), 7.08 (d,8 Hz, 2H), 7.30 (m,3H), 7.5–7.8 (m,6H), 8.00 (d,8 Hz, 1H).

FAB-MS: calculated for $C_{28}H_{29}N_7O_4S$ 559; found 560 (M+H,100%).

EXAMPLE 48

3-Amino-3-methyl-N-[3,4-dihydro-1,4-dioxo-5-[[2'-(1H-tetrazol-5-yl)[1,1'-biphenyl]-4-yl]methyl]-1,5-benzothiazepin-3(S)-yl]-butanamide, trifluoroacetate [diastereomer A]

Step A:
3-t-Butoxycarbonylamino-3-methyl-N-[3,4-dihydro-1,4-dioxo-1,5-benzothiazepin-3(S)-yl]-butanamide, diastereomers A and B A solution of 179 mg (0.46 mmol) of 3-t-butoxycarbonylamino-3-methyl-N-[3,4-dihydro-4-oxo-1,5-benzothiazepin-3(S)-yl]-butanamide (Example 46, Step A) in 4.5 mL of methanol/water (5:1) was treated with 102 mg (0.48 mmol, 1.05 eq) of sodium periodate and stirred at room temperature for 48 hours. The reaction mixture was filtered and the filtrate concentrated under vacuum. The residue was redissolved in chloroform, dried over potassium carbonate, filtered and concentrated under vacuum. Purification by flash chromatography on silica, eluting with ethyl acetate, afforded 47 mg (0.12 mmol, 25%) of the less polar, minor diastereomer A in addition to 105 mg (0.26 mmol, 56%) of the more polar, major diastereomer B.

$^1$H NMR (diastereomer A; 200 MHz, CDCl$_3$): 1.37 (s,3H), 1.38 (s,3H), 1.45 (s,9H), 2.51 (d,13 Hz, 1H), 2.79 (d,13 Hz, 1H), 3.80 (m,2H), 4.78 (m,1H), 4.95 (br s,1H), 7.14 (m,2H), 7.59 (m,2H), 7.93 (m,1H), 8.18 (br s,1H). FAB-MS: calculated for $C_{19}H_{27}N_3O_5S$ 409; found 410 (M+H,29%).

Step B:
3-t-Butoxycarbonylamino-3-methyl-N-[3,4-dihydro-1,4-dioxo-5-[[2'-(N-triphenylmethyl)-tetrazol-5-yl][1,1'-biphenyl]-4-yl]methyl]-1,5-benzothiazepin-3(S)-yl]-butanamide, diastereomer A Prepared from diastereomer A obtained in Step A and N-triphenylmethyl-5-[2-(4'-bromomethylbiphen-4-yl)] tetrazole by the procedure described in Example 1, Step K. $^1$H NMR (200 MHz, CDCl$_3$): 1.35 (s,3H), 1.36 (s,3H), 1.44 (s,9H), 2.45 (d,13 Hz, 1H), 2.72 (d,13 Hz, 1H), 3.61 (m,2H), 4.63 (m,1H), 4.86 (m,2H), 6.9–7.6 (m,25H), 7.81 (m,1H), 7.90 (m,1H). FAB-MS (Li$^+$ spike): calculated for $C_{52}H_{51}N_7O_5S$ 886; found 893 (M+Li,95%).

Step C:
3-Amino-3-methyl-N-[3,4-dihydro-1,4-dioxo-5-[[2'-(1H-tetrazol-5-yl)[1,1'-biphenyl]-4-yl]-methyl]-1,5-benzothiazepin-3(S)-yl]-butanamide, trifluoroacetate, diastereomer A The title compound was prepared from the intermediate obtained in Step B by the procedure described in Example 31, Step H. $^1$H NMR (200 MHz, CD$_3$OD): 1.32 (br s,6H), 2.51 br s,2H), 3.32 (dd;8,11 Hz; 1H), 3.95 (t,11 Hz, 1H), 4.55 (dd;8,11 Hz; 1H), 4.85 (d,15 Hz, 1H), 5.22 (d,15 Hz, 1H), 7.01 (d,8 Hz, 2H), 7.17 (d,8 Hz, 2H), 7.4–7.8 (m,8H). FAB-MS: calculated for $C_{28}H_{29}N_7O_3S$ 543; found 544 (M+H,100%).

EXAMPLE 49

3-Amino-3-methyl-N-[3,4-dihydro-1,4-dioxo-5-[[2'-(1H-tetrazol-5-yl)[1,1'-biphenyl]-4-yl]methyl]-1,5-benzothiazepin-3(S)-yl]-butanamide, trifluoroacetate [diastereomer B]

Step A:
3-t-Butoxycarbonylamino-3-methyl-N-[3,4-dihydro-1,4-dioxo-1,5-benzothiazepin-3(S)-yl]-butanamide, diastereomer B Prepared from 3-t-butoxycarbonylamino-3-methyl-N-[3,4-dihydro-4-oxo-1,5-benzothiazepin-3(S)-yl]-butanamide (Example 46, Step A) by the procedure described in Example 48, Step A. $^1$H NMR (diastereomer B; 200 MHz, CDCl$_3$): 1.37 (s,3H), 1.38 (s,3H), 1.44 (s,9H), 2.48 (d,14 Hz, 1H), 2.68 (d,14 Hz, 1H), 3.30 (dd;11,15 Hz; 1H), 4.14 (dd;8,15 Hz; 1H), 4.86 (m,1H), 7.1 (d,8 Hz, 1H), 7.25 (m, 1H), 7.41 (m,1H), 7.55 (m,1H), 8.81 (br s,1H). FAB-MS: calculated for $C_{19}H_{27}N_3O_5S$ 409; found 410 (M+H,38%).

Step B:
3-t-Butoxycarbonylamino-3-methyl-N-[3,4-dihydro-1,4-dioxo-5-[[2'-(N-triphenylmethyl)-tetrazol-5-yl][1,1'-biphenyl]-4-yl]methyl]-1,5-benzothiazepin-3(S)-yl]-butanamide, diastereomer B Prepared from the intermediate obtained in Step A and N-triphenylmethyl-5-[2-(4'-bromomethylbiphen-4-yl)] tetrazole by the procedure described in Example 1, Step K. $^1$H NMR (200 MHz, CDCl$_3$): 1.38 (s,6H), 1.45 (s,9H), 2.50 (d,14 Hz, 1H), 2.72 (c,14 Hz, 1H), 3.10 (dd;10,15 Hz; 1H), 4.05 (m,2H), 4.85 (m,1H), 5.08 (br s,1H), 5.68 (d,15 Hz, 1H), 6.9–7.5 (m,26H), 7.92 (m,1H). FAB-MS (Li$^+$ spike): calculated for $C_{52}H_{51}N_7O_5S$ 886; found 893 (M+li,64%).

Step C:
3-Amino-3-methyl-N-[3,4-dihydro-1,4-dioxo-5-[[2'-(1H-tetrazol-5-yl)[1,1'-biphenyl]-4-yl]-methyl]-1,5-benzothiazepin-3(S)-yl]-butanamide, trifluoroacetate, [diastereomer B]

The title compound was prepared from the intermediate obtained in Step B by the procedure described in Example 31, Step H. $^1$H NMR (200 MHz, CD$_3$OD): 1.33 (br s,6H), 2.53 (br s,2H), 3.29 (dd;11,14 Hz; 1H), 3.89 (dd,7,14; 1H), 4.48 (d,16 Hz, 1H), 4.82 (m,1H), 5.33 (d,16 Hz, 1H), 7.0–7.7 (m,12H). FAB-MS: calculated for $C_{28}H_{29}N_7O_3S$ 543; found 544 (M+H,100%).

EXAMPLE 50

3-Amino-3-methyl-N-[3,4-dihydro-3-oxo-4-[[2'-(1H-tetrazol-5-yl)[1,1'-biphenyl]-4-yl]methyl]-2H-1,4-benzothiazin-2-yl]-butanamide, mono(trifluoroacetate)

Step A:
2-Amino-3,4-dihydro-3-oxo-2H-1,4-benzothiazine

Anhydrous ammonia gas was bubbled for one hour through a suspension of 500 mg (2.5 mmol) of 2-chloro-3,4-dihydro-3-oxo-2H-1,4-benzothiazine (prepared by the method of Worley, et al; J. Org. Chem., 40, 1731–1734 (1975)) in 5 mL of methylene chloride. The mixture was filtered through Celite and the filtrate evaporated under vacuum. The residue was triturated with 20 mL of chloroform, filtered and the filtrate evaporated under vacuum. Purification by flash chromatography on silica, eluting with ethyl acetate, afforded 185 mg (1.0 mmol, 41%) of the product. $^1$H NMR (200 MHz, CDCl$_3$): 2.00 (br s,2H), 4.68 (br s,1H), 6.9–7.4 (m,4H), 9.05 (br s,1H). FAB-MS: calculated for C$_8$H$_8$N$_2$OS 180; found 181 (M+h,54%).

Step B:
3-t-Butoxycarbonylamino-3-methyl-N-[3,4-dihydro-3-oxo-2H-1,4-benzothiazin-2-yl]-butanamide Prepared from 2-amino-3,4-dihydro-3-oxo-2H-1,4-benzothiazine (Step A) and 3-t-butoxycarbonyl-amino-3-methylbutanoic acid (Example 31, Step E) by the procedure described in Example 1, Step F. $^1$H NMR (200 MHz, CD$_3$OD): 1.26 (s,6H), 1.36 (s,9H), 2.47 (d,13 Hz, 1H), 2.57 (d,13 Hz, 1H), 5.52 (br s,1H), 6.31 (br s,1H), 7.00 (m,2H), 722 (m,2H). FAB-MS: calculated for C$_{18}$H$_{25}$N$_3$O$_4$S 379; found 380 (M+H,26%).

Step C:
3-t-Butoxycarbonylamino-3-methyl-N-[3,4-dihydro-3-oxo-4-[[2'-(N-triphenylmethyl)-tetrazol-5-yl][1,1'-biphenyl]-4-yl]methyl]-2H-1,4-benzothiazin-2-yl]-butanamide Prepared from the intermediate obtained in Step B and N-triphenylmethyl-5-[2-(4'-bromomethyl-biphen-4-yl)] tetrazole by the procedure described in Example 1, Step K. $^1$H NMR (200 MHz, CDCl$_3$): 1.40 (s,6H), 1.42 (s,9H), 2.53 (d,14 Hz, 1H), 2.92 (d,14 Hz, 1H), 4.86 (d,16 Hz, 1H), 4.92 (d,8 Hz, 1H), 5.29 (d,16 Hz, 1H), 5.49 (d,8 Hz, 1H), 6.85–7.50 (m,26H), 7.92 (m,1H).

Step D:
3-Amino-3-methyl-N-[3,4-dihydro-3-oxo-4-[[2'-(1H-tetrazol-5-yl)[1,1'-biphenyl]-4-yl]-methyl]-2H-1,4-benzothiazin-2-yl]-butanamide, trifluoroacetate The title compound was prepared from the intermediate obtained in Step C by the procedure described in Example 31, Step H. $^1$H NMR (200 MHz, CD$_3$OD): 1.40 (s,6H), 2.62 (s,2H), 5.34 (s,2H), 5.73 (s,1H), 7.0–7.7 (m,12H). FAB-MS: calculated for C$_{27}$H$_{27}$N$_7$O$_2$S 513; found 514 (M+H,100%).

EXAMPLE 51

3-Amino-3-methyl-N-[2,3,4,5-tetrahydro-2-oxo-1-[2-phenylethyl]-1H-1-benzazepin-3-yl]-butanamide, trifluoroacetate Step A:
3-Benzyloxycarbonylamino-3-methyl-N-[2,3,4,5-tetrahydro-2-oxo-1H-1-benzazepin-3-yl]-butanamide Prepared from 3-amino-2,3,4,5-tetrahydro-1H[1]benzazepin-2-one (Example 1, Step A) and 3-benzyloxycarbonylamino-3-methylbutanoic acid (Example 1, Step E) by the procedure described in Example 1, Step F. $^1$H NMR (200 MHz, CDCl$_3$): 1.38 (s,3H), 1.39 (s,3H), 1.82 (m,1H), 2.52 (s,2H), 2.5–3.0 (m,3H), 4.51 (m,1H), 5.07 (br s,2H), 5.58 (br s,1H), 6.68 (d,7 Hz, 1H), 6.96 (d,8 Hz, 1H), 7.1–7.4 (m,8H), 7.62 (br s, 1H). FAB-MS: calculated for C$_{23}$H$_{27}$N$_3$O$_4$ 409; found 410 (M+H,100%).

Step B
3-Benzyloxycarbonylamino-3-methyl-N-[2,3,4,5-tetrahydro-2-oxo-1-[2-phenylethyl]-1H-1-benzazepin-3-yl]-butanamide Prepared from the intermediate obtained in Step A and 2-phenethyl bromide by the procedure described in Example 3, Step A. $^1$H NMR (200 MHz, CDCl$_3$): 1.37 (s,6H), 1.68 (m,2H), 2.50 (m,4H), 2.7–3.0 (m,2H), 3.70 (m,1H), 4.48 (m,2H), 5.05 (s,2H), 5.66 (s,1H), 6.99 (m,1H), 7.0–7.4 (m,14H). FAB-MS: calculated for C$_{31}$H$_{35}$N$_3$O$_4$ 513; found 514 (M+H,100%).

Step C
3-amino-3-methyl-N-[2,3,4,5-tetrahydro-2-oxo-1-[2-phenylethyl]-1H-1-benzazepin-3-yl]-butanamide, trifluoroacetate The title compound was prepared from the intermediate obtained in Step B by the procedure described in Example 3, Step B. $^1$H NMR (200 MHz, CD$_3$OD): 1.34 (s,3H), 1.42 (s,3H), 2.0–2.4 (m,1H), 2.58 (m,3H), 2.85 (m,2H), 3.90 (m,1H), 4.58 (m,1H), 4.90 (d,15 Hz, 1H), 5.0 (m,1H), 5.15 (d,15 Hz, 1H), 7.0–7.5 (m,9H). FAB-MS: calculated for C$_{23}$H$_{29}$N$_3$O$_2$ 379; found 380 (M+1,100%).

EXAMPLE 52

3-Amino-3-methyl-N-[2,3,4,5-tetrahydro-2-oxo-1-[3-phenylpropyl]-1H-1-benzazepin-3-yl]-butanamide, trifluoroacetate Step A
3-Benzyloxycarbonylamino-3-methyl-N-[2,3,4,-5-tetrahydro-2-oxo-1-[3-phenylpropyl]-1H-1-benzazepin-3-yl]-butanamide Prepared from 3- benzyloxycarbonylamino-3-methyl-N-[2,3,4,5tetrahydro-2-oxo-1H-1-benzazepin-3-yl]-butanamide (Example 51, Step A) and 3-phenylpropyl bromide by the procedure described in Example 3, Step A. $^1$H NMR (200 MHz, CDCl$_3$): 1.38 (s,6H), 1.82 (m,4H), 2.4–2.9 (m,7H), 3.45 (m,1H), 4.36 (m,1H), 5.02 (s,2H), 5.64 (s,1H), 6.69 (d,8 Hz,1H), 6.9–7.4 (m,14H). FAB-MS: calculated for C$_{32}$H$_{37}$N$_3$O$_4$ 527; found 528 (M+H,100%).

Step B
3-Amino-3-methyl-N-[2,3,4,5-tetrahydro-2-oxo-1-[3-phenylpropyl]-1H-1-benzazepin-3-ly]-butanamide, trifluoroacetate The title compound was prepared from the intermediate obtained in Step A by the procedure described in Example 3, Step B. $^1$H NMR (200 MHz, CD$_3$OD): 1.21 (s,6H), 1.7–2.1 (m,2H), 2.1–2.4 (m,2H), 2.5–2.9 (m,6H), 3.46 (m,1H), 4.37 (m,2H), 6.9–7.3 (m,9H). FAB-MS: calculated for C$_{24}$H$_{31}$N$_3$O$_2$ 393; found 394 (M+1,100%).

EXAMPLE 53

4-Amino-4-methyl-N-[2,3,4,5-tetrahydro-2-oxo-1-[[2'-(1H-tetrazol-5-yl)[1,1'-biphenyl]-4-yl]methyl]-1H-1-benzazepin-3-yl]-pentanamide, trifluoroacetate Step A:
3-Amino-2,3,4,5-tetrahydro-1-[[2'-(1H-tetrazol-5-yl)[1,1'-biphenyl]-4-yl]methyl]-2H-1-benzazepin-2-one, hydrochloride Prepared from 3-amino-2,3,4,5-tetrahydro-1H-1-benzazepin-2-one (Example 1, Step A) by the procedures described in Example 4, Steps A, B and C. $^1$H NMR (200 MHz, CD$_3$OD): 2.17 (m,1H), 2.3–2.6 (m,3H), 3.80 (dd;8,12 Hz; 1H), 4.78 (d,15 Hz, 1H), 5.38 (d,15 Hz, 1H), 6.95 (d,8 Hz, 2H), 7.17 (d,8 Hz, 2H), 7.28 (m,2H), 7.38 (m,2H), 7.5–7.7 (m,4H). FAB-MS: calc. for C$_{24}$H$_{22}$N$_6$O 410; found 411 (M+H,100%).

Step B: 4-Benzyloxycarbonylamino-4-methylpentanoic acid

Prepared from 2,2-dimethylglutaric acid by the procedures described in Example 1, Steps C, D and E. $^1$H NMR (200 MHz, CDCl$_3$): 1.29 (s,6H), 2.02 (t,6 Hz, 2H), 2.34 (t, 6 Hz, 2H), 5.06 (s,2H), 7.34 (s,5H), 10.5 (br s,1H).

Step C:
4-Benzyloxycarbonylamino-4-methyl-N-[2,3,4,-5-tetrahydro-2-oxo-1-[[2'-(1H-tetrazol-5-yl)-[1,1'-biphenyl]-4-yl]methyl-1H-benzazepin-3-yl]-pentanamide Prepared from the intermediates obtained in Steps A and B by the procedure described in Example 4, Step D. $^1$H NMR (200 MHz, CD$_3$OD): 1.30 (s,6H), 1.9–2.6 (m,8H), 4.38 (m,1H), 4.86 (d,13 Hz, 1H), 4.98 (s,2H), 5.16 (d,13 Hz, 1H), 6.97 (d,8 Hz, 2H), 7.1–7.3 (m,11H), 7.4–7.7 (m,4H). FAB-MS: calculated for C$_{38}$H$_{39}$N$_7$O$_4$ 657; found 658 (m+H,20%).

Step D:
4-Amino-4-methyl-N-[2,3,4,5-tetrahydro-2-oxo-1-[[2'-(1H-tetrazol-5-yl)[1,1'-biphenyl]-4-yl]methyl]-1H-1-benzazepin-3-yl]-pentanamide, trifluoroacetate The title compound was prepared from the intermediate obtained in Step C by the procedure described in Example 1, Step H. $^1$H NMR (200 MHz, CD$_3$OD): 1.29 (s,3H), 1.31 (s,3H), 1.8–2.6 (m,8H), 4.29 (dd;8,12 Hz; 1H), 4.94 (d,13 Hz, 1H), 5.16 (d,13 Hz, 1H), 6.99 (d,8 Hz, 2H), 7.1–7.3 (m,6H), 7.4–7.7 (m,4H). FAB-MS: calculated for C$_{30}$H$_{33}$N$_7$O$_2$ 523; found 524 (M+H,100%)

EXAMPLE 54

Piperidine-N'-[2,3,4,5-tetrahydro-2-oxo-1-[[2'-(1H-tetrazol-5-yl)[1,1'-biphenyl]-4-yl]methyl]-1H-1-benzazepin-3-yl]-4-carboxamide, trifluoroacetate Step A: N-(t-Butoxycarbonyl)piperidine-4-carboxylic acid To a suspension of 1.0 g (7.74 mmol) of piperidine-4-carboxylic acid in 20 mL of methylene chloride at room temperature was added 1.13 mL of triethylamine (0.82 g, 8.1 mmol, 1.05 eq) followed by 1.87 mL of di-t-butyl-dicarbonate (1.77 g, 8.1 mmol, 1.05 eq). The mixture was stirred at room temperature for 48 hours then concentrated under vacuum. The residue was redissolved in ethyl acetate and the solution washed with 5% citric acid and brine, then dried over magnesium sulfate, filtered and evaporated under vacuum to afford 1.75 g (7.63 mmol, 98%) of the product. $^1$H NMR (200 MHz, CD$_3$OD): 1.42 (s,9H), 1.50 (m,2H), 1.84 (m,2H), 2.46 (m,1H), 2.86 (t,9 Hz, 2H), 3.91 (t,3 Hz, 1H), 3.98 (t,3 Hz, 1H). FAB-MS: calculated for C$_{11}$H$_{19}$NO$_4$ 229; found 230 (M+H,17%).

Step B:
N-(t-butoxycarbonyl)piperidine-N'-[2,3,4,5-tetrahydro-2-oxo-1-[[2'-(1H-tetrazol-5-yl)-[1,1'-biphenyl]-4-yl]methyl]-1H-1-benzazepin-3-yl]-piperidine-4-carboxamide Prepared from N-(t-butoxycarbonyl)piperidine-4-carboxylic acid and 3-amino-1,3,4,5-tetrahydro-1-[[2'-(1H-tetrazol-5-yl)[1,1'-biphenyl]-4-yl]methyl]-2H-1-benzazepin-2-one hydrochloride (Example 53, Step A) by the procedure described in Example 4, Step D. $^1$H NMR (200 MHz, CD$_3$OD): 1.42 (s,9H), 1.4–2.9 (m,11H), 4.05 (m,3H), 4.30 (m,1H), 4.81 (d,15 Hz, 1H), 5.22 (d,15 Hz, 1H), 6.98 (d,8 Hz, 2H), 7.1–7.3 (m,6H), 7.4–7.7 (m,4H). FAB-MS: calculated for C$_{35}$H$_{39}$N$_7$O$_4$ 621; found 622 (M+H,7%).

Step C:
Piperidine-N'-[2,3,4,5-tetrahydro-2-oxo-1-[[2'-(1H-tetrazol-5-yl)[1,1'-biphenyl]-4-yl]-methyl]-1H-1-benzazepin-3-yl]-4-carboxamide, trifluoroacetate The title compound was prepared from the intermediate obtained in Step B by the procedure described in Example 31, Step H. $^1$H NMR (200 MHz, CD$_3$OD): 1.7–2.7 (m,8H), 3.00 (m,3H), 3.38 (m,2H), 4.31 (dd;8,12 Hz; 1H), 4.86 (d,15 Hz, 1H), 5.20 (d,15 Hz, 1H), 6.99 (d,8 Hz, 2H), 7.1–7.4 (m,6H), 7.4–7.7 (m,4H). FAB-MS: calculated for C$_{30}$H$_{31}$N$_7$O$_2$ 521; found 522 (M+H,100%).

EXAMPLE 55

Piperidine-N'-[2,3,4,5-tetrahydro-2-oxo-1-[[2'-(1H-tetrazol-5-yl)[1,1'-biphenyl]-4-yl]methyl]-1H-1-benzazepin-3-yl]-3-carboxamide, trifluoroacetate The title compound was prepared from piperidine-3-carboxylic acid and 3-amino-1,3,4,5-tetrahydro-1-[[2'-(1H-tetrazol-5-yl)[1,1'-biphenyl]-4-ly]methyl]-2H-1-benzazepin-2-one hydrochloride (Example 53, Step A) by the procedures described in Example 54. $^1$H NMR (200 MHz, CD$_3$OD): 1.6–2.2 (m,5H), 2.28 (m,1H), 2.50 (m,2H), 2.79 (m,1H), 3.19 (m,4H), 4.30 (m,1H), 4.86 (d,14 Hz, 1H), 5.17 (d,14 Hz, 1H), 6.99 (m,4H), 7.20 (m,4H), 7.55 (m,3H), 8.38 (m,1H). FAB-MS: calculated for C$_{30}$H$_{31}$N$_7$O$_2$ 521; found 522 (M+H,100%).

EXAMPLE 56

Quinuclidine-N'-[2,3,4,5-tetrahydro-2-oxo-1-[[2'-(1H-tetrazol-5-yl)[1,1'-biphenyl]-4-yl]methyl]-1H-1-benzazepin-3-yl]-3-carboxamide, trifluoroacetate The title compound, as a mixture of four diastereomers, was prepared from racemic quinuclidine-3-carboxylic acid and 3-amino-1,3,4,5-tetrahydro-1-[[2'-(1H-tetrazol-5-yl)[1,1'-biphenyl]-4-yl]methyl]-2H-1-benzazepin-2-one hydrochloride (Example 53, Step A) by the procedures described in Example 4, Step D. $^1$H NMR (200 MHz, CD$_3$OD): 1.7–2.7 (m,8H), 3.0–3.7

(m,8H), 4.32 (m,1H), 4.8–5.2 (m,2H), 7.00 (d,8 Hz, 2H), 7.1–7.4 (m,6H), 7.4–7.7 (m,4H). FAB-MS: calculated for $C_{32}H_{33}N_7O_2$ 547; found 531 (22%).

EXAMPLE 57

3-Amino-3-methyl-N-[2,3,4,5-tetrahydro-2-oxo-1-[[[1,1'-biphenyl]-4-yl]methyl]-1H-1-benzazepin-3(R)-yl]-butanamide, trifluoroacetate

Step A:
3-t-Butoxycarbonylamino-3-methyl-N-[2,3,4,5-tetrahydro-2-oxo-1H-1-benzazepin-3(R)-yl]-butanamide Prepared from 3-t-butoxycarbonylamino-3-methyl-butanoic acid (Example 31, Step E) and 3(R)-amino-2,3,4,5-tetrahydro-1H-1-benzazepin-2-one (Example 1, Step B) by the procedure described in Example 1, Step F. $^1$H NMR (200 MHz, CDCl$_3$): 1.37 (s,6H), 1.44 (s,9H), 1.95 (m,1H), 2.46 (d,15 Hz, 1H), 2.59 (d,15 Hz, 1H), 2.6–3.0, (m,3H), 4.53 (m,1H), 5.30 (br s,1H), 6.72 (d,7 Hz, 1H), 6.98 (d,8 Hz,1H), 7.1–7.3 (m,3H), 7.82 (br s,1H). FAB-MS: calculated for $C_{20}H_{29}N_3O_4$ 375; found 376 (M+H,70%).

Step B:
3-t-Butoxycarbonylamino-3-methyl-N-[2,3,4,5-tetrahydro-2-oxo-1-[[[1,1'-biphenyl]-4-yl]-methyl]-1H-1-benzazepin-3(R)-yl]-butanamide Prepared from the intermediate obtained in Step A and 4-chloromethylbiphenyl by the procedure described in Example 1, Step K. FAB-MS: calculated for $C_{33}H_{39}N_3O_4$ 541; found 542 (M+H,31%).

Step C:
3-amino-3-methyl-N-[2,3,4,5-tetrahydro-2-oxo-1-[[[1,1'-biphenyl]-4-yl]methyl]-1H-1-benzazepin-3(R)-yl]-butanamide, trifluoroacetate The title compound was prepared from the intermediate obtained in Step B by the procedure described in Example 31, Step H. $^1$H NMR (200 MHz, CD$_3$OD): 1.33 (s,3H), 1.36 (s,3H), 2.0–2.6 (m,6H), 4.38 (dd;8,12 Hz; 1H), 4.89 (d,15 Hz, 1H), 5.24 (d,15 Hz, 1H), 7.1–7.6 (m,13H). FAB-MS: calculated for $C_{28}H_{31}N_3O_2$ 441; found 442 (M+H,100%).

EXAMPLE 58

3-amino-3-methyl-N-[2,3,4,5-tetrahydro-2-oxo-1-[[2'-carboxy][1,1'-biphenyl]-4-yl]methyl]-1H-1-benzazepin-3-yl]-butanamide

Step A:
3-t-butoxycarbonylamino-3-methyl-N-[2,3,4,5-tetrahydro-2-oxo-1H-1-benzazepin-3-yl]-butan-amide Prepared from 3-t-butoxycarbonylamino-3-methyl-butanoic acid (Example 31, Step E) and 3-amino-2,3,4,5-tetrahydro-1H-1-benzazepin-2-one (Example 1, Step A) by the procedure described in Example 1, Step F. $^1$H NMR (300 MHz, CDCl$_3$): 1.34 (s,6H), 1.41 (s,9H), 1.90 (m,1H), 2.45 (d,15 Hz, 1H), 2.56 (d,15 Hz, 1H), 2.65 (m,1H), 2.76 (m,1H), 2.92 (m,1H), 4.53 (m,1H), 5.20 (br s,1H), 6.62 (d,15 Hz, 1H), 6.97 (d,8 Hz, 1H), 7.10–7.25 (m,3H), 7.35 (br s,1H). FAB-MS: calculated for $C_{20}H_{29}N_3O_4$ 375; found 376 (M+H,45%).

Step B:
3-t-butoxycarbonylamino-3-methyl-N-[2,3,4,5-tetrahydro-2-oxo-1-[[2'-t-butoxycarbonyl]-[1,1'-biphenyl]-4-yl]methyl]-1H-1-benzazepin-3-yl]-butanamide Prepared from the intermediate obtained in Step A and t-butyl 4'-bromomethylbiphenyl-2-carboxylate (prepared by the method of D. J. Carini, et al, EPO publication 324,377) by the procedure described in Example 1, Step K. $^1$H NMR (300 MHz, CDCl$_3$): 1.17 (s,9H), 1.34 (s,6H), 1.40 (s,9H), 1.86 (m,1H), 2.40–2.65 (m,5H), 4.51 (m,1H), 4.81 (d,14 Hz, 1H), 5.31 (s,1H), 5.35 (d,14 Hz, 1H), 6.68 (d,7 Hz, 1H), 7.1–7.5 (m,11H), 7.71 (m,1H). FAB-MS: calculated for $C_{38}H_{47}N_3O_6$ 641; found 642 (M+h,15%).

Step C:
3-amino-3-methyl-N-[2,3,4,5-tetrahydro-2-oxo-1-[[2'-carboxy][1,1'-biphenyl]-4-yl]methyl]-1H-1-benzazepin-3-yl]-butanamide The intermediate obtained in Step B (500 mg, 0.78 mmol) dissolved in 2 mL of glacial acetic acid was treated with 2 mL of 6N HCl and the mixture heated at 50° C. for 3 hours. The mixture was concentrated under vacuum to a minimum volume, redissolved in 3 mL of distilled water and lyophilized. The crusty solid was redissolved in 2 mL of methanol and treated dropwise with stirring with 5 mL of propylene oxide. The mixture was stirred at room temperature for 5 hours then filtered; the filter cake was washed with either, air dried, then dried under vacuum to give 278 mg (0.57 mmol, 73%) of the title compound. $^1$H NMR (300 MHz, D$_2$O): 1.43 (s,3H), 1.47 (s,3H), 2.0–2.5 (m,4H), 2.66 (m,2H), 4.28 (dd;7,11 Hz; 1H), 4.70 (d,15 Hz, 1H), 5.29 (d,15 Hz, 1H), 6.92 (m,1H), 7.0–7.4 (m,10H), 7.70 (m,1H). FAB-MS: calculated for $C_{29}H_{31}N_3O_4$ 485; found 486 (M+H,100%).

EXAMPLE 59

3-amino-3-methyl-N-[7-methoxy-2,3,4,5-tetrahydro-2-oxo-1-[[2'-(1H-tetrazol-5-yl)[1,1'-biphenyl]-4-yl]methyl]-1H-1-benzazepin-3-yl]-butanamide, trifluoroacetate

Step A:
7-Methoxy-2,3,4,5-tetrahydro-1H-1-benzazepin-2-one

Prepared from 6-methoxy-1-tetralone by the procedure described in Example 31, Step A. $^1$H NMR (200 MHz, CDCl$_3$): 2.1–2.4 (m,4H), 2.72 (t,7 Hz, 2H), 3.77 (s,3H), 6.71 (d,8 Hz, 2H), 6.73 (s,1H), 6.89 (d,8 Hz, 1H), 7.80 (br s, 1H). FAB-MS: calculated for $C_{11}H_{13}NO_2$ 191; found 191 (M+,60%).

Step B:
3-Iodo-7-methoxy-2,3,4,5-tetrahydro-1H-1-benzazepin-2-one

Prepared from 7-methoxy-2,3,4,5-tetrahydro-1H-1-benzazepin-2-one by the procedure described in Example 31, Step B. $^1$H NMR (200 MHz, CDCl$_3$): 2.5–3.0 (m,4H), 3.89 (s,3H), 4.64 (t,8 Hz, 1H), 6.75 (s,1H), 6.77 (d,8 Hz, 1H), 6.94 (d,8 Hz, 1H), 7.70 (br s, 1H). FAB-MS: calculated for $C_{11}H_{12}INO_2$ 317; found 317 (M+,100%).

Step C:
3-Azido-7-methoxy-2,3,4,5-tetrahydro-1H-1-benzazepin-2-one

3-Iodo-7-methoxy-2,3,4,5-tetrahydro-1H-1-benzazepin-2-one (4.074 g, 12.85 mmol) and sodium azide (4.178 g, 64.3 mmol, 5 eq.) were dissolved in 50 mL of dimethylformamide and heated with stirring at 60° for 2 hours. The solvent was evaporated under vacuum at room temperature and the residue redissolved in 150 mL of ethyl acetate and washed with water (3×50 mL) and brine (1×50 mL). The organic layer was separated, dried over MgSO4, filtered and evaporated to dryness under vacuum to yield 2.538 g (10.94 mmol, 85%) of product. $^1$H NMR (200 MHz, CDCl$_3$): 2.2–2.7 (m,3H), 2.90 (m,1H), 3.75 (s,3H), 3.80 (m,1H), 6.75 (m,2H), 6.95 (d,8 Hz, 2H), 8.22 (br s,1H). FAB-MS: calculated for $C_{11}H_{12}N_4O_2$ 232; found 233 (M+H,30%).

Step D:
3-Amino-7-methoxy-2,3,4,5-tetrahydro-1H-1-benzazepin-2-one

Prepared from 3-azido-7-methoxy-2,3,4,5-tetrahydro-1H-1-benzazepin-2-one by the procedure described in Example 31, Step D. $^1$H NMR (200 MHz, CDCl$_3$): 1.86 (m,1H), 2.4–2.6 (m,2H), 2.86 (m,1H), 3.39 (m,1H), 3.76 (s,3H), 6.72 (d,8 Hz, 1H), 6.74 (s,1H), 6.88 (d,8 Hz, 1H), 7.62 (br s,1H). FAB-MS: calculated for $C_{11}H_{14}N_2O_2$ 206 found 208 (100%).

Step E:
3-t-Butoxycarbonylamino-3-methyl-N-[7-methoxy-2,3,4,5-tetrahydro-2-oxo-1H-1-benzazepin-3-yl]-butanamide Prepared from 3-t-butoxycarbonylamino-3-methyl-butanoic acid (Example 31, Step E) and the amine obtained in Step D by the procedure described in Example 1, Step F. $^1$H NMR (200 MHz, CDCl$_3$): 1.32 (s,6H), 1.38 (s,9H), 1.86 (m,1H), 2.4–3.0 (m,5H), 3.77 (s,3H), 4.49 (m,1H), 5.25 9br s,1H), 6.68 (d,8 Hz, 1H), 6.70 (s,1H), 6.89 (d,8 Hz, 1H), 7.55 (br s,1H). FAB-MS: calculated for $C_{21}H_{31}N_3O_5$ 405; found 428 (m+na,100%), 406 M+H,23%).

Step F:
3-t-Butoxycarbonylamino-3-methyl-N-[7-methoxy-2,3,4,5-tetrahydro-2-oxo-1-[[2'-(N-triphenylmethyl)-tetrazol-5-yl][1,1'-biphenyl]-4-yl]methyl-1H-1-benzazepin-3-yl]-butanamide Prepared from the intermediate obtained in Step E and N-triphenylmethyl-5-[2-(4'-bromomethyl-biphen-4-yl)] tetrazole by the procedure described in Example 1, Step G. $^1$H NMR (200 MHz, CDCl$_3$): 1.31 (s,3H), 1.32 (s,3H), 1.37 (s,9H), 1.70 (m,1H), 2.2–2.6 (m,5H), 3.72 (s,3H), 4.43 (m,1H), 4.61 (d,15 Hz, 1H), 5.06 (d,15 Hz, 1H), 5.35 (br s,1H), 6.62 (m,3H), 6.9 (m,10H), 7.25 (m,12H), 7.83 (m,1H).

Step G:
3-Amino-3-methyl-N-[7-methoxy-2,3,4,5-tetrahydro-2-oxo-1-[[2'-(1H-tetrazol-5-yl)[1,1'-biphenyl]-4-yl]methyl]-1H-1-benzazepin-3-ly]-butanamide, mono(trifluoroacetate)

The title compound was prepared from the intermediate obtained in Step F by the procedure described in Example 31, Step H. $^1$H NMR (200 MHz, CD$_3$OD): 1.35 (s,3H), 1.39 (s,3H), 2.05 (m,1H), 2.3–2.6 (m,5H), 3.81 (s,3H), 4.37 (dd;7,11 Hz; 1H), 4.76 (d,15 Hz, 1H), 5.22 (d,15 Hz, 1H), 6.80 (d,3 Hz, 1H), 6.88 (dd;3,8 Hz; 1H), 7.01 (d,8 Hz, 2H), 7.17 (d,8 Hz, 2H), 7.22 (d,8 Hz, 1H), 7.5–7.7 (m,4H). FAB-MS: calculated for $C_{30}H_{33}N_7O_3$ 539; found 540 (M+H,100%).

EXAMPLE 60

3-Amino-3-methyl-N-[7-methoxy-2,3,4,5-tetrahydro-2-oxo-1-[[2'-(1H-tetrazol-5-yl)[1,1'-biphenyl]-4-yl]-methyl]-1H-1-benzazepin-3-yl]-butanamide, trifluoroacetate 240 mg (0.27 mmol) of 3-t-butoxycarbonylamino-3-methyl-N-[7-methoxy-2,3,4,5-tetrahydro-2-oxo-1-[[2'-(N-triphenylmethyl)-tetrazol-5-yl][1,1'-biphenyl]-4-yl]methyl-1H-1-benzazepin-3-yl]-butanamide (Example 59, Step F) was dissolved in 4 mL of methylene chloride and the solution treated with 1.35 mL of 1.0M boron tribromide in methylene chloride (1.35 mmol, 5 eq.) and the mixture stirred at room temperature for 4 hours then quenched by the addition of 15 mL of ice water. The mixture was extracted with ethyl acetate (20×20 mL) and the combined organic phases were washed with brine, dried over magnesium sulfate, filtered and solvents removed in vacuo. The residue was purified by reverse phase medium pressure liquid chromatography on C8, eluting with methanol/0.1% aqueous trifluoroacetic acid (55:45). In this manner, 56 mg (0.087 mmol, 32%) of the title compound was obtained as a colorless glass. $^1$H NMR (200 MHz, CD$_3$OD): 1.39 (s,3H), 1.43 (s,3H), 2.07 (m,1H), 2.3–2.6 (m,5H), 4.42 (dd:5,8 Hz, 1H), 4.79 (d,11 Hz, 1H), 5.24 (d,11 Hz, 1H), 6.68 (d,2 Hz, 1H), 6.78 (dd;2,7 Hz; 1H), 7.06 (d,7 Hz, 2H), 7.18 (d,7 Hz, 1H), 7.21 (d,7 Hz, 2H), 7.5–7.7 (m,4H). FAB-MS: calculated for $C_{29}H_{31}N_7O_3$ 525; found 526 (M+H,87%).

EXAMPLE 61

3-Amino-3-methyl-N-benzyl-N-[2,3,4,5-tetrahydro-2-oxo-1-[[2'-(1H-tetrazol-5-yl)[1,1'-biphenyl]-4-yl]-methyl]-1H-1-benzazepin-3(R)-yl]-butanamide, trifluoroacetate

Step A:
3(R)-(Benzylamino)-2,3,4,5-tetrahydro-1H-1-benzazepin-2-one

A solution of 528 mg (3.0 mmol) of 3(R)-amino-2,3,4,5-tetrahydro-1H-1-benzazepin-2-one (Example 1, Step B) in 45 mL of absolute methanol at room temperature was treated with 4.5 g of powdered 3A molecular sieves followed by dropwise addition of a solution of 954 mg (9.0 mmol, 3 eq.) of benzaldehyde in 15 mL of methanol. The pH of the mixture was adjusted to 7 by addition of trifluoroacetic acid then stirred at room temperature for 2 hours. Sodium cynaoborohydride (18 mL of 1.0M THF solution: 18 mmol, 6 eq.) was added and the mixture stirred at room temperature for 18 hours. The mixture was filtered and the filtrate treated with 3 mL of trifluoroacetic acid with stirring for 3 hours, then all volatiles removed under vacuum and the residue dissolved in 50 mL of ethyl acetate. The ethyl acetate solution was washed with water (3×15 mL), saturated aqueous sodium bicarbonate (2×15 mL) and 15 mL of brine then dried over magnesium sulfate, filtered and solvents removed under vacuum. The residue was purified by chromatography on silica, eluting with ethyl acetate/hexane (70:30), to afford 410 mg (1.54 mmol, 51%) of the product. $^1$H NMR (200MHz,CDCl$_3$): 2.05 (m,1H), 2.5-3.0 (m,3H), 3.37 (dd;7.11Hz;1H), 3.57 (d,12Hz,1H), 3.90 (d,12Hz,1H), 7.05 (d,8Hz,1H), 7.1-7.4 (m,8H), 7.75 (br s,1H). FAB-MS: calculated for C$_{17}$H$_{18}$N$_2$O 266; found 267 (M+H,75%).

Step B:
3-t-Butoxycarbonylamino-3-methyl-N-benzyl-N-[2,3,4,5-tetrahydro-2-oxo-1H-1-benzazepin-3-(R)-yl]-butanamide A solution of 90 mg (0.34 mmol) of 3(R)-(benzylamino)-2,3,4,5-tetrahydro-1H-1-benzazepin-2-one in 1.5 mL of tetrahydrofuran under nitrogen at room temperature was treated with 73 mg (0.34 mmol, 1 eq.) of 3-t-butoxycarbonylamino-3-methylbutanoic acid (Example 31, Step E) followed by 94 mg (0.38 mmol, 1.1 eq.) of 2-ethoxy-1-ethoxycarbonyl-1,2-dihydroquinoline (EEDQ). Most of the solvent was evaporated under a stream of nitrogen and the resulting reaction mixture (thick syrup approx. 0.3 mL) was stirred for 3 days. The mixture was evaporated to dryness under vacuum and the residue purified by medium pressure liquid chromatography on silica, eluting with ethyl acetate/hexane (1:1) to afford 45 mg (mmol, 33%) of product. $^1$H NMR (200MHz, CDCl$_3$): 1.28 (s,3H), 1.32 (s,3H), 1.35 (s,9H), 2.16 (m,2H), 2.35 (d,14Hz,1H), 2.58 (d,14Hz,1H), 2.60 (m,1H), 2.81 (m,1H), 4.70 (d,18Hz,1H), 4.99 (d,18Hz,1H), 5.37 (t,10Hz,1H), 5.83 (br s,1H), 6.98 (d,7Hz,1H), 7.05-7.45 (m,5H), 7.50-7.85 (m,3H), 8.13 (t,8Hz,1H), 8.90 (m,1H). FAB-MS: calculated for C$_{27}$H$_{35}$N$_3$O$_4$ 465; found 466 (M+H)48%).

Step C:
3-Amino-3-methyl-N-benzyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from the intermediate obtained in Step B and N-triphenylmethyl-5-[2-(4'-bromomethylbiphenyl-4-yl)]tetrazole by the methods described in Example 1, Step K and Example 31, Step H. $^1$H NMR (400 MHz, CD$_3$CN): 1.35 (s,3H), 1.36 (s,3H), 2.19 (m,1H), 2.38 (m,1H), 2.47 (d,17Hz,1H), 2.7-2.9 (m,2H), 2.90 (d,17Hz,1H), 4.75 (d,16Hz,1H), 4.93 (d,19Hz,1H), 5.03 (d,19Hz,1H), 5.22 (dd;8,12Hz;1H), 5.48 (d,16Hz,1H), 7.2-7.5 (m,10H), 7.6-7.8 (m,6H), 7.85 (br s,1H). FAB-MS: calculated for C$_{36}$H$_{37}$N$_7$O$_2$ 599; found 600 (M+H,30%).

EXAMPLE 62
3-Amino-3-methyl-N-methyl-N-[2,3,4,5-tetrahydro-2-oxo-1-[[2'-(1H-tetrazol-5-yl)[1,1'-biphenyl]-4-yl]-methyl]-1H-1-benzazepin-3(R)-yl]-butanamide, trifluoroacetate

Step A:
3(R)-N-Methyl-N-benzylamino-2,3,4,5-tetrahydro-1H-1-benzazepin-2-one A solution of 150 mg (0.56 mmol) of 3(R)-(benzylamino)-2,3,4,5-tetrahydro-1H-1-benzazepin-2-one (Example 61, Step A) in 0.6 mL of formic acid was treated with 0.047 mL (0.56 mmol, 1 eq.) of 36% aqueous formaldehyde and the mixture heated at 80° with stirring for 24 hours. The mixture was cooled, treated with 0.8 mL of 6N HCl, and all volatiles removed under vacuum. The residue was partitioned between 10 mL of water and 10 mL of methylene chloride; 1 mL of 10% aqueous sodium carbonate was then added and the mixture shaken. The organic layer was separated and the aqueous layer extracted with an additional 20 mL of methylene chloride. The combined extracts were dried over magnesium sulfate, filtered and solvents removed under vacuum. The residue was purified by medium pressure liquid chromatography on silica, eluting with 2.5% methanol in ethyl acetate, to give 98 mg (0.35 mmol, 63%) of product. $^1$H NMR (200 MHz, CDCl$_3$): 2.35 (s,3H), 2.35 (m,2H), 2.69 (m,1H), 2.88 (m,1H), 3.37 (dd;8,11Hz;1H), 3.80 (d,14Hz,1H), 3.90 (d,14Hz,1H), 6.90 (d,8Hz,1H), 7.05-7.35 (m,8H). FAB-MS: calculated for C$_{18}$H$_{20}$N$_2$O 280; found 281 (M+H,100%).

STEP B;
3(R)-(methylamino)-2,3,4,5-tetrahydro-1H-1-benzazepin-2-one

A solution of 98 mg (0.35 mmol) of 3(R)-(N-methyl-N-benzyl)amino-2,3,4,5-tetrahydro-1H-1-benzazepin-2-one (Step A) in 10 mL of methanol was treated with one drop of concentrated sulfuric acid and the resulting solution hydrogenated at room temperature and 30-40 psi over 20 mg of 10% Pd/C for 20 hours. The mixture was filtered and the filtrate evaporated under vacuum. The residue was treated with 15 mL of ethyl acetate. 4 mL of water and 2 mL of 10% aqueous sodium carbonate then shaken. The organic layer was separated, and the aqueous phase re-extracted with an additional 10 mL of ethyl acetate. The combined extracts were washed with brine, dried over magnesium sulfate, filtered and the filtrate evaporated under vacuum to give 68 mg (0.35 mmol, 100%) of product. $^1$H NMR (200MHz,CDCl$_3$): 1.85 (m,1H), 2.30 (s,3H), 2.35-2.65 (m,2H), 2.73 (m,1H), 3.10 (dd;8,12Hz;1H), 6.97 (d,8Hz,1H), 7.1-7.3 (m,3H), 7.5 (br s,1H).

Step C:
3-t-Butoxycarbonylamino-3-methyl-N-methyl-N-[2,3,4,5-tetrahydro-2-oxo-1H-1-benzazepin-3-(R)-yl]-butanamide Prepared from 3-t-butoxycarbonylamino-3-methyl-butanoic acid (Example 31, Step E) and the amine obtained in Step B by the produce described in Example 1, Step F. $^1$H NMR (200MHz, CDCl$_3$): 1.30 (br s,15H), 2.19 (m,1H), 2.42 (m,1H), 2.5-2.8 (m,3H), 2.91 (m,1H), 3.15 (s,3H), 5.32 (dd;6,8Hz;1H), 5.52 (br s,1H), 6.97 (d,5Hz,1H), 7.1–7.3 (m,3H), 7.35 (br s,1H).

Step D:
3-Amino-3-methyl-N-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate Prepared from the intermediate obtained in Step C and N-triphenylmethyl-5-[2-(4'-bromomethylbiphenyl-4-yl)] tetrazole by the procedures described in Example 1, Step K and Example 31 Step H. $^1$H NMR (200MHz, CD$_3$OD): 1.34 (s,3H), 1.38 (s,3H), 2.10 (m,1H), 2.3–2.8 (m,5H), 3.16 (s,3H), 4.90 (d,15Hz,1H), 5.01 (dd;7,11Hz;1H), 5.13 (d,15Hz,1H), 7.02 (d,8Hz,2H), 7.19 (d,8Hz,2H), 7.2–7.4 (m,4H), 7.5–7.7 (m,4H). FAB-MS: calculated for C$_{30}$H$_{33}$N$_7$O$_2$ 523; found 524 (M+H,22%).

EXAMPLE 63
2-Amino-2-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, trifluoroacetate

Step A:
2-(t-Butoxycarbonylamino)-2-methyl-N-[2,3,4,5-tetrahydro-2-oxo-1H-1-benzazepin-3(R)-yl]-propanamide Prepared from 2-(t-butoxycarbonylamino)-2-methylpropanoic acid and 3(R)-amino-2,3,4,5-tetrahydro-1H-[1]benzazepin-2-one (Example 1, Step B) by the procedure described in Example 1, Step F. $^1$H NMR (200MHz, CDCl$_3$): 1.42 (s,12H), 1.46 (s,3H), 1.90 (m,1H), 2.5–3.0 (m,3H), 4.48 (m,1H), 5.01 (br s,1H), 6.97 (d,8Hz,1H), 7.1–7.3 (m,3H), 7.9 (br s,1H). FABMS: calculated for C$_{19}$H$_{27}$N$_3$O$_4$ 361; found 362 (M+H,30%).

Step B:
2-(t-Butoxycarbonylamino)-2-methyl-N-[2,3,4,5-tetrahydro-2-oxo-1-[[2'-[N-(triphenylmethyl)-tetrazol-5-yl][1,1'-biphenyl]-4-yl]methyl]-1H-1-benzazepin-3(R)-yl]-propanamide Prepared from the intermediate obtained in Step A and N-triphenylmethyl-5-[2-(4'-bromomethylbiphenyl-4-yl)] tetrazole by the procedure described in Example 1, Step K. $^1$H NMR (200MHz, CDCl$_3$): 1.42 (s,9H), 1.43 (s,3H), 1.46 (s,3H), 1.77 (m,1H), 2.2–2.7 (m,3H) 4.43 (m,1H), 4.72 (d,15Hz,1H), 4.93 (br s,1H), 5.09 (d,15Hz,1H), 6.9–7.5 (m,26H), 7.86 (m,1H).

Step C:
2-Amino-2-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, mono(trifluoroacetate)

The title compound was prepared from the intermediate obtained in Step B by the procedure described in Example 31, Step H with final purification performed by reverse phase medium pressure liquid chromatography on C-8, eluting with methanol/0.1% aqueous trifluoroacetic acid (55:45). $^1$H-NMR (200MHz, CD$_3$OD): 1.52 (s,3H), 1.61 (s,3H), 2.1–2.6 (m,4H), 4.33 (dd;8,11Hz;1H), 4.85 (d,15Hz,1H), 5.18 (d,15Hz,1H), 6.99 (d,8Hz,2H), 7.15 (d,8Hz,2H), 7.2–7.4 (m,4H), 7.5–7.7 (m,4H). FAB-MS: calculated for C$_{28}$H$_{29}$N$_7$O$_2$ 495; found 496 (M+H,32%).

EXAMPLE 64
Quinuclidine-N'-[2,3,4,5-tetrahydro-2-oxo-1-[[2'-(1H-tetrazol-5-yl)[1,1'-biphenyl]-4-yl]methyl]-1H-1-benzazepin-3(R)-yl]-3-carboxamide, trifluoroacetate The title compound, as a mixture of two diastereomers, was prepared from racemic quinuclidine-3-carboxylic acid and 3(R)-amino-1,3,4,5-tetrahydro-1-[[2'-(1H-tetrazol-5-yl)[1,1'-biphenyl]-4-yl]methyl]-2H-1-benzazepin-2-one hydrochloride (Example 4, Step C) by the procedure described in Example 4, Step D, with final purification by reverse phase medium pressure liquid chromatography on C-8, eluting with acetonitrile/0.1% aqueous trifluoroacetic acid (35:65). $^1$H NMR (200MHz, CD$_3$OD); 1.7–2.6 (m,8H), 3.00 (m,1H), 3.1–3.3 (m,6H), 3.65 (m,1H), 4.32 (m,1H), 4.8–5.2 (m,2H), 7.00 (d,8Hz,2H), 7.1–7.3 (m,6H), 7.5–7.7 (m,4H). FAB-MS: calculated for C$_{32}$H$_{33}$N$_7$O$_2$ 547; found 548 (M+H,100%).

EXAMPLE 65
3-Amino-2,2-dimethyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, trifluoroacetate

Step A:
3-(Benzyloxycarbonylamino)-2,2-dimethylpropanoic acid

Prepared from 3-[benzyloxycarbonylamino]-2,2-dimethylpropanoic acid, methyl ester (Example 1, Step D) by the procedure described in Example 1, Step E. $^1$H NMR (200MHz, CDCl$_3$): 1.25 (s,6H), 3.30 (d,7Hz,2H), 5.10 (s,2H), 7.34 (s,5H).

Step B:
3-(Benzyloxycarbonylamino)-2,2-dimethyl-N-[2,3,4,5-tetrahydro-2-oxo-1H-1-benzazepin-3(R)-yl]-propanamide Prepared from 3-(benzyloxycarbonylamino)-2,2-dimethylpropanoic acid and 3(R)-amino-2,3,4,5-tetrahydro-1H-[1]benzazepin-2-one (Example 1, Step E) by the procedure described in Example 1, Step F. $^1$H NMR (200MHz, CDCl$_3$): 1.19 (s,6H), 1.90 (m,1H), 2.6–3.0 (n,3H), 3.26 (d,6Hz,2H), 4.46 (m,1H), 5.07 (s,2H), 5.7 (br t,1H), 6.62 (d,7Hz,1H), 6.97 (d,8Hz,1H), 7.1–7.3 (m,3H), 7.3 (s,5H), 8.14 (br s,1H). FAB-MS: calculated for C$_{23}$H$_{27}$N$_3$O$_4$ 409; found 410 (M+H,100%).

Step C:
3(t-Butoxycarbonylamino)-2,2-dimethyl-N-[2,3,4,5-tetrahydro-2-oxo-1H-1-benzazepin-3(R)-yl]-propanamide A solution of 170 mg (0.42 mmol) of the intermediate obtained in Step B in 5 mL of absolute methanol and one drop of trifluoroacetic acid was hydrogenated at room temperature and 1 atmosphere over 35 mg of 20% palladium hydroxide on carbon for 4 hours. The mixture was filtered through Celite and solvent removed under vacuum to afford 165 mg (0.42 mmol, 100%) of the amine trifluoroacetate salt as a pale yellow solid.

The above intermediate was dissolved in 2 mL of methylene chloride and treated with 108 mg (0.49 mmol. 1.2 eq.) of di-t-butyl-dicarbonate followed by 0.12 mL of triethylamine (87 mg, 0.86 mmol, 2 eq.). After two hours at room temperature, the mixture was added to 20 mL of ethyl acetate and washed with 5% aqueous citric acid, saturated aqueous sodium bicarbonate and brine. The organic layer was separated, dried over magnesium sulfate, filtered and solvents removed under vacuum. The residue was purified by medium pressure liquid chromatography on silica, eluting with ethyl acetate/hexane (3:2) to afford 156 mg (0.41 mmol, 98%) of the product as a white solid. $^1$H NMR (200MHz, CDCl$_3$): 1.18 (s,6H), 1.39 (s,9H), 1.92 (m,1H), 2.6-3.0 (m,3H), 3.17 (d,6Hz,2H, 4.46 (m,1H), 5.25 (br s,1H), 6.69 (d,7Hz,1H), 6.98 (d,8Hz,1H), 7.1-7.3 (m,3H), 8.22 (br s,1H), FAB-MS: calc. for C$_{20}$H$_{29}$N$_3$O$_4$ 375; found 376 (M+H,10%).

Step D:
3-(t-Butoxycarbonylamino)-2,2-dimethyl-N-[2,3,4,5-tetrahydro-2-oxo-1-[[2'-[N-(triphenylmethyl)tetrazol-5-yl][1,1'-biphenyl]-4-yl]methyl]-1H-1-benzazepin-3(R)-yl]-propanamide Prepared from the intermediate obtained in Step C and N-triphenylmethyl-5-[2-(4'-bromomethylbiphen-4-yl)] tetrazole by the procedure described in Example 1, Step K, $^1$H NMR (200MHz, CDCl$_3$): 1.16 (s,3H), 1.17 (s,3H), 1.40 (s,9H), 1.74 (m,1H), 2.3-2.5 (m,3H), 3.16 (d,7Hz,2H), 4.40 (m,1H), 4.62 (d,15Hz,1H), 5.22 (d,15Hz,1H), 5.28 (br s,1H), 6.68 (d,7Hz,1H), 6.9-7.5 (m,26H), 7.85 (m,1H).

Step E:
3-Amino-2,2-dimethyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, trifluoroacetate The title compound was prepared from the intermediate obtained in Step D by the procedure described in Example 31, Step H with final purification performed by reverse phase medium pressure liquid chromatography on C-8, eluting with methanol/0.1% aqueous trifluoroacetic acid (55:45). $^1$H NMR (200MHz, CD$_3$OD): 1.24 (s,3H), 1.33 (s,3H), 2.1-2.6 (m,4H), 2.99 (br s,2H), 4.30 (dd;8,11Hz;1H), 4.85 (d,15Hz,1H), 5.21 (d,15Hz,1H), 7.00 (d,8Hz,2H), 7.1-7.4 (m,6H), 7.4-7.7 (m,4H). FAB-MS: calculated for C$_{29}$H$_{31}$N$_7$O$_2$ 509; found 510 (M+H,100%).

EXAMPLE 66

3-Amino-3-methyl-N-[2,3,4,5-tetrahydro-2-oxo-1-[[2'-(1H-tetrazol-5-yl)[1,1'-biphenyl]-4-yl]methyl]-1H-1-benzazepin-4(S)-yl]-butanamide, trifluoroacetate Step A:
3-Benzyloxycarbonylamino-3-methyl-N-[2,3,4,5-tetrahydro-2-oxo-1H-1-benzazepin-3-(S)-yl]-butanamide Prepared from 3(S)-amino-2,3,4,5-tetrahydro-1H-1-benzazepin-2-on (Example 1, Step B) and 3-benzyloxycarbonylamino-3-methylbutanoic acid (Example 1, Step E) by the procedure described in Example 1, Step F. FAB-MS: calculated for C$_{23}$H$_{27}$N$_3$O$_4$ 409; found 410 (M+H,100%). [a]$_D$=$-160°$ (C=1,CHCl$_3$).

Step B:
3-Benzyloxycarbonylamino-3-methyl-N-[2,3,4,5-tetrahydro-2-oxo-1-[[2'-(N-triphenylmethyl)-tetrazol-5-yl][1,1'-biphenyl]-4-yl]methyl-1H-benzazepin-3(S)-yl]-butanamide Prepared from the intermediate obtained in Step A and N-triphenylmethyl-5-[4'-bromomethylbiphenyl-2-yl)tetrazole by the procedure described in Example 1, Step K, $^1$H NMR (200MHz,CDCl$_3$): 1.38 (s,3H), 1.40 (s,3H), 1.67 (m,1H), 2.2-2.5 (m,5H), 4.44 (m,1H), 4.67 (d,14Hz,1H), 5.06 (s,2H), 5.12 (d,14Hz,1H), 5.63 (br s,1H), 6.64 (d,7Hz,1H), 6.9-7.5 (m,31H), 7.85 (m,1H).

Step C:
3-Amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(S)-yl]-butanamide, trifluoroacetate The title compound was prepared from the intermediate obtained in Step B by the procedure described in Example 1, Step L. $^1$H NMR (200MHz,CD$_3$OD): 1.34 (s,3H), 1.38 (s,3H), 2.0-2.6 (m,6H), 4.34 (dd;7,11Hz;1H), 4.86 (d,15Hz,1H), 5.20 (d,15Hz,1H), 6.99 (d,8Hz,2H), 7.1-7.3 (m,6H), 7.45-7.70 (m,4H). FAB-MS: calculated for C$_{29}$H$_{31}$N$_7$O$_2$ 509; found 510 (M+H,100%). [a]$_D$=$-98°$ (c=5,CH$_3$OH).

EXAMPLE 67

3-(2-Fluoropropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide, trifluoroacetate To a cold ($-78°$ C.) solution of 3-(2-hydroxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide (Example 22, 20 mg, 0.029 mmol) in 1.5 mL of hydrogen fluoride-pyridine under a nitrogen atmosphere, 0.2 mL of DAST (diethylaminosulfur trifluoride) was slowly added. The reaction mixture was brought to room temperature and stirred for 48 hours. Additional DAST (0.2 mL) was added at 24 hour intervals until no further reaction was detected by HPLC. The reaction mixture was repeatedly purified by reverse phase HPLC to afford 4 mg of product. FAB-MS: calculated for C$_{32}$H$_{36}$N$_7$O$_2$F 569; found 570 (M+H, 100%). The product was converted into its hydrochloride salt by repeated evaporation of an aqueous 6N HCl/methanol solution. $^{19}$F NMR (CD$_3$OD): $-75.4$.

EXAMPLE 68

3-Amino-3-methyl-N-[2,3,4,5-tetrahydro-2-oxo-1-[[2-(1H-tetrazol-5-yl)[1,1'-biphenyl]-4-yl]methyl]-1H-1-benzazepin-3(R)-yl]butanamide, trifluoroacetate Step A: 3-Nitro-4-phenyltoluene To a cold (0° C.) solution of 4-methyl-2-nitroaniline (3.8 g) in 11 mL of HBF$_4$, an aqueous solution of sodium nitrite (1.7 g in 3.4 mL) was added dropwise. The reaction mixture was stirred for 10 minutes. The precipitate was collected and washed with cold aqueous HBF$_4$ (3 mL), ethanol and ether to yield 1.72 g of diazonium salt. The diazonium salt was suspended in benzene (76 mL) and acetonitrile (7.6 mL). Potassium acetate (1.53 g)

was added and the resulting mixture stirred under nitrogen in the dark at room temperature for 1.5 hr. The solid was removed by filtration and the filtrate washed with water (2×) and brine. The solution was dried with anhydrous sodium sulfate and then concentrated to afford 1.49 g of crude product which could be chromatographed on silica gel (2:1 hexanes:CH$_2$Cl$_2$).

Step B: 3-Amino-4-phenyltoluene

A solution of 2.4 g of 3-nitro-4-phenyltoluene in 25 mL of methanol was hydrogenated at room temperature and 40 psi over 0.30 g of 5% Pd/C catalyst. The solution was filtered and the filtrate concentrated to give 1.98 g of product. EI-MS: calculated for C$_{13}$H$_{13}$N: 183; found 183.

Step C: 3-Cyano-4-phenyltoluene

To a cold (0° C.) suspension of 3-amino-4-phenyltoluene (1.97 g) in 2.65 mL of water and 2.65 mL of 12N HCl was slowly added a solution of a sodium nitrite (738 mg) in 2 mL of water. To this yellowish slurry, 10 mL of flouoroboric acid was added with stirring. The cold mixture was filtered and the solid (2.02 g) washed with cold fluoroboric acid, ethanol and ether. A solution of this diazonium salt (2.02 g) in 5 mL of DMSO was added dropwise with cooling to a mixture of CuCN and NaCN in DMSO (13.3 mL). The reaction mixture was then diluted with water (20 mL) and extracted repeatedly with benzene. The combined organic layers were washed with water (2×) and brine and then dried over anhydrous MgSO$_4$. Concentration under vacuum gave a reddish oil which was chromatographed on silica gel to give 0.788 g of product.

Step D:
N-Triphenylmethyl-5-[2'-(4'-methylbiphenyl-4-yl)]tetrazole

A solution of 3-cyano-4-phenyltoluene (390 mg) and trimethyltin azide (525 mg) in 2.5 mL of toluene was heated at reflux for 24 hr under nitrogen. The reaction mixture was concentrated and the residue suspended in 3.5 mL of toluene. Tetrahydrofuran (0.25 mL) was added followed by HCl gas until the solution became homogeneous. The mixture was concentrated and the residue (307 mg) dissolved in 5 mL of CH$_2$Cl$_2$ and treated with 504 mg of triphenylmethyl chloride and 233 mg of triethylamine under nitrogen. The mixture was stirred overnight and then diluted with CH$_2$Cl$_2$ and water. The layers were separated and the aqueous layer further extracted with CH$_2$Cl$_2$. The combined organic layers were washed with water and brine, then dried over anhydrous magnesium sulfate. Concentration under vacuum afforded 935 mg which was chromatographed on silica gel eluting with hexanes:ethyl acetate (9:1) to give 615 mg of product.

Step E:
N-Triphenylmethyl-5-[2'-(4'-bromomethylbiphenyl-4-yl)]tetrazole

A solution of N-triphenylmethyl-5-[2'-(methylbiphenyl-4-yl)]tetrazole (95.7 mg), N-bromo-succinimide (35.5 mg) and AIBN (2 mg) in 4 mL of CCl$_4$ was heated at reflux for 4 hr. The reaction mixture was filtered and the filtrate concentrated to give 129 mg of product.

Step F:
3-t-Butoxycarbonylamino-3-methyl-N-[2,3,4,5-tetrahydro-2-oxo-1-[[2-(N-triphenylmethyl)-tetrazol-5-yl][1,1'-biphenyl]-4-yl]methyl-1H-benzazepin-3(R)-yl]butanamide To a solution of 33.7 mg of 3-t-butoxycarbonylamino-3-methyl-N-[2,3,4,5,-tetrahydro-2-oxo-1H-1-benzaepin-3(R)-yl]butanamide (Example 57, Step A) in 0.5 mL of dry dimethylformamide at room temperature was added 3.6 mg of 60% sodium hydride oil dispersion under nitrogen. After 30 minutes, N-triphenylmethyl-5-[2'-(4'-bromomethylbiphenyl-4-yl)]-tetrazole (129 mg) in 0.2 mL of dry dimethylformamide was added and the resulting mixture stirred for 8 hr at room temperature. The mixture was diluted with ethyl acetate and washed with water (2×) and brine. The organic layer was dried over magnesium sulfate, filtered and concentrated under vacuum. The crude product was chromatographed on silica gel eluting with ethyl acetate:hexanes (2:1) to give 16 mg of pure product. FAB-MS: calculated for C$_{53}$H$_{53}$N$_7$O$_2$ 851; found 858 (M+Li).

Step G:
3-Amino-3-methyl-N-[2,3,4,5-tetrahydro-2-oxo-1-[[2-(1H-tetrazol-5-yl)[1,1'-biphenyl]-4-yl]methyl-1H-1-benzazepin-3(R)-yl]butanamide A solution of 3-t-butoxycarbonylamino-3-methyl-N-[2,3,4,5-tetrahydro-2-oxo-1-[[2-(N-triphenylmethyl)-tetrazol-5-yl][1,1'-biphenyl]-4-yl]methyl-1H-benzaepin-3(R)-yl]butanamide (14 mg) in 0.3 mL of methanol and 0.3 mL of 9N HCl was stirred overnight at room temperature and under nitrogen. The reaction mixture was diluted with benzene and freeze-dried to give 12 mg of crude product which was purified by RP-HPLC on a Dynamax C18 column, eluting with methanol/0.1% aqueous trifluoroacetic acid (linear gradient; 60% methanol to 20% methanol in ten minutes) to give 9.0 mg of the title compound. FAB-MS: calculated for C$_{29}$H$_{31}$N$_7$O$_2$ 510; found 511 (M+1). $^1$H NMR (400MHz,CD$_3$OD): 1.35 (s,3H), 1.38 (s,3H), 2.1–2.85 (m,6H), 4.39 (dd;8,13Hz;1H), 4.95 (d,16Hz,1H), 5.39 (d,16Hz,1H), 7.1 (m,2H), 7.2–7.32 (m,7H), 7.55–7.70 (m,3H).

EXAMPLE 69

4'-[[3(R)-[(3-Amino-3-methyl-1-oxobutyl)amino]-2,3,4,5-tetrahydro-2-oxo-1H-1-benzazepin-1-yl]methyl]-[1,1'-biphenyl]-2-carboxamide, trifluoroacetate Step A: 4-Methylphenyltrimethylstannane 41.4L of 1.0 M p-tolylmagnesium bromide in diethyl ether (41.4 mol) was added dropwise, maintaining the temperature below −5° C., over 4 hours to a solution of 546 g (2.79 mol) of trimethyltin chloride in tetrahydrofuran (4L) under nitrogen at −10 C. The suspension was allowed to warm slowly to room temperature over 12 h then saturated ammonium chloride solution (1L) was added followed by sufficient water (approximately 1L) to dissolve the precipitate. The solution was extracted with ether-hexane (1:1) (1×4L, 3×2L). The combined organic phases were washed with brine, dried over magnesium sulfate and the solvents removed under vacuum. Purification by flash chromatography on silica gel eluting with hexane/ethyl acetate (95:5) gave a pale yellow oil containing white crystals of 4,4'-dimethylbiphenyl which were removed by filtration to leave 711.3 g (100%) of product. $^1$H NMR (300MHz,CDCl$_3$): 0.30 (s,9H), 2.34 (s,3H), 7.19 (d,7.7Hz,2H), 7.40 (d,7.7Hz,2H).

Step B: 4'-Methyl-1,1'-biphenyl-2-nitrile

A solution of 2.0 g (10.98 mmol) of 2-bromobenzonitrile, 2,93 g (11.5 mmol) of 4-methylphenyltrimethylstannane (Step A) and 0.385 g (0.55 mmol) of bis-triphenylphosphine palladium (II) chloride in 50 mL of dry dimethylformamide under nitrogen was heated at 100° C. for 5.5 hours. The reaction was cooled to room temperature. The reaction was poured into 150 mL of water and extracted with ether (3×150 mL). The combined either extracts were washed with water (4×100 mL) and brine (100 mL), dried over magnesium sulfate, filtered and the solvents removed under vacuum. Purification by flash chromatography on silica gel, eluting with hexane/ether (85:15), afforded 1.69 g (80%) of the product contaminated with about 10% of 2-methylbenzonitrile. $^1$H NMR (200 MHz, CDCl$_3$): 2.40 (s,3H), 7.27 (d,7Hz,2H), 7.30–7.65 (m,5H), 7.72 (d,6Hz,1H), FAB-MS: calculated for C$_{14}$H$_{11}$N 193; found 193 (M+, 100%).

Step C: 4'-Bromomethyl-1,1'-biphenyl-2-nitrile

To a solution of 699 mg (3.62 mmol) of the intermediate obtained in step B in 15 mL of carbon tetrachloride under nitrogen was added 708.3 mg (3.98 mmol, 1.1 eq) of N-bromosuccinimide and 59 mg (0.36 mmol, 0.1 eq) of azobisisobutyronitrile (AIBN). The resulting mixture was heated in the dark for 4 hours. The mixture was cooled to room temperature and filtered. The filtrate was concentrated under vacuum to afford 948 mg (96%) of the product as a yellow solid. $^1$H NMR (200MHz,CDCl$_3$): 4.51 (s,2H), 7.25–7.80 (m,8H). FAB-MS: calculated for C$_{14}$H$_{10}$BrN 272; found 272,274 (M+). $^1$H NMR indicates the presence of minor amounts of starting material and dibromo derivative.

Step D:
3-[[1-[[2'-Cyano-[1,1'-biphenyl]-4-yl]methyl]-2,3,4,5-tetrahydro-2-oxo-1H-benzazepin-3(R)-yl]amino]-1,1-dimethyl-3-oxopropylcarbamic acid, 1,1-dimethylethyl ester To a solution of 0.83 g (2.21 mmol) of 3-t-butoxycarbonylamino-3-methyl-N-[2,3,4,5-tetrahydro-2-oxo-1H-1-benzazepin-3(R)-yl]-butanamide (Example 57, Step A) in 6 mL of dry dimethylformamide at room temperature under nitrogen was added 97 mg of 60% sodium hydride dispersion in oil (58 mg NaH, 2.43 mmol, 1.1 eq). After stirring for 1 hour, a solution of 780 mg (2.88 mmol, 1.3 eq) of 4'-bromomethyl-1,1'-biphenyl-2-nitrile (Step C) in 2.0 mL of dimethylformamide was added via cannula. The flask which originally contained the bromide was washed with 1 mL of dry dimethylformamide which was then added to the reaction mixture via cannula. After stirring at room temperature for 3 hours, the reaction was diluted with 200mL of ethyl acetate, washed with 50 mL of water and 50 mL of brine. The organic layer was separated, dried over magnesium sulfate, filtered and the solvent removed under vacuum. The residue was purified by flash chromatography on silica gel, eluting with ethyl acetate/hexane (6:4), to afford 1.13 g (90%) of the product as a white foam. $^1$H NMR (200MHz,CDCl$_3$); 1.32 (s,3H), 1.40 (s,12H), 1.85 (m,1H), 2.35–2.70 (m,5H), 4.52 (m,1H), 4.90 (d,12Hz,1H), 5.21 (d,12Hz,1H), 6.70 (d,5Hz,1H), 7.10–7.65 (m,12H), 7.72 (d,6Hz,1H). FAB-MS: calculated for C$_{34}$H$_{38}$N$_4$O$_4$ 566; found 567 (M+H).

Step E:
4'-[[3(R)-[(3-t-Butoxycarbonylamino-3-methyl-1-oxobutyl)amino]-2,3,4,5-tetrahydro-2-oxo-1H-1-benzazepin-1-yl]methyl][1,1'-biphenyl]-2-carboxamide To a solution of 600 mg (1.06 mmol) of intermediate from Step D in 3.0 mL of dimethylsulfoxide was added 15 mg (0.106 mmol) of anhydrous potassium carbonate followed by 0.88 mL of 30% aqueous hydrogen peroxide. The resulting mixture was stirred at room temperature for 24 hours. The reaction was diluted with 100 mL of chloroform and washed with water (30 mL), 50% saturated aqueous sodium bisulfite (30 mL) and brine (30 mL). The organic layer was dried over sodium sulfate, filtered and the solvent removed under vacuum. The residue was purified by flash chromatography on silica gel, eluting with ethyl acetate, to afford 551.4 mg (90%) of the product as a white solid. $^1$H NMR (200MHz,CDCl$_3$): 1.30 (s,3H), 1.37 (s,12H), 1.85 (m,1H), 2.45–2.70 (m,5H), 4.50 (m,1H), 4.85 (d,12Hz,1H), 5.18 (s,1H), 5.25 (d,12Hz,1H), 5.65 (s,1H), 6.78 (d,5Hz,1H), 7.2–7.5 (m,12H), 7.70 (dd;5,1Hz;1H). FAB-MS: calculated for C$_{34}$H$_{40}$N$_4$O$_5$ 584; found 586.

Step F:
4'-[[(3(R)-[(3-Amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate To a slurry of 551 mg (0.942 mmol) of intermediate from Step E in 2 mL of the dry methylene chloride was added 5 drops of anisole followed by 2 mL of trifluoroacetic acid. After stirring for 2 hours at room temperature all volatiles were removed under vacuum. The resulting material was purified by reverse phase medium pressure liquid chromatography on C-8 eluting with methanol/0.1% aqueous trifluoroacetic acid (55:45) to afford 535 mg (95%) of the title compound as a white solid. $^1$H NMR (200MHz,CD$_3$OD): 1.42 (s,3H), 1.48 (s,3H), 2.00–2.65 (m,6H), 4.42 (dd;7,10Hz;1H), 4.95 (d,14Hz,1H), 5.25 (d,14Hz,1H), 7.2–7.6 (m,12H). FAB-MS: calculated for C$_{29}$H$_{32}$N$_4$O$_3$ 484; found 485 (M+H,100%).

EXAMPLE 70

4'-[[2,3,4,5-Tetrahydro-3(R)-[[3-[(2(R)-hydroxypropyl)amino]-3-methyl-1-oxobutyl]amino-2-oxo-1H-1-benzazepin-1-yl]methyl][1,1'-biphenyl]-2-carboxamide, trifluoroacetate To a solution of 0.75 g (1.25 mmol) of 4'-[[3(R)-[(3-amino-3-methyl-1-oxobutyl)amino]-2,3,4,5-tetrahydro-2-oxo-1H-1-benzazepin-1-yl]methyl]-[1,1'-biphenyl]-2- carboxamide, trifluoroacetate (Example 69) in 15 mL dry methanol was added 0.35 mL (2.50 mmol) of triethylamine, 4.0 g of dry 4A powdered molecular sieves followed by a solution of 1.3 g (7.5 mmol) of 2(R)-benzyloxypropanol (prepared according to the procedure of Hanessian and Kloss, Tetrahedron Lett. 1985, 26, 1261-1264.) in 5 mL of dry methanol. The pH of the mixture was carefully adjusted to 6.5 with glacial acetic acid. The reaction was stirred for 5 hours at which time 7.5 mL (7.5 mmol) of a 1.0 M solution of sodium cyanoborohydride in tetrahydrofuran was added by syringe. The reaction was stirred for 3 days then filtered through a pad of Celite. To the filtrate was added 5.0 mL of trifluoroacetic acid (CAUTION! evolution of hydrogen cyanide) and the resulting mixture stirred for three hours. The solvent was removed under vacuum to afford 5.0 g of a clear oil.

The crude intermediate was dissolved in 30 mL of methanol and placed in a shaker bottle. To the solution was added 1 mL of trifluoroacetic acid followed by 1.2 g of 30% palladium on carbon. The mixture was hydrogenated at room temperature and 40 psi for 36 hours. The mixture was filtered through Celite and the solvent removed under vacuum. The resulting material was purified by reverse phase medium pressure liquid chromatography on C-8 eluting with methanol/0.1% aqueous trifluoroacetic acid (60:40) to afford 640 mg (78%) of the title compound as a white solid. $^1$H NMR (200MHz,CD$_3$OD): 1.22 (d,8Hz,3H), 1.35 (s,3H), 1.39 (s,3H), 2.12 (m,2H), 2.32 (m,2H), 2.62 (m,4H), 2.80 (dd;8,11Hz;1H), 3.08 (dd;3,11Hz;1H), 3.92 (m,1H), 4.39 (dd;7.12Hz;1H), 5.02 (d,14Hz,1H), 5.18 (d,14Hz,1H), 7.20-7.55 (m,12H), FAB-MS: calculated for C$_{32}$H$_{38}$N$_4$O$_4$ 542; found 544 (N+H,100%).

EXAMPLE 71

4'-[[3(R)-[(2(S),3-Dihydroxypropyl)amino]-3-methyl-1-oxobutyl]amino]-2,3,4,5-tetrahydro-2-oxo-1H-1-benzazepin-1-yl]methyl][1,1'-biphenyl]-2-carboxamide, trifluoroacetate To a solution of 0.585 g (0.98 mmol) of 4'-[[3(R)-[(3-amino-3-methyl-1-oxobutyl)amino]-2,3,4,5-tetrahydro-2-oxo-1H-1-benzazepin-1-yl]methyl]-[1,1'-biphenyl]-2-carboxamide, trifluoroacetate (Example 69) in 15 mL dry methanol was added 0.27 mL (1.95 mmol) of triethylamine, 2.5 g of dry 4A powdered molecular sieves followed by a solution of 1.3 g (10 mmol) of D-glyceraldehyde acetonide (used crude as prepared according to the procedure of Hertel, L. W.; Grossman, C. S.; Kroin, J. S. Synth. Conn. 1991, 21, 151-154.) in 5 mL of dry methanol. The pH of the mixture was carefully adjusted to 6.5 with glacial acetic acid (7 drops). The reaction was stirred for 3 hours at which time 4.9 mL (4.9 mmol) of a 1.0M solution of sodium cyanoborohydride in tetrahydrofuran was added via syringe. The reaction was stirred for 20 hours then filtered through a pad of Celite. To the filtrate was added 5.0 mL of trifluoroacetic acid (CAUTION! hydrogen cyanide evolved), 5.0 mL of water and 5 drops of concentrated hydrochloric acid. The resulting mixture was stirred for 24 hours. The solvent was removed under vacuum to afford a clear oil which was purified by reverse phase medium pressure liquid chromatography on C-8 eluting with methanol/0.1% aqueous trifluoroacetic acid (60:40) to afford 590 mg (90%) of the title compound as a white solid. $^1$H NMR (200MHz,CD$_3$OD); 1.35 (s;3H), 1.30 (s,3H), 2.12 (m,1H), 2.31 (m,1H), 2.60 (m,4H), 2.98 (dd;8,12Hz;1H), 3.19 (dd;3,12Hz;1H), 3.55 (dd;3.6Hz;2H), 3.83 (m,1H), 4.40 (dd;8,11Hz;1H), 5.02 (d,15Hz,1H), 5.15 (d,15Hz,1H), 7.20-7.55 (m,12H). FAB-MS; calculated for C$_{32}$H$_{38}$N$_4$O$_5$ 558; found 560 (100%).

EXAMPLE 72

N-Ethyl-4'-[[3(R)-[(3-amino-3-methyl-1-oxobutyl)amino]-2,3,4,5-tetrahydro-2-oxo-1H-1-benzazepin-1-yl]-methyl][1,1'-biphenyl]-2-carboxamide, trifluoroacetate Step A:
4'-[[2,3,4,5-Tetrahydro-3(R)-[[3-methyl-1-oxo-3-[[(benzyloxy)carbonyl]amino]butyl]-amino]-2-oxo-1H-1-benzazepin-1-yl]methyl][1,1'-biphenyl]-2-carboxylic acid 1,1-dimethylethyl ester To a solution of 1.22 g (3.0 mmol) of 3-benzyloxycarbonylamino-3-methyl-N-[2,3,4,5-tetrahydro-2-oxo-1H-1-benzazepin-3(R)-yl]-butanamide (Example 1, Step F) in 10 mL of dry dimethylformamide under nitrogen was added 131.6 mg (3.92 mmol) of 60% sodium hydride in oil. After stirring for 20 minutes, a solution of 1.14 g (3.29 mmol) of t-butyl 4'-bromomethyl-1,1'-biphenyl-2-carboxylate (prepared according to the procedure of D. J. Carini, et. al. EPO publication 324.377) in 2.5 mL of dimethylformamide was added by cannula. The flask which originally contained the bromide was rinsed with 2.5 mL dimethylformamide which was added to the reaction mixture. After stirring at room temperature for 2 hours, the reaction has diluted with 400 mL of ethyl acetate, washed with 100 mL of water and 100 mL of brine. The organic layer was dried over magnesium sulfate, filtered and the solvent removed under vacuum. The residue was purified by flash chromatography on silica gel eluting with ethyl acetate/hexane (55:45) to afford 1.74 g (96%) of the product as a white foam. $^1$H NMR (200MHz,CDCl$_3$): 1.15 (s,9H), 1.45 (s,3H), 1.48 (s,3H), 1.76 (m,1H), 2.35-2.62 (m,5H), 4.48 (m,1H), 4.79 (d,14Hz,1H), 5.04 (t,12Hz,2H), 5.35 (d, 14Hz,1H), 6.70 (d,6Hz,1H), 7.10-7.45 (m,17H), 7.72 (m,1H). FAB-MS: calculated for C$_{41}$H$_{45}$N$_3$O$_6$ 675; found 683 (M+Li).

Step B:
4'-[[2,3,4,5-Tetrahydro-3(R)-[[3-methyl-1-oxo-3-[[(benzyloxy)carbonyl]amino]butyl]amino]-2-oxo-1H-1-benzazepin-1-yl]methyl][1,1'-biphenyl]-2-carboxylic acid To a solution of 150 mg (0.22 mmol) of the intermediate from Step A in 1 mL of dry methylene chloride was added 2 drops of anisole followed by 1 mL of trifluoroacetic acid. The solution was stirred for 4 hours at room temperature. The solvent was removed under vacuum and the resulting oil was azeotroped with carbon tetrachloride (3×20 mL) to afford 140 mg (100%) of product as a white foam. $^1$H NMR (200MHz,CDCl$_3$): 1.38 (s,6H), 1.65 (m,1H), 2.10-2.40 (m,3H), 2.61 (s,2H), 4.45 (m,1H), 4.62 (d,14Hz,1H), 5.06 (s,2H), 5.27 (d,14Hz,1H), 7.00-7.36 (m,15H), 7.42 (m,1H), 7.55

(m,1H), 7.68 (d,7Hz,1H), 7.95 (dd;2,8Hz;1H), 8.18 (br s,1H). FAB-MS: calculated for $C_{37}H_{37}N_3O_6$ 619; found 642 (M+Na).

Step C:
N-Ethyl-4'-[[3(R)-[[3-(benzyloxycarbonyl)amino-3-methyl-1-oxobutyl]amino]-2,3,4,5-tetrahydro-2-oxo-1H-1-benzazepin-1-yl]-methyl][1,1'-biphenyl]-2-carboxamide To a slurry of 14 mg (0.169 mmol) of ethylamine hydrochloride in 1 mL of dry methylene chloride under nitrogen at 0° C. was added 0.047 mL (0.339 mmol) of triethylamine followed by a solution of 70 mg (0.113 mmol) of the intermediate from Step B in 1 mL of methylene chloride. To this mixture was added 75 mg (0.169 mmol) of benzotriazol-1-yloxytris(dimethylamino)phosphonium hexafluorophosphate. The reaction mixture was slowly warmed to room temperature. After 2 hours the reaction was diluted with 75 mL of ethyl acetate, washed with 25 mL of 5% aqueous citric acid, 25 mL of saturated aqueous sodium bicarbonate and 25 mL of brine. The organic layer was dried over magnesium sulfate, filtered and the solvent removed under vacuum. The residue was purified by flash chromatography on silica gel eluting with ethyl acetate/hexane (9:1) to afford 74 mg (100%) of the product as a white foam. $^1$H NMR (200MHz,CDCl$_3$): 0.75 (t,6Hz,3H), 1.35 (s,3H), 1.38 (s,3H), 1.76 (m,2H), 2.35-2.62 (m,5H), 3.10 (m,2H), 4.48 (m,1H), 4.82 (d,14Hz,1H), 5.04 (m,3H), 5.30 (d,14Hz,1H), 5.57 (s,1H), 6.65 (d,6Hz,1H), 7.10-7.45 (m,15H), 7.62 (m,1H), FAB-MS: calculated for $C_{39}H_{42}N_4O_5$ 646; found 669 (M+Na).

Step D:
N-Ethyl-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate To a solution of 74 mg (0.114 mmol) of the intermediate obtained in Step C in 5 mL of dry methanol was added 3 drops of trifluoroacetic acid and 15 mg of 20% palladium hydroxide on carbon. The mixture was hydrogenated at room temperature and 40 psi for 3 hours. The catalyst was removed by filtration through Celite and the solvent removed under vacuum. The resulting material was purified by reverse phase medium pressure liquid chromatography on C-8 eluting with methanol/0.1% aqueous trifluoroacetic acid (60:40) to afford 64 mg (90%) of the title compound as a white solid. $^1$H NMR (200MHz,CD$_3$OD): 0.85 (t,7Hz,3H), 1.35 (s,3H), 1.39 (s,3H), 2.1 (m,1H), 2.3 (m,1H), 2.50-2.65 (m,4H), 3.09 (q,7Hz,2H), 4.40 (dd;6,13Hz;1H), 4.92 (d,15Hz,1H), 5.30 (d,15Hz,1H), 7.20-7.52 (m,12H). FAB-MS: calculated for $C_{31}H_{36}N_4O_3$ 512; found 514 (100%).

EXAMPLE 73
N-Ethyl-4'-[[3(R)-[[3-[(2(S),3-dihydroxypropyl)amino]-3-methyl-1-oxobutyl]amino]-2,3,4,5-tetrahydro-2-oxo-1H-1-benzazepin-1-yl]methyl][1,1'-biphenyl]-2-carboxamide, trifluoroacetate The title compound was prepared from N-ethyl-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate (Example 72) and D-glyceraldehyde acetonide (used crude as prepared according to the procedure of Hertel, L. W.; Grossman, C. S.; Kroin, J. S., Synth. Comm. 1991, 21, 151-154.) by the procedure described in Example 71. $^1$H NMR (200MHz,CD$_3$OD): 0.87 (t,7Hz,3H), 1.35 (s,3H), 1.39 (s,3H), 2.10 (m,1H), 2.35 (m,1H), 250-2.65 (m,4H), 2.85-3.25 (m,4H), 3.55 (m,2H), 3.83 (m,1H), 4.40 (dd;8,12Hz;1H), 5.00 (d,15Hz,1H), 5.25 (d,15Hz,1H), 7.20-7.52 (m,12H). FAB-MS: calculated for $C_{34}H_{42}H_4O_5$ 586; found 588 (100%).

EXAMPLE 74
N-(2-Hydroxyethyl)-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate

Step A:
N-(2-Hydroxyethyl)-4'-[[3(R)-[[3-(benzyloxycarbonyl)amino-3-methyl-1-oxobutyl]amino]-2,3,4,5-tetrahydro-2-oxo-1H-1-benzazepin-1-yl]methyl][1,1'-biphenyl]-2-carboxamide To a solution of 70 mg (0.11 mmol) of 4'-[[2,3,4,5-tetrahydro-3(R)-[[3-methyl-1-oxo-3-[(benzyloxycarbonyl)amino]butyl]amino]-2-oxo-1H-1-benzazepin-1-yl]methyl][1,1'-biphenyl]-2-carboxylic acid (Example 72, Step B) in 2 mL of dry methylene chloride under nitrogen at 0° C. was added 0.023 mL (0.17 mmol) of triethylamine followed by 55 mg (0.12 mmol) of benzotriazol-1-yloxy-tris(dimethylamino)phosphonium hexafluorophosphate. After 5 minutes, 0.010 mL (0.33 mmol) of ethanolamine was added to the reaction by syringe. The reaction mixture was slowly warmed to room temperature. After 2 hours, the reaction was diluted with 75 mL of ethyl acetate, washed with 25 mL of 5% aqueous citric acid, 25 mL of saturated sodium bicarbonate and 25 mL of brine. The organic layer was dried over magnesium sulfate, filtered and the solvent removed under vacuum. The residue was purified by flash chromatography on silica gel eluting with ethyl acetate/methanol (97:3) to afford 58 mg (78%) of the product as a white foam. $^1$H NMR (200 MHz,CDCl$_3$): 1.30 (s,3H), 1.35 (s,3H), 1.80 (m,1H), 2.20-2.75 (m,7H), 3.10-3.40 (m,4H), 4.51 (m,1H), 4.92 (d, 14 Hz, 1H), 5.00 (s,2H), 5.10 (d,14 Hz, 1H), 5.68 (s,1H), 6.53 (d,6 Hz, 1H), 7.12-7.48 (m,16H), 7.65 (d;1.6 Hz;1H). FAB-MS: calculated for $C_{39}H_{42}N_4O_6$ 662; found 686 (M+Na).

Step B:
N-(2-Hydroxyethyl)-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate The title compound was prepared from the intermediate obtained in Step A by the procedure described in Example 72, Step D. $^1$H NMR (200 MHz,CD$_3$OD): 1.35 (s,3H), 1.39 (s,3H), 2.00-2.40 (m,2H), 2.41-2.68 (m,4H), 3.21 (t,5 Hz,2H), 3.41 (t,5 Hz,2H), 4.40 (dd;6,10 Hz;1H), 4.95 (d,15 Hz,1H), 5.26 (d,15 Hz,1H), 7.20-7.52 (m,12H). FAB-MS: calculated for $C_{31}H_{36}N_4O_4$ 528; found 530 (100%).

EXAMPLE 75

N-(Phenylmethyl)-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate

Step A:

N-(Phenylmethyl)-4'-[[3(R)-[[3-(benzyloxycarbonyl)amino-3-methyl-1-oxobutyl]amino]-2,3,4,5-tetrahydro-2-oxo-1H-1-benzazepin-1-yl]methyl][1,1'-biphenyl]-2-carboxamide The title compound was prepared from 4'-[[2,3,4,5-tetrahydro-3(R)-[[3-methyl-1-oxo-3-[(benzyloxycarbonyl)amino]butyl]amino-]-2-oxo-1H-1-benzazepin-1yl]methyl][1,1'-biphenyl]-2-carboxylic acid (Example 72, Step B) and benzylamine according to the procedure described in Example 74, Step A. $^1$H NMR (200 MHz,CDCl$_3$): 1.31 (s,3H), 1.35 (s,3H), 1.75 (m,1H), 2.30–2.65 (m,5H), 4.23 (d,5 Hz,2H), 4.47 (m,1H), 4.83 (d,14 Hz,1H), 5.02 (s,2H), 5.45 (m,1H), 5.60 (s,1H), 6.68 (d,6Hz,1H), 6.90 (m,2H), 7.10–7.50 (m,20H), 7.65 (m,1H). FAB-MS: calculated for C$_{44}$H$_{44}$N$_4$O$_5$ 708; found 709 (M+H), 731 (M+Na, 100%).

Step B:

N-(Phenylmethyl)-4'-[[3(R)-[(3-amino-3-methyl-1oxobutyl)amino]-2,3,4,5-tetrahydro-2-oxo-1H-1-benzazepin-1-yl]methyl][1,1'-biphenyl]-2-carboxamide, trifluoroacetate The title compound was prepared from the intermediate obtained in Step A according to the procedure described in Example 72, Step D. $^1$H NMR (200 MHz,CD$_3$OD): 1.35 (s,3H), 1.39 (s,3H), 2.00–2.45 (m,2H), 2.48–2.68 (m,4H), 4.28 (m,2H), 4.40 (dd;8,12 Hz;1H), 4.95 (d,15 Hz,1H), 3.26 (d,1 Hz,1H), 7.05 (m,2H), 7.15–7.55 (m,15H), 8.47 (t,6 Hz,1H). FAB-MS: calculated for C$_{36}$H$_{38}$N$_4$O$_3$ 574; found 576 (100%).

EXAMPLE 76

N-[(4-Methoxyphenyl)methyl]-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate

Step A:

N-[(4-Methoxyphenyl)methyl]-4'-[[3(R)-[[3-(benzyloxycarbonyl)amino-3-methyl-1-oxo-butyl]amino]-2,3,4,5-tetrahydro-2-oxo-1H-1-benzazepin-1-yl]methyl][1,1'-biphenyl]-2-carboxamide The title compound was prepared from 4'-[[2,3,4,5-tetrahydro-3(R)-[[3-methyl-1-oxo-3-[[(benzyloxyoxy)carbonyl]amino]butyl]amino]-2-oxo-1H-1-benzazepin-1-yl]methyl][1,1'-biphenyl]-2-carboxylic acid (Example 72, Step B) and 4-methoxybenzylamine by the procedure described in Example 74, Step A. $^1$H NMR (200 MHz,CD$_3$OD) 1.40 (s,6H), 2.00 (m,1H), 2.31 (m,1H), 2.50–2.75 (m,4H), 3.82 (s,3H), 4.27 (s,2H), 4.43 (dd;7,11 Hz;1H), 4.95 (d,15 Hz,1H), 5.05 (d,12 Hz,1H), 5.15 (d,12 Hz,1H), 5.37 (d,15 Hz,1H), 6.87 (m,3H), 7.03 (d,8 Hz,2H), 7.20–7.57 (m,19H). FAB-MS: calculated for C$_{45}$H$_{46}$N$_4$O$_6$ 738; found 7.40.

Step B:

N-[(4-Methoxyphenyl)methyl]-4'-[[3(R)-[(3-amino-3-methyl-(oxobutyl)amino]-2,3,4,5-tetrahydro-2-oxo-1H-1-benzazepin-1-yl]-methyl][1,1'-biphenyl]-2-carboxamide, trifluoroacetate The title compound was prepared from the intermediate obtained in Step A by the procedure described in Example 72, Step D. $^1$H NMR (200 MHz,CD$_3$OD): 1.32 (s,3H), 1.37 (s,3H), 2.00–2.45 (m,2H), 2.48–2.68 (m,4H), 3.75 (s,3H), 4.20 (s,2H), 4.40 (dd;8,12 Hz;1H), 4.95 (d,14 Hz,1H), 5.25 (d,14 Hz,1H), 6.80 (d,8 Hz,2H), 6.97 (d,8 Hz,2H), 7.19–7.52 (m,12H). FAB-MS: calculated for C$_{37}$H$_{40}$N$_4$O$_4$ 604; found 606 (100%).

EXAMPLE 77

N-[(4-Hydroxyphenyl)methyl]-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate To a solution of 60.5 mg (0.084 mmol) of N-[(4-methoxyphenyl)methyl]-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate (Example 76) in 3 mL of dry methylene chloride under nitrogen was added 0.42 mL (0.42 mmol) of 1.0M solution of boron tribromide in methylene chloride. The reaction mixture was stirred for 2 hours then 2 mL of water was added followed by sufficient methanol to dissolve any remaining precipitate. The solvent was removed under vacuum. The resulting material was purified by reverse phase medium pressure liquid chromatography on C-8 eluting with methanol/0.1% aqueous trifluoroacetic acid (60:40) to afford 53 mg (89%) of the title compound as a white solid. $^1$H NMR (200 MHz,CD$_3$OD): 1.39 (s,3H), 1.45 (s,3H), 2.10–2.50 (m,2H), 2.52–2.72 (m,4H), 4.23 (s,2H), 4.48 (dd;8,12 Hz;1H), 5.02 (d,14 Hz,1H), 5.30 (d,14 Hz,1H), 6.72 (d,8 Hz,2H), 6.94 (d,8 Hz,2H), 7.20–7.57 (m,12H). FAB-MS: calculated for C$_{36}$H$_{38}$N$_4$O$_4$ 590; found 592 (100%).

EXAMPLE 78

N,N-Diethyl-4'-[[3(R)-[(3-amino-3-methyl-1-oxobutyl)amino]-2,3,4,5-tetrahydro-2-oxo-1H-1-benzazepin-1-yl]-methyl][1,1'-biphenyl]-2-carboxamide, trifluoroacetate

Step A:

N,N-Diethyl-4'-[[3(R)-[[3-(benzyloxycarbonyl)amino-3-methyl-1-oxobutyl)amino]-2,3,4,5-tetrahydro-2-oxo-1H-1-benzazepin-1-yl]methyl][1,1'-biphenyl]-2-carboxamide Prepared from 4'-[[2,3,4,5-tetrahydro-3(R)-[[3-methyl-1-oxo-3-[[(benzyloxy)carbonyl]amino]butyl]amino]-2-oxo-1H-1benzazepin-1-yl]methyl][1,1'-biphenyl]-2-carboxylic acid (Example 72, Step B) and diethylamine according to the procedure described in Example 74, Step A. $^1$H NMR (200 MHz,CDCl$_3$): 0.65 (t,6 Hz,3H), 0.72–1.00 (m,3H), 1.35 (s,6H), 1.96 (m,1H), 2.27 (m,1H), 2.40–2.68 (m,6H), 2.80–3.12 (m,2H), 3.55 (m,1H), 4.35 (dd;6,10 Hz;1H), 4.82 dd,6,15 Hz;1H), 5.04 (dd;3,16 Hz;2H), 5.40 (dd;8,14 Hz;1H, 7.15–7.55 (m,17H). FAB- MS: calculated for $C_{41}H_{46}N_4O_5$ 674; found 676, 698 (M+Na).

Step B:
N,N-Diethyl-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate The title compound was prepared from the intermediate obtained in Step A by the procedure described in Example 72, Step D. $^1$H NMR (200 MHz,CD$_3$OD): 0.67 (t,7 Hz,3H), 0.75–1.00 (m,3H), 1.34 (s,3H), 1.39 (s,3H), 2.00–2.80 (m,7H), 2.80–3.15 (m,2H), 3.55 (m,1H), 4.40 (dd;7,12 Hz;1H), 4.87 (d,15 Hz,1H), 5.36 (d,15 Hz,1H), 7.20–7.55 (m,12H). FAB-MS: calculated for $C_{33}H_{40}N_4O_3$ 540; found 542 (100%).

EXAMPLE 79

3-Amino-3-methyl-N-[2,3,4,5-tetrahydro-2-oxo-1-[[2'-carboxy[1,1'-biphenyl]-4-yl]methyl]-1H-benzazepin-3(R)-yl]butanamide, trifluoroacetate To a slurry of 54 mg (0.086 mmol) of 4'-[[2,3,4,5-tetrahydro-3(R)-[[3-methyl-1-oxo-3-[(benzyloxycarbonyl)amino]butyl]amino]-2-oxo-1H-1-benzazepin-1-yl]methyl][1,1'-biphenyl]-2-carboxylic acid (Example 72, Step B) in 2 mL of dry methylene chloride under nitrogen was added 0.5 mL (0.5 mmol) of 1.0M solution of boron tribromide in methylene chloride. The reaction mixture was stirred at room temperature for 30 minutes then quenched by the addition of 2 mL of water. The remaining solids were dissolved by the addition of 2 mL of methanol and the solvent were removed under vacuum. The resulting material was purified by reverse phase medium pressure liquid chromatography on C-8 eluting with methanol/0.1% aqueous trifluoroacetic acid (60:40) to afford 38 mg (74%) of the title compound as an off-white solid. $^1$H NMR (200 MHz,CD$_3$OD): 1.34 (s,3H), 1.39 (s,3H), 2.00–2.46 (m,2H), 2.50–2.70 (m,4H), 4.42 (dd;7,11 Hz;1H), 4.99 (d,14 Hz,1H), 5.23 (d,14 Hz),1H), 7.2–7.6 (m,11H), 7.76 (dd;1,7 Hz;1H). FAB-MS: calculated for $C_{29}H_{31}N_3O_4$ 485; found 486 (M+H, 100%).

EXAMPLE 80

3-Amino-3-methyl-N-[2,3,4,5-tetrahydro-2-oxo-1-[[2'-hydroxymethyl[1,1'-biphenyl]-4-yl]methyl]-1H-benzazepin-3-(R)-yl]butanamide, trifluoroacetate Step A:
3-[(Benzyloxycarbonyl)amino]-3-methyl-N-[2,3,4,5-tetrahydro-2-oxo-1-[[2'-hydroxymethyl[1,1'-biphenyl]-4-yl]methyl]-1H-benzazepin-3(R)-yl]butanamide To a solution of 124 mg (0.20 mmol) of 4'-[[2,3,4,5-tetrahydro-3(R)-[[3-methyl-1-oxo-3-[(benzyloxycarbonyl)amino]butyl]amino]-2-oxo-1H-1-benzazepin-1-yl]methyl][1,1'-biphenyl]-2-carboxylic acid (Example 72, Step B) in 1.5 mL of dry 1,2-dimethoxyethane at 0° C. was added 0.046 mL (0.421 mmol) of N-methylmorpholine followed by 0.055 mL (0.42 mmol) of isobutyl chloroformate. The reaction mixture was stirred at 0° C. for 1 hour then filtered. Solids were rinsed with 1,2-dimethoxyethane (2×1 mL) and the filtrates combined. To the filtrate at 0° C. was added by syringe a solution of 30.3 mg (0.801 mmol) of sodium borohydride in 0.3 mL of water. The reaction mixture was stirred at 0° C. for 15 minutes then diluted with ethyl acetate (75 mL). The organic layer was washed with saturated aqueous ammonium chloride (25 mL) and brine (25 mL), then dried over magnesium sulfate, filtered and the solvent was removed under vacuum. The residue was purified by flash chromatography on silica gel eluting with ethyl acetate/hexane (75:25) to afford 86 mg (71%) of the product as a white solid. $^1$H NMR (200 MHz,CDCl$_3$): 1.35 (s,3H), 1.37 (s,3H), 2.80 (m,2H), 2.50 (m,4H), 4.50 (m,3 H), 4.90 (d,15 Hz,1H), 5.03 (dd;10,12 Hz;2H), 5.18 (d,15 Hz,1H), 5.77 (s,1H), 6.70 (d,8 Hz,1H), 7.10–7.40 (m,16H), 7.53 (m,1H). FAB-MS: calculated for $C_{37}H_{39}N_3O_5$ 605; found 607 (30%).

Step B:
3-Amino-3-methyl-N-[2,3,4,5-tetrahydro-2-oxo-1-[[2'-hydroxymethyl[1,1'-biphenyl]-4-yl]methyl]-1H-benzazepin-3(R)-yl]butanamide, trifluoroacetate To a solution of 40 mg (0.066 mmol) of the intermediate obtained in Step A in 2 mL of methanol was added 5 mg of 20% palladium hydroxide on carbon catalyst. The resulting mixture was hydrogenated at room temperature and 1 atmosphere for 30 minutes. The catalyst was removed by filtration through Celite and the solvent removed under vacuum. The residue was purified by reverse phase medium pressure liquid chromatography on C-8 eluting with methanol/0.1% aqueous trifluoroacetic acid (60:40) to afford 36 mg (95%) of the title compound as a white solid. $^1$H NMR (200 MHz,CD$_3$OD): 1.34 (s,3H), 1.37 (s,3H), 2.0–2.7 (m,6H), 4.44 (m,3H), 4.95 (d,15 Hz,1H), 5.25 (d,15 Hz,1H), 7.1–7.5 (m,11H), 7.55 (d,6 Hz,1H). FAB-MS: calculated for $C_{29}H_{33}N_3O_3$ 471; found 472 (M+H, 100%).

EXAMPLE 81

3-Amino-3-methyl-N-[2,3,4,5-tetrahydro-2-oxo-1-[[2'-methyl[1,1'-biphenyl]-4-yl]methyl]-1H-benzazepin-3(R)-yl]butanamide, trifluoroacetate To a solution of 30 mg (0.066 mmol) of 3-[(benzyloxycarbonyl)amino]-3-methyl-N-[2,3,4,5-tetrahydro-2-oxo-1-[[2'-hydroxymethyl[1,1'-biphenyl]-4-yl]methyl]-1H-benzazepin-3(R)-yl]butanamide (Example 80, Step A) in 2 mL of methanol was added 5 mg of 20% palladium hydroxide on carbon catalyst and 1 drop of trifluoroacetic acid. The resulting mixture was hydrogenated at room temperature and 1 atmosphere for 4 hours. The catalyst was removed by filtration through Celite and the solvent removed under vacuum. The residue was purified by reverse phase medium pressure liquid chromatography on C-8 eluting with methanol/0.1% aqueous trifluoroacetic acid (65:35) to afford 30 mg (100%) of the title compound as a white solid. $^1$H NMR (200 MHz,CD$_3$OD): 1.35 (s,3H), 1.40 (s,3H), 2.0–2.7 (m,6H), 2.10 (s,3H), 4.42 (dd;8,12 Hz;1H), 4.95 (d,14 Hz,1H), 5.27 (d,14 Hz,1H), 7.1–7.4 (m,12H). FAB-MS: calculated for $C_{29}H_{33}N_3O_2$ 455; found 456 (M+H,100%).

EXAMPLE 82

4'-[[3(R)-[[3-[(2(S),3(S),4-Trihydroxybutylamino]-3-methyl-1-oxobutyl]amino-9-2,3,4,5-tetrahydro-2-oxo-1H-1-benzazepin-lyl-9-methyl][1,1'-biphenyl]-2-carboxamide, trifluoroacetate

Step A:
1-t-Butyldimethylsilyl-2,3-isopropylidene-D-threitol

To a solution of 1.0 g (6.2 mmol) of 2,3-isopropylidene-D-threitol in 6.0 mL of dry dimethylformamide at 0° C. was added 0.44 g (6.5 mmol) of imidazole followed by dropwise addition of a solution of 0.93 g (6.2 mmol) of t-butyldimethylsilyl chloride in 6.0 mL of dimethylformamide. The reaction mixture was stirred at 0° C. for 30 minutes then at room temperature for 1 hour. The reaction mixture was poured into 75 mL water and extracted with ether (3×75 mL). The combined ether extracts were washed with saturated aqueous sodium bicarbonate and with brine. The organic layer was dried over magnesium sulfate, filtered and the solvent removed under vacuum. The resulting oil was purified by flash chromatography on silica gel, eluting with hexanes/ethyl acetate (75:25) to afford 0.70 g (41%) of product as a clear oil. $^1$H NMR (200 MHz,CDCl$_3$): 0.07 (s,6H), 0.90 (s,9H), 1.39 (s,3H), 1.41 (s,3H), 3.60–4.00 (m,7H). FAB-MS: calculated for $C_{13}H_{28}O_4Si$ 276; found 261 (M-15,10%)

Step B:
5(S)-t-Butyldimethylsilyloxymethyl-2,2-dimethyl-1,3-dioxolan-4(R)-carboxaldehyde To a solution of 0.676 g (2.44 mmol) of the intermediate obtained in Step A in 35 mL of dry methylene chloride was added 3 mL of dry dimethylsulfoxide followed by 2.8 mL (20.2 mmol) of triethylamine. To this solution was added 1.61 g (10.1 mmol) of pyridine sulfur trioxide complex in three portions over a 5 minute period. The reaction mixture was stirred at room temperature for 2 hours at which time it was diluted with 250 mL of ethyl acetate. The mixture was transferred to a separatory funnel and washed with 1N HCl (2×50 mL), saturated aqueous sodium bicarbonate (50 mL) and brine (5 mL). The organic layer was dried over magnesium sulfate, filtered, and the solvent removed under vacuum to afford 672 mg (100%) of product which was used in the next reaction without further purification. $^1$H NMR (200 MHz,CDCl$_3$): 0.09 (s,6H), 0.87 (s,9H), 1.40 (s,3H), 1.45 (s,3H), 3.78 (d,4 Hz,2H), 4.10 (m,1H), 4.30 (dd;2,6 Hz;1H), 9.85 (d,2 Hz,1H).

Step C:
4'-[[3(R)-[[3-[(2(S),3(S),4-Trihydroxybutylamino-]-3-methyl-1-oxobutyl]amino-]-2,3,4,5-tetrahydro-2-oxo-1H-1-benzazepin-1-yl]methyl][1,1'-biphenyl]-2-carboxamide, trifluoroacetate The title compound was prepared from 4'-[[3(R)-[(3-amino-3-methyl-1-oxobutyl)amino]-2,3,4,5-tetrahydro-2-oxo-1H-1-benzazepin-1-yl]methyl]]1,1'-biphenyl]-2-carboxamide, trifluoroacetate (Example 69) and the intermediate obtained in Step B by the procedure described in Example 71. $^1$H NMR (200 MHz,CD$_3$OD); 1.37 (s,3H), 1.41 (s,3 H), 2.12–2.40 (m,2H), 2.55–2.71 (m,4H), 3.05–3.25 (m,2H), 3.59 (m,3H), 3.92 (m,1H), 4.40 (dd;7,12 Hz;1H), 5.02 (d,15 Hz,1H), 5.15 (d,15 Hz,1H), 7.20–7.58 (m,12H). FAB-MS: calculated for $C_{33}H_{40}N_4O_6$ 588; found 589 (M+H,70%).

EXAMPLE 83

4'-[[3(R)-[(2(R)-Amino-3-hydroxy-1-oxopropyl)amino]-2,3,4,5-tetrahydro-2-oxo-1H-1-benzazepin-1-yl]methyl][1,1'-biphenyl]-2-carboxamide, trifluoroacetate

Step A:
2(R)-t-Butoxycarbonylamino-3-(t-butoxy)-N-[2,3,4,5-tetrahydro-2-oxo-1H-1-benzazepin-3(R)-yl]propanamide To a solution of 200 mg (1.13 mmol) of 3(R)-amino-2,3,4,5-tetrahydro-1H-1-benzazepin-2-one (Example 1, Step B) in 8 mL of dry methylene chloride was added 0.206 mL (1.48 mmol) of triethylamine, 553 mg (1.25 mmol) of BOC-D-serine t-butyl ether followed by 602 mg (1.36 mmol) of benzotriazol-1-yloxytris(dimethylamino)phosphonium hexafluorophosphate. The reaction mixture was stirred at room temperature for 2 hours then diluted with 100 mL of ethyl acetate, washed with 25 mL of 5% aqueous citric acid, 25 mL of saturated sodium bicarbonate and 25 mL of brine. The organic layer was dried over magnesium sulfate, filtered and the solvents removed under vacuum. The residue was purified by flash chromatography on silica gel, eluting with ethyl acetate-hexane (55:45) to afford 480 mg (200%) of the product as a white foam. $^1$H NMR (200 MHz,CDCl$_3$): 1.20 (s,9H), 1.47 (s,9H), 1.92 (m,1H), 2.55–3.02 (m,3H), 3.38 (t,8 Hz,1H), 3.78 (m,1H), 4.15 (m,1H), 4.52 (m,1H), 5.45 (s,1H), 7.00 (m,1H), 7.10–7.35 (m,3H), 7.68 (d,4 Hz,1H), 8.05 (s,1H). FAB-MS: calculated for $C_{22}H_{33}N_3O_5$ 419; found 420 (M+H,205), 426 (M+Li,40%).

Step B:
2(R)-t-Butoxycarbonylamino-3-(t-butoxy)-N-[2,3,4,5-tetrahydro-2-oxo-1-[[2'-cyano[1,1'-biphenyl]-4-yl]methyl]-1H-1-benzazepin-3(R)-yl]propanamide Prepared from the intermediate obtained in Step A and 4'-bromomethyl-1,1'-biphenyl-2-nitrile (Example 69, Step C) by the procedure described in Example 69, Step D. $^1$H NMR (200 MHz,CDCl$_3$): 1.20 (s,9H), 1.47 (s,9H), 1.88 (m,1H), 2.45–2.75 (m,3H), 3.38 (dd;6,8 Hz;1H), 3.78 (m,1H), 4.15 (m,1H), 4.52 (m,1H), 4.97 (d,14 Hz,1H), 5.21 (d,14 Hz,1H), 5.40 (s,1H), 7.1–7.5 (m,11H), 7.6–7.8 (m,2H). FAB-MS: calculated for $C_{36}H_{42}N_4O_5$ 610; found 618 (M+Li,30%).

Step C:
4'-[[3(R)-[[2(R)-(t-Butoxycarbonyl)amino-3-hydroxy-1-oxopropyl]amino-]-2,3,4,5-tetrahydro-2-oxo-1H-1-benzazepin-1-yl]methyl]-[1,1,'-biphenyl]-2-carboxamide Prepared from the intermediate obtained in Step B by the procedure described in Example 69, Step E. $^1$H NMR (400 MHz,CDCl$_3$): 1.18 (s,9H), 1.45 (s,9H, 1.85 (m,1H), 2.45 (m,1H), 2.62 (m,2H), 3.38 (dd;6,8 Hz,1H), 3.72 (m,1H), 9.12 (m,1H), 4.47 (m,1H), 4.92 (d,14 Hz,1H), 5.13 (s,1H), 5.20 (d,14 Hz,1H), 5.37 (s,2H), 7.17 (m,3H), 7.2–7.4 (m,6H), 7.40 (m,1H), 7.47 (m,1H), 7.60 (s,1H), 7.72 (d,8 Hz,1H). FAB-MS: calculated for $C_{36}H_{44}N_4O_6$ 628; found 636 (M+Li;40%).

Step D:
4'-[[3(R)-[(2)(R)-Amino-3-hydroxy-1-oxo-propyl-)amino]-2,3,4,5-tetrahydro-2-oxo-1H-1-benzazepin-1-yl]methyl][1,1'-biphenyl]-2-carboxamide, trifluoroacetate The title compound was prepared from the intermediate obtained in Step C by the procedure described in Example 69, Step F. $^1$H NMR (200 MHz,CD$_3$OD): 2.10 (m,1H), 2.37 (m,1H), 2.62 (m,2H), 3.8–4.1 (m,3H), 4.42 (dd;6,11 Hz;1H), 4.95 (d,14 Hz,1H), 5.27 (d,14 Hz,1H), 7.2–7.6 (m,12H). FAB-MS: calculated for C$_{27}$H$_{28}$N$_4$O$_4$ 472; found 473 (M+H,100%).

EXAMPLE 84

4'-[[3(R)-[(2-Amino-2-methyl-1-oxopropyl)amino]-2,3,4,5-tetrahydro-2-oxo-1H-1-benzazepin-1-yl]methyl][1,1'-biphenyl]-2-carboxamide, trifluoroacetate

Step A:
2-t-Butoxycarbonylamino-2-methyl-N-[2,3,4,5-tetrahydro-2-oxo-1-[[2'-cyano[1,1,'-biphenyl]-4-yl]methyl]-1H-1-benzazepin-3(R)-yl]propanamide Prepared from 2-t-butoxycarbonylamino-2-methyl-N-[2,3,4,5-tetrahydro-2-oxo-1H-1-benzazepin-3(R)-yl]propanamide (Example 68, Step A) and 4'-bromomethyl-1-1'-biphenyl-2-nitrile (Example 69, Step C) by the procedure described in Example 69, Step D. $^1$H NMR (200 MHz,CDCl$_3$): 1.39 (s,9H), 1.41 (s,3H), 1.45 (s,3H), 1.83 (m,1H), 2.4–2.8 (m,3H), 4.48 (m,1H), 4.90 (d,16 Hz,1H), 4.93 (s,1H), 5.22 (d,16 Hz,1H), 7.1–7.5 (m,10H), 7.60 (m,1H), 7.72 (d,6 Hz,1H). FAB-MS: calculated for C$_{33}$H$_{36}$N$_4$O$_4$ 552; found 554 (20%).

Step B:
4'-[[3(R)-[[2-(t-Butoxycarbonyl)amino-2-methyl-1-oxopropyl]amino]-2,3,4,5-tetrahydro-2-oxo-1H-1-benzazepin-1-yl]methyl][1,1'-biphenyl]-2-carboxamide Prepared from the intermediate obtained in Step A by the procedure described in Example 69, Step E. $^1$H NMR (200 MHz,CDCl$_3$); 1.40 (s,12H), 1.43 (s,3H), 1.83 (m,1H), 2.4–2.8 (m,3H), 4.48 (m,1H), 4.85 (d,14 Hz,1H), 4.97 (s,1H), 5.20 (s,1H), 5.22 (d,14 Hz,1H), 5.57 (s,1H), 7.1–7.5 (m,11H), 7.70 (dd;1,6 Hz;1H).

Step C:
4'-[[3(R)-[(2-Amino-2-methyl-1-oxopropyl)amino]-2,3,4,5-tetrahydro-2-oxo-1H-1benzazepin-1-yl]methyl][1,1,'-biphenyl]-2-carboxamide, trifluoroacetate The title compound was prepared from the intermediate described in Example 69, Step F. $^1$H NMR (200 MHz,CD$_3$OD): 1.52 (s,3H), 1.65 (s,3H), 2.25 (m,2H), 2.60 (m,2H), 4.40 (m,1H), 5.00 (d,7 Hz,1H), 5.20 (d,7 Hz,1H), 7.2–7.6 (m,12H). FAB-MS: calculated for C$_{28}$H$_{30}$N$_4$O$_3$ 470; found 471 (M+H,100%).

EXAMPLE 85

3-(2-Aminoethyl)amino-3-methyl-N-[2,3,4,5-tetrahydro-2-oxo-1-[[2'-carboxy[1,1'-biphenyl]-4-yl]methyl]-1H-benzazepin-3-(R)-yl]butanamide, dihydrochloride

Step A:
4'-[[2,3,4,5-Tetrahydro-3(R)-[[3-methyl-1-oxo-3-amino]butyl]amino]-2-oxo-1H-1-benzazepin-1-yl]methyl][1,1'-biphenyl]-2-carboxylic acid, 1,1-dimethylethyl ester, acetate To a solution of 400 mg (0.592 mmol) of 4'-[[2,3,4,5-tetrahydro-3(R)-[[3-methyl-1-oxo-3-[(benzyloxycarbonyl)amino]butyl]amino]-2-oxo-1H-1-benzazepin-1-yl]methyl][1,1'-biphenyl]-2-carboxylic acid, 1,1-dimethylethyl ester (Example 72, Step A) in 10 mL of methanol was added 0.043 mL (0.59 mmol) of acetic acid and 80 mg of 20% palladium hydroxide on carbon catalyst. The resulting mixture was hydrogenated at room temperature and 1 atmosphere for 4 hours. The catalyst was removed by filtration through Celite and the filtrate concentrated under vacuum to afford 345 mg (97%) of the product as a white solid. $^1$H NMR (400 MHz,CD$_3$OD): 1.17 (s,9H), 1.35 (s,3H), 1.42 (s,3H), 1.95 (s,3H), 2.15 (m,1H), 2.35 (m,1H), 2.50 (d,12 Hz,1H), 2.5–2.78 (m,3H), 4.42 (dd;8,11 Hz;1H), 5.02 (d,15 Hz,1H), 5.37 (d,15 Hz,1H), 7.1–7.6 (m,11H), 7.67 (d,8 Hz,1H). FAB-MS: calculated for C$_{33}$H$_{39}$N$_3$O$_4$ 541; found 542 (M+H,100%).

Step B: 2-(t-Butoxycarbonylamino)acetaldehyde

To a solution of 700 mg (4.34 mmol) of 2-(t-butoxycarbonylamino)ethanol in 35 mL of dry methylene chloride was added 4.0 mL of dimethylsulfoxide and 4.8 mL (35 mmol) of triethylamine, followed by 2.8 g (17 mmol) of pyridine sulfur trioxide complex in three portions over 5 minutes. The reaction was stirred at room temperature for 3 hours then diluted with 500 mL of ether. The mixture was transferred to a separatory funnel and washed with 1N HCl (2×50 ml), saturated aqueous sodium bicarbonate (100 mL), and brine (100 mL). The organic layer was dried over magnesium sulfate, filtered, and the solvent removed under vacuum to afford 550 mg (80%) of product which was used without further purification. $^1$H NMR (200 MHz,CDCl$_3$): 1.40 (s,9H), 4.05 (d,7 Hz,2H), 5.17 (s,1H), 9.62 (s,1H).

Step C:
3-(2-Aminoethyl)amino-3-methyl-N-[2,3,4,5-tetrahydro-2-oxo-1-[[2'-carboxy-[[1,1'-biphenyl]-4-yl]methyl]-1H-benzazepin-3-(R)-yl]butanamide, dihydrochloride To a solution of 345 mg (0.573 mmol) of the intermediate obtained in Step A in 10 mL of dry methanol was added 0.088 mL (0.63 mmol) of triethylamine, 3.4 g of dry 4A powdered molecular sieves followed by a solution of 540 mg (3.4 mmol) of 2-(t-butoxycarbonylamino)acetaldehyde (Step B) in 5 mL of dry methanol. The pH of the mixture was carefully adjusted to 6.5 with glacial acetic acid (7 drops). The reaction was stirred for 3 hours at which time 3.4 mL (3.4 mmol) of a 1.0M solution of sodium cyanoborohydride in tetrahydrofuran was added by syringe. The reaction was stirred for 20 hours then filtered through a pad of Celite. To the filtrate was added 2.0 mL of acetic acid (CAUTION! evolution of hydrogen cyanide). The resulting mixture was stirred for 3 hours. The solvent was removed under vacuum to afford a clear oil which was dissolved in 5 mL of methylene chloride. To this solution was added 5 drops of anisole followed by 5 mL of trifluoroacetic acid. The mixture was stirred for 4 hours at room temperature then all volatiles removed under vacuum to give an oil which was purified by reverse phase medium pressure liquid chromatography on C-8 eluting with methanol/0.1% aqueous trifluoroacetic acid (55:45). The product thus obtained was converted to its dihydrochloride salt by dissolving it in 10 mL of 6N HCl followed by evaporation under vacuum. The cycle was repeated three times to afford 273 mg (79%) of the title compound as an off-white solid. $^1$H NMR (200 MHz,CD$_3$OD): 1.45 (s,3H), 1.51 (s,3 H), 2.1–2.5 (m,2H), 2.5–2.7 (m,4H), 3.2–3.5 (m,4H), 4.42 (dd;8,11 Hz;1H), 5.00 (d,15 Hz,1H), 5.22 (d,15 Hz,1H), 7.2–7.6 (m,11H), 7.78 (d,6 Hz,1H). FAB-MS: calculated for $C_{31}H_{36}N_4O_4$ 528; found 529 (M+H,100%).

EXAMPLE 86

3-[(2(S)-Hydroxypropyl)amino]3-methyl-N-[2,3,4,5-tetrahydro-2-oxo-1-[[2'-(1H-tetrazol-5-yl)[1,1'-biphenyl-]-4-yl]methyl]-1H-1-benzazepin-3(R)-yl]butanamide, trifluoroacetate Step A:
3-[(2-(S)-Benzyloxypropyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide, trifluoroacetate To a solution of 0.20 g (0.34 mmol) of 3-amino-3-methyl-N-[2,3,4,5-tetrahydro-2oxo-1-[[2'-(1H-tetrazol-5-yl)[1,1'-biphenyl]-4-yl]methyl]-1H-1-benzazepin-3(R)-yl]-butanamide, trifluoroacetate (Example 1) in 8 mL of dry methanol was added 0.096 mL (2.50 mmol) of triethylamine, 1.0 g of dry 4a powered molecular sieves followed by a solution of 0.296 g (1.80 mmol) of (S)-2-benzyloxpropanol (prepared from ethyl-L-lactate according to the procedure of Hanessian and Kloss, Tetrahedron Lett. 1985, 26, 1261–1265.) in 2 mL of dry methanol. The pH of the mixture was carefully adjusted to 6.5 with glacial acetic acid. The reaction was stirred for 2 hours at which time 2.06 mL (2.06 mmol) of a 1.0M solution of sodium cyanoborohydride in tetrahydrofuran was added by syringe. The reaction was stirred for 24 hours then filtered through a pad of Celite. To the filtrate was added 5.0 mL of trifluoroacetic acid (CAUTION! evolution of hydrogen cyanide) and the resulting mixture was stirred for three hours. The solvent was removed under vacuum to afford 1.6 g of a clear oil which was purified by reverse phase medium pressure liquid chromatography on C-8 eluting with methanol/0.1% aqueous trifluoroacetic acid (65:35) to afford 254 mg (100%) of the product as a white solid. $^1$H NMR( 200 MHz,CD$_3$OD): 1.28 (d,6 Hz,3H), 1.35 (s,3H), 1.40 (s,3 H), 2.10 (m,1H), 2.2–2.7 (m,5H), 2.95 (m,1H), 3.20 (m,1H), 3.83 (m,1H), 4.42 (m,1H), 4.50 (d,11 Hz,1H), 4.63 (d,11 Hz,1H), 5.20 (d,15 Hz,1H), 6.95 (d,8 Hz,2H), 7.1–7.7 (m,15H). FAB-MS: calculated for $C_{39}H_{43}N_7O_3$ 657; found 658 (M+H,100%).

Step B:
3-[(2(S)-Hydroxypropyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate A solution of 250 mg (0.324 mmol) of the intermediate prepared in Step A in 5 mL of methanol was placed in a shaker bottle. To the solution was added 3 drops of trifluoroacetic acid and 0.1 g of 30% palladium on carbon. The mixture was hydrogenated at room temperature and 40 psi for 3 days. The catalyst was removed by filtration through Celite and the filtrate evaporated under vacuum. The resulting material was purified by reverse phase medium pressure liquid chromatography on C-8 eluting with methanol/0.1% aqueous trifluoroacetic acid (60:40) to afford 149 mg (64%, Steps A + B) of the title compound as a white solid. $^1$H NMR (200 MHz,CD$_3$OD): 1.20 (d,6 Hz,3H), 1.35 (s,3 H), 1.40 (s,3H), 2.10 (m,1H), 2.2–2.6 (m,5H), 2.78 (m,1H), 3.08 (m,1H), 3.92 (m,1H), 4.35 (dd;7,10 Hz;1H), 4.95 (d,14 Hz,1H), 5.18 (d,14 Hz,1H), 7.00 (d,8 Hz,2H), 7.1–7.4 (m,6H), 7.5–7.7 (m,4H). FAB-MS: calculated for $C_{32}H_{37}N_7O_3$ 567; found 568 (M+H,100%).

EXAMPLE 87

3-[[2-(t-Butoxycarbonylamino)ethyl]amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate To a solution of 485 mg (0.833 mmol) of 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate (Example 1) in 8 mL of dry methanol was added 0.232 mL (1.67 mmol) of triethylamine, 2.5 g of dry 4A powdered molecular sieves followed by a solution of 200 mg (1.25 mmol) of 2-(t-butoxycarbonylamino)acetaldehyde (Example 85, Step B) in 1 mL of dry methanol. The pH of the mixture was carefully adjusted to 6.5 with glacial acetic acid. The reaction was stirred for 2 hours at which time 5.0 mL (5.0 mmol) of a 1.0M solution of sodium cyanoborohydride in tetrahydrofuran was added by syringe. The reaction was stirred for 20 hours then filtered through a pad of Celite. To the filtrate was added 1.0 mL of acetic acid (CAUTION! evolution of hydrogen cyanide). The resulting mixture was stirred for 30 minutes. The solvent was removed under vacuum to afford a clear oil which was purified by reverse phase high pressure liquid chromatography on C-18 eluting with methanol/0.1% aqueous trifluoroacetic acid (65:35) to afford 347 mg (54%) of the title compound as a white solid. $^1$H NMR (200 MHz,CD$_3$OD): 1.30 (s,9H), 1.35 (s,3H), 1.39 (s,3H), 2.10 (m,1H), 2.2–2.6 (m,5H), 3.10 (m,2H), 3.35 (m,2H), 4.39 (dd;8,11 Hz;1H), 4.95 (d,15 Hz,1H), 5.21 (d,15 Hz,1H), 7.05 (m,2H), 7.2–7.5 (m,7H), 7.5–7.7 (m,3H). FAB-MS: calculated for $C_{36}H_{44}N_8O_4$ 652; found 654 (100%).

EXAMPLE 88

3-[(2-Aminoethyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, di(trifluoroacetate)

The title compound was prepared from 3-[[(2-t-butoxycarbonylamino)ethyl]amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3-(R)-yl]-butanamide, monotrifluoroacetate (Example 87) by the procedure described in Example 69, Step F. $^1$H NMR (200 MHz,CD$_3$OD): 1.38 (s,3H), 1.42 (s,3H), 2.12 (m,1H), 2.2–2.7 (m,5H), 3.33 (m,4H), 4.35 (dd;6,11 Hz;1H), 7.1–7.4 (m,7H,), 7.5–7.7 (m,3H). FAB-MS: calculated for $C_{31}H_{36}N_8O_2$ 552; found 553 (M+H,100%).

EXAMPLE 89

3-Amino-3-methyl-N-[2,3,4,5-tetrahydro-2-oxo-1-[[-2'-[1-(carboxymethyl)tetrazol-5-yl][1,1'-biphenyl]-4-yl]-methyl]-1H-1-benzazepin-3(R)-yl]-butanamide, trifluoroacetate Step A:
3-(t-Butoxycarbonylamino)-3-methyl-N-[2,3,4,5-tetrahydro-2-oxo-1-[[2'-[1-(carboxymethyl)tetrazol-5-yl][1,1'-biphenyl]-4-yl]methyl]-1H-1-benzazepin-3(R)-yl]-butanamide, t-butyl ester and,
3-(t-Butoxycarbonylamino)-3-methyl-N-[2,3,4,5-tetrahydro-2-oxo-1-[[2'-[2-(carboxymethyl)tetrazol-5-yl][1,1'-biphenyl]-4-yl]methyl]-1H-1-benzazepin-3(R)-yl]-butanamide, t-butyl ester To a solution of 101 mg (0.166 mmol) of 3-(t-butoxycarbonylamino)-3-methyl-N-[2,3,4,5-tetrahydro-2-oxo-1-[[2'-(1H-tetrazol-5-yl)1,1'-biphenyl]-4-yl]methyl]-1H-1-benzazepin-3(R)-yl]butanamide (Example 16, Step A), in 1 mL of acetone was added 0.028 mL (0.20 mmol) of triethylamine followed by dropwise addition of 0.029 mL (0.18 mmol) of t-butyl bromoacetate. The reaction mixture was stirred at room temperature for 1 hour then the solvent was removed under vacuum. The residue was dissolved in 50 mL of methylene chloride, washed with saturated aqueous sodium bicarbonate, dried over magnesium sulfate and filtered. The filtrate was evaporated under vacuum to afford 139 mg (100%) of product as a mixture of N-1 and N-2 tetrazole isomers. $^1$H NMR of mixture (200 MHz,CDCl$_3$): 1.30 (s,6H), 1.40 (s,6H), 1.50 (m,36H), 1.90 (m,2H), 2.4–2.7 (m,8H), 3.80 (s,2H), 4.07 (s,2H), 4.52 (m,2H), 4.80 (m,2H), 5,37 (m,2H), 6.72 (m,2H), 7-.0–7.4 (m,16H), 7.14–7.8 (m,6H). FAB-MS calculated for $C_{40}H_{49}N_7O_6$ 723; found 724 (M+H,20%).

Step B:
3-Amino-3-methyl-N-[2,3,4,5-tetrahydro-2-oxo-1-[[2'-[1-(carboxymethyl)tetratzol-5-yl][1,1'-biphenyl]-4-yl]methyl]-1H-1-benzazepin-3(R)-yl]-butanamide, trifluoroacetate Prepared from the intermediate obtained in Step A by the procedure described in Example 69, Step F. Separation of isomers by reverse phase high pressure liquid chromatography on C-18 eluting with methanol/0.1% aqueous trifluoroacetic acid afforded the title compound in addition to the N-2 isomer. $^1$H NMR (200 MHz,CD$_3$OD): 1.39 (s,3H), 1.42 (s,3H), 2.0–2.7 (m,6H), 4.40 (dd;8,11 Hz;1H), 4.48 (s,2H), 4.85 (d,15 Hz,1H), 5.35 (d,15 Hz,1H), 7.05 (d,8 Hz,2H), 7.2–7.4 (m,7H), 7.5–7.9 (m,3H). FAB-MS: calculated for $C_{31}H_{33}N_7O_4$ 567; found 568 (M+H,100%).

EXAMPLE 90

3-Amino-3-methyl-N-[2,3,4,5-tetrahydro-2-oxo-1-[[2'-[2-(carboxymethyl)tetrazol-5-yl][1,1'-biphenyl]-4-yl]methyl]-1H-1-benzazepin-3(R)-yl]-butanamide trifluoroacetate The title compound was prepared from 3-(t-butoxycarbonylamino)-methyl-N-[2,3,4,5-tetrahydro-2-oxo-1-[[2'-[2-(carboxymethyl)-tetrazol-5-yl][1,1'-biphenyl]-4-yl]methyl]-1H-1-benzazepin-3(R)-yl]-butanamide, t-butyl ester (Example 89, Step A) by the procedure described in Example 89, Step B. $^1$H NMR (200 MHz,CD$_3$OD): 1.35 (s,3H), 1.42 (s,3H), 2.0–2.6 (m,6H), 4.39 (dd;7,11 Hz;1H), 4.90 (d,14 Hz,1H), 5.20 (d,14 Hz,1H), 5.42 (s,2H), 7.04 (d,6 Hz,2H), 7.15 (d,6 Hz,2H), 7.2–7.6 (m,7H), 7.75 (m,1H). FAB-MS: calculated for $C_{31}H_{33}N_7O_4$ 567; found 568 (M+H,100%).

EXAMPLE 91

3-Amino-3-methyl-N-[2,3,4,5-tetrahydro-2,5-dioxo-1-[[2'-(1H-tetrazol-5-yl)[1,1'-biphenyl]-4-yl]methyl]-1H-1-benzazepin-3-yl]-butanamide, trifluoroacetate Step A:
3-t-Butoxycarbonylamino-3-methyl-N-[2,3,4,5-tetrahydro-2,5-dioxo-1H-1-benzazepin-3-yl]-butanamide To a solution of 120 mg (0.531 mmol) of 3-t-butoxycarbonylamino-2,3,4,5-tetrahydro-1H-1-benzazepin-2,5-dione (prepared by the procedure of F. Stewart, Australian J. Chem. 1980, 33, 633–640.) in 2 mL of methanol was added 2 mL of 9N hydrochloric acid. The mixture was stirred at room temperature for 24 hours and solvent was removed under vacuum.

To the resulting solid in 3 mL of dry methylene chloride was added 0.22 mL (1.6 mmol) of triethylamine, 115 mg (0.531 mmol) of 3-t-butoxycarbonylamino-3-methyl butanoic acid (Example 31, Step E), followed by 235 mg (0.531 mmol) of benzotriazol-1-yloxy-tris(dimethylamino)phosphonium hexafluorophosphate. The reaction mixture was stirred at room temperature for 2 hours. The reaction was diluted with 75 mL of ethyl acetate, washed with 25 Ml of 5% aqueous citric acid, 25 mL of saturated aqueous sodium bicarbonate and 25 mL of brine. The organic layer was dried over magnesium sulfate, filtered and the solvent removed under vacuum. The residue was purified by flash chromatography on silica gel eluting with ethyl acetate/hexanes (65:35) to afford 109 mg (51%) of the product as a white foam. $^1$H NMR (200 MHz,CDCl$_3$): 1.33 (s,3H), 1.39 (s,12H), 2.49 (d,12 Hz,1H), 2.75 (d,12 Hz,1H), 2.9 (m,1H), 3.27 (dd;2,16 Hz;1H), 5.05 (m,2H), 7.05 (t,6 Hz,1H), 7.24 (t,6 Hz,1H), 7.50 (m,1H), 7.82 (dd;2,8 Hz;1H), 8.85 (s,1H). FAB-MS: calculated for $C_{20}H_{27}N_3O_5$ 389; found 390 (M+H,60%).

Step B:
3-(t-Butoxycarbonylamino)-3-methyl-N-[2,3,4,5-tetrahydro-2,5-dioxo-1-[[2'-(N-triphenylmethyl)tetrazol-5-yl)[1,1'-biphenyl]-4-yl]methyl]-1H-1-benzazepin-3-yl]-butanamide Prepared from the intermediate obtained in Step A and N-triphenylmethyl-5-[2-(4'-bromomethylbiphen-4-yl)] tetrazole (Example 1, Step J) by the procedure described in Example 1, Step K. $^1$H NMR (200 MHz,CDCl$_3$): 1.35 (s,3H), 1.40 (s,12H), 2.49 (d,14 Hz,1H), 2.6–2.9 (m,2H), 3.27 (m,1H), 4.82 (d,15 Hz,1H), 4.92 (d,15 Hz,1H), 5.05 (s,1H), 5.15 (m,1H), 6.8–7.6 (m,26H), 7.90 (m,1H). FAB-MS: calculated for C$_{53}$H$_{51}$N$_7$O$_5$ 865; found 873 (M+Li).

Step C:
3-Amino-3-methyl-N-[2,3,4,5-tetrahydro-2,5-dioxo-1-[[2'-(1H-tetrazol-5-yl)[1,1'-biphenyl]-4-yl]-methyl]-1H-1-benzazepin-3-yl]-butanamide, trifluoroacetate To a solution of 68 mg (0.078 mmol) of the intermediate obtained in Step B in 3 mL of methanol was added 14 mg of palladium hydroxide catalyst. The mixture was hydrogenated at room temperature and 1 atmosphere for 20 hours at which time the solids were filtered and the solvent removed under vacuum.

The resulting solid was dissolved in 3 mL of methylene chloride. To this solution was added 3 drops of anisole followed by 2 mL of trifluoroacetic acid. The reaction mixture was stirred for 2 hours at room temperature, then all volatiles removed under vacuum. The resulting material was purified by reverse phase high pressure liquid chromatography on C-18, eluting with methanol/0.1% aqueous trifluoroacetic acid (linear gradient; 50% methanol increased to 55% methanol over 12 minutes) to afford 16.5 mg (335) of the title compound as a white solid. $^1$H NMR (200 MHz,CD$_3$OD): 1.37 (s,3H), 1.40 (s,3H), 2.59 (dd;14,16 Hz,2H), 2.9–3.2 (m,2H), 4.97 (d,15 Hz,1H), 5.17 (dd;4,12 Hz;1H), 5.25 (d,15 Hz,1H), 7.00 (d,8 Hz,2H), 7.12 (d,8 Hz,2H), 7.37 (m,2H), 7.4–7.7 (m,6H). FAB-MS: calculated for C$_{29}$H$_{29}$N$_7$O$_3$ 523; found 524 (M+H,100%).

EXAMPLE 92

3-Amino-3-methyl-N-[5-hydroxy-2,3,4,5-tetrahydro-2-oxo-1-[[2'-(1H-tetrazol-5-yl)[1,1'-biphenyl]-4-yl]methyl]-1H-1-benzazepin-3-yl]-butanamide, trifluoroacetate To a solution of 23 mg (0.036 mmol) of 3-amino-3-methyl-N-[2,3,4,5-tetrahydro-2,5-dioxo-1-[[2'-(1H-tetrazol-5-yl)[1,1'-biphenyl]-4-yl]methyl]-1H-1-benzazepin-3-yl]-butanamide, trifluoroacetate (Example 91) in 1 mL of methanol/water (4:1) was added 14 mg (0.36 mmol) of sodium borohydride. The reaction mixture was stirred for 1 hour then quenched by the addition of 5 drops of trifluoroacetic acid. The solvent was removed under vacuum and the resulting material was purified by reverse phase high pressure liquid chromatography on C-18 eluting with methanol/0.1% aqueous trifluoroacetic acid (55:45) to afford 18 mg (78%) of the title compound as a white solid. $^1$H NMR (200 MHz,CD$_3$OD): 1.37 (s,3H), 1.40 (s,3H), 2.17 (m,1H), 2.3–2.6 (m,3H), 4.30 (dd;8,10 Hz;1H), 4.67 (dd;6,10 Hz;1H), 4.95 (d,15 Hz,1H), 5.23 (d,15 Hz,1H), 7.00 (d,8 Hz,2H), 7.20 (d,8 Hz,2H), 7.35 (m,3H), 7.5–7.7 (m,5H). FAB-MS: calculated for C$_{29}$H$_{31}$N$_7$O$_3$ 525; found 526 (M+H,100%).

EXAMPLE 93

4'-[[3(R)-[3-Amino-3-methyl-1-oxobutyl)amino]-2,3,4,5-tetrahydro-2-oxo-1H-1-benzazepin-1-yl]methyl][1,1'-biphenyl]-2-thioamide, trifluoroacetate

Step A:
4'-[[3(R)-[(3-t-Butoxycarbonylamino-3-methyl-1-oxobutyl)amino]-2,3,4,5-tetrahydro-2-oxo-1H-1-benzazepin-1-yl]methyl][1,1'-biphenyl]-2-thioamide A solution of 380 mg (0.67 mmol) of 3-[[1-[[2'-cyano-[1,1'-biphenyl]-4-yl]methyl]-2,3,4,5-tetrahydro-2-oxo-1H-benzazepin-3(R)-yl]amino]-1,1-dimethyl-3-xopropylcarbamic acid, 1,1-dimethylethyl ester (Example 69, Step D), in 5 mL of pyridine was placed in a bomb and treated with 5 mL of triethylamine and excess hydrogen sulfide was introduec under pressure. The bomb was sealed and heated for 12 hours at 90° C. The bomb was vented into 5M sodium hydroxide and the contents poured into 40 mL of water, then extracted with ether (3×). The combined extracts were washed with water (3×), dried over magnesium sulfate, filtered and evaporated under vacuum to afford 330 mg (0.53 mmol, 82%) of product. $^1$H NMR (200 MHz, CDCl$_3$): 1.38 (s,6H), 1.45 (s,9H), 1.90 (m,1H), 2.4–2.7 (m,4H), 2.92 (m,1H), 4.55 (m,1H), 4.94 (d,15 Hz, 1H), 5.22 (d, 15 Hz,1H), 5.31 (br s,1H), 6.50 (br s,1H), 6.70 (m,1H), 7.1–7.5 (m,12H), 7.82 (m,1H). FAB-MS (Li+ spike): calculated for C$_{34}$H$_{40}$N$_4$O$_4$S 600; found 607 (M+Li,65%).

Step B:
4'-[[3(R)-[(3-Amino-3-methyl-1-oxobutyl)amino]-2,3,4,5-tetrahydro-2-oxo-1H-1-benzazepin-1-yl]methyl][1,1'-biphenyl]-2-thioamide, trifluoroacetate A suspension of 80 mg (0.13 mmol) of the intermediate prepared in Step A in 10 mL of methylene chloride at room temperature was treated with 5 mL of trifluoroacetic acid. After 45 minutes, all volatiles were removed under vacuum and the residue placed under high vacuum. Purification by preparative thin layer chromatography on a 1 mm silica plate eluting with methylene chloride/methanol/acetic acid (9:1:0.1) afforded 43 mg of the free amine which was converted to the trifluoroacetate salt by dissolving in 3 mL of methanol and adding 0.5 mL of trifluoroacetic acid, followed by removal of volatiles under vacuum. In this manner, 30 mg (0.05 mmol, 37%) of the title compound was obtained. $^1$H NMR (400 MHz, CD$_3$OD): 1.35 (s,3H), 1.39 (s,3H), 2.111 (m,1H), 2.31 (m,1H), 2.45–2.65 (m,4H), 4.40 (dd;7,11 Hz;1H), 4.94 (d,15 Hz,1H), 5.24 (d,15 Hz,1H), 7.20–7.55 (m,12H). FAB-MS: calculated for C$_{29}$H$_{32}$N$_4$O$_2$S 500; found 501 (M+H,100%).

EXAMPLE 94

N-Hydroxy-4'-[[3(R)-[(3-amino-3-methyl-1-oxobutyl)amino]2,3,4,5-tetrahydro-2-oxo-1H-1-benzazepin-1-yl]methyl]-[1,1'-biphenyl]-2-carboxamide, trifluoroacetate Step A:
N-Hydroxy-4'-[[2,3,4,5-Tetrahydro-3(R)-[[3-methyl-1-oxo-3-[[(benzyloxy)carbonyl]amino]butyl]-amino]-2-oxo-1H-1-benzazepin-1-yl]methyl]-[1,1'-biphenyl]-2-carboxamide Prepared from 4'-[[2,3,4,5-Tetrahydro-3(R)-[[3-methyl-1-oxo-3-[[(benzyloxy)carbonyl]amino]butyl]amino]-2-oxo-1H-1-benzazepin-1-yl]methyl][1,1'-biphenyl]-2-carboxylic acid (Example 72, Step B) and (0-trimethylsilyl)hydroxylamine by the procedure described in Example 72, Step C. $^1$H NMR (200 MHz,CDCl$_3$): 1.33 (s,3H), 1.36 (s,3H0, 1.77 (m,1H), 2.3–2.5 (m,4H), 4.46 (m,1H), 4.68 (d,15 Hz,1H), 5.02 (s,2H), 5.14 (d,15 Hz,1H0, 5.73 (br s,1H), 6.82 (d,7 Hz,1H), 7.1–7.5 (m,16H), 7.60 (d,8 Hz,1H). FAB-MS: calc. for $C_{37}H_{38}N_4O_6$ 634; found 635 (M+H,1%).

Step B:
N-Hydroxy-4'-[[3(R)-[(3-amino-3-methyl-1-oxo-butyl) amino]-2,3,4,5-tetrahydro-2-oxo-1H-1-benzazepin -1-yl]methyl][1,1'-biphenyl]-2-carboxamide, trifluoroacetate The title compound was prepared from the intermediate obtained in Step A by the procedure described in Example 79. $^1$H NMR (200 MHz, CD$_3$OD): 1.36 (s,3H), 1.39 (s,3H), 2.0–2.7 (m,hH), 4.41 (dd;7,11 Hz;1H), 5.03 (d,15 Hz,1H), 5.18 (d,15 Hz), 7.2–7.6 (m,12H), FAB-MS: calculated for $C_{29}H_{32}N_4O_4$ 500; found 502 (100%).

EXAMPLE 95

4'-[[3(R)-[(3-Amino-3-methyl-1-oxobutyl)amino]2,3,4,5-tetrahydro-2-oxo-1H-1-benzazepin-1-yl]methyl]-2-nitro-1,1'-biphenyl, trifluoroacetate Step A: 4'-Methyl-2-nitro-1,1'-biphenyl Prepared from 4-methylphenyltrimethylstannane (Example 69, Step A) and 2-bromonitrobenzene by the procedure described in Example 69, Step B. $^1$H NMR (200 MHz,CDCl$_3$): 2.39 (s,3H), 7.23 (m,3H), 7.45 (m,3H), 7.58 (t,7 Hz,1H), 7.80 (d,7 Hz,1H).

Step B: 4'-Bromomethyl-2-nitro-1,1'-biphenyl

Prepared from 4'-methyl-2-nitro-1,1'-biphenyl by the procedure described in Example 69, Step C. $^1$H NMR (200 MHz,CDCl$_3$): 4.53 (s,2H), 7.2–7.7 (m,7H), 7.85 (m,1H). FAB-MS: calculated for $C_{14}H_{10}BrN$ 272; found 272,274 (M+). $^1$H NMR indicates the presence of minor amounts of starting material and dibromo derivative.

Step C:
3-[[1-[[2'-Nitro-[1,1'-biphenyl]-4-yl]methyl]-2,3,4,5-tetrahydro-2-oxo-1H-benzazepin -3(R)-yl]amino]-1,1-dimethyl-3-oxopropyl]carbamic acid, 1,1-dimethyethyl ester Prepared from 4'-bromomethyl-2-nitro-1,1'-biphenyl and 3-t-butoxycarbonylamino-3-methyl-N -[2,3,4,5-tetrahydro-2-oxo-1H-1-benzazepin-3(R)-yl]butanamide (Example 57, Step A) by the procedure described in Example 69, Step D. $^1$H NMR (200 MHz,CDCl$_3$): 1.34 (s,6H), 1.41 (s,9H), 1.83 (m,1H), 2.35–2.70 (m,5H), 4.50 (m,1H), 4.84 (d,15 Hz,1H), 5.23 (d,15 Hz,1H), 5.27 (s,1H), 6.64 (d,7 Hz,1H), 7.1–7.6 (m,11H), 7.80 (d,8 Hz,1H).

Step D:
4'-[[3(R)-[(3-Amino-3-methyl-1-oxobutyl)amino-9 -2,3,4,5-tetrahydro-2-oxo-1H-1benzazepin -1yl]methyl]-2-nitro-1,1'-biphenyl, trifluoroacetate Prepared from the intermediate obtained in Step C by the procedure described in Example 69, Step F. $^1$H NMR (400 MHz,CD$_3$OD): 1.34 (s,3H), 1.38 (s,3H), 2.11 (m,1H), 2.32 (m,1H), 2.4–2.7 (m,4H), 4.40 (dd;8,11 Hz;1H), 4.99 (d,15 Hz,1H), 5.21 (d,15 Hz,1H), 7.1–7.4 (m,8H), 7.45 (d,8 Hz,1H), 7.54 (t,8 Hz,1H), 7.67 (t,8 Hz,1H), 7.85 (d,8 Hz,1H). FAB-MS: calculated for $C_{28}H_{30}N_4O_4$ 486; found 487 (M+H, 90%).

EXAMPLE 96

2-Amino-4'-[[3(R)-[(3-amino-3-methyl-1-oxobutyl)amino]-2,3,4,5-tetrahydro-2-oxo-1H-1-benzazepin-1-yl]methyl]-1,1'-biphenyl, trifluoroacetate A solution of 200 mg (0.34 mmol) of the intermediate obtained in Example 95 (Step C) in 3 mL of methanol was hydrogenated at room temperature and 40 psi over 50 mg of 5% palladium on carbon for 90 minutes. The catalyst was removed by filtration through Celite and the filtrate evaporated to dryness under vacuum to afford 189 mg (0.34 mmol,100%) of product.

The above intermediate (90 mg, 0.16 mmol) was dissolved in 5 mL of methylene chloride and treated with 0.25 mL of trifluoroacetic acid. The mixture was stirred at room temperature for 14 hours then all volatiles removed under vacuum to give 46 mg (0.10 mmol, 62%) of the title compound. $^1$H NMR (400 MHz,CD$_3$OD): 1.38 (s,3H), 1.42 (s,3H), 2.13 (m,1H), 2.32 (m,1H), 2.45–2.70 (m,4H), 4.40 (dd;7,11 Hz;1H), 5.00 (d,15 Hz,1H), 5.29 (d,15 Hz,1H), 7.05–7.45 (m,12H). FAB-MS: calculated for $C_{28}H_{32}N_4O_2$ 456; found 457 (M+H,100%).

EXAMPLE 97

4'-[[3(R)-[(3-Amino-3-methyl-1-oxobutyl)amino]-2,3,4,5-tetrahydro-2-oxo-1H-1-benzazepin-1-yl]methyl][1,1'-biphenyl]-2-carboxylic acid-N(2)-formylhydrazide, trifluoroacetate Step A:
4'-[[3(R)-[(3-t-Butoxycarbonylamino-3-methyl-1-oxobutyl)amino]-2,3,4,5-tetrahydro-2-oxo-1H-1-benzazepin-1-yl]methyl][1,1'-biphenyl]-2-carboxylic acid-N(2)-formylhydrazide A solution of 100 mg (0.17 mmol) of 4'-[[3(R)-[(3-t-butoxycarbonylamino-3-methyl-1-oxobutyl)amino]-2,3,4,5-tetrahydro-2-oxo-1H-1benzazepin-1-yl]methyl]-[1,1'-biphenyl]-2-thioamide (Example 93, Step A) in 6 mL of tetrahydrofuran was treated with 0.08 mL of methyl iodide and the resulting solution stirred at room temperature for 14 hours. The mixture was evaporated under vacuum to give the product which was used in the next step without purification.

A solution of 40 mg (0.68 mmol) of formic hydrazide in 2 mL of dry dimethylformamide was added to the intermediate obtained above and the resulting solution stirred at room temperature for 14 hours. An additional 80 mg (1.4 mmol) of formic hydrazide was added and stirring continued for another 5 hours. The reaction mixture was added to ethyl acetate and washed with water (4×). The organic layer was separated, dried over magnesium sulfate, filtered and solvents removed under vacuum. Purification by preparative thin layer chromatography on silica, eluting with methylene chloride/methanol (9:1), afforded 32 mg (0.05 mmol, 30%) of product. $^1$H NMR (200 MHz,CDCl$_3$): 1.30 (s,6H), 1.37 (s,9H), 1.84 (m,1H), 2.3–2.6 (m,5H), 4.50 (m,1H), 4.76 (d,15 Hz,1H), 4.98 (br s,2H), 5.24 (d,15 Hz,1H), 5.53 (br s,1H), 7.1–7.6 (m,12H), 8.34 (br s,1H).

Step B: 4'-[[3(R)-[(3-Amino-3-methyl-1-oxobutyl)amino]-2,3,4,5-tetrahydro-2-oxo-1H-1-benzazepin-1-yl]methyl][1,1'-biphenyl]-2-carboxylic acid-N(2)-formyl hydrazide, trifluoroacetate Prepared from the intermediate obtained in Step A by the procedure described in Example 69, Step F. $^1$H NMR (400 MHz,CD$_3$OD): 1.35 (s,3H), 1.39 (s,3H), 2.12 (m,1H), 2.22 (m,1H), 2.35–2.70 (m,4H), 4.39 (m,1H), 4.9 (m,1H), 5.3 (m,1H), 7.2–7.8 (m,12H), 8.20 (s,1H). FAB-MS: calculated for C$_{30}$H$_{33}$N$_5$O$_4$ 527; found 534 (M+Li,10%).

EXAMPLE 98

4'-[[3(R)-[(3-Amino-3-methyl-1-oxobutyl)amino]-2,3,4,5-tetrahydro-2-oxo-1H-1-benzazepin-1-yl]methyl]-2-(hydroxyacetyl)-1,1'-biphenyl, trifluoroacetate

Step A: 4'-Methyl-2-acetyl-1,1'-biphenyl

Prepared from 4-methylphenyltrimethylstannane (Example 69, Step A) and 2'-bromoacetophenone by the procedure described in Example 69, Step B. $^1$H NMR (200 MHz,CDCl$_3$): 1.98 (s,3H), 2.37 (s,3H), 7.20 (s,4H), 7.3–7.5 (m,4H). FAB-MS: calculated for C$_{15}$H$_{14}$O 210; found 211 (M+H,100%).

Step B: 4'-Methyl-2-(bromoacetyl)-1,1'-biphenyl

A solution of 4'-methyl-2-acetyl-1,1'-biphenyl (2.06 g, 9.79 mmol) in 10 mL of glacial acetic acid was treated dropwise with a solution of bromine (1.722 g, 1.07 mmol) dissolved in 3.0 mL of glacial acetic acid. After initiating the reaction with the first few drops of the bromine/acetic acid reagent by heating the reaction mixture at 30° C., the remainder of the bromine solution was added dropwise at 25°–30° C. The reaction mixture was stirred at room temperature until the consumption of bromine was complete (approximately 2 hrs). The reaction mixture was diluted with 150 mL of hexane then washed with water (3×50 mL). The organic layer was removed, dried over magnesium sulfate, filtered and evaporated under vacuum to give 2.92 g of an oil that was used in the next step without purification. $^1$H NMR (crude product) (200 MHz,CDCl$_3$): 2.38 (s,3H), 3.66 (s,2H), 7.21 (s,4H), 7.3–7.6 (m,4H).

Step C: 4'-Methyl-2-(acetoxyacetyl)-1,1'-biphenyl

A solution of 1.44 g (4.98 mmol) of 4'-methyl-2-(bromoacetyl)-1,1'-biphenyl in 3.0 mL of polyethyleneglycol-400 was added to a solution of 500 mg of potassium acetate in 3.0 mL of polyethyleneglycol-400. The suspension was heated at 100° C. for 30 minutes, then cooled and diluted with 100 mL of water. The resultant mixture was extracted with ether; the combined ether extracts were diluted with an equal volume of hexane and washed with water. The organic layer was separated, dried over magnesium sulfate, filtered, and the solvent was removed under vacuum to yield an oil which was purified by silica chromatography, eluting with hexane/ethyl acetate (8:1) to give 444 mg (1.66 mmol, 33%) of product as an oil. $^1$H NMR (200 MHz,CDCl$_3$): 2.06 (s,3H), 2.39 (s,3H), 4.46 (s,2H), 7.23 (s,4H), 7.3–7.6 (m,4H).

Step D: 4'-Bromomethyl-2-(acetoxyacetyl)-1,1'-biphenyl

Prepared from 4'-methyl-2-(acetoxyacetyl)-1,1'-biphenyl by the procedure described in Example 69, Step C. $^1$H NMR (200 MHz,CDCl$_3$): 2.01 (s,3H), 4.49 (s,4H), 7.15–7.55 (m,8H).

Step E: 3-[[1-[[2'-(acetoxyacetyl)-[1,1'-biphenyl]-4-yl]methyl]-2,3,4,5-tetrahydro-2-oxo-1H-benzazepin-3(R)-yl]amino]-1,1-dimethyl-3-oxo-propylcarbamic acid, 1,1-dimethylethyl ester Prepared from 4'-bromoethyl-2-(acetoxyacetyl)-1,1'-biphenyl and 3-t-butoxycarbonylamino-3-methyl-N-[2,3,4,5-tetrahydro-2-oxo-1H-1-benzazepin-3(R)-yl]-butanamide (Example 57, Step A) by the procedure described in Example 69, Step D. $^1$H NMR (200 MHz,CDCl$_3$): 1.33 (s,6H), 1.39 (s,9H), 1.87 (m,1H), 2.03 (s,3H), 2.35–2.70 (m,5H), 4.36 (s,2H), 4.51 (m,1H), 4.85 (d,15 Hz,1H), 5.28 (d,15 Hz,1H), 6.66 (m,1H), 7.1–7.6 (m,12H).

Step F: 4'-[[3(R)-[(3-Amino-3-methyl-1-oxobutyl)amino]-2,3,4,5-tetrahydro-2-oxo-1H-1-benzazepin-1-yl]methyl]-2-(hydroxyacetyl)-1,1'-biphenyl, trifluoroacetate The title compound was prepared from the intermediate obtained in Step E by the procedure described in Example 69, Step F. $^1$H NMR (200 MHz,CD$_3$OD): 1.30 (s,3H), 1.34 (s,3H), 2.08 (m,1H), 2.28 (m,1H), 2.4–2.6 (m,4H), 4.01 (s,2H), 4.36 (dd;8,11 Hz;1H), 4.95 (d,15 Hz,1H), 5.17 (d,15 Hz;1H), 7.1–7.5 (m,12), FAB-MS (Li+spike): calculated for C$_{30}$H$_{33}$N$_3$O$_4$ 499; found 500 (M+H,18%), 506 (M+Li,100%).

EXAMPLE 99

4'-[[3(R)-[(3-Amino-3-methyl-1-oxobutyl)amino]-2,3,4,5-tetrahydro-2-oxo-1H-1-benzazepin-1-yl]methyl]-2-hydroxy-1,1'-biphenyl, trifluoroacetate

Step A: 4'-Methyl-2-hydroxy-1,1'-biphenyl

A solution of 4.2 g (20.0 mmol) of 4'-methyl-2-acetyl-1-1'-biphenyl (Example 98, Step A) in methylene chloride, under a nitrogen atmosphere, was treated with 8.98 g of 85% m-chloroperbenzoic acid. The resultant suspension was cooled to 0° C. and treated dropwise with 1.54 mL of trifluoroacetic acid over a 10 minute period. The reaction mixture was stirred at room temperature for 16 hours. The reaction mixture was diluted with 50 mL of methylene chloride and the solution was washed successively with 50 mL of 10% sodium silfite, 50 mL of saturated aqueous potassium carbonate and water (3×50 mL). The organic layer was removed and dried over magnesium sulfate, then evaporated under vacuum to yield 4.1 g of an oil. The off was dissolved in 20 mL of methanol and treated with 2.0 mL of 5N aqueous sodium hydroxide. The reaction mixture was stirred at room temperature for 1 hour. The pH of the solution was adjusted to 5–6 with acetic acid. After the methanol was removed under vacuum, the residue was taken up in ether, washed with water, dried over magnesium sulfate, filtered and evaporated under vacuum to yield 3.0 g of crude product which was purified by preparative high pressure liquid chromatography on silica, eluting with hexane/ethyl acetate (10:1). In this manner, 1.85 g (10.0 mmol, 50%) of the product was obtained as an oil. $^1$H NMR (200 MHz, CDCl$_3$): 2.40 (s,3H), 5.22 (br s,1H), 6.96 (m,2H), 7.2–7.4 (m,6H). EI-MS: calculated for C$_{13}$H$_{12}$O 184; found 184 (M+,100%).

Step B: 4'-Methyl-2-acetoxy-1,1'-biphenyl

A solution of 1.0 g (5.4 mmol) of 4'-methyl-2-hydroxy-1,1'-biphenyl in 2.0 mL of pyridine was treated with 2 mL of acetic anhydride. The reaction mixture was stirred at room temperature for 5 hours. The solvent was removed under vacuum to yield 1.11 g (4.9 mmol, 90%) of the product as an oil. $^1$H NMR (200 MHz, CDCl$_3$): 2.07 (s,3H), 2.36 (s,3H), 7.07 (dd;3,8 Hz;1H), 7.15 (d,8 Hz,2H), 7.2–7.4 (m,5H).

Step C: 4'-Bromomethyl-2-acetoxy-1,1'-biphenyl

Prepared from 4-'-methyl-2-acetoxy-1,1'-biphenyl by the procedure described in Example 69, Step C. $^1$H NMR (200 MHz, CDCl$_3$): 2.05 (s,3H), 4.50 (s,2H), 7.08 (m,1H), 7.20–7.45 (m,7H).

Step D:
3-[[1-[[2'-acetoxy-[1,1'-biphenyl]-4-yl]methyl]-2,3,4,5-tetrahydro-2-oxo-1H-benzazepin-3(R)-yl]amino]-1,1-dimethyl-3-oxopropylcarbamic acid, 1,1-dimethyethyl ester Prepared from 4-'-bromomethyl-2-acetoxy-1,1'-biphenyl and 3-t-butoxycarbonylamino-3-methyl-N-[2,3,4,5-tetrahydro-2-oxo-1H-1-benzazepin-3(R)-yl]-butanamide (Example 57, Step A) by the procedure described in Example 69, Step D. $^1$H NMR (200 MHz, CDCl$_3$): 1.38 (s,6H), 1.45 (s,9H), 1.85 (m,1H), 2.02 (s,3H), 2.35–2.65 (m,5H), 4.52 (m,1H), 4.84 (d,15 Hz,1H), 5.30 (d,15 Hz,1H), 6.71 (d,7 Hz,1H), 7.1–7.4 (m, 12 H).

Step E:
4'-[[3(R)-[(3-Amino-3-methyl-1-oxobutyl)amino]-2,3,4,5-tetrahydro-2-oxo-1H-1-benzazepin-1-yl]methyl]-2-hydroxy-1,1'-biphenyl, trifluoroacetate A solution of 468 mg (0.78 mmol) of the intermediate obtained in Step D in 25 mL of methanol was treated with 4.0 mL of 5N aqueous sodium hydroxide and the resultant solution stirred at roomt emperature for 1 hour. The solvent was removed under vacuum to yield the crude intermediate which was used without purification.

The intermediate obtained above was treated as described in Example 69, Step F to afford the title compound. $^1$H NMR (400 MHz,CD$_3$OD): 1.34 (s,3H), 1.39 (s,3H), 2.11 (m,1H), 2.32 (m,1H), 2.45–2.70 (m,4H), 4.41 (dd;8,11 Hz;1H), 4.95 (d,15 Hz,1H), 5.23 (d,15 Hz,1H), 6.86 (d,8 Hz,2H), 7.11 (m,1H), 7.15–7.25 (m,5H), 7.35 (m,2H), 7.45 (d,8 Hz,2H).

EXAMPLE 100

4'-[[3(R)-[(3-Amino-3-methyl-1-oxobutyl)amino]-2,3,4,5-tetrahydro-2-oxo-1H-1-benzazepin-1-yl]methyl]-2(4-aminophenoxy)-1,1'-biphenyl, di(trifluoroacetate)

Step A: 4'-Methyl-2-(4-nitrophenoxy)-1,1'-biphenyl

A solution of 450 mg (2.44 mmol) of 4'-methyl-2-hydroxy-1-1'-biphenyl (Example 99, Step A) in 7.0 mL of dimethylformamide was treated with 135 mg of 60% sodium hydride (3.3 mmol). The reaction mixture was stirred at room temperature for 30 minutes then treated with 428 mg (3.03 mmol) of 1-fluoro-2-nitrobenzene. The reaction mixture was heated at 100° C. for 2 hours. The reaction mixture was cooled, poured into 100 mL of water and the resultant mixture was extracted with ethyl ether (3×60 mL). The combined extracts were washed with water (4×50 mL), dried over magnesium sulfate, filtered and evaporated under vacuum. The residue was chromatographed on silica, eluting with hexane/ethyl acetate (10:1) to give 737 mg (99%) of the product. $^1$H NMR (200 MHz, CDCl$_3$): 2.28 (s,3H), 6.83 (d,8 Hz,2H), 7.08 (d,8 Hz,2H), 7.3–7.5 (m,6H), 8.05 (d,8 Hz,2H).

Step B:
4'-Bromomethyl-2-(4-nitrophenoxy)-1,1'-biphenyl

Prepared from 4'-methyl-2-(4-nitrophenoxy)-1,1'-biphenyl by the procedure described in Example 69, Step C. $^1$H NMR (200 MHz, CDCl$_3$): 4.43 (s,2H), 6.83 (d,8 Hz,2H), 7.09 (d,8 Hz,1H), 7.3–7.5 (m, 7H), 8.04 (d,8 Hz,2H).

Step C:
3-[[1-[[2'-nitrophenoxy-[1,1'-biphenyl]-4-yl]methyl]-2,3,4,5-tetrahydro-2-oxo-1H-benzazepin-3(R)-yl]amino]-1,1-dimethyl-3-oxopropylcarbamic acid, 1,1-dimethyethyl ester Prepared from 4'-bromoethyl-2-(4-nitrophenoxy)-1,1'-biphenyl and 3-t-butoxycarbonylamino-3-methyl-N-[2,3,4,5-tetrahydro-2-oxo-1H-1-benzazepin-3-(R)-yl]-butanamide (Example 57, Step A) by the procedure described in Example 69, Step D. $^1$NMR (200 MHz, CDCl$_3$): 1.32 (s,6H), 1.38 (s,9H), 1.78 (m,1H), 2.3–2.7 (m,5H), 4.47 (m,1H), 4.75 (d,15 Hz,1H), 5.13 (d,15 Hz,1H), 6.63 (d,7 Hz,1H), 6.75 (d,8 Hz,2H), 7.05–7.50 (m,/11H), 7.97 (s,1H), 7.98 (d,8 Hz,2H).

Step D:

4'-[[3(R)-[(3-Amino-3-methyl-1-oxobutyl)amino]-2,3,4,5-tetrahydro-2-oxo-1H-1-benzazepin-1-yl]methyl]-2(4-aminophenoxy)-1,1'-biphenyl, di(trifluoroacetate)

The intermediate obtained in Step C (140 mg, 0.21 mmol) was dissolved in 16 mL of methanol and hydrogenated at room temperature and 40 psi over 20 mg of 10% palladium on carbon for 2 hours. The catalyst was removed by filtration through Celite and the filtrate evaporated under vacuum to yield 140 mg of crude product which was used in the next step without purification.

The crude intermediate obtained above was converted to the title compound by treatment with trifluoroacetic acid according to the procedure described in Example 69, Step F. $^1$H NMR (200 MHz, CD$_3$OD): 1.38 (s,3H), 1.42 (s,3H), 2.11 (m,1H), 2.32 (m,1H), 2.45–2.65 (m,4H), 4.41 (dd;8,12 Hz;1H), 4.88 (d,15 Hz,1H), 5.25 (d,15 Hz,1H), 6.90 (d,8 Hz,2H), 7.09 (d,8 Hz,1H), 7.15–7.50 (m,13H).

EXAMPLE 101

3-[[3(R)-[(3-Amino-3-methyl-1-oxobutyl)amino]-2,3,4,5-tetrahydro
-2-oxo-1H-benzazepin-1-yl]methyl]phenylacetamide, trifluoroacetate Step A: 3-(Bromomethyl)phenylacetonitrile Prepared from 3-(methyl)phenylacetonitrile by the procedure described in Example 69, Step C. $^1$H NMR (300 MHz,CDCl$_3$): 3.73 (s,2H), 4.45 (s,2H), 7.24 (m,1H), 7.33 (m,3H).

Step B:
3-[[1-[[1-(Cyanomethyl)phenyl-3-yl]methyl]-2,3,4,5-tetrahydro-2-oxo-1H-benzazepin-3(R)-yl]amino]1,1-dimethyl-3-oxopropylcarbamic acid, 1,1-dimethylethyl ester Prepared from 3-(broomomethyl)phenylacetonitrile and 3-t-butoxycarbonylamino-3-methyl-N-[2,3,4,5-tetrahydro-2-oxo-1H-1-benzazepin-3(R)-yl]butanamide (Example 57, Step A) by the procedure described in Example 69, Step D. $^1$H NMR (400 MHz,CDCl$_3$): 1.33 (s,3H), 1.34 (s,3H), 1.40 (s,9H), 1.83 (m,1H), 2.4–2.6 (m,5H), 3.65 (s,2H), 4.48 (m,1H), 4.86 (d,15 Hz,1H), 5.12 (d,15 Hz,1H), 5.23 (br s,1H), 6.60 (d,7 Hz,1H), 7.1–7.3 (m,8H). FAB-MS: calculated for C$_{29}$H$_{36}$N$_4$O$_4$ 504; found 505 (M+H,10%).

Step C:
3-[[3(R)-[(3-t-Butoxycarbonylamino-3-methyl-1-oxobutyl)amino]-2,3,4,5-tetrahydro-2-oxo-1H-1-benzazepin-1-yl]methyl]phenylacetamide Prepared from the intermediate obtained in Step B by the procedure described in Example 69, Step E. $^1$H NMR (400 MHz,CDCl$_3$): 1.32 (s,6H), 1.39 (s,9H), 1.90 (m,1H), 2.4–2.6 (m,5H), 3.46 (d,15 Hz,1H), 3.50 (d,15 Hz,1H), 4.48 (m,1H), 4.93 (d,15 Hz,1H), 5.07 (d,15 Hz,1H), 5.49 (br s,1H), 5.93 (br s,1H), 6.65 (d,7 Hz,1H), 7.05–7.25 (m,8H). FAB-MS: calculated for C$_{29}$H$_{38}$N$_4$O$_4$ 506; found 507 (M+H,15%).

Step D:
3-[[3(R)-[(3-Amino-3-methyl-1-oxobutyl)amino]-2,3,4,5-tetrahydro-2-oxo-1H-1-benzazepin -1-yl]methyl]phenylacetamide, trifluoroacetate The title compound was prepared from the intermediate obtained in Step C by the procedure described in Example 69, Step F. $^1$H NMR (200 MHz, CD$_3$OD): 1.30 (s,3H), 1.33 (s,3H), 2.07 (m,1H), 2.26 (m,1H), 2.4–2.6 (m,4H), 3.39 (s,2H), 4.33 (dd;8,11 Hz;1H), 4.90 (d,15 Hz,1H), 5.11 (d,15 Hz,1H), 7.08 (d,8 Hz,1H), 7.1–7.2 (m,5H), 7.25 (d,2 Hz,2H). FAB-MS: calculated for C$_{23}$H$_{28}$N$_4$O$_3$ 422; found 423 (M+H,100%).

EXAMPLE 102

3-[(2(R)-Hydroxypropyl)amino]-3-methyl-N-[2,3,4,5-tetrahydro
-2-oxo-1-[[2'-(1H-tetrazol-5-yl)[1,1'-biphenyl]-4-yl]methyl]-1H-1-benzazepin-3(R)-yl]butanamide, trifluoroacetate Step A:
3-[(2(R)-Benzyloxypropyl)amino]-3-methyl-N-[2,3,4,5-tetrahydro-2-oxo-1-[[2'-(1H-tetrazol
-5-yl)[1,1'-biphenyl]-4-yl]methyl]-1H-1-benzazepin
-3(R)-yl]butanamide, trifluoroacetate Prepared from 3-amino-3-methyl-N-[2,3,4,5-tetrahydro -2-oxo-1-[[2'-(1H-tetrazol-5-yl)[1,1'-biphenyl]-4-yl]methyl]-1H-1-benzazepin-3(R)-yl]butanamide, trifluoroacetate (Example 1) and (R)-2-benzyloxlpropanal (prepared from ethyl-D-lactate according to the procedure of Hanessian and Kloss, Tetrahedron Lett. 1985, 26, 126-1264. ) by the procedure described in Example 86, Step A. $^1$H NMR (200 MHz,CD$_3$OD): 1.25 (d,6 Hz,3H), 1.35 (s,6H), 2.11 (m,1H), 2.32 (m,1H), 2.5–2.7 (m,4H), 2.95 (m,1H), 3.17 (m,1H), 3.80 (m,1H), 4.40 (m,1H), 4.44 (d,11 Hz,1H), 4.64 (d,11 Hz,1H), 4.90 (d,15 Hz,1H), 5.02 (d,15 Hz,1H), 6.99 (d,8 Hz,2H), 7.1–7.7 (m,15H). FAB-MS: calculated for C$_{39}$H$_{43}$N$_7$O$_3$ 657; found 658 (M+H,100%).

Step B:
3-[(2(R)-Hydroxypropyl)amino]-3-methyl-N-[2,3,4,5-tetrahydro-2-oxo-1-[[2'-(1H-tetrazol
-5-yl)[1,1'-biphenyl]-4-yl]methyl]-1H-1-benzazepin
-3(R)-yl]butanamide, trifluoroacetate The title compound was prepared fro mthe intermediate obtained in Step A by the procedure described in Example 86, Step B. $^1$H NMR (400 MHz,CD$_3$OD): 1.22 (d,6 Hz,3H), 1.37 (s,3H), 1.39 (s,3H), 2.10 (m,1H), 2.31 (m,1H), 2.45–2.70 (m,4H), 2.81 (dd;10,12 Hz;1H), 3.08 (dd;4,12 Hz;1H), 3.92 (m,1H), 4.36 (dd;7,11 Hz;1H), 4.93 (d,15 Hz,1H), 5.17 (d,15 Hz,1H), 7.04 (d,8 Hz,2H), 7.19 (d,8 Hz,2H), 7.20–7.35 (m,4H), 7.54 (m,2H), 7.65 (m,2H). FAB-MS: calculated for C$_{32}$H$_{37}$N$_7$O$_3$ 567; found 568 (M+H,45%).

EXAMPLE 103

2-[(2(R)-Hydroxypropyl)amino]-3-methyl-N-[2,3,4,5-tetrahydro -2-oxo-1-[[2'-(1H-tetrazol-5-yl)[1,1'-biphenyl]-4-yl]methyl]-1H-1-benzazepin-3(R)-yl]propanamide, trifluoroacetate The title compound was prepared from 2-amino-2-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-propanamide, trifluoroacetate (Example 63) and (R)-2-benzyloxypropanal (prepared from ethyl-D-lactate according to the procedure of Hanessian and Kloss, Tetrahedron Lett. 1985, 26, 1261-1264.) by the procedure described in Example 86. $^1$H NMR (200 MHz,CD$_3$OD): 1.16 (d,6 Hz,3H), 1.55 (s,3H), 1.64 (s,3H), 2.22 (m,2H), 2.49 (m,2H), 2.74 (dd;9,12 Hz;1H), 2.92 (dd;4,12 Hz;1H), 3.94 (m,1H), 4.31 (m,1H), 4.88 (d,15 Hz,1H), 5.17 (d,15 Hz,1H), 6.98 (d,8 Hz,2H), 7.16 (d,8 Hz,2H), 7.2-7.4 (m,4H), 7.45-7.70 (m,4H). FAB-MS: calculated for C$_{31}$H$_{35}$N$_7$O$_3$ 553; found 554 (M+H,45%).

EXAMPLE 104

3-[(2(R)-Acetoxypropyl)amino]-3-methyl-N-[2,3,4,5-tetrahydro -2-oxo-1-[[2'-(1H-tetrazol-5-yl)[1,1'-biphenyl]-4-yl]methyl]-1H-1-benzazepin-3(R)-yl]butanamide, trifluoroacetate To a stirred solution of 20 mg (0.028 mmol) of 3-[(2(R)-hydroxypropyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate (Example 102) in 2 mL of methylene chloride at room temperature was added 8.8 mg of acetic anhydride (3 eq.) followed by 13 mg (4 eq.) of 4-dimethylaminopyridine. The mixture was stirred for one hour then concentrated under vacuum and the residue purified by reverse phase high pressure liquid chromatography on C18, eluting with methanol/0.1% aqueous trifluoroacetic acid (70:30) to afford the title compound.

$^1$NMR (400 MHz,CD$_3$OD): 1.30 (d,6 Hz,3H), 1.36 (s,3H), 1.39 (s,3H), 2.01 (s,3H), 2.10 (m,1H), 2.29 (m,1H), 2.4-2.7 (m,4H), 3.15 (dd;9,13 Hz;1H), 3.25 (dd;4,13 Hz;1H), 4.36 (dd;8,12 Hz;1H), 4.9 (d,15 Hz,1H), 5.07 (m,1H), 5.19 (d,15 Hz,1H), 7.04 (d,8 Hz,2H), 7.19 (d,8 Hz,2H), 7.20-7.35 (m,4H), 7.54 (m,2H), 7.65 (m,2H). FAB-MS: calculated for C$_{34}$H$_{39}$N$_7$O$_4$ 609; found 610 (M+H,75%).

EXAMPLE 105

3-[(2(R)-Hydroxypropyl)amino]-3-methyl-N-[2,3,4,5-tetrahydro -2-oxo-1-[[2'-(1H-tetrazol-5-yl)[1,1'-biphenyl]-4-yl]methyl]-1H-1-benzazepin-3(R) -yl]butanamide, trifluoroacetate Step A: 3-[(2(R)-Benzyloxypropyl)amino]-3-methyl-N -[2,3,4,5-tetrahydro-2-oxo-1-[[2'-(1-methyltetrazol -5-yl)[1,1'-biphenyl]-4-yl]methyl]-1H-1-benzazepin-3(R)-yl]butanamide, trifluoroacetate Prepared from 3-amino-3-methyl-N-[2,3,4,5-tetrahydro -2-oxo-1-[[2'-(1-methyltetrazol-5-yl)[1,1'-biphenyl]-4-yl]methyl]-1H-1-benzazepin-3(R)-yl]butanamide, trifluoroacetate (Example 16) by the procedure describeb in Example 86, Step A. $^1$H NMR (200 MHz,CD$_3$OD): 1.29 (d,7 Hz,3H), 1.35 (s,6H), 2.12 (m,1H), 2.35 (m,1H), 2.5-2.7 (m,4H), 3.00 (dd;9,13 Hz;1H), 3.14 (s,3H), 3.20 (m,1H), 3.85 (m,1H), 4.44 (m,1H), 4.48 (d,11 Hz,1H), 4.67 (d,11 Hz,1H), 4.90 (d,15 Hz,1H), 5.25 (d,15 Hz,1H), 7.00 (d,8 Hz,2H), 7.1-7.5 (m,12H), 7.6 (m,2H), 7.75 (m,1H). FAB-MS: calculated for C$_{40}$H$_{45}$N$_7$O$_3$ 671; found 672 (M+H,100%).

Step B:
3-[(2(R)-Hydroxypropyl)amino]-3-methyl-N-[2,3,4,5-tetrahydro-2-oxo-1-[[2'-(1methyltetrazol -5-yl)[1,1'-biphenyl]-4-yl]methyl]-1H-1-benzazepin-3(R)-yl]butanamide, trifluoroacetate The title compound was prepared from the intermediate obtained in Step A by the procedure described in Example 86, Step B. $^1$H NMR (200 MHz,CD$_3$OD): 1.21 (d,6 Hz,3H), 1.34 (s,3H), 1.36 (s,3H), 2.10 (m,1H), 2.20-2.70 (m,5H), 2.78 (dd;10,12 Hz,1H), 3.09 (dd;4,12 Hz;1H), 3.16 (s,3H), 3.92 (m,1H), 4.35 (dd;8,12 Hz;1H), 4.85 (d,15 Hz,1H), 5.32 (d,15 Hz,1H), 7.00 (d,8 Hz,2H), 7.15-7.35 (m,6H), 7.55-7.75 (m,4H). FAB-MS: calculated for C$_{33}$H$_{39}$N$_7$O$_3$ 581; found 582 (M+H,100%).

EXAMPLE 106

3-[(2(R)-Methoxypropyl)amino]-3-methyl-N-[2,3,4,5-tetrahydro -2-oxo-1-[[2'-(1H-tetrazol-5-yl)[1,1'-biphenyl]-4-yl]methyl]-1H-1-benzazepin-3(R)-yl]butanamide, trifluoroacetate Step A: 2(R)-Methoxypropionaldehyde To a solution of 1.00 g (9.6 mmol) of (R)-(+)-methyl lactate in 2 mL of methyl iodide was added 4.45 g (19.2 mmol) of silver (I) oxide and the resulting mixture heated at reflux for 2 hours. The mixture was cooled, filtered and the excess methyl iodide removed under vacuum at 0° C. to afford 0.5 g of crude methyl [2(R)-methoxy]propionate which was used in the next step without purification.

To a stirred solution of 3.5 g (4.2 mmol) of the intermediate obtained above is 5 mL of ether at 0° C. was added 5.0 mL of 1.0M solution of lithium aluminum hydride in ether over 5 minutes. The resulting mixture was treated with 1 mL of 1N sodium hydroxide, filtered, dried over magnesium sulfate and concentrated under vacuum at 0° C. to give 0.36 g of crude 2(R)-methoxypropanol which was used directly in the next step.

To a stirred suspension of 2.7 g (12.6 mmol) of pyridinium chlorochromate on Celite (1 g) in 8 mL of methylene chloride was added 0.36 g of crude 2(R)-methoxypropanol and the resulting mixture stirred at room temperature for 3 hours. The reaction mixture was filtered, dried over sodium sulfate, filtered and concentrated under vacuum at 0° C. to give approximately 0.3 g of crude product which was used in the next step without purification.

Step B:
3-[(2(R)-Methoxypropyl)amino]-3-methyl-N-[2,3,4,5-tetrahydro-2-oxo-1-[[2'-(1H-tetrazol -5-yl)[1,1'-biphenyl]-4-yl]methyl]-1H-1-benzazepin -3(R)-yl]butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin -3(R)-yl]butanamide, trifluoroacetate (Example 1) and 2(R)-methoxypropionaldehyde (Step A) by the procedure described in Example 86, Step A. $^1$H NMR (200 MHz,CD$_3$OD): 1.17 (d,6 Hz,3H), 1.36 (br s,6H), 2.11 (m,1H), 2.31 (m,1H), 2.45–2.65 (m,4H), 2.87 (m,1H), 3.14 (m,1H), 3.31 (s,3H), 3.59 (m,1H), 4.37 (dd;7,11 Hz,1H), 4.95 (d,15 Hz,1H), 5.15 (d,15 Hz,1H), 7.03 (d,8 Hz,2H), 7.1–7.4 (m,6H), 7.5–7.7 (m,4H). FAB-MS: calculated for C$_{33}$H$_{39}$N$_7$O$_3$ 581; found 582 (M+H,100%).

EXAMPLE 107
3-[(2(R)-Hydroxy-2-methylpropyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide, trifluoroacetate

Step A: 2-Benzyloxy-2-methyl-3-butene

To a stirred suspension of 18.6 g of 60% sodium hydride oil dispersion (0.46 mol) in 50 mL of dry tetrahydrofuran at 0° C. was added 40 g (0.46 mol) of 2-methyl-3-buten-2-ol over 30 minutes. The resulting mixture was warmed to room temperature and stirred for 3 hours, then heated at reflux for an additional 30 minutes. The mixture was cooled to 0° C., treated with 80 g (0.46 mol) of benzyl bromide, then heated at reflux for 5 hours. The reaction mixture was cooled, filtered and concentrated under vacuum. The residue was purified by distillation under reduced pressure to give 42 g (0.24 mol,52%) of product, b.p. 88°–89° C. (2 mm). $^1$H NMR (200 MHz,CDCl$_3$): 1.38 (s,6H), 4.39 (s,2H), 5.20 (m,2H), 5.95 (m,1H), 7.2–7.4 (m,5H).

Step B: 2-Benzyloxy-2-methylpropionaldehyde

A mixture of 100 mL of water, 200 mL of dioxane, 20 g (0.11 mol) of 2-benzyloxy-2-methyl-3-butene and 1 g of osmium tetroxide was stirred at room temperature for 30 minutes then 51 g (0.22 mol) of finely ground sodium periodate was added in portions over 30 minutes. Stirring was continued for 2 hours then the mixture filtered and the filtrate extracted with several portions of ether. The combined extracts were dried over magnesium sulfate, filtered and the filtrate concentrated under vacuum. Distillation afforded 7.3 g (0.041 mol, 37%) of product, b.p. 85°–88° C. (2 mm).

Step C: 3-Amino-3-methyl-N-[2,3,4,5-tetrahydro-2-oxo 1H-1-benzazepin-3(R)-yl]butanamide, trifluoroacetate To a solution of 150 mg (0.40 mmol) of 3-t-butoxycarbonylamino -3-methyl-N-[2,3,4,5-tetrahdyro-2-oxo-1H-1-benzazepin-3(R)-yl]-butanamide (Example 57, Step A) in 2 mL of methylene chloride at 0° C. was added 2 mL of trifluoroacetic acid and the mixture stirred at room temperature for 1 hour. All volatiles were removed under vacuum to give 130 mg (0.33 mmol, 84%) of the product.

$^1$H NMR (200 MHz,CD$_3$OD): 1.33 (s,3H), 1.37 (s,3H), 2.12 (m,1H), 2.3–2.6 (m,3H), 2.6–3.0 (m,2H), 4.37 (dd;8,12 Hz;1H), 7.02 (d,8 Hz,1H), 7.1–7.3 (m,3H). FAB-MS: calculated for C$_{15}$H$_{21}$N$_3$O$_2$ 275; found 276 (M+H,100%).

Step D:
3-(2-Benzyloxy-2-methylpropyl)amino-3-methyl-N -[2,3,4,5-tetrahydro-2-oxo-1H-1-benzazepin-3-(R)-yl]-butanamide Prepared from the intermediate obtained in Step C and 2-benzyloxy-2-methylpropionaldehyde by the procedure described in Example 86, Step A. $^1$H NMR (200 MHz, CD$_3$OD): 1.32 (s,3H), 1.38 (s,9H), 2.10 (m,1H), 2.41 (m,1H), 2.65 (s,2H), 2.7–2.9 (m,2H), 3.09 (s,2H), 4.40 (m,1H), 4.48 (s,2H), 7.0–7.2 (m,4H), 7.2–7.4 (m,5H). FAB-MS: calculated for C$_{26}$H$_{35}$N$_3$O$_3$ 437; found 438 (M+H,100%).

Step E:
3-[(2-Benzyloxy-2-methylpropyl)amino]-3-methyl -N-[2,3,4,5-tetrahydro-2-oxo-1-[[2'-(1H-tetrazol-5-yl)[1,1'-biphenyl]-4yl]-methyl]-1H-1-benzazepin-3)(R)-yl]-butanamide, trifluoroacetate To a stirred solution of 145 mg (0.332 mmol) of the intermediate obtained in Step D in 2 mL of dry dimethylformamide at room temperature under nitrogen was added 67 mg of 60% sodium hydride oil dispersion (1.67 mmol,5 eq.). After 30 minutes, a solution of 277 mg (0.41 mmol, 1.2 eq.) of N-triphenylmethyl-5-[2-(4'-bromomethylbiphen -4-yl)]tetrazole in 2 mL of dry dimethyleformamide was added and the mixture stirred at room temperature for 1 hour. The reaction mixture was added to 100 mL of ethyl acetate and washed with water (2×) and brine. The organic layer was separated, dried over magnesium sulfate, filtered and concentrated under vacuum.

The residue was dissolved in 5 mL of methanol and treated with 5 mL of 9N HCl. The mixture was stirred at room temperature for 2 hours then washed with hexanes (5×) to remove triphenylmethanol. The aqueous layer was removed, filtered and evaporated under vacuum; the residue was purified by reverse phase medium pressure liquid chromatography on C8, eluting with methanol/0.1% aqueous trifluoroacetic acid (65:35) to afford 245 mg (0.31 mmol,94%) of product.

$^1$H NMR (200 MHz,CD$_3$OD): 1.32 (s,3H), 1.38 (s,9H), 2.10 (m,1H), 2.31 (m,1H), 2.4–2.7 (m,2H), 2.66 (s,H), 4.39 (dd;7.11 Hz;1H), 4.50 (s,2H), 4.94 (d,15 Hz,1H), 5.16 (d,15 Hz,1H), 6.99 (d,8 Hz,2H), 7.05–7.25 (m,5H), 7.25–7.45 (m,6H), 7.55–7.70 (m,4H). FAB-MS: calculated for C$_{40}$H$_{45}$N$_7$O$_3$ 671; found 672 (M+H,100%).

Step F:
3-[(2-Benzyloxy-2-methylpropyl)amino]-3-methyl-N -[2,3,4,5-tetrahydro-2-oxo-1-[[2'-(1H-tetrazol -5-yl)[1,1'-biphenyl]-4yl]-methyl]-1H-1-benzazepin -3)(R)-yl]-butanamide, trifluoroacetate The title compound was prepared from the intermediate obtained in Step E by the procedure described in Example 86, Step B.

¹H NMR (200 MHz, CD₃OD): 1.29 (s,6H), 1.36 (s,3H), 1.40 (s,3H), 2.1-2.5 (m,4H), 2.68 (s,2H), 2.98 (s,2H), 4.37 (dd;7,11 Hz;1H), 4.94 (d,15 Hz,1H), 5.17 (d,15 Hz,1H), 7.04 (d,8 Hz,2H), 7.20 (d,8 Hz,2H), 7.20-7.35 (m,4H), 7.5-7.7 (M,4H). FAB-MS: calculated for $C_{33}H_{39}N_7O_3$ 581; found 582 (M+H,70%).

EXAMPLE 108

3-[(2(S)-Hydroxy-3-methylbutyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate

Step A:
3-[(2(S)-Benzyloxy-3-methylbutyl)amino]-3-methyl-N-[2,3,4,5-tetrahydro-2-oxo-1-[[2'-(1H-tetrazol-5-yl)[1,1'-biphenyl]-4-yl]-methyl]-1H-1-benzazepin-3(R)-yl]-butanamide, trifluoroacetate Prepared from 2(S)-benzyloxy-3-methylbutanal (prepared from L-valine by the method of Li, et al; J. Amer. Chem. Soc., 112, 7659 (1990)) and 3-amino-3-methyl-N-[2,3,4,5-tetrahydro-2-oxo-1-[[2'-(1H-tetrazol -5-yl)[1,1'-biphenyl]-4-yl]methyl]-1H-1-benzazepin -3(R)-yl]-butanamide, trifluoroacetate (Example 1), by the procedure described in Example 86, Step A.

¹H NMR (200 MHz, CD₃OD): 0.92 (d,7 Hz,3H), 0.98 (d,7 Hz,3H), 1.31 (s,3H), 1.38 (s,3H), 2.0-2.6 (m,5H), 2.62 (s,2H), 2.95 (dd;9,12 Hz;1H), 3.15 (dd;3,12 Hz;1H), 3.55 (m,1H), 4.40 (dd;7,11 Hz;1H), 4.52 (d,12 Hz,1H), 4.61 (d,12 Hz, 1H), 4.89 (d,15 Hz,1H), 5.18 (d,15 Hz,1H), 6.97 (d,8 Hz,2H), 7.1-7.7 (m,15H). FAB-MS: calculated for $C_{41}H_{47}N_7O_3$ 685; found 687 (100%).

Step B:
3-[(2(S)-Hydroxy-3-methylbutyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate Prepared from the intermediate obtained in Step A by the procedure described in Example 86, Step B.

¹H NMR (200 MHz,CD₃OD): 0.86 (d,7 Hz,3H), 0.92 (d,7 Hz,3H), 1.35 (s,3H), 1.40 (s,3H), 1.67 (m,1H), 2.0-2.6 (m,4H), 2.64 (s,2H), 2.82 (dd;10,12 Hz,1H), 3.12 (dd;3,12 Hz;1H), 3.48 (m,1H), 4.37 (dd;8,12 Hz;1H), 4.9 (d,15 Hz,1H), 5.19 (d,15 Hz,1H), 7.04 (d,8 Hz,2H), 7.15-7.35 (m,6), 7.5-7.7 (m,4H). FAB-MS: calculated for $C_{34}H_{41}N_7O_3$ 595; found 597 (100%).

EXAMPLE 109

3-[(2(R)-Hydroxy-3-methylbutyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from D-valine and 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate (Example 1), by the procedures described in Example 108.

¹H NMR (200 MHz,CD₃OD): 0.86 (d,7 Hz,3H), 0.88 (d,7 Hz,3H), 1.32 (s,3H), 1.33 (s,3H), 1.65 (m,1H), 2.00-2.66 (m,6H), 2.78 (dd;10,12 Hz,1H), 3.10 (dd;2,12 Hz;1H), 3.45 (m,1H), 4.34 (dd;8,12 Hz,1H), 4.90 (d,15 Hz,1H), 5.1 (d,15 Hz,1H), 7.02 (d,8 Hz,2H), 7.1-7.3 (m,6H), 7.45-7.70 (m,4H). FAB-MS: calculated for $C_{34}_{41}N_7O_3$ 595; found 597 (100%).

EXAMPLE 110

4-[[3(R)-[3-Amino-3-methyl-1-oxobutyl)amino]-2,3,4,5-tetrahydro-2-oxo-1H-1-benzazepin-1-yl]-methyl]-2-phenyl-1,1'-biphenyl, trifluoroacetate

Step A: 2-Bromobiphenyl

A solution of 8.8 mL of isoamylnitrite in 120 mL of benzene at 45° C. was treated dropwise over 30 minutes with a solution of 7.5 g of 2-bromoaniline in 30 mL of benzene. After the addition was complete, the mixture was heated at reflux for 90 minutes then cooled and concentrated under vacuum. The product was purified by preparative high pressure liquid chromatography on silica, eluting with hexanes. ¹H NMR (200 MHz,CDCl₃): 7.23 (m,2H), 7.35 (m,1H), 7.44 (s,5H), 7.70 (d,8 Hz,1H).

Step B: 4'-Methyl-2-phenyl-1,1'-biphenyl

Prepared from 2-bromobiphenyl and 4-methylphenyltrimethylstannane by the procedure described in Example 69, Step B.

¹H NMR (200 MHz,CDCl₃): 2.30 (s,3H), 7.06 (s,4H), 7.23 (m,5H), 7.44 (s,4H).

Step C: 4'-Bromomethyl-2-phenyl-1,1'-biphenyl

Prepared from 4'-methyl-2-phenyl-1,1'-biphenyl by the procedure described in Example 69, Step C.

Step D:
4'-[[3(R)-[(3-Amino-3-methyl-1-oxobutyl)-amino]-2,3,4,5-tetrahydro-2-oxo-1H-1-benzazepin-1-yl]methyl]-2-phenyl-1,1'-biphenyl, trifluoroacetate The title compound was prepared from 3-t-butoxycarbonylamino-3-methyl-N-[2,3,4,5-tetrahydro-2-oxo-1H-1-benzazepin-3(R)-yl]-butanamide (Example 57, Step A) and 4'-bromomethyl-2-phenyl-1,1'-biphenyl by the procedures described in Example 69, Steps D and F.

¹H NMR (300 MHz,CD₃OH): 1.32 (s,3H), 1.36 (s,3H), 2.0-2.6 (m,6H), 4.37 (dd;8,12 Hz;1H), 4.78 (d,15 Hz,1H), 5.28 (d,15 Hz,1H), 6.9-7.45 (m,17H).

EXAMPLE 111

3-[[2-Hydroxy-3-(4-hydroxyphenyl)-propyl]amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate

Step A: Ethyl 2-hydroxy-3-(4-hydroxyphenyl)propionate

To a stirred solution of 0.5 g (2.74 mmol) of D,L 3-(4-hydroxyphenyl) lactic acid hydrate in 10 mL of ethanol was added a catalytic amount of concentrated hydrochloric acid. The mixture was heated at reflux for 2 hours then cooled to room temperature and concentrated under vacuum. The residue was dissolved in 50 mL of ether and washed with saturated aqueous sodium bicarbonate (1×50 mL) and brine (1×50 mL). The organic layer was removed, dried over magnesium sulfate, filtered and evaporated under vacuum to afford 0.54 g (2.57 mmol,94%) of the ethyl ether. ¹H NMR (200 MHz,CDCl₃): 1.26 (t,7 Hz,3H), 2.86 (dd;7,14

Hz;1H); 3.03 (dd;4,14 Hz; 1H), 4.19 (q,7 Hz,2H), 4.38 (dd;4,7 Hz;1H), 5.60 (br s,1H), 6.66 (d,8 Hz,2H), 7.03 (d,8 Hz,2H).

Step B: Ethyl 2-(t-butyldimethylsiloxy)-3-[4-(t-butyldimethylsiloxyphenyl)]propionate To a stirred solution of 0.57 g (7.4 mmol) of ethyl 2-hydroxy-3-(4-hydroxyphenyl)propionate in 10 mL of methylene chloride at −78° C. was added 2 mL of 2,6-lutidine (4 eq.) followed by 2.52 mL of t-butyldimethylsilyl trifluoromethanesulfonate (4 eq.). The reaction mixture was warmed to room temperature and stirred for 16 hours. The reaction mixture was diluted with 50 mL of methylene chloride and washed with 10% hydrochloric acid (2×100 mL), saturated aqueous sodium bicarbonate and brine. The organic layer was removed, dried over magnesium sulfate, filtered and concentrated under vacuum to give 1.12 g of crude product. A 250 mg sample was purified by preparative thin layer chromatography on silica, eluting with hexane/ethyl acetate (90:10) to afford 210 mg of pure product. $^1$H NMR (200 MHz,CDCl$_3$): 0.13 (s,6H), 0.76 (s,9H), 0.94 (s,9H), 2.76 (dd;10,14 Hz;1H), 2.97 (dd;4,14 Hz;1H), 4.24 (dd;4,10 Hz;1H), 6.73 (d,8 Hz,2H), 7.05 (d,8 Hz,2H).

Step C: 2-(t-Butyldimethylsiloxy)-3-[4-(t-butyldimethylsiloxyphenyl)]propanal To a stirred solution of 210 mg (0.48 mmol) of ethyl 2-(t-butyldimethylsiloxy)-3-[4-(t-butyldimethylsiloxyphenyl)]propionate in 10 mL of ether at −78° C. was added dropwise over 5 minutes 1 mL of 1.0M solution of diisobutylaluminum hydride in hexane (2 eq.). The reaction mixture was poured, with rapid stirring, into 50 mL of 10% hydrochloric acid. After stirring for 5 minutes, the mixture was extracted with ether (2×30 mL) and the combined extracts dried over magnesiumsulfate, filtered and concentrated under vacuum to give approximately 200 mg of the product which was used immediately and without further purification.

$^1$H NMR (200 MHz,CDCl$_3$): 0.14 (s,6H), 0.80 (s,9H), 0.95 (s,9H), 2.76 (dd;10,14 Hz;1H), 2.90 (dd;4,14 Hz;1H), 4.24 (ddd;2,4,10 Hz;1H), 6.73 (d,8 Hz,2H), 7.02 (d,8 Hz,2H), 9.61 (d,2 Hz,1H).

Step D: 3-[(2-Hydroxy-3-(4-hydroxyphenyl)-propyl)amino]-3-methyl-N-[2,3,4,5-tetrahydro-2-oxo-1-[[2'-(1H-tetrazol-5-yl)[1,1'-biphenyl]-4-yl]-methyl]-1H-benzazepin-3(R)-yl]-butanamine, trifluoroacetate The title compound was prepared as a mixture of two diastereomers from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate (Example 1) and 2-(t-butyldimethylsiloxy)-3-[4-(t-butyldimethylsiloxyphenyl)]propanal (Step C) by the procedure described in Example 86, Step A.

$^1$H NMR (200 MHz,CD$_3$OD): 1.35 (m,6H), 2.10 (m,1H), 2.29 (m,1H), 2.40–2.75 (m,6H), 2.85 (m,1H), 3.07 (m,1H), 3.90 (m,1H), 4.33 (dd;8,12 Hz;1H), 4.9 (m,1H), 5.1 (m,1H), 6.67 (d,8 Hz,2H), 7.02 (m,4H), 7.15–7.35 (m,6H), 7.75–7.7 (m,4H). FAB-MS: calculated for C$_{38}$H$_{41}$N$_7$O$_4$ 659; found 659 (40%).

EXAMPLE 112

3-[[2(R)-Hydroxy-2-phenylpropyl]amino]-3-methyl-N-[2,3,4,5-tetrahydro-2-oxo-1-[[2'-(1H-tetrazol-5-yl)[1,1'-biphenyl]-4-yl]methyl]-1H-1-benzazapin-3(R)-yl]-butanamide, trifluoroacetate

Step A: 2(R)-Benzyloxy-2-phenylacetaldehyde

Prepared from (R)-(−)-mandelic acid by the procedures described in Example 111 (Steps A, C) and Example 107, Step A.

$^1$H NMR (200 MHz,CDCl$_3$): 4.51 (d,12 Hz,1H), 4.65 (d,12 Hz,1H), 4.77 (d,2 Hz,1H), 7.35 (m,10H), 9.61 (d,2 Hz,1H).

Step B: 3-[(2(R)-Benzyloxy-2-phenylethyl)amino]-3-methyl-N-[2,3,4,5-tetrahydro-2-oxo-1-[[2'-(1H-tetrazol-5-yl)[1,1'-biphenyl]-4-yl]-methyl]-1H-1-benzazepin-3(R)-yl]-butanamide, trifluoroacetate Prepared 2(R)-benzyloxy-2-phenyl acetaldehyde and 3-amino-3-methyl-N-[2,3,4,5-tetrahydro-2-oxo-1-[[2'-(1H-tetrazol-5-yl)[1,1'-biphenyl]-4-yl]methyl]-1H-benzazepin-3(R)-yl]-butanamide, trifluoroacetate (Example 1) by the procedure described in Example 86, Step A. $^1$H NMR (200 MHz,CD$_3$OD): 1.35 (s,6H), 2.12 (m,1H), 2.32 (m,1H), 2.5–2.7 (m,4H), 3.22 (m,2H), 4.32 (d,12 Hz,1H), 4.43 (d,12 Hz,1H), 4.45 (m,1H), 4.67 (t,7 Hz,1H), 4.99 (d,14 Hz,1H), 5.13 (d,14 Hz,1H), 7.02 (d,8 Hz,2H), 7.10–7.45 (m,16H), 7.5–7.7 (m,4H). FAB-MS: calculated for C$_{44}$H$_{45}$N$_7$O$_3$ 719; found 720 (M+H,35%).

Step C: 3-[[2(R)-Hydroxy-2-phenylpropyl]amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from the intermediate obtained in Step B by the procedure described in Example 86, Step B.

$^1$H NMR (400 MHz,CD$_3$OD): 1.38 (s,3H), 1.39 (s,3H), 2.10 (m,1H), 2.3 (m,1H), 2.4–2.7 (m,4H), 3.05 (m,1H), 3.22 (m,1H), 4.39 (m,1H), 4.95 (d,15 Hz,1H), 5.18 (d,15 Hz,1H), 7.08 (d,8 Hz,2H), 7.20–7.45 (m,11H), 7.5–7.7 (m,4H). FAB-MS: calculated for C$_{37}$H$_{39}$N$_7$O$_3$ 629; found 630 (M+H,85%).

EXAMPLE 113

3-Amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, hydrochloride, dihydrate

Step A: 1-Tetralone oxime

To 4.6 L of water at room temperature in a 4-neck 50 L flask stirring in a steam bath apparatus equipped with an overhead stirrer, a temperature probe and reflux condenser was added 3.72 Kg (27.36 mol) of sodium acetate with stirring, followed by 1.9 Kg of hydroxylamine hydrochloride (27.36 mol). To this slurry at room temperature, 12 L of ethanol was added followed by 1.994 Kg (13.68 mol) of 1-tetralone. Additional ethanol (1.7 L) was used to rinse off the funnel and added to the reaction mixture. The resulting light orange slurry was heated to 75° C. over 40 minutes and maintained at 75°–85° C. for another 75 minutes. The reaction mixture was cooled with the aid of ice packed around the flask. When the internal temperature reached 32° C., the reaction mixture was pumped over 15 minutes into 60 L of ice contained in a 200 L vessel. The reaction vessel was washed with an additional 12 L of water which was added to the 200 L vessel. When the ice melted, the mixture was filtered through a filter pad and the wet cake washed with 4 L of water. The wet cake was suction dried for 1 hour then transferred to two trays and dried under vacuum at 40' C. for 2 days to give 2.094 Kg (13.01 mol, 95%) of product. $^1$H NMR (250 MHz,CDCl$_3$): 1.90 (m,2H), 2.80 (t,6 Hz,2H), 2.88 (t,6 Hz,2H), 7.15–7.35 (m,3H), 7.90 (d,8 Hz,1H), 8.9 (br s,1H).

Step B: 2,3,4,5-Tetrahydro-1H-1-benzazepin-2-one

To 10 L of methanesulfonic acid in a 22 L 3-neck flask equipped with an overhead stirrer, a temperature probe, nitrogen inlet and reflux condenser was added 2.6 Kg (18.61 mol) of phosphorus pentoxide. An additional 1.6 L of methanesulfonic acid was used to wash wall the phosphorus pentoxide into the vessel. The mixture was heated at 90° C. for 2.5 hours then cooled to 50° C. using an ice bath and treated with 2.00 Kg (12.41 mol) of 1-tetralone oxime in several portions over 15 minutes. The mixture was heated at 63° C. for 10 minutes then slowly heated to 80° C. and kept at 80° C. for 3 hours. The reaction mixture was pumped into 70 L of ice then treated slowly with 11.25 L of 50% aqueous sodium hydroxide over 90 minutes at such a rate so as to maintain the temperature below 28° C. The mixture was filtered and 4 L of the filtrate was used to rinse the vessel. The wet cake (pink) was washed with 8 L of water then suction dried for 45 minutes then transferred to two trays and dried under vacuum at 40° C. for 2 days to give 1.9 Kg (11.79 mol, 95%) of product. $^1$H NMR (250 MHz,CDCl$_3$): 2.24 (m,2H), 2.38 (t,6 Hz,2H), 2.82 (t,6 Hz,2H), 7.03 (d,8 Hz,1H), 7.13 (m,1H), 7.24 (m,2H), 8.63 (br s,1H).

Step C:
3-Iodo-2,3,4,5-tetrahydro-1H-1-benzazepin-2-one

A suspension of 1.8 Kg (11.17 mol) of 2,3,4,5-terahydro-1H-1-benzazepin-2-one in a mixture of 22.33 L of methylene chloride and 11.78 L (55.83 mol) of hexamethyldisilazane was heated at reflux for 10 minutes then cooled to 30° C. and treated with 8.503 Kg (33.5 mol) of iodine in one portion. The mixture was heated at reflux for 2.5 hours then cooled to room temperature. Aqueous sodium sulfite containing 4.926 Kg of sodium sulfite in 44 L of water was cooled to 0° C. and into it was poured the reaction mixture in several portions with vigorous stirring while maintaining the temperature below 10° C. The reaction vessel was rinsed with 3 L of methylene chloride and the washing transferred to the quenching mixture. Methylene chloride (17 L) was added to the quenching mixture and it was stirred vigorously and the layers allowed to separate. The aqueous layer was removed and reextracted with 12 L of methylene chloride. The combined organic layers were washed with 11 L of water and concentrated under vacuum to a final volume of approximately 5 L. The residue was treated with 55 L of toluene and concentrated under vacuum to a final volume of 10 L. The resulting slurry was removed by filtration and the filter cake washed with an additional 5 L of toluene and dried under vacuum at ambient temperature for 24 hours to give 1.842 Kg (6.42 mol, 57%) of product.

$^1$H NMR (200 MHz,CDCl$_3$): 2.6–2.8 (m,3H), 2.93 (m,1H), 4.64 (t,8 Hz,1H), 6.97 (d,8 Hz,1H), 7.10–7.35 (m,3H), 7.55 (br s,1H).

Step D:
3(R)-Amino-2,3,4,5-tetrahydro-1H-1-benzazepin-2-one, D-tartrate

3-Iodo-2,3,4,5-tetrahydro-1H-1-benzazepin-2-one (1.79 Kg, 6.24 mol) was slurried in 6.2 L of methanol and the slurry charged into an autoclave. Condensed ammonia (1.55 L) was added and the autoclave closed, with stirring, and heated to 100° C. over 1 hour. Heating at 100° C. was continued for 2 hours then the autoclave was allowed to cool to room temperature over 1 hour, during which time the internal pressure was 150–155 psi. The reaction mixture was transferred to a polyethylene jug and the autoclave rinsed with 2×8 L of methanol. The washings were concentrated under vacuum at 30° C. then combined with the reaction mixture and concentrated to near dryness under vacuum at 30° C. The resulting residue was dissolved in 4 L of ethyl acetate then concentrated to dryness under vacuum at 30° C.

Sodium chloride (712 g) was dissolved in 2 L of water and 1.0 Kg of sodium carbonate was dissolved in 6 L of water. Two liters of the sodium carbonate solution was added to the concentrated residue and the resulting slurry transferred to an extraction flask. Another 2 L portion of the sodium carbonate solution was added to the residue flask and the solution transferred to the extraction flask. The remaining sodium carbonate solution was used in the same way. The sodium chloride solution was added to the sodium carbonate/aminolactam emulsion and the resulting mixture stirred for 10 minutes then extracted with four 6 L portions of methylene chloride. The combined methylene chloride layers were concentrated to dryness; the residue was treated with 2 L of 200 proof ethanol and the resulting slurry concentrated to dryness under vacuum to give 1.171 Kg of crude product.

The crude product was slurried in 8 L of ethanol and treated with 900 g of D-tartaric acid in one portion. Water (7 L) was added and the mixture heated to 77° C., then additional ethanol (45 L) was added and heating continued. The solution was cooled to 43° C. and treated with the seed slurry. (The seed slurry was prepared by the route described above starting with 10.50 g of crude product and 9.1 g of D-tartaric acid.) The solution was aged at room temperature for 48 hours. The slurry formed was removed by filtration and the wet cake washed with 1.8 L of ethanol. The resulting filter cake was suction dried with nitrogen bleeding for 20 hours then transferred into a drying tray and dried under vacuum for 24 hours to give 254 g (1.085 mol, 17.4%) of the product. $^1$H NMR (250 MHz,CDCl$_3$): 2.13 (m,1H), 2.51 (m,2H), 2.73 (m,2H), 3.68 (t,6 Hz,1H), 3.98 (s,2H), 7.05 (d,8 Hz,1H), 7.16 (t,8 Hz,1H), 7.30 (m,2H), 7.6 (br s,5H), 10.26 (br s,1H).

Step E:
3(R)-Amino-2,3,4,5-tetrahydro-1H-1-benzazepin-2-one

A solution of 229.23 g (0.700 mol) of 3(R)-amino-2,3,4,5-tetrahydro-1H-1-benzazepin-2-one, D-tartrate in 4.1 L of water was treated with 194 g (1.40 mol) of potassium carbonate. Subsequent portions of 100 g and 135 g of potassium carbonate were added until the pH was 10.5. The mixture was extracted with four 4 L portions of methylene chloride which were then combined and dried over magnesium sulfate. The aqueous layer was treated with 1.4 Kg of sodium chloride and reextracted with four 4 L portions of methylene chloride which were then combined and dried over magnesium sulfate. The two 16 L batches of extracts were combined, filtered and concentrated to dryness under vacuum to give 115.5 g of product which contained 1.6% of an impurity identified as 7-iodo-3(R)-amino-2,3,4,5-tetrahydro-1H-1-benzazepin-2-one.

A solution of 107.02 g (0.607 mol) of the intermediate obtained above in 1.712 L of ethanol was hydrogenated at room temperature and 40 psi over 4.00 g of 10% palladium on carbon for 4 hours. The catalyst was removed by filtration through solkaflok and the filtrate concentrated to dryness under vacuum to give 101.08 g (0.574 mol, 94.4%) of product.

Step F: N-Chlorosulfonyl-4,4-dimethylazetidin-2-one

To a 3-neck 12 L flask equipped with an overhead stirrer, a 250 mL addition funnel topped with a nitrogen inlet and a rubber septum to allow a temperature probe and isobutylene needle was charged 450 mL of isobutylene. The flask was cooled in a dry ice-acetone bath. Ethyl ether (450 mL) was added and the resulting solution at −60° C. was treated with 210 mL (2.41 mol) of chlorosulfonyl isocyanate over 5 minutes at a rate so as to maintain the internal temperature below −50° C. The mixture was stirred at −50° C. to −62° C. for 30 minutes then allowed to warm slowly to room temperature and treated with 2250 mL of ether. The resulting solution was treated with 750 mL of 10% aqueous sodium carbonate slowly in 3 portions. The mixture was transferred into a 4 L separatory funnel and the aqueous layer removed. The organic layer was washed with 500 mL of water, then removed and treated with 750 mL of hexane. As crystallization began, additional hexane (250 mL) was added and the mixture concentrated under partial vacuum to a final volume of 3100 mL. The solid that formed was removed by filtration with the aid of 200 mL of hexane for rinsing. After air drying, the wet cake was dried under vacuum at 40° C. overnight to give 253 g (1.28 mol,53%) of product as a pale yellow crystalline solid. Recycling of the mother liquors gave an additional 100 g (19%) of product as a white crystalline solid. $^1$H NMR (250 MHz,CDCl$_3$): 1.89 (s,6H), 3.05 (s,2H).

Step G:
3-Methoxysulfonylamino-3-methyl-N-[2,3,4,5-tetrahydro-2-oxo-1H-1-benzazepin-3(R)-yl]butanamide A suspension of 98.31 g (0.530 mol) of 3(R)-amino-2,3,4,5-tetrahydro-1H-1-benzazepin-2-one in 1600 mL of methanol at room temperature was treated with 155 mL (1.112 mol) of triethylamine. The resulting suspension was cooled to 0° C. and treated with a solution of 110.01 g (0.557 mol) of N-chlorosulfonyl-4,4-dimethylazetidin-2-one in 960 mL of methanol over 20 minutes maintaining the internal temperature below 10° C. Additional methanol (100 mL) was used to rinse the flask and the rinse was transferred into the reaction vessel. The reaction mixture was warmed to room temperature and stirred for 90 minutes.

The reaction mixture was concentrated under vacuum to a slurry (600 mL) which was diluted with 3180 mL of ethyl acetate and treated with 1 L of saturated aqueous ammonium chloride and 1 L of water. The organic layer was separated, washed with 2 L of 1:1 saturated aqueous ammonium chloride/water then 2 L of brine. The organic layer was removed and concentrated under vacuum to a final volume of 1.6 L. The resulting slurry was treated with 1.6 L of hexane and then aged at room temperature for 2.5 hours. The solid was removed by filtration and the cake washed with 1 L of hexane. The material was air dried at 40° C. for 48 hours to give 163.81 g (0.444 mol, 83.7%) of product as a white solid.

$^1$H NMR (250 MHz,CDCl$_3$): 1.39 (s,3H), 1.42 (s,3H), 2.04 (m,1H), 2.37 (d,15 Hz,1H), 2.58 (d,15 Hz,1H), 2.69 (m,2H), 2.95 (m,1H), 3.81 (s,3H), 4.55 (m,1H), 6.83 (m,2H), 7.01 (d,8 Hz,1H), 7.25 (m,3H), 8.20 (br s,1H).

Step H:
3-Methoxysulfonylamino-3-methyl-N-[2,3,4,5-tetrahydro-2-oxo-1-[[2'-(N-triphenylmethyl)-tetrazol-5-yl][1,1'-biphenyl]-4-yl]methyl-1H-1-benzazepin-3(R)-yl]-butanamide To a suspension of 155.0 g (0.4197 mol) of the intermediate obtained in Step G in 800 mL of tetrahydrofuran was added 140 mL of dimethylformamide and the resulting solution cooled to 0° to −5° C. and treated with 19.1 g of 95% sodium hydride 0.796 mol). Additional tetrahydrofuran (40 mL) was used to rinse the addition funnel. The mixture was stirred for 30 minutes at 0° C. then treated with a solution of 269.0 g (0.4825 mol) of N-triphenylmethyl-5-[2-(4'-bromomethylbiphen-4-yl)] in 800 mL of tetrahydrofuran over 20 minutes. After the addition was complete, the reaction mixture was warmed to room temperature and stirred for 5 hours. An additional 1.0 g of 95% sodium hydride was added an stirring continued for another 3.5 hours.

The reaction mixture was poured into a mixture of 3 L of ethyl acetate and 2.5 L of water. Additional water (300 mL) and ethyl acetate (500 mL) were used for rinsing. The aqueous layer was removed and the organic layer washed with 2 L of brine. The organic layer was separated, dried over sodium sulfate, filtered and concentrated under vacuum to a viscous oil. The oil was further concentrated under vacuum to form a pale yellow solid which was purified by chromatography on silica, eluting with ethyl acetate/hexanes (1:1 to 3:1) to afford 330.6 g (0.3908 mmol, 89.3%) of product as a white solid.

Step I:
3-Amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, mono(hydrochloride), di(hydrate)

To 900 mL of hot (70° C.) ethanol was added, with vigorous stirring, 190.0 g (0.2246 mol) of the intermediate obtained in Step H by a solid addition funnel. Additional ethanol (50 mL) was used to rinse the funnel. To the clear solution at 70° C. was added 380 mL of 6N hydrochloric acid over 10 minutes. The mixture was stirred at 70° C. for 4.5 hours then allowed to cool to room temperature. The reaction mixture was poured into a mixture of 1900 mL of water and 3L of ethyl acetate/hexane (2:1). The aqueous layer was removed and washed with 3 L of ethyl acetate/hexane (2:1) then 2.5 L of hexane. The aqueous layer was separated and filtered, then concentrated under vacuum at 40° C. to a final volume of 3500 mL and allowed to age overnight at ambient temperature. The white suspension was removed by filtration and the wet cake washed with 250 mL of a solution of 15 mL of concentrated hydrochloric acid in 500 mL of water. The product was dried under vacuum at 35°–40° C. overnight then allowed to equilibrate in ambient humidity to give 110.25 g (0.189 mol, 90.7%) of the title compound as a white powdery slid. $^1$H NMR (250 MHz,CD$_3$OD): 1.36 (s,3H), 1.40 (s,3H), 2.12 (m,1H), 2.30 (m,1H), 2.50 (m,2H), 2.55 (m,2H), 4.36 (dd;8,12 Hz;1H), 4.87 (d,15 Hz,1H), 5.21 (d,15 Hz,1H), 7.00 (m,2H), 7.17 (m,2H), 7.22 (m,2H), 7.31 (m,2H), 7.51 (m,1H), 7.53 (m,1H), 7.61 (m,2H).

EXAMPLE 114

3-[(2,2-Dimethyl-1,3-dioxolane-4(S)-yl)methyl]amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, mono(trifluoroacetate)

To a stirred solution of 116 mg (0.20 mmol) of 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, hydrochloride, dihydrate (Example 113) in 5 mL of dry methanol was added 0.5 g of dry 3A powdered molecular sieves followed by a solution of 131 mg (1.0 mmol) of D-glyceraldehyde acetonide (used crude as prepared according to the procedure of Hertel, L. W.; Grossman, C. S.; Kroin, J. S. Synth. Comm. 1991, 21, 151–154) in 1 mL of dry methanol. The pH of the mixture was carefully adjusted to 6.5 with glacial acetic acid and triethylamine. The reaction was stirred at room temperature for 3 hours at which time 1.0 mL (1.0 mmol) of a 1.0M solution of sodium cyanoborohydride in tetrahydrofuran was added dropwise by syringe. The reaction was stirred overnight then filtered through a pad of Celite. The filtrate was diluted with 50% aqueous trifluoroacetic acid and stirred for 3 hours at room temperature. The solution was concentrated under vacuum and the residue purified by preparative reverse phase high pressure liquid chromatography on C18, eluting with methanol/0.1% aqueous trifluoroacetic acid (linear gradient; 60% methanol to 85% methanol over 10 minutes). The title compound was thus obtained in addition to the faster eluting major product 3-(2(S),3-dihydroxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide. $^1$H NMR (200 MHz,CD$_3$OD): 1.35–1.40 (m,12H), 2.05–2.75 (m,6H), 3.01 (dd;8,12 Hz;1H), 3.26 (dd;3,12 Hz;1H), 3.78 (dd;5,10 Hz;1H), 4.15 (dd;6,8 Hz;1H), 4.36 (m,2H), 4.85 (d,15 Hz,1H), 5.15 (d,15 Hz,1H), 7.03 (d,8 Hz,2H), 7.2–7.4 (m,6H), 7.5–7.7 (m,4H).

EXAMPLE 115

3-(2(S),3-Dihydroxypropyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, hydrochloride, dihydrate (Example 113) and D-glyceraldehyde acetonide by the procedure described in Example 114.
$^1$H NMR (200 MHz,CD$_3$OD): 1.37 (s,3H), 1.39 (s,3H), 2.05–2.75 (m,6H), 2.95 (dd;8,11 Hz;1H), 3.19 (dd;3,11 Hz;1H), 3.56 (m,2H), 3.84 (m,1H), 4.35 (dd;8.12 Hz;1H), 4.93 (d,15 Hz,1H), 5.16 (d,15 Hz,1H), 7.04 (d,8 Hz,2H), 7.15–7.35 (m,6H), 7.5–7.7 (m,4H). FAB-MS: calculated for C$_{32}$H$_{37}$N$_7$O$_4$ 583; found 585 (100%).

EXAMPLE 116

3-(2(S),3(S),4-Trihydroxybutyl)amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The title compound was prepared from 3-Amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, hydrochloride, dihydrate (Example 113) and 5(S)-t-butyldimethylsilyloxymethyl-2,2-dimethyl-1,3-dioxolan-4(R)-carboxaldehyde (Example 82) by the procedure described in Example 71. $^1$H NMR (400 MHz,CD$_3$OD): 1.36 (s,3H), 1.40 (s,3H), 2.09 (m,1H), 2.30 (m,1H), 2.46 (m,1H), 2.57 (dd;7,11 Hz;1H), 2.64 (s,2H), 3.13 (m,2H), 3.59 (br s,3H), 3.92 (m,1H), 4.35 (dd;7,12 Hz;1H), 4.9 (d,15 Hz,1H), 5.18 (d,15 Hz,1H), 7.02 (d,8 Hz,2H), 7.18 (d,8 Hz,2H), 7.22 (m,2H), 7.30 (m,2H), 7.53 (m,2H), 7.63 (m,2H). FAB-MS: calculated for C$_{33}$H$_{39}$N$_7$O$_5$ 613; found 614 (100%).

EXAMPLE 117

3-Amino-3-methyl-N-[2,3,4,5-tetrahydro-2-oxo-1-[[2'-(1-benzyltetrazol-5-yl)[1,1'-biphenyl]-4-yl]methyl]-1H-1-benzazepin-3(R)-yl]-butanamide, trifluoroacetate To a stirred solution of 174 mg (0.20 mmol) of 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, hydrochloride, dihydrate (Example 113) in 3 mL of tetrahydrofuran and 1 mL of dimethylformamide was added 0.22 mL (5 eq.) of triethylamine followed by 0.043 mL (1.2 eq.) of benzyl bromide. The mixture was stirred for 2 hours at room temperature then concentrated under vacuum. Initial purification by reverse phase high pressure liquid chromatography on C18, eluting with methanol/0.1% aqueous trifluoroacetic acid (75:25) afforded a major product (1-benzyl isomer) followed by a minor product (2-benzyl isomer). Repurification of each product by reverse phase high pressure liquid chromatography on C18, eluting with methanol/0.1% aqueous trifluoroacetic acid (70:30) afforded 9 mg of the title compound in addition to 8 mg of the 2-benzyl isomer.

$^1$H NMR (200 MHz,CD$_3$OD): 1.35 (s,3H), 1.39 (s,3H), 2.05–2.65 (m,6H), 4.38 (dd;7,11 Hz;1H); 4.82 (d,15 Hz,1H), 4.85 (s,2H), 5.35 (d,15 Hz,1H), 6.77 (dd;2,8 Hz;2H), 6.94 (d,8 Hz,2H), 7.1–7.8 (m,13H). FAB-MS: calculated for C$_{36}$H$_{37}$N$_7$O$_2$ 599; found 601 (100%).

EXAMPLE 118

3-Amino-3-methyl-N-[2,3,4,5-tetrahydro-2-oxo-1-[[2'-(2-benzyltetrazol-5-yl)[1,1'-biphenyl]-4-yl]methyl]-1H-1-benzazepin-3(R)-yl]-butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, hydrochloride, dihydrate (Example 113) and benzyl bromide by the procedure described in Example 117.

$^1$H NMR (200 MHz,CD$_3$OD): 1.35 (s,3H), 1.39 (s,3H), 2.00–2.65 (m,6H), 4.40 (dd;7,11 Hz;1H), 4.88 (d,15 Hz,1H), 5.26 (d,15 Hz,1H), 5.74 (s,2H), 6.96 (d,8 Hz,2H), 7.10 (d,8 Hz,2H), 7.25 (m,3H), 7.30–7.65 (m,9H), 7.73 (dd;2,7 Hz;1H). FAB-MS: calculated for C$_{36}$H$_{37}$N$_7$O$_2$ 599; found 601 (100%).

EXAMPLE 110

3-(3(R)-Hydroxybutyl)amino-3-methyl-N-[2,3,4,5-tetrahydro-2-oxo-1-[[2'-(1H-tetrazol-5-yl)[[1,1'-biphenyl]-4-yl]methyl]-1H-1-benzazepin-3(R)-yl]-butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, hydrochloride, dihydrate (Example 113) and 3(R)-hydroxybutanol-O-tetrahydropyranyl ether (prepared from methyl 3(R)-hydroxybutyrate by the method of Sato: Heterocycles, 24, 2173 (1986)) by the procedure described in Example 71.

$^1$H NMR (200 MHz,CD$_3$OD): 1.12 (d,6 Hz,3H), 1.33 (s,3H), 1.36 (s,3H), 1.70 (m,3H), 2.00–2.60 (m,3H), 3.09 (m,2H), 3.82 (m,1H), 4.34 (dd;7,11 Hz;1H), 4.85 (d,15 Hz,1H), 5.18 (d,15 Hz,1H), 7.00 (d,8 Hz,2H), 7.1–7.3 (m,6H), 7.5–7.7 (m,4H). FAB-MS: calculated for C$_{33}$H$_{39}$N$_7$O$_3$ 581; found 583 (100%).

EXAMPLE 120

3-(3(S)-Hydroxybutyl)amino-3-methyl-N-[2,3,4,5-tetrahydro-2-oxo-1-[[2'-(1H-tetrazol-5-yl)[[1,1'-biphenyl]-4-yl]methyl]-1H-1-benzazepin-3(R)-yl]-butanamide, trifluoroacetate The title compound was prepared from 3-amino-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, hydrochloride, dihydrate (Example 113) and 3(S)-hydroxybutanol-O-tetrahydropyranyl ether (prepared from methyl 3(S)-hydroxybutyrate by the method of Sato: Heterocycles, 24, 2173 (1986)) by the procedure described in Example 71.

$^1$H NMR (200 MHz,CD$_3$OD): 1.15 (d,6 Hz,3H), 1.33 (s,3H), 1.36 (s,3H), 1.70 (m,3H), 1.9–2.6 (m,5H), 3.10 (m,2H), 3.84 (m,1H), 4.33 (dd;8,12 Hz;1H), 4.85 (d,15 Hz,1H), 5.19 (d,15 Hz,1H), 7.00 (d,8 Hz,2H), 7.10–7.35 (m,6H), 7.45–7.70 (m,4H). FAB-MS: calculated for C$_{33}$H$_{39}$N$_7$O$_3$ 581; found 583 (100%).

EXAMPLE 121

3-Amino-3-methyl-N-[2,3,4,5-tetrahydro-2-oxo-1-[[3-bromo-2'-(1H-tetrazol-5-yl)[1,1'-biphenyl]-4-yl]methyl]-1H-1-benzazepin-3(R)-yl]-butanamide, trifluoroacetate Step A: 2-Bromo-4-iodotoluene A well stirred solution of 18.6 g (0.10 mol) of 3-bromo-p-toluidine in 80 mL of 6N HCl at 0° C. was treated with a solution of 7.35 g (0.11 mol) of sodium nitrite in 15 mL of water at a rate that maintained the temperature <10° C. The mixture was stirred for 45 minutes then cautiously treated with 33.2 g (0.20 mol) of potassium iodide at 0° C. The mixture was treated with 300 mL of ether and washed (3×) with saturated aqueous sodium bisulfite. The organic layer was separated, dried over magnesium sulfate, filtered and concentrated under vacuum. The residue was redissolved in 50 mL of hexane, filtered through 30 g of silica and concentrated under vacuum to afford 15.6 g (0.053 mol, 53%) of the product which was determined to be 65% pure by $^1$H NMR. $^1$H NMR (200 MHz,CDCl$_3$): 2.33 (s,3H), 6.97 (d,8 Hz,1H), 7.51 (dd;2,8 Hz;1H), 7.86 (d,2 Hz,1H).

Step B: 2'-[(N-Triphenylmethyl)tetrazol-5-yl]-2-bromo-1-methyl-1,1'-biphenyl

A solution of 6.0 g (15 mmol) of 5-phenyl-2-trityltetrazole (Example 1, Step H) in 60 mL of tetrahydrofuran at −15° C. to −10° C. was treated with 6.5 mL of 2.5M n-butyllithium in hexane (16.3 mmol,1.05 eq) and the resulting mixture stirred for 1.5 hours at −5° C. to −10° C. then treated with 9.2 mL of 1.0M solution of zinc chloride in ether (9.2 mmol,0.6 eq). The mixture was warmed to room temperature and treated with: 0.3 g of bis(trphenylphosphine) nickel dichloride, 0.3 mL of a 3M solution of methylmagnesium chloride in tetrahydrofuran and finally, a solution of 8.5 g (29 mmol) of 2-bromo-4-iodotoluene in 12 mL of tetrahydrofuran. The mixture was stirred overnight at room temperature then treated with an additional 1.5 g of 2-bromo-4-iodotoluene and heated briefly to 40° C. The mixture was cooled and partitioned between ether and saturated citric acid. The organic layer was separated, washed with brine (2×), dried over magnesium sulfate, filtered and concentrated under vacuum. The residue was dissolved in methylene chloride, passed through a short plug of silica, and concentrated under vacuum. The gummy residue was dissolved in ether and treated with an equal volume of hexane to precipitate the product. By this method, 4.3 g (7.7 mmol, 51%) of product was obtained as a white powder. $^1$H NMR (400 MHz,CDCl$_3$): 2.29 (s,3H), 6.83 (t,8 Hz,2H), 6.89 (d,8 Hz,6H), 7.2–7.4 (m,11H), 7.45 (m,2H), 7.92 (dd;2,8 Hz;1H).

Step C
2'-[(N-Triphenylmethyl)tetrazol-5-yl]-2-bromo-1-bromomethyl-1,1'-biphenyl Prepared from the intermediate obtained in Step B by the procedure described in Example 69, Step C. $^1$H NMR (200 MHz,CDCl$_3$): 4.48 (s,2H), 6.85–7.05 (m,8H), 7.20–7.55 (m,13H), 8.03 (m,1H). $^1$H NMR indicates the product thus obtained contains approximately 20% starting material.

Step D:
3-t-butoxycarbonylamino-3-methyl-N-[2,3,4,5-tetrahydro-2-oxo-1-[[3-bromo-2'-(N-triphenylmethyl)tetrazol-5-yl][1,1'-biphenyl]-4-yl]methyl-1H-1-benzazepin-3(R)-yl]-butanamide Prepared from 3-t-butoxycarbonylamino-3-methyl-N-[2,3,4,5-tetrahydro-2-oxo-1H-1-benzazepin-3(R)-yl]-butanamide (Example 57, Step A) and 2'-[(N-triphenylmethyl)tetrazol-5-yl]-2-bromo-1-bromomethyl-1,1'-biphenyl by the procedure described in Example 1, Step K. $^1$H NMR (200 MHz,CDCl$_3$): 1.34 (s,3H), 1.35 (s,3H), 1.40 (s,9H), 1.90 (m,1H), 2.43 (d,14 Hz,1H), 2.55 (d,14 Hz,1H), 2.5–2.8 (m,3H), 4.57 (m,3H), 4.97 (d,15 Hz,1H), 5.14 (d,15 Hz,1H), 5.31 (br s,1H), 6.66 (d,7 Hz,1H), 6.95–7.15 (m,13H), 7.20–7.40 (m,10H), 7.46 (m,2H), 7.93 (m,1H).

Step E:
3-Amino-3-methyl-N-[2,3,4,5-tetrahydro-2-oxo-1-[[3-bromo-2'-(1H-tetrazol-5-yl)[1,1'-biphenyl]-4-yl]methyl]-1H-1-benzazepin-3(R)-yl]-butanamide, trifluoroacetate The title compound was prepared from the intermediate obtained in Step D by the procedure described in Example 31, Step H.

$^1$H NMR (200 MHz, CD$_3$OD): 1.32 (s,3H), 1.37 (s,3H), 2.0–2.9 (m,6H), 4.40 (dd;8,12 Hz;1H), 4.90 (d,15 Hz,1H), 5.26 (d,15 Hz,1H), 6.96 (dd;2,8 Hz,1H), 7.10–7.45 (m,6H), 7.45–7.70 (m,4H). FAB-MS: calculated for C$_{29}$H$_{30}$BrN$_7$O$_2$ 587,589; found 589 (98%); 591 (100%).

EXAMPLE 122
3-[(2(R)-Hydroxypropyl)amino]-3-methyl-N-[2,3,4,5-tetrahydro-2-oxo-1-[[3-bromo-2'-(1H-tetrazol-5-yl)[1,1'-biphenyl]-4-yl]methyl]-1H-1-benzazepin-3(R)-yl]-butanamide, hydrochloride

Step A:
3-[2(R)-Benzyloxypropyl]amino-3-methyl-N-[2,3,4,5-tetrahydro-2-oxo-1H-1-benzazepin-3(R)-yl]-butanamide Prepared from 3-amino-3-methyl-N-[2,3,4,5-tetrahydro-2-oxo-1H-1-benzazepin-3(R)-yl]-butanamide, trifluoroacetate (Example 107, Step C) and (R)-2-benzyloxypropanol (prepared from ethyl-D-lactate according to the procedure of Hanessian and Kloss, Tetrahedron Lett. 1985, 26, 1261–1264.) by the procedure described in Example 86, Step A. $^1$H NMR (200 MHz,CD$_3$OD): 1.31 (d,6 Hz,3H), 1.4 (s,3H), 1.43 (s,3H), 2.17 (m,1H), 2.30 (m,1H), 2.6–3.1 (m,5H), 3.22 (dd;3,12 Hz;1H), 3.86 (m,1H), 4.48 (dd;7,12 Hz;1H), 4.50 (d,12 Hz,1H), 4.70 (d,12 Hz,1H), 7.11 (d,8 Hz,1H), 7.15–7.45 (m,8H). FAB-MS: calculated for C$_{25}$H$_{33}$N$_3$O$_3$ 423; found 424 (M+H, 100%).

Step B:
3-[2(R)-Hydroxypropyl]amino-3-methyl-N-[2,3,4,5-tetrahydro-2-oxo-1H-1-benzazepin-3(R)-yl]-butanamide A solution of 750 mg (1.40 mmol) of the intermediate obtained in Step A in methanol containing 2 drops of trifluoroacetic acid was hydrogenated at room temperature and 40 psi in the presence of 300 mg of 30% palladium on carbon for 3 days. The catalyst was removed by filtration through Celite and the filtrate concentrated under vacuum to give 600 mg (1.34 mmol, 96%) of product. $^1$H NMR (200 MHz, CD$_3$OD): 1.22 (d,7 Hz,3H), 1.37 (s,3H), 1.39 (s,3H), 2.14 (m,1H), 2.3–3.0 (m,6H), 3.09 (dd;2,11 Hz;1H), 3.93 (m,1H), 4.38 (dd;8,12 Hz;1H), 7.05 (d,8 Hz,1H), 7.10–7.35 (m,3H).

Step C:
3-[2(R)-Triethylsiloxypropyl]amino-3-methyl-N-[2,3,4,5-tetrahydro-2-oxo-1H-1-benzazepin-3(R)-yl]-butanamide To a stirred solution of 660 mg (1.48 mmol) of the intermediate obtained in Step B in 3 mL of methylene chloride at room temperature was added 1.1 mL of N,N-diisopropylethylamine (0.81 g, 4.2 eq.) followed by 0.71 mL of triethylsilyl trifluoromethanesulfonate (0.83 g, 2.1 eq.). The resulting mixture was stirred at room temperature for 2 hours then partitioned between ethyl acetate and saturated aqueous sodium chloride (buffered to pH 9 with 2 drops of ammonium hydroxide). The organic layer was separated, washed with buffered brine, dried over magnesium sulfate, filtered and solvents evaporated under vacuum. The residue was purified by preparative high pressure liquid chromatography on silica, eluting with ethyl acetate/0.1% ammonium hydroxide in methanol (85:15), to afford 480 mg (1.07 mmol, 72%) of product. $^1$H NMR (200 MHz,CD$_3$OD): 0.63 (q,8 Hz,6H), 0.97 (t,8 Hz,9H), 1.14 (s,6H), 1.18 (d,6 Hz,3H), 2.05 (m,1H), 2.28 (d,2Hz,2H), 2.35–3.00 (m,5H), 4.01 (m,1H), 4.44 (dd;8,12 Hz;1H), 7.05 (d,8 Hz,1H), 7.10–7.35 (m,3H). FAB-MS: calculated for C$_{24}$H$_{41}$N$_3$O$_3$Si 447; found 448 (M+H, 100%).

Step D:
3-[(2(R)-Hydroxypropyl)amino]-3-methyl-N-[2,3,4,5-tetrahydro-2-oxo-1H-[[3-bromo-2'-(1H-tetrazol-5-yl)[1,1'-biphenyl]-4-yl]methyl]-1H-1-benzazepin-3(R)-yl]butanamide, hydrochloride To a stirred solution of 94 mg (0.21 mmol) of the intermediate obtained in Step C in 0.5 mL of dimethylformamide was added 6 mg of 60% sodium hydride oil dispersion (3.6 mg NaH, 1.2 eq.). The resulting solution was stirred for 15 minutes then treated with a solution of 201 mg (0.31 mmol, 1.5 eq.) of 2'-[(N-Triphenylmethyl)tetrazol-5-yl]-2-bromo-1-bromomethyl-1,1'-biphenyl (Example 121, Step C) in 0.5 mL of dimethylformamide. The resulting solution was stirred at room temperature for 2 hours then added to 50 mL of ethyl acetate and washed with brine (2×). The organic layer was separated, dried over sodium sulfate, filtered an solvents removed under vacuum.

The residue was dissolved in 2 mL of methanol and treated with 10 mL of 9N HCl and 10 mL of hexane. This mixture was stirred vigorously for 2 hours then the layers allowed to separate. The aqueous layer was removed by pipet, washed once with hexane, filtered and evaporated under vacuum. The residue was triturated with methanol to give a white solid that was removed by filtration. Thus, 101 mg (0.15 mmol, 71%) of the title compound was obtained as a white solid. $^1$H NMR (300 MHz,CD$_3$OD): 1.23 (d,6 Hz,3H), 1.40 (s,3H), 1.41 (s,3H), 2.24 (m,1H), 2.40 (m,1H), 2.61 (d,15 Hz,1H), 2.69 (d,15 Hz,1H), 2.7–3.0 (m,5H), 3.13 (dd;3,11 Hz;1H), 3.96 (m,1H), 4.47 (dd;7,12 Hz;1H), 4.9 (d,15 Hz,1H), 5.38 (d,15 Hz,1H), 7.17 (d,8 Hz,2H), 7.25–7.40 (m,3H), 7.45 (d,8 Hz,1H), 7.48 (d,2 Hz,1H), 7.64 (m,2H), 7.74 (m,2H). FAB-MS: calculated for C$_{32}$H$_{36}$BrN$_7$O$_3$ 645,647; found 646(50%), 648(55%).

EXAMPLE 123

3'-Bromo-4'-[[3(R)-[(3-amino-3-methyl-1-oxobutyl)amino]-2,3,4,5-tetrahydro-2-oxo-1H-1-benzazepin-1yl]methyl][1,1'-biphenyl]-2-carboxamide, trifluoroacetate

Step A: 3'-Bromo-4'-methyl-1,1'-biphenyl-2-nitrile

A solution of 5.2 g (27 mmol) of 4'-methyl-1,1'-biphenyl-2-nitrile (Example 69, Step B) in 60 mL of methylene chloride at 0° C. was treated with 6.7 g of silver trifluoroacetate (30 mmol). When all the silver trifluoroacetate was dissolved, 1.6 mL of bromine was added dropwise (4.95 g, 31 mmol) with vigorous stirring. After two hours, the reaction mixture was filtered and the solid washed with methylene chloride. The combined organic layers were washed once with dilute (<1N) aqueous sodium hydroxide and once with brine. The organic layer was removed, dried over magnesium sulfate, filtered and concentrated under vacuum. The residue was purified by preparative high pressure liquid chromatography on silica, eluting with 10% ether/hexane to give 3 g (41%) of product. $^1$H NMR (200 MHz, CDCl$_3$): 2.46 (s, 3H), 7.2–7.8 (m,7H).

Step B:
3'-Bromo-4'-bromomethyl-1,1'-biphenyl-2-nitrile

Prepared from the intermediate obtained in Step A by the procedure described in Example 69, Step C. NMR analysis shows product to contain small amounts of starting material and dibromomethyl compound. $^1$H NMR (200 MHz, CDCl$_3$): 4.64 (s,2H), 7.4–7.8 (m,7H). FAB-MS: calculated for C$_{14}$H$_9$Br$_2$N 351; found 352 (100%); 271 (100%)

Step C:
3-[[1-[[3-Bromo-2'-cyano-[1,1'-biphenyl]-4-yl]methyl]-2,3,4,5-tetrahydro-2-oxo-1H-benzazepin-3(R)yl]amino]-1,1-dimethyl-3-oxo-propylcarbamic acid, 1,1-dimethylethyl ester Prepared from 3-t-butoxycarbonylamino-3-methyl-N-[2,3,4,5-tetrahydro-2-oxo-1H-1-benzazepin-3(R) -yl]-butanamide (Example 57, Step A) and 3'-bromo-4'-bromomethyl-1,1'-biphenyl-2-nitrile by the procedure described in Example 69, Step D. $^1$H NMR (200 MHz, CDCl$_3$): 1.33 (s,3H), 1.34 (s,3H), 1.40 (s,9H), 1.91 (m,1H), 2.43 (d,14Hz,1H), 2.55 (d,14Hz,1H), 2.55–2.90 (m,3H), 4.62 (m,1H), 4.95 (d,16Hz,1H), 5.28 (s,1H), 5.34 (d,16Hz,1H), 6.63 (d,7Hz,1H), 7.10–7.25 (m,4H), 7.45 (m,4H), 7.64 (m,1H), 7.75 (m,2H). FAB-MS (Li spike): calculated for C$_{34}$H$_{37}$BrN$_4$O$_4$ 644, 646; found 651 (13%); 653 (15%).

Step D:
3'-Bromo-4'-[[3(R)-[(3-t-butoxycarbonylamino-3-methyl-1-oxobutyl)amino]-2,3,4,5-tetrahydro-2-oxo-1H-1-benzazepin-1-yl]methyl][1,1'-biphenyl]-2-carboxamide The title compound was prepared from the intermediate obtained in Step C by the procedure described in Example 69, Step E. $^1$H NMR (200 MHz, CDCl$_3$): 1.34 (br, s,6H), 1.40 (s,9H), 1.93 (m,1H), 2.43 (d,13Hz,1H), 2.56 (d,13Hz,1H), 2.55–2.90 (m,3H), 4.62 (m,1H), 4.96 (d,16Hz,1H), 5.30 (d,16Hz,1H), 5.34 (br s,1H), 5.65 (br s,1H), 6.69 (d,7Hz,1H), 7.05–7.55 (m,9H), 7.63 (s,1H), 7.71 (dd;2,8Hz;1H). FAB-MS: calculated for C$_{34}$H$_{39}$BrN$_4$O$_5$ 662, 664; found 663 (2%); 665 (3%).

Step E:
3+-Bromo-4'-[[3(R)-[(3-amino-3-methyl-1-oxobutyl)amino]-2,3,4,5-tetrahydro-2-oxo-1H-1-benzazepin-1-yl]methyl][1,1'-biphenyl]-2-carboxamide, trifluoroacetate The title compound was prepared from the intermediate obtained in Step D by the procedure described in Example 69, Step F. $^1$H NMR (200 MHz, CD$_3$OD): 1.35 (s,3H), 1.37 (s,3H), 2.10–3.00 (m,6H), 4.48 (dd;8,12Hz;1H), 4.93 (d,16Hz,1H), 5.33 (d,16Hz,1H), 7.15–7.60 (m,10H), 7.67 (d,2Hz,1H). FAB-MS: calculated for C$_{29}$H$_{31}$BrN$_4$O$_3$ 562, 564; found 563 (38%); 565 (37%).

EXAMPLE 124

3'-Bromo-4'-[[3(R)-[[3-[(2(S),3-dihydroxypropyl)amino]-3-methyl-1-oxobutyl]amino]-2,3,4,5-tetrahydro-2-oxo-1H-1-benzazepin-1-yl]methyl][1,1'-biphenyl]-2-carboxamide, trifluoroacetate The title compound was prepared from 3'-bromo-4'-[[3(R)-[(3-amino-3-methyl-1-oxo-butyl)amino]2,3,4,5-tetrahydro-2-oxo -1H-1-benzazepin-1-yl]m ethyl][1,1'-biphenyl]-2-carboxamide, trifluoroacetate (Example 123) and D-glyceraldehyde acetonide by the procedure described in Example 71. $^1$H NMR (200 MHz, CD$_3$OD): 1.36 (s,6H), 2.1–3.0 (m,6H), 3.17 (dd;4,12Hz;1H), 3.50 (m,2H), 3.83 (m,1H), 4.46 (dd;8,12Hz;1H), 4.82 (d,16Hz,1H), 5.40 (d,16Hz,1H), 7.10–7.60 (m,10H), 7.70 (s,1H). FAB-MS: calculated for C$_{32}$H$_{37}$BrN$_4$O$_5$ 636, 638; found 637 (35%); 639 (35%).

EXAMPLE 125

3-Amino-3-methyl-N-[2,3,4,5-tetrahydro-2-oxo-1-[[2'-carbomethoxy-[1,1'-biphenyl]-4-yl]methyl]-1H-1-benzazepin-3-yl]-butanamide, trifluoroacetate

Step A:
3-Benzyloxycarbonylamino-3-methyl-N-[2,3,4,5-tetrahydro-2-oxo-1-[[2'-carbomethoxy-[1,1'-biphenyl]-4-yl]methyl]-1H-1-benzazepin-3-yl]-butanamide Prepared from 3-benzyloxycarbonylamino-3-methyl-N-[2,3,4,5-tetrahydro-2-oxo-1H-1-benzazepin-3-yl ]- butanamide (Example 51, Step A) and methyl 4'-bromomethyl-1,1'-biphenyl-2-carboxylate (prepared by the method of D. J. Carinie et al, EPO publication 324,377) by the procedure described in Example 1, Step K. $^1$H NMR (300 MHz, CDCl$_3$): 1.37 (s,3H), 1.39 (s,3H), 1.75 (m,1H), 2.3–2.6 (m,5H), 3.52 (s,3H), 4.50 (m,1H), 4.80 (d,14Hz,1H), 5.06 (s,2H), 5.34 (d,14Hz,1H), 5.65 (s,1H), 6.72 (d,7Hz,1H), 7.1–7.4 (m,15H), 7.48 (dt;2,8Hz;1H), 7.78 (dd;2,8Hz;1H). FAB-MS: calculated for C$_{38}$H$_{39}$N$_3$O$_6$ 633; found 634 (M+H,60%).

Step B:
3-Amino-3-methyl-N-[2,3,4,5-tetrahydro-2-oxo-1-[[2'-carbomethoxy-[1,1'-biphenyl]-4-yl]methyl]-1H-1-benzazepin-3-yl]-butanamide, trifluoroacetate The title compound was prepared from the intermediate obtained in Step A by the procedure described in Example 1, Step L. $^1$H NMR (300 MHz, CD$_3$OD): 1.40 (s,3H), 1.44 (s,3H), 2.17 (m,1H), 2.38 (m,1H), 2.5–2.7 (m,4H), 3.56 (s,3H), 4.46 (dd;8,12Hz;1H), 4.98 (d,15Hz,1H), 5.37 (d,15Hz,1H), 7.22 (d,8Hz,2H), 7.25–7.50 (m,8H), 7.59 (dt;2,8Hz;1H), 7.78 (dd;2,8Hz;1H). FAB-MS: calculated for C$_{30}$H$_{33}$N$_3$O$_4$ 499; found 500 (M+H,100%).

EXAMPLE 126

3-Amino-3-methyl-N-[2,3,4,5-tetrahydro-2-oxo-1-[[2'-cyano-[1,1'-biphenyl]-4-yl]methyl]-1H-benzazepin-3-yl]butanamide, trifluoroacetate Step A:
3-Benzyloxycarbonylamino-3-methyl-N-[2,3,4,5-tetrahydro-2-oxo-1-[[2'-cyano-[1,1'-biphenyl]-4-yl]methyl]-1H-1-benzazepin-3-yl]-butanamide Prepared from 3-benzyloxycarbonylamino-3-methyl-N-[2,3,4,5-tetrahydro-2-oxo-1H-1-benzazepin-3-yl ]-butanamide (Example 51, Step A) and 4'-bromomethyl-1,1'-biphenyl-2-nitrile (Example 69, Step C) by the procedure described in Example 1, Step K. FAB-MS: calculated for C$_{37}$H$_{36}$N$_4$O$_4$ 600; found; 601 (M+H,100%).

Step B:
3-Amino-3-methyl-N-[2,3,4,5-tetrahydro-2-oxo-1-[[2'-cyano-[1,1'-biphenyl]-4-yl]methyl]-1H-1-benzazepin-3-yl]-butanamide, trifluoroacetate The title compound was prepared from the intermediate obtained in Step A by the procedure described in Example 1, Step L. $^1$H NMR (300 MHz,CD$_3$OD): 1.40 (s,3H), 1.43 (s,3H), 2.18 (m,1H), 2.38 (m,1H), 2.5–2.7 (m,4H), 4.47 (dd;8,12Hz;1H), 5.11 (d,15Hz,1H), 5.28 (d,15Hz,1H), 7.30 (m,2H), 7.35–7.65 (m,8H), 7.76 (dt;2,8Hz;1H), 7.86 (dd;2,8Hz;1H). FAB-MS: calculated for C$_{29}$H$_{30}$N$_4$O$_2$ 466; found 467 (M+H,100%).

EXAMPLE 127

3-Amino-3-methyl-N-[2,3,4,5-tetrahydro-2-oxo-1-[[2'-trifluoromethyl-[1,1'-biphenyl ]-4-yl]methyl]-1H-1-benzazepin-3-yl]-butanamide, trifluoroacetate Step A: 2-Trifluoromethyl-4'-methyl-1,1'-biphenyl A solution of 388 mg (1.52 mmol, 1.4 eq.) of 4-methylphenyltrimethylstannane (Example 69, Step A) in 5 mL of toluene under a nitrogen atmosphere was treated with 238 mg of 2-bromobenzotrifluoride (1.06 mmol) and 64 mg of tetrakis(triphenylphosphine) palladium(O) and the resulting solution heated at reflux for 14 hours. The mixture was cooled, filtered and concentrated under vacuum to give an amber oil that was chromatographed on silica, eluting with hexane, to give the product. $^1$H NMR (300 MHz, CDCl$_3$): 2.41 (s,3), 7.2–7.8 (m,8H). EI-MS: calculated for C$_{14}$H$_{11}$F$_3$ 236; found 236 (M+,100%).

Step B:
4'-Bromomethyl-2-trifluoromethyl-1,1'-biphenyl

Prepared from 2-trifluoromethyl-4'-methyl-1,1'-biphenyl by the procedure described in Example 69, Step C. EI-MS: calculated for C$_{14}$H$_{10}$BrF$_3$ 314,316; found 314 (5%),316 (5%).

Step C:
3-Benzyloxycarbonylamino-3-methyl-N-[2,3,4,5-tetrahydro-2-oxo-1-[[2'-trifluoromethyl [1,1'-biphenyl]-4-yl]methyl]-1H-1-benzazepin-3-yl]-butanamide Prepared from 3-benzyloxycarbonylamino-3-methyl-N-[2,3,4,5-tetrahydro-2-oxo-1H-1-benzazepin-3-yl ]-butanamide (Example 51, Step A) and 4'-bromomethyl-2-trifluoromethyl-1,1'-biphenyl by the procedure described in Example 1, Step K. $^1$H NMR (300 MHz,CDCl$_3$): 1.37 (s,3H), 1.39 (s,3H), 1.73 (m,1H), 2.2–2.6 (m,5H), 4.50 (m,1H), 4.82 (d,15Hz,1H), 5.06 (s,2H), 5.29 (d,15Hz,1H), 5.65 (s,1H), 6.70 (d,7Hz,1H), 7.1–7.4 (m,14H), 7.44 (t,8Hz,1H), 7.52 (t,8Hz,1H), 7.71 (d,8Hz,1H). FAB-MS: calculated for C$_{37}$H$_{36}$F$_3$N$_3$O$_4$ 643; found 644 (M+H,55%).

Step D:
3-Amino-3-methyl-N-[2,3,4,5-tetrahydro-2-oxo-1-[[2'-trifluoromethyl-[1,1'-biphenyl]-4-yl]methyl]-1H-1-benzazepin-3-yl]-butanamide, trifluoroacetate The intermediate obtained in Step C (92 mg, 0.14 mmol) was treated with 1.62 mL of 30% hydrogen bromide in acetic acid at room temperature for 2 hours. The mixture was concentrated under vacuum to give a dark yellow residue. Purification by preparative reverse phase high pressure liquid chromatography on C18, eluting with methanol/0.1% aqueous trifluoroacetic acid (linear gradient: 75% methanol increased to 85% over 10 minutes) afforded 71 mg (0.11 mmol, 81%) of the title compound as a colorless glass.

$^1$H NMR (300MHz,CD$_3$OD): 1.39 (s,3H), 1.44 (s,3H), 2.16 (m,1H), 2.38 (m,1H), 2.5–2.7 (m,4H), 4.47 (dd;8,12Hz;1H), 5.04 (d,15Hz,1H), 5.34 (d,15Hz,1H), 7.20–7.45 (m,9H), 7.56 (t,8Hz,1H), 7.66 (t,8Hz,1H), 7.79 (d,8Hz,1H), FAB-MS: calculated for C$_{29}$H$_{31}$F$_3$N$_3$O$_2$ 509; found (M+H,100%).

EXAMPLE 128

3-Amino-3-methyl-N-[7-methylthio-2,3,4,5-tetrahydro-2-oxo-1-[[2'-(1H-tetrazol-5-yl)[1,1'-biphenyl]-4-yl]methyl]-1H-1-benzazepin-3-yl]-butanamide, hydrochloride

Step A: 6-Methylthio-1-tetralone oxime

Prepared from 6-methylthio-1-tetralone (prepared by the method described in EPO 0 325,963 Al) by the procedure described in Example 113, Step A. $^1$H NMR (200MHz,CDCl$_3$): 1.89 (m,2H), 2.52 (s,3H), 2.78 (m,4H), 7.02 (d,2Hz,1H), 7.08 (dd;2,8Hz;1H), 7.81 (d,8Hz,1H).

Step B: 7-Methylthio-2,3,4,5-tetrahydro-1H-1-benzazepin-2-one

Prepared from 6-methylthio-1-tetralone oxime by the procedure described in Example 113, Step B. $^1$H NMR (200MHz,CDCl$_3$): 2.23 (m,2H), 2.36 (m,2H), 2.49 (s,3H), 2.78 (t,8Hz,2H), 6.94 (d,8Hz,1H), 7.14 (m,2H), 7.75 (br s,1H).

Step C: 3-Iodo-7-methylthio-2,3,4,5-tetrahydro-1H-1-benzazepin-2-one

Prepared from 7-methylthio-2,3,4,5-tetrahydro-1H-1-benzazepin-2-one by the procedure described in Example 31, Step B. $^1$H NMR (200MHz,CDCl$_3$): 2.51 (s,3H), 2.6–2.9 (m,3H), 2.50 (s,3H), 2.97 (m,1H), 4.68 (t,9Hz,1H), 6.95 (d,8Hz,1H), 7.15 (m,2H), 7.5 (br s,1H).

Step D: 3-Amino-7-methylthio-2,3,4,5-tetrahydro-1H-1-benzazepin-2-one

A mixture of 0.5 g of 3-iodo-7-methylthio-2,3,4,5-tetrahydro-1H-1-benzazepin-2-one and 15 g of ammonia in 20 mL of chloroform was shaken in a bomb at 100° C. for 3 hours. The bomb was cooled, vented and the contents transferred to a separatory funnel. The mixture was washed with water, dried over magnesium sulfate, filtered and solvents removed under vacuum to give the product. $^1$H NMR (200 MHz,CDCl$_3$): 1.90 (m,1H), 2.3–2.7 (m,2H), 2.45 (s,3H), 2.85 (m,1H), 3.39 (dd;8,11Hz;1H), 6.89 (d,8Hz,1H), 7.10 (m,2H), 8.3 (br s,1H).

Step E: 3-t-Butoxycarbonylamino-3-methyl-N-[7-methylthio-2,3,4,5-tetrahydro-2-oxo-1H-1-benzazepin-3-yl]-butanamide Prepared from the intermediate obtained in Step D and 3-t-butoxycarbonylamino-3-methyl-butanoic acid (Example 31, Step E) by the procedure described in Example 1, Step F. $^1$H NMR (200MHz,CDCl$_3$): 1.33 (s,6H), 1.40 (s,9H), 1.91 (m,1H), 2.4–3.0 (m,5H), 2.48 (s,3H), 4.50 (m,1H), 5.22 (br, s1H), 6.68 (d,7Hz,1H), 6.90 (d,8Hz,1H), 7.11 (m,2H), 7.66 (br, s,1H).

Step F: 3-t-Butoxycarbonylamino-3-methyl-N-[7-methylthio-2,3,4,5-tetrahydro-2-oxo-1-[[2°-(N-triphenylmethyl)-tetrazol-5-yl][1,1'-biphenyl]-4-yl]methyl-1H-1-benzazepin-3-yl]-butanamide Prepared from the intermediate obtained in Step E by the procedure described in Example 1, Step K. $^1$H NMR (200MHz,CDCl$_3$): 1.37 (s,6H), 1.43 (s,9H), 1.78 (m,1H), 2.2–2.7 (m,5H), 2.44 (s,3H), 4.49 (m,1H), 4.69 (d,15Hz,1H), 5.12 (d,15Hz,1H), 5.34 (br s,1H), 6.69 (d,7Hz,1H), 6.9–7.1 (m,12H), 7.2–7.5 (m,13H), 7.87 (m,1H).

Step G: 3-Amino-3-methyl-N-[7-methylthio-2,3,4,5-tetrahydro-2-oxo-1-[[2'-(1H -tetrazol-5-yl)[1,1'-biphenyl]-4-yl]methyl]-1H-1-benzazepin-3-yl]-butanamide, hydrochloride The title compound was prepared from the intermediate obtained in Step F by the procedure described in Example 34, Step K. $^1$H NMR (200MHz,DMSO-d$_6$): 1.24 (s,3H), 1.25 (s,3H), 2.0–2.6 (m,6H), 2.47 (s,3H), 4.25 (m,1H), 4.78 (d,15Hz,1H), 5.15 (d,15Hz,1H), 6.97 (d,8Hz,2H), 7.05–7.30 (m,5H), 7.45–7.70 (m,4H), 7.92 (br s,2H), 8.68 (d,7Hz,1H).

EXAMPLE 129

3-Amino-3-methyl-N-[7-methylsulfinyl-2,3,4,5-tetrahydro-2-oxo-1-[[2'-(1H-tetrazol -5-yl)[1,1'-biphenyl]-4-yl]methyl]-1H-1-benzazepin-3-yl]-butanamide, hydrochloride

Step A: 3-t-Butoxycarbonylamino-3-methyl-N-[7-methylsulfinyl-2,3,4,5-tetrahydro-2-oxo-1-[[2'-(N-triphenylmethyl)-tetrazol-5-yl][1,1'-biphenyl]-4-yl]methyl-1H-1-benzazepin-3-yl]-butanamide Prepared as a mixture of two racemic diastereomers from the intermediate obtained in Example 128, Step F by the procedure described in Example 48, Step A. $^1$H NMR (200MHz,CDCl$_3$): 1.37 (s,6H), 1.44 (s,9H), 1.90 (m,1H), 2.4–2.9 (m,5H), 2.78 (s,3H), 4.54 (m,1H), 4.76 (two doublets,15Hz,total of 1H), 5.18 (two doublets,15Hz,total of 1H), 5.32 (br s,1H), 6.9–7.1 (m,9H), 7.2–7.6 (m,15H), 7.90 (m,1H), 7.98 (d,8Hz,1H), 8.08 (br s,1H).

Step B: 3-Amino-3-methyl-N-[7-methylsulfinyl-2,3,4,5-tetrahydro-2-oxo-1-[[2'-(1H-tetrazol-5-yl)[1,1'-biphenyl]-4-yl]methyl]-1H-1-benzazepin-3-yl]-butanamide, hydrochloride The title compound was prepared as a mixture of two racemic diastereomers from the intermediate obtained in Step A by the procedure described in Example 34, Step K.

$^1$H NMR (200MHz,DMSO-d$_6$): 1.24 (s,3H), 1.26 (s,3H), 2.0–2.8 (m,6H), 2.78 (s,3H), 4.25 (m,1H), 4.94 (d,15Hz,1H), 5.19 (d,15Hz,1H), 7.01 (d,8Hz,2H), 7.16 (d,8Hz,2H), 7.5–7.7 (m,7H), 7.95 (br s,2H), 8.75 (d,7Hz,1H).

EXAMPLE 130

3-[(2(R)-Hydroxypropyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate

Step A:
3-Methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]but-2-eneamide To a suspension of 1.18 g (2.64 mmol) of 3(R)-amino-2,3,4,5-tetrahydro-1-[[2'-(1H-tetrazol-5-yl) [1,1'-biphenyl]-4-yl]methyl]-2H-1-benzazepin-2-one, hydrochloride (Example 4, Step C) in 30 mL of methylene chloride under nitrogen at −15° C. was added 0.923 mL (2.64 mmol) of triethylamine followed by 0.294 mL (2.64 mmol) of 3,3-dimethylacryloyl chloride. The reaction mixture was stirred at −15° C. for 2 hours then quenched by the addition of 1N hydrochloric acid. The mixture was diluted with 50 mL of methylene chloride and washed with 50 mL of 1N hydrochloric acid and brine. The organic layer was removed and concentrated to dryness under vacuum. The residue was redissolved in 30 mL of methanol and treated with 1.5 mL of 9N hydrochloric acid. After stirring for 30 minutes, the mixture was concentrated to dryness under vacuum to give 1.3 g (2.63 mmol, 99%) of the product as a white solid.

$^1$H NMR (400MHz,CD$_3$OD): 1.85 (s,3H), 2.06 (s,3H), 2.08 (m,1H), 2.29 (m,1H), 2.44 (m,1H), 2.55 (m,1H), 4.40 (dd;7,11Hz;1H), 4.85 (d,15Hz,1H), 5.26 (d,15Hz,1H), 5.77 (s,1H), 7.00 (d,8Hz,2H), 7.18 (d,8Hz,2H), 7.2–7.4 (m,4H), 7.54 (m,2H), 7.64 (m,2H).

Step B:
3-[(2(R)-Hydroxypropyl)amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]-butanamide, trifluoroacetate The intermediate obtained in Step A (18 mg, 0.037 mmol) was dissolved in 2 mL of (R)-(−)-1-amino-2-propanol and the resulting solution heated under nitrogen at 120° C. for 5 hours. The reaction mixture was cooled, concentrated under vacuum at 50° C. and the residue purified by medium pressure liquid chromatography on C8, eluting with methanol/0.1% aqueous trifluoroacetic acid (50:50), to give 14 mg (0.021 mmol,57%) of the title compound as a colorless glass. The material thus obtained was identical by 400 MHz NMR (CD$_3$OD), FAB-MS and reverse phase analytical high pressure liquid chromatography to the material obtained in Example 102.

EXAMPLE A

Utilizing the general procedures described in Example 1 to 130, the following compounds of Formula I can be prepared from the appropriately substituted starting materials and reagents.

| $R_1$ | $R^{3a}$ | $R^4$ | x | m |
|---|---|---|---|---|
| H | tetrazole (N–N / N–N–H) | OH / –CH$_2$CHCH$_3$ | 1 | 0 |
| H | tetrazole | OH (▼) / –CH$_2$CHCH$_3$ | 1 | 0 |
| H | tetrazole | –CH$_2$CH$_2$CHCH$_3$ / OH | 1 | 0 |
| H | tetrazole | H | 0 | 0 |
| H | tetrazole | OH / –CH$_2$CHCH$_3$ | 1 | 1 |
| H | tetrazole | OH (▼) / –CH$_2$CHCH$_3$ | 1 | 1 |
| H | tetrazole | –CH$_2$CH$_2$CHCH$_3$ / OH | 1 | 1 |
| H | tetrazole | OCH$_3$ / –CH$_2$CHCH$_3$ | 1 | 0 |
| 8-F | tetrazole | OH / –CH$_2$CHCH$_3$ | 1 | 0 |
| 8-CF$_3$ | tetrazole | OH / –CH$_2$CHCH$_3$ | 1 | 0 |

-continued

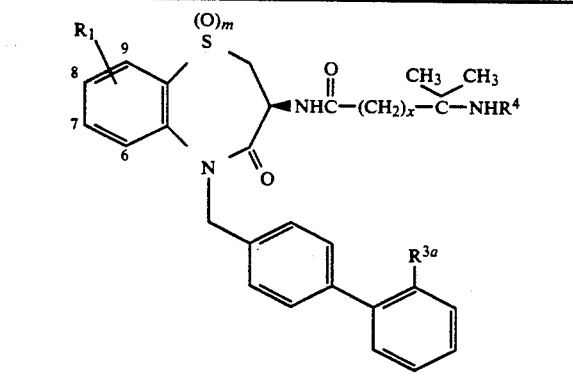

| R₁ | R³ᵃ | R⁴ | x | m |
|---|---|---|---|---|
| 9-F | 5-methyl-tetrazole (N-H) | —CH₂CHCH₃ (OH) | 1 | 0 |
| 8-OCH₃ | 5-methyl-tetrazole (N-H) | —CH₂CHCH₃ (OH) | 1 | 0 |
| 8-SCH₃ | 5-methyl-tetrazole (N-H) | —CH₂CHCH₃ (OH) | 1 | 0 |
| H | —CO₂NH₂ | H | 1 | 0 |
| H | —CO₂NH₂ | H | 1 | 1 |
| H | —CO₂NH₂ | —CH₂CHCH₃ (OH) | 1 | 0 |
| H | —CO₂NH₂ | —CH₂CHCH₂OH (OH) | 1 | 0 |
| H | —CO₂NHEt | H | 1 | 0 |
| H | —CO₂NHEt | —CH₂CHCH₃ (OH) | 1 | 0 |
| H | —CO₂NHEt | —CH₂CHCH₂OH (OH) | 1 | 0 |
| H | —CH₂CONH₂ | —CH₂CHCH₃ (OH) | 1 | 0 |
| H | —CH₂CONHEt | —CH₂CHCH₂OH (OH) | 1 | 0 |
| H | 2-hydroxyphenyl | H | 1 | 0 |

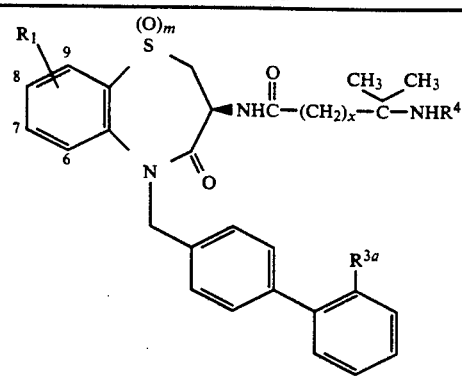

| R₁ | R³ᵃ | R⁴ | x | m |
|---|---|---|---|---|
| H | 2-hydroxy-methylphenyl | —CH₂CHCH₃ (OH) | 1 | 0 |
| H | 2-hydroxyphenoxy | H | 1 | 0 |
| H | 2-carboxamidophenoxy | H | 1 | 0 |
| H | 2-(2H-tetrazol-5-yl)phenoxy | H | 1 | 0 |
| H | 5-methyl-tetrazole (N-H) | —CH₂CHCHCH₂OH (OH, OH) | 1 | 0 |
| H | —CONH₂ | H | 0 | 0 |
| H | —CONHEt | H | 0 | 0 |
| H | —CH₂OH | H | 1 | 0 |
| H | —CH₂OH | —CH₂CHCH₃ (OH) | 1 | 0 |
| H | —CH₂OH | —CH₂CHCH₃ (OH) | 1 | 1 |
| H | —CH₂OH | —CH₂CHCH₂OH (OH) | 1 | 0 |
| H | —CH₂NH₂ | —CH₂CHCH₃ (OH) | 1 | 0 |
| H | —CH₂NHCOCH₃ | H | 1 | 0 |

5,310,737

151
-continued

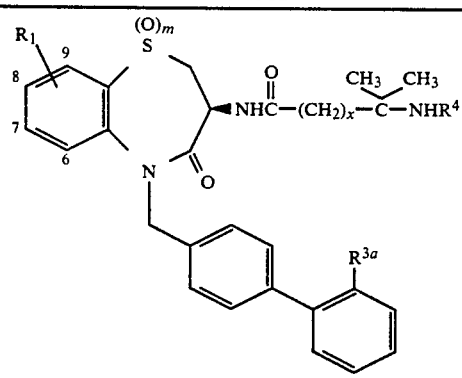

| R₁ | R³ᵃ | R⁴ | x | m |
|---|---|---|---|---|
| H | —CH₂NHCOPh | H | 1 | 0 |
| H | —CH₂NHCOCH₃ | —CH₂CHCH₃ with OH | 1 | 0 |
| H | —CH₂NHCOCH₃ | —CH₂CHCH₂OH with OH | 1 | 0 |
| H | tetrazole (N—N, N, N, NH) | —CH₂C(CH₃)₂ with OH | 1 | 0 |
| H | tetrazole | —CH₂C(CH₃)₂ with OH | 1 | 1 |
| H | —CONHOH | —CH₂CHCH₃ with OH | 1 | 0 |

EXAMPLE B

Utilizing the general procedures described in Example 1 to 130, the following compounds of Formula I can be prepared from the appropriately substituted starting materials and reagents.

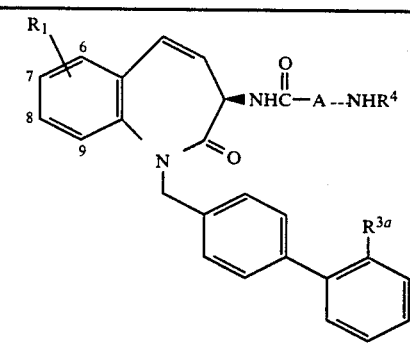

| R₁ | R³ᵃ | R⁴ | A |
|---|---|---|---|
| H | tetrazole | H | —CH₂—C(Me)(Me)— |

152
-continued

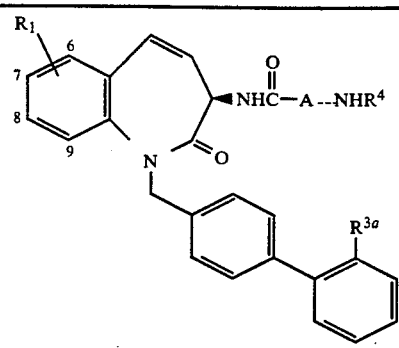

| R₁ | R³ᵃ | R⁴ | A |
|---|---|---|---|
| H | tetrazole | H | —C(Me)(Me)— |
| H | tetrazole | —CH₂CHCH₃ with OH | —CH₂—C(Me)(Me)— |
| H | tetrazole | —CH₂CHCH₃ with OH | —CH₂—C(Me)(Me)— |
| H | tetrazole | —CH₂CH₂CHCH₃ with OH | —CH₂—C(Me)(Me)— |
| 7-F | tetrazole | —CH₂CHCH₃ with OH | —CH₂—C(Me)(Me)— |
| 7-SCH₃ | tetrazole | —CH₂CHCH₃ with OH | —CH₂—C(Me)(Me)— |
| 7-S(O)CH₃ | tetrazole | —CH₂CHCH₃ with OH | —CH₂—C(Me)(Me)— |
| 7-OCH₃ | tetrazole | —CH₂CHCH₃ with OH | —CH₂—C(Me)(Me)— |
| H | —CONH₂ | H | —CH₂—C(Me)(Me)— |
| H | —CONH₂ | —CH₂CHCH₃ with OH | —CH₂—C(Me)(Me)— |
| H | —CONHMe | —CH₂CHCH₃ with OH | —CH₂—C(Me)(Me)— |

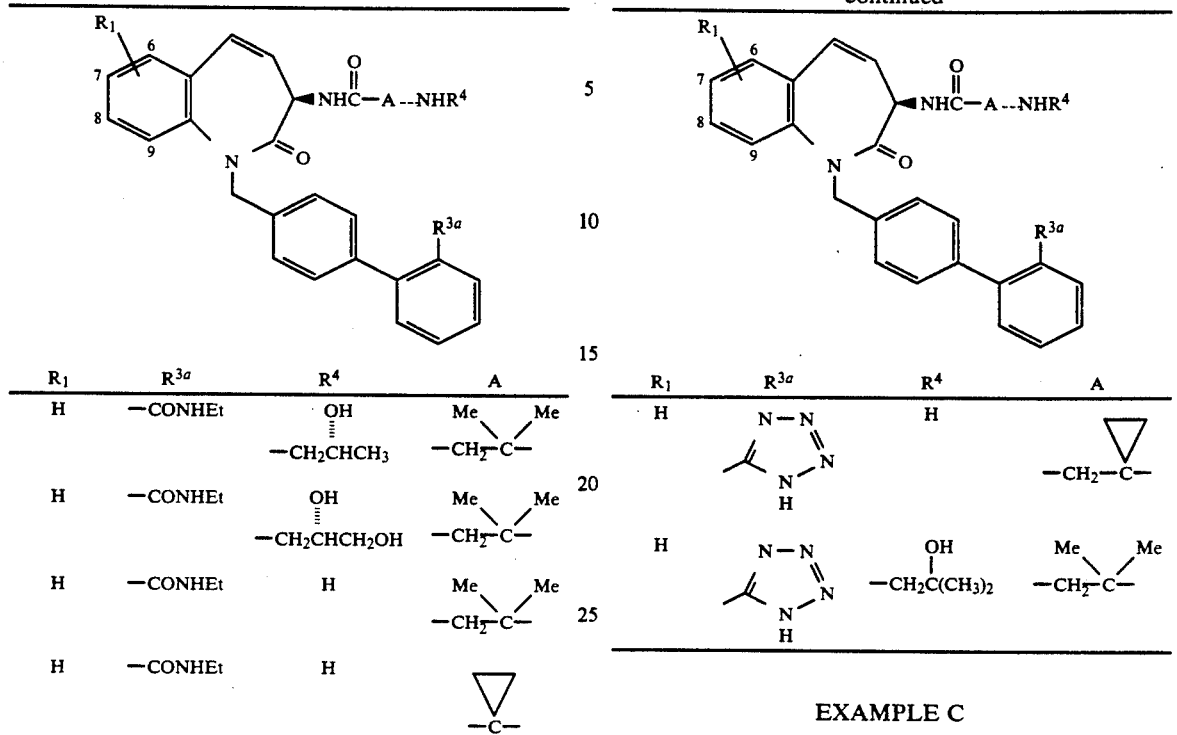

| R₁ | R³ᵃ | R⁴ | A |
|---|---|---|---|
| H | —CONHEt | —CH₂CHCH₃ (OH) | —CH₂—C(Me)(Me)— |
| H | —CONHEt | —CH₂CHCH₂OH (OH) | —CH₂—C(Me)(Me)— |
| H | —CONHEt | H | —CH₂—C(Me)(Me)— |
| H | —CONHEt | H | —C⟨▷ (cyclopropyl) |

| R₁ | R³ᵃ | R⁴ | A |
|---|---|---|---|
| H | tetrazolyl-NH | H | —CH₂—C⟨▷ |
| H | tetrazolyl-NH | —CH₂C(CH₃)₂ (OH) | —CH₂—C(Me)(Me)— |

EXAMPLE C

Utilizing the general procedures described in Example 1 to 130, the following compounds of Formula I can be prepared from the appropriately substituted starting materials and reagents.

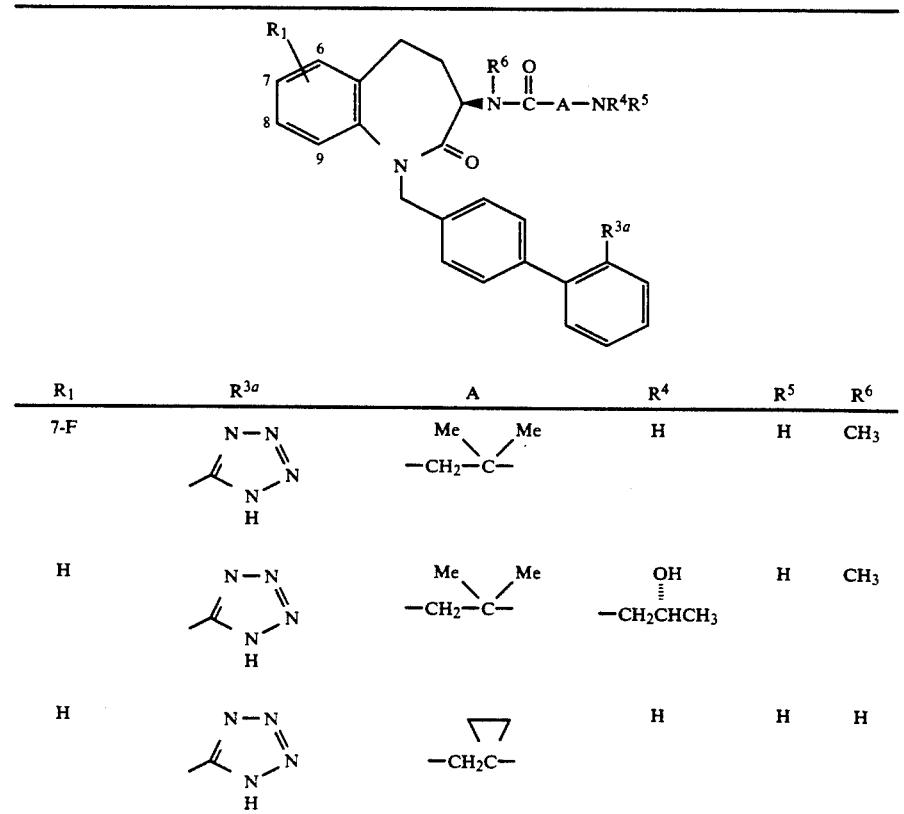

| R₁ | R³ᵃ | A | R⁴ | R⁵ | R⁶ |
|---|---|---|---|---|---|
| 7-F | tetrazolyl-NH | —CH₂—C(Me)(Me)— | H | H | CH₃ |
| H | tetrazolyl-NH | —CH₂—C(Me)(Me)— | —CH₂CHCH₃ (OH) | H | CH₃ |
| H | tetrazolyl-NH | —CH₂C—⟨▷ | H | H | H |

-continued
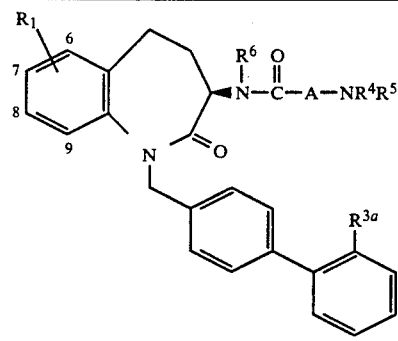
| R₁ | R³ᵃ | A | R⁴ | R⁵ | R⁶ |
|---|---|---|---|---|---|
| H | tetrazole (NH) | cyclopropyl –C– | H | H | H |
| H | tetrazole (NH) | cycloheptyl –C– | H | H | H |
| H | tetrazole (NH) | –CH– with (CH₂)₄NH₂ | H | H | H |
| H | tetrazole N-CH₂CH(OH)CH₃ | –CH₂–C(Me)₂– | –CH₂CH(OH)CH₃ | H | H |
| H | –C≡N | –CH₂–C(Me)₂– | –CH₂CH(OH)CH₃ | H | H |
| H | –CF₃ | –CH₂–C(Me)₂– | H | H | H |
| H | tetrazole (NH) | –CH₂C(Me)(CH₂OH)– | H | H | H |
| H | tetrazole N-CH₂CH(OH)CH₃ | –CH₂–C(Me)₂– | –CH₂CH(OH)CH₃ | H | H |
| 7-F | tetrazole N-CH₂CH(OH)CH₃ | –CH₂–C(Me)₂– | H | H | H |

-continued

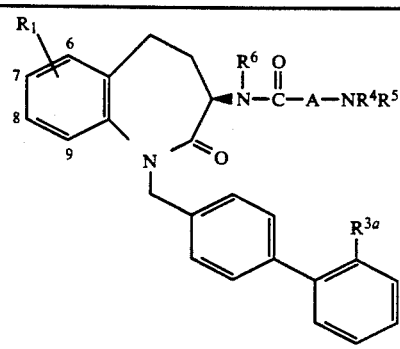

| $R_1$ | $R^{3a}$ | A | $R^4$ | $R^5$ | $R^6$ |
|---|---|---|---|---|---|
| 7-F | 5-methyl-2-(2-hydroxypropyl)tetrazole | $-CH_2-C(Me)(Me)-$ | H | H | H |
| H | 5-methyl-1-(2-hydroxypropyl)tetrazole | $-CH_2-C(Me)(Me)-$ | $-CH_2CH_2OH$ | H | H |
| H | 5-methyl-2-(2-hydroxypropyl)tetrazole | $-CH_2-C(Me)(Me)-$ | $-CH_2CH_2OH$ | H | H |
| H | 5-methyltetrazole (NH) | $-C(Me)(CH_2OH)-$ | H | H | H |
| H | 5-methyl-2-(carboxymethyl)tetrazole | $-CH_2-C(Me)(Me)-$ | H | H | H |
| H | 5-methyltetrazole (NH) | $-CH_2-C(Me)(Me)-$ | H | $CH_3$ | H |
| H | 5-methyltetrazole (NH) | $-CH_2-C(Me)(Me)-$ | $-CH_2C(OH)(CH_3)_2$ | H | H |
| H | $-CONH_2$ | $-CH_2-C(Me)(Me)-$ | $-CH_2C(OH)(CH_3)_2$ | H | H |
| H | $-CONHEt$ | $-CH_2-C(Me)(Me)-$ | $-CH_2C(OH)(CH_3)_2$ | H | H |
| 7-$OCH_3$ | 5-methyltetrazole (NH) | $-CH_2-C(Me)(Me)-$ | H | H | H |

-continued

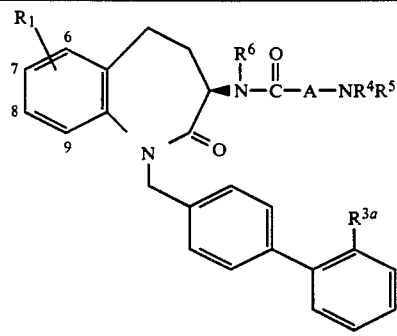

| R$_1$ | R$^{3a}$ | A | R$^4$ | R$^5$ | R$^6$ |
|---|---|---|---|---|---|
| 7-OH | 5-tetrazolyl (NH) | —CH$_2$—C(Me)$_2$— | H | H | H |
| 7-OCH$_3$ | 5-tetrazolyl (NH) | —CH$_2$—C(Me)$_2$— | —CH$_2$C(CH$_3$)$_2$OH | H | H |
| 7-OH | 5-tetrazolyl (NH) | —CH$_2$—C(Me)$_2$— | —CH$_2$C(CH$_3$)$_2$OH | H | H |
| H | 5-tetrazolyl (N-Bn) | —CH$_2$—C(Me)$_2$— | H | H | H |
| H | 5-tetrazolyl (N-Bn) | —CH$_2$—C(Me)$_2$— | —CH$_2$C(CH$_3$)$_2$OH | H | H |
| H | 5-tetrazolyl (NH) | —CH$_2$—C(Me)$_2$— | —CH$_2$CH$_2$OCH$_2$CH$_2$— | | H |
| H | —CONHCH$_3$ | —CH$_2$C(Me)$_2$— | —CH$_2$CH(OH)CH$_3$ | H | H |
| H | —CONHEt | —C(Me)$_2$— | CH$_2$CH$_2$CH(OH)CH$_3$ | H | H |
| H | —CONHOH | —C(Me)$_2$— | CH$_2$CH$_2$CH(OH)CH$_3$ | H | H |
| H | —CONHOH | —CH$_2$C(Me)$_2$— | CH$_2$CH$_2$CH(OH)CH$_3$ | H | H |
| H | 5-tetrazolyl (NH) | —C(Me)$_2$— | —CH$_2$CH(OH)CH$_3$ | H | H |

-continued

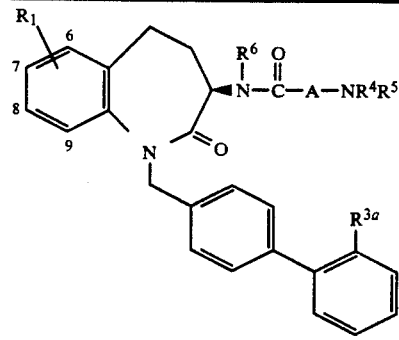

| $R_1$ | $R^{3a}$ | A | $R^4$ | $R^5$ | $R^6$ |
|---|---|---|---|---|---|
| H | 5-tetrazolyl (N—N / N—N—H with Me) | $-CH_2C(Me)_2-$ | $-CH_2CH_2CHCH_3$ with OH | H | H |
| H | —CONHOH | $-CH_2C(Me)_2-$ | $-CH_2CHCH_3$ with OH | H | H |
| 7-F | —CONHOH | $-CH_2C(Me)_2-$ | $-CH_2CHCH_3$ with OH | H | H |

EXAMPLE D

Utilizing the general procedures described in Example 1 to 10, the following compounds of Formula I can be prepared from the appropriately substituted starting materials and reagents.

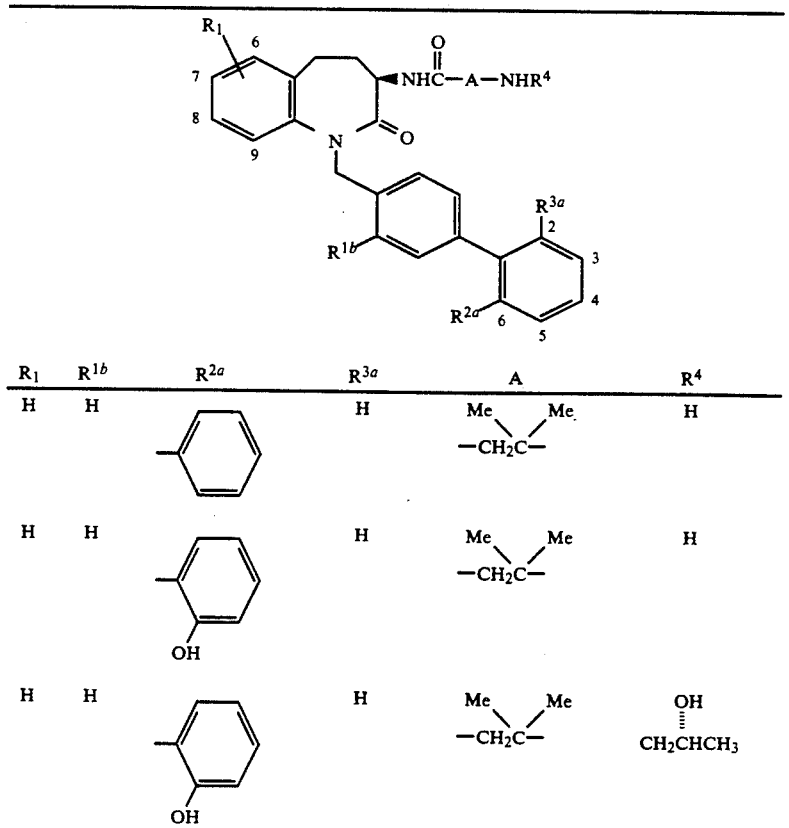

| $R_1$ | $R^{1b}$ | $R^{2a}$ | $R^{3a}$ | A | $R^4$ |
|---|---|---|---|---|---|
| H | H | phenyl | H | $-CH_2C(Me)_2-$ | H |
| H | H | 2-hydroxyphenyl | H | $-CH_2C(Me)_2-$ | H |
| H | H | 2-hydroxyphenyl | H | $-CH_2C(Me)_2-$ | $CH_2CHCH_3$ with OH |

-continued

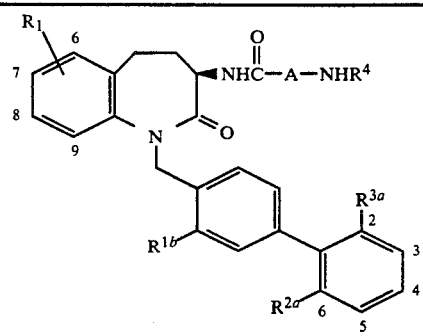

| $R_1$ | $R^{1b}$ | $R^{2a}$ | $R^{3a}$ | A | $R^4$ |
|---|---|---|---|---|---|
| H | H | 3-hydroxyphenyl | H | $-CH_2C(Me)_2-$ | $\overset{OH}{\underset{}{CH_2CHCH_3}}$ |
| H | Br | H | tetrazol-5-yl (NH) | $-CH_2C(Me)_2-$ | H |
| H | Br | H | tetrazol-5-yl (NH) | $-CH_2C(Me)_2-$ | $\overset{OH}{\underset{}{CH_2CHCH_3}}$ |
| H | H | H | tetrazol-5-yl (NH) | $-C(Me)_2CH_2-$ | H |
| H | H | H | tetrazol-5-yl (NH) | $-C(Me)_2-$ | $\overset{OH}{\underset{}{CH_2CHCH_3}}$ |
| H | H | H | tetrazol-5-yl (NH) | $-CH_2C(Me)_2-$ | $\overset{OH}{\underset{}{CH_2CH(CH_3)_2}}$ |
| H | H | H | tetrazol-5-yl (NH) | $-CH_2C(Me)_2-$ | $\overset{OH}{\underset{}{CH_2CH_2OH}}$ |
| H | H | H | 1-methyltetrazol-5-yl | $-CH_2C(Me)_2-$ | $\overset{OH}{\underset{}{CH_2CHCH_3}}$ |
| H | H | H | tetrazol-5-yl (NH) | $-CH_2C(Me)_2-$ | $\overset{OCH_3}{\underset{}{CH_2CHCH_3}}$ |
| H | Br | H | $-CONH_2$ | $-CH_2C(Me)_2-$ | H |

EXAMPLE E
Utilizing the general procedures described in Example 1 to 130, the following compounds of Formula I can be prepared from the appropriately substituted starting materials and reagents.
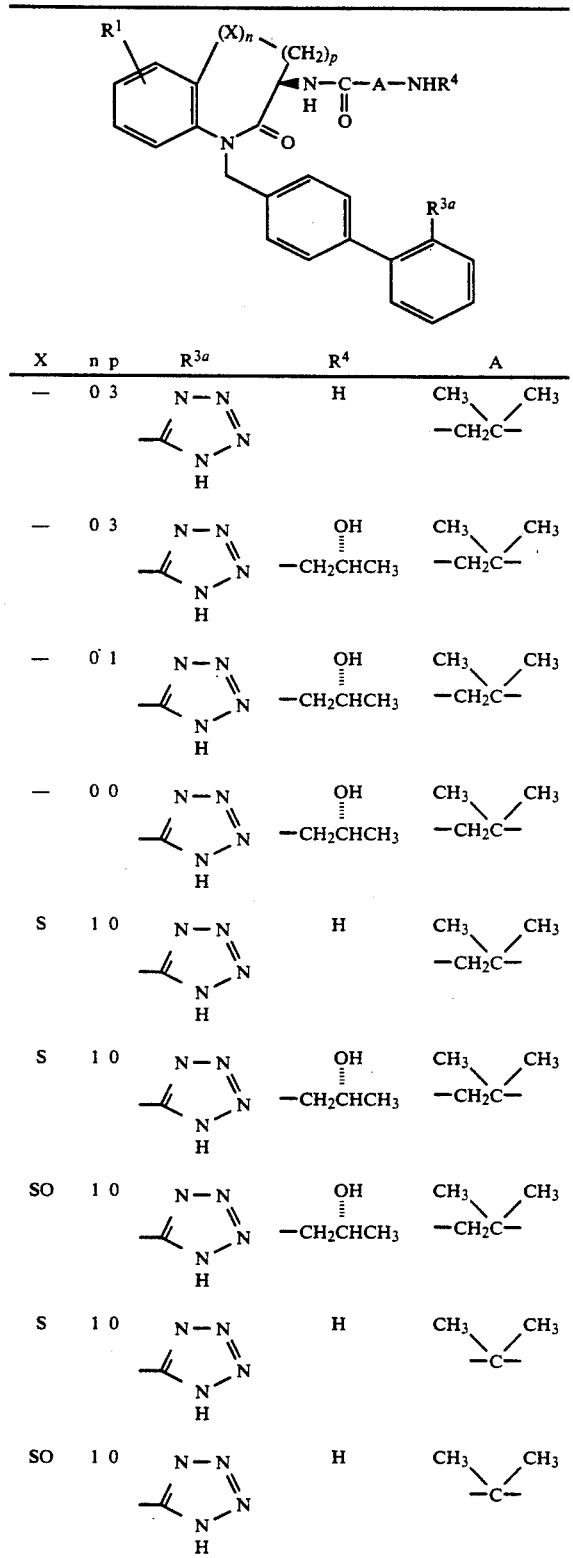
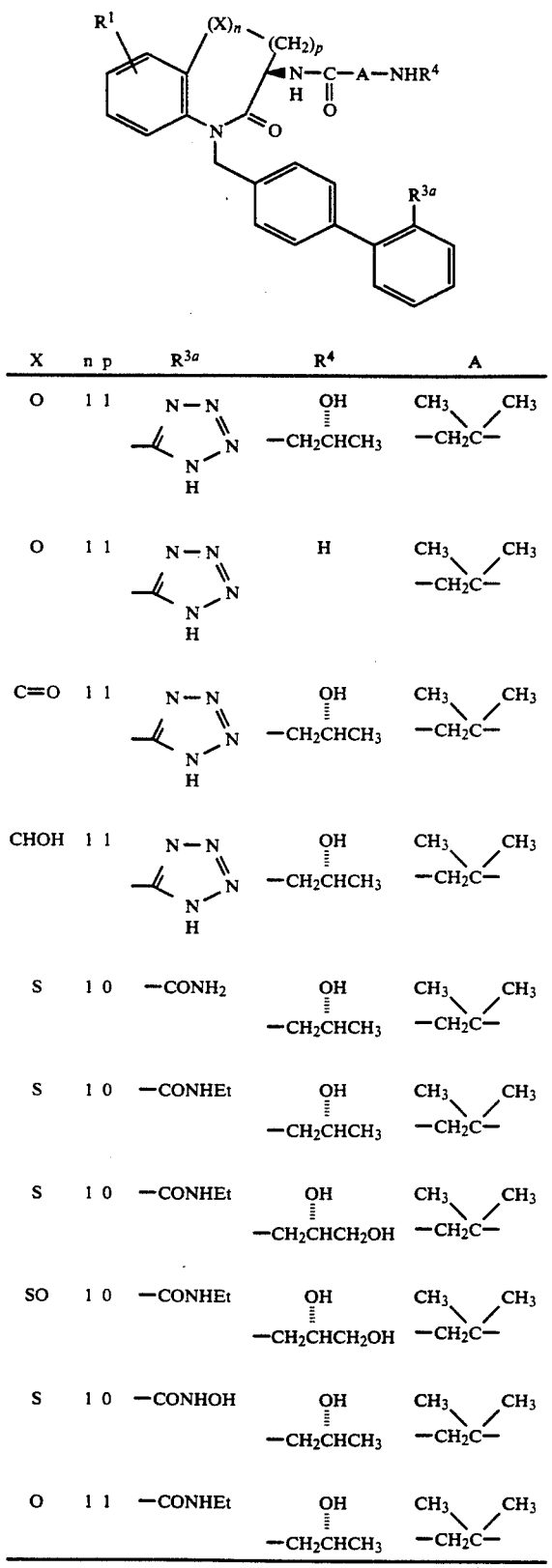
What is claimed is:
1. A compound having the formula:

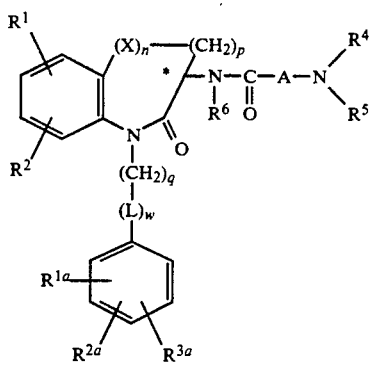

where L is

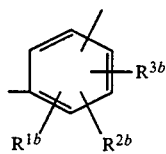

n i 1;
p is 1;
q is 0 to 4;
w is 0 to 1;
X is $S(O)_m$,
m is 0 to 2;
$R^1$, $R^2$, $R^{1a}$, $R^{2a}$, $R^{1b}$, and $R^{2b}$ are independently hydrogen, halogen, $C_1$–$C_7$ alkyl, $C_1$–$C_3$ perfluoroalkyl, $C_1$–$C_3$ perfluoroalkoxy, —$S(O)_m R^{7a}$, cyano, nitro, $R^{7b}O(CH_2)_v$—, $R^{7b}COO(CH_2)_v$—, $R^{7b}OCO(CH_2)_v$, phenyl or substituted phenyl where the substituents are from 1 to 3 of halogen, $C_1$–$C_6$ alkyl, $C_1$–$C_6$ alkoxy, or hydroxy;

$R^{7a}$ and $R^{7b}$ are independently hydrogen, $C_1$–$C_3$ perfluoroalkyl, $C_1$–$C_6$ alkyl, substituted $C_1$–$C_6$ alkyl, where the substituents are phenyl or substituted phenyl; phenyl or substituted phenyl where the phenyl substituents are from 1 to 3 of halogen, $C_1$–$C_6$ alkyl, $C_1$–$C_6$ alkoxy, or hydroxy and v is 0 to 3; $R^{3a}$ and $R^{3b}$ are independently hydrogen, $R^9$, $C_1$–$C_6$ alkyl substituted with $R^9$, phenyl substituted with $R^9$ or phenoxy substituted with $R^9$;
$R^9$ is

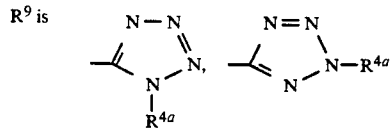

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^4R^5N(CH_2)_v$—j, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^4R^5NN(R^5)CS(CH_2)_v$—, $R^{7b}CON(R^4)N(R^5)CO(CH_2)_v$—, $R^{7b}CON(R^4)N(R^5)CS(CH_2)_v$—, $R^4N(OR^{7b})CO(CH_2)_v$— or $R^{7a}CON(OR^{7b})CO(CH_2)_v$—;
and v is as defined above;
$R^4$, $R^{41}$, $R^5$ are independently hydrogen, phenyl, substituted phenyl, $C_1$–$C_{10}$ alkyl, substituted $C_1$–$C_{10}$ alkyl, $C_3$–$C_{10}$ alkenyl, substituted $C_3$–$C_{10}$ alkenyl, $C_3$–$C_{10}$ alkynyl, or substituted $C_3$–$C_{10}$ alkynyl where the substituents on the phenyl, alkyl, alkenyl or alkynyl are from 1 to 5 of hydroxy, $C_1$–$C_6$ alkoxy, $C_3$–$C_7$ cycloalkyl, phenyl $C_1$–$C_3$ alkoxy, fluoro, $R^1$ substituted or $R^1$, $R^2$ independently disubstituted phenyl $C_1$–$C_3$ alkoxy, phenyl, $R^1$ substituted or $R^1$, $R^2$ independently disubstituted phenyl, where the substituents on the phenyl are as defined above, $C_1$–$C_5$-alkanoyloxy, $C_1$–$C_5$ alkoxycarbonyl, carboxy, formyl, or —$NR^{10}R^{11}$ where $R^{10}$ and $R^{11}$ are independently hydrogen, $C_1$–$C_6$ alkyl, phenyl, phenyl $C_1$–$C_6$ alkyl, $C_1$–$C_5$-alkoxycarbonyl or $C_1$–$C_5$-alkanoyl-$C_1$–$C_6$ alkyl; or $R^4$ and $R^5$ can be taken together to form —$(CH_2)_rB(CH_2)_s$— where B is $CH_2$, O or $S(O)_m$ or $N$-$R^{10}$, r and s are independently 1 to 3, and $R^{10}$ is as defined above;

$R^6$ is hydrogen, $C_1$–$C_{10}$ alkyl, phenyl or phenyl $C_1$–$C_{10}$ alkyl;

A is

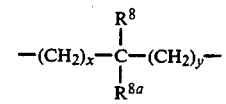

where x and y are independently 0-3;
$R^8$ and $R^{8a}$ are independently hydrogen, $C_1$–$C_{10}$ alkyl, trifluoromethyl, phenyl, substituted $C_1$–$C_{10}$ alkyl where the substituents are from 1 to 3 of imidazolyl, indolyl, hydroxy, fluoro, $S(O)_m R^{7a}$, $C_1$–$C_6$ alkoxy, $C_3$–$C_7$ cycloalkyl, phenyl $C_1$–$C_3$ alkoxy, $R^1$ substituted or $R^1$, $R^2$ independently disubstituted phenyl $C_1$–$C_3$ alkoxy, phenyl, $R^1$ substituted or $R^1$, $R^2$ independently disubstituted phenyl, $C_1$–$C_5$-alkanoyloxy, $C_1$–$C_5$ alkoxycarbonyl, carboxy, formyl, or —$NR^{10}R^{11}$ where $R^{10}$ and $R^{11}$ are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;
and pharmaceutically acceptable salts thereof.

2. A compound of claim 1 wherein:
n is 1;
p is 1;
q is 0 to 2;
w is 0 or 1;
X is $S(O)_m$,
m is 0 to 2;
$R^1$, $R^2$, $R^{1a}$, $R^{2a}$, $R^{1b}$, and $R^{2b}$ are independently hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$, phenyl or substituted phenyl where the substituents are from 1 to 3 of halogen, $C_1$–$C_6$ alkyl, $C_1$–$C_6$ alkoxy, or hydroxy;

$R^{7a}$ and $R^{7b}$ are independently hydrogen, $C_1$–$C_3$ perfluoroalkyl, $C_1$–$C_6$ alkyl, substituted $C_1$–$C_6$ alkyl, where the substituents are phenyl; phenyl and v is 0 to 2;

$R^{3a}$ and $R^{3b}$ are independently hydrogen, $R^9$, $C_1$–$C_6$ alkyl substituted with $R^9$, phenyl substituted with $R^9$ or phenoxy substituted with $R^9$;

$R^9$ is

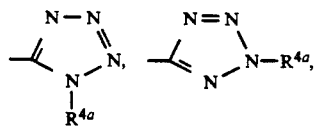

$R^{7b}O(CH_2)_v$—, $R^{7b}COO(CH_2)_v$—, $R^{7b}OCO(CH_2)_v$—, $R^{7b}CO(CH_2)_v$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^{7b}CON(R^4)N(R^5)CO(CH_2)_v$—, $R^4N(OR^{7b})CO(CH_2)_v$— or $R^{7a}CON(OR^{7b})CO(CH_2)_v$—; where v is as defined above; $R^4$, $R^{4a}$, $R^5$ are independently hydrogen, $C_1$-$C_{10}$ alkyl, substituted $C_1$-$C_{10}$ alkyl, where the substituents on the alkyl are from 1 to 5 of hydroxy, $C_1$-$C_6$ alkoxy, $C_3$-$C_7$ cycloalkyl, phenyl $C_1$-$C_3$ alkoxy, fluoro, $R^1$ substituted or $R^1$, $R^2$ independently disubstituted phenyl $C_1$-$C_3$ alkoxy, phenyl, $R^1$ substituted or $R^1$, $R^2$ independently disubstituted phenyl, where the substituents on the phenyl are as defined above, $C_1$-$C_5$-alkanoyloxy, $C_1$-$C_5$ alkoxycarbonyl, carboxy or formyl, $R^4$ and $R^5$ can be taken together to form —$(CH_2)_rB(CH_2)_s$— where B is $CH_2$, O or $S(O)_m$ or N-$R^{10}$ r and s are independently 1 to 3 and $R^{10}$ is as defined above;

$R^6$ is hydrogen, $C_1$-$C_{10}$ alkyl or phenyl $C_1$-$C_{10}$ alkyl;
A is

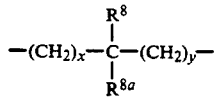

where x and y are independently 0-2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, phenyl, $R^1$ substituted or $R^1$, $R^2$ independently disubstituted phenyl, $C_1$-$C_5$-alkanoyloxy, $C_1$-$C_5$ alkoxycarbonyl, carboxy, formyl, —$NR^{10}R^{11}$ where $R^{10}$ and $R^{11}$ are independently hydrogen, $C_1$-$C_6$ alkyl, or $C_1$-$C_5$ alkanoyl-$C_1$-$C_6$ alkyl; or $R^8$ and $R^{8a}$ can be taken together to form —$(CH_2)_t$— where t is 2 to 4; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

3. A compound of claim 2 wherein:
n is 1;
p is 1;
q is 0 to 2;
w is 0 to 1;
X is $S(O)_m$,
m is 0 or 1;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl, substituted $C_1$-$C_6$ alkyl, where the substituents are phenyl and v is 0 to 2;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$;

$R^9$ is

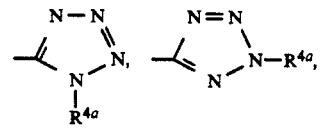

$R^{7b}O(CH_2)_v$—, $R^{7b}COO(CH_2)_v$—, $R^{7b}OCO(CH_2)_v$—, $R^{7b}CO(CH_2)_v$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4N(OR^{7b})CO(CH_2)_v$— or $R^{7a}CON(OR^{7b})CO(CH_2)_v$—; where v is as defined above; $R^4$, $R^{4a}$, $R^5$ are independently hydrogen, $C_1$-$C_{10}$ alkyl, substituted $C_1$-$C_{10}$ alkyl, where the substituents on the alkyl, are from 1 to 5 of hydroxy, $C_1$-$C_6$ alkoxy, fluoro, phenyl, $R^1$ substituted or $R^1$, $R^2$ independently disubstituted phenyl, where the substituents on the phenyl are as defined above, $C_1$-$C_5$-alkanoyloxy, $C_1$-$C_5$ alkoxycarbonyl, carboxy;

$R^6$ is hydrogen, $C_1$-$C_{10}$ alkyl;
A is

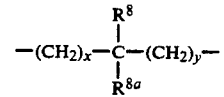

where x and y are independently 0-2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, phenyl, $R^1$ substituted or $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form —$(CH_2)_t$— where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

4. A compound of claim 3 wherein:
n is 1;
p is 1;
q is 1;
w is 1;
X is $S(O)_m$;
m is 0 or 1;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}(COO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl, substituted $C_1$-$C_6$ alkyl, where the substituents are phenyl, phenyl and v is 0 to 1;

$R^{3a}$ and $R^{3b}$ are independently hydrogen or $R^9$;
$R^9$ is $R^9$ is 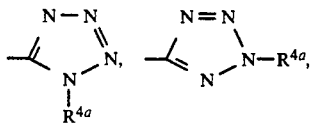

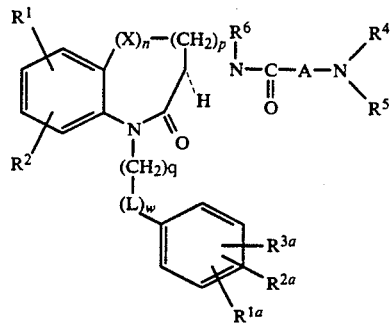

$R^{7b}O(CH_2)_v-$, $R^{7b}COO(CH_2)_v-$, $R^{7b}OCO(CH_2-)_v-$, $R^{7b}CO(CH_2)_v-$, $R^4R^5N(CH_2)_v-$, $R^{7b}CON(R^4)(CH_2)_v-$, $R^4R^5NCO(CH_2)_v-$ or $R^4N(OR^{7b})CO(CH_2)_v-$; where v is as defined above;

$R^4$, $R^5$ are independently hydrogen, $C_1-C_{10}$ alkyl, substituted $C_1-C_{10}$ alkyl, where the substituents on the alkyl are from 1 to 3 of hydroxy, $C_1-C_3$ alkoxy, fluoro, phenyl, $R^1$ substituted or $R^1$, $R^2$ independently disubstituted phenyl, where the substituents on the phenyl are as defined above;

$R^{4a}$ is hydrogen, $C_1-C_{10}$ alkyl, substituted $C_1-C_{10}$ alkyl where the substituents on the alkyl are from 1 to 3 of hydroxy.

$R^6$ is hydrogen;

A is

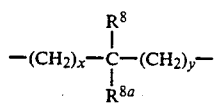

where x and y are independently 0-1;

$R^8$ and $R^{8a}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_mR^{7a}$, $C_1-C_6$ alkoxy, phenyl, $R^1$ substituted or $R^1$, $R^2$ independently disubstituted phenyl, $C_1-C_5$-alkanoyloxy, $C_1-C_5$ alkoxycarbonyl, carboxy; or $R^8$ and $R^{8a}$ can be taken together to form $-(CH_2)_t-$ where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

5. A stereospecific compound of claim 1 having the following structural formula:

where $R^1$, $R^2$, X, n, p, q, L, w, $R^{1a}$, $R^{2a}$, $R^{3a}$, $R^4$, $R^5$, A and $R^6$ are as defined in claim 1.

6. A compound of claim 1 which is:
3-amino-3-methyl-N-[3,4-dihydro-4-oxo-5-[[2'-(1H-tetrazol-5-yl)[1,1'-biphenyl]-4-yl]methyl]-1,5-benzothiazepin-3(S)-yl]-butanamide;
3-(2(R)-hydroxypropyl)amino-3-methyl-N-[3,4-dihydro-4-oxo-5-[[2'-(1H-tetrazol-5-yl)[1,1'-biphenyl]-4-yl]methyl]-1,5-benzothiazepin-3(S)-yl]-butanamide;
3-(2(S)-hydroxypropyl)amino-3-methyl-N-[3,4-dihydro-4-oxo-5-[[2'-(1H-tetrazol-5 yl)[1,1'-biphenyl]-4-yl]methyl]-1,5-benzothiazepin-3(S)-yl]-butanamide;
N-ethyl-4'-[[3(S)-[[3-[[2(S),3-dihydroxypropyl)amino[-3-methyl-1-oxobutyl ]amino]-3,4-dihydro-4-oxo-1,5-benzothiazepin-5(2H)-yl]methyl]-1,1'-biphenyl]-2-carboxamide
4'-[[3(S)-[(3-amino-3-methyl-1-oxobutyl)amino]-3,4-dihydro-4-oxo-1,5 -benzothiazepin-5(2H)-yl]-methyl]-[1,1'-biphenyl]-2-carboxamide
3-(2(R)-hydroxypropyl)amino-3-methyl-N-[3,4-dihydro-1,4-dioxo-5-[[2'-(1H-tetrazol -5-yl)[1,1'-biphenyl]-4-yl]methyl]-1,5-benzothiazepin-3(S)-yl]-butanamide;
3-amino-3-methyl-N-[3,4-dihydro-1,4-dioxo-5-[[2'-(1H-tetrazol-5-yl)[1,1'-biphenyl]-4-yl]-1,5-benzothiazepin-3(S)-yl]-butanamide;
3-amino-3-methyl-N-[7-methylthio-2,3,4,5-tetrahydro-2-oxo-1-[[2'-(1H-tetrazol-5 -yl)[1,1'-biphenyl]-4-yl]methyl]-1H-1-benzazepin-3(R)-yl]butanamide
and pharmaceutically acceptable salts of such compounds.

7. A method for increasing levels of endogenous growth hormone in a human or an animal which comprises administering to such human or animal an effective amount of a compound of claim 1.

8. A composition useful for increasing the endogenous production or release of growth hormone in a human or an animal which comprises an inert carrier and an effective amount of a compound of claim 1.

9. A composition useful for increasing the endogenous production/release of growth hormone in a human or an animal which comprises an inert carrier and an effective amount of a compound of claim 1 used in combination with other growth hormone secretagogues such as, GHRP-6 or GHRP-1, growth hormone releasing factor (GRF) or one of its analogs, IGF-1 or IGF-2, or B-HT920.

* * * * *